(12) United States Patent
Zhang et al.

(10) Patent No.: US 8,088,806 B2
(45) Date of Patent: *Jan. 3, 2012

(54) THIAZOLE COMPOUNDS AND METHODS OF USE

(75) Inventors: Suoming Zhang, Madison, CT (US);
Avinash Phadke, Branford, CT (US);
Cuixian Liu, Madison, CT (US);
Xiangzhu Wang, Branford, CT (US);
Jesse Quinn, Windsor, CT (US); Dawei Chen, Middletown, CT (US); Venkat Gadhachanda, Hamden, CT (US);
Shouming Li, Chesire, CT (US); Milind Deshpande, Madison, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/431,155

(22) Filed: May 9, 2006

(65) Prior Publication Data

US 2007/0004711 A1    Jan. 4, 2007

Related U.S. Application Data

(60) Provisional application No. 60/679,133, filed on May 9, 2005.

(51) Int. Cl.
*A61K 31/426* (2006.01)
*A61K 31/44* (2006.01)
(52) U.S. Cl. .................................. 514/370; 514/342
(58) Field of Classification Search .................. None
See application file for complete search history.

(56) References Cited

U.S. PATENT DOCUMENTS

| | | | |
|---|---|---|---|
| 2,474,194 A | 6/1949 | Thurston | |
| 3,458,526 A | 7/1969 | Lednicer | |
| 3,467,666 A | 9/1969 | Dexter et al. | |
| 3,933,838 A | 1/1976 | Manghisi et al. | |
| 5,104,889 A | 4/1992 | Kanai et al. | |
| 5,298,515 A | 3/1994 | Schubert et al. | |
| 5,856,347 A | 1/1999 | Hashiguchi et al. | |
| 6,583,163 B2 | 6/2003 | Chihiro et al. | |
| 6,586,453 B2 | 7/2003 | Dhanoa et al. | |
| 7,115,746 B2 | 10/2006 | Snoonian et al. | |
| 7,163,952 B2 | 1/2007 | Inaba et al. | |
| 7,169,931 B2 | 1/2007 | Takemoto et al. | |
| 7,232,838 B2 | 6/2007 | Love et al. | |
| 2001/0044545 A1 | 11/2001 | Dhanoa et al. | |
| 2002/0016471 A1 | 2/2002 | Salituro et al. | |
| 2003/0158199 A1 | 8/2003 | Stieber et al. | |
| 2003/0203897 A1 | 10/2003 | Love et al. | |
| 2003/0220380 A1 | 11/2003 | Dhanoa et al. | |
| 2004/0014789 A1 | 1/2004 | Lau et al. | |
| 2004/0053982 A1 | 3/2004 | Press et al. | |
| 2004/0110810 A1 | 6/2004 | Ciafolini et al. | |
| 2004/0157845 A1 | 8/2004 | Doherty et al. | |
| 2004/0186148 A1 | 9/2004 | Shankar et al. | |
| 2004/0198773 A1 | 10/2004 | Hart et al. | |
| 2004/0209924 A1 | 10/2004 | Hart et al. | |
| 2004/0236110 A1 | 11/2004 | Ladouceur et al. | |
| 2004/0254191 A1 | 12/2004 | Love et al. | |
| 2004/0254236 A1 | 12/2004 | Dong et al. | |
| 2004/0267017 A1 | 12/2004 | Bierer et al. | |
| 2005/0065196 A1 | 3/2005 | Inaba et al. | |

FOREIGN PATENT DOCUMENTS

| | | |
|---|---|---|
| DD | 271258 A1 | 8/1989 |
| EP | 0790057 B1 | 5/2002 |
| EP | 1321463 | 6/2003 |
| EP | 1354603 | 10/2003 |
| EP | 1452530 | 9/2004 |
| EP | 1599468 B1 | 3/2007 |

(Continued)

OTHER PUBLICATIONS

Moyer et al., American Family Physician, (Jan. 15, 1999), 59(2), pp. 349-354 (1-7).*

(Continued)

*Primary Examiner* — Laura L. Stockton
(74) *Attorney, Agent, or Firm* — Cantor Colburn LLP

(57) ABSTRACT

The present invention provides compounds, salts and hydrates of Formula I,

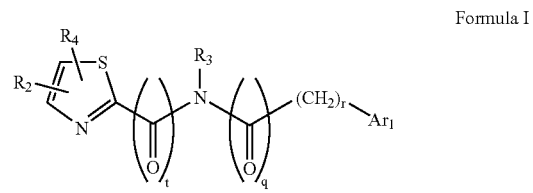

Formula I wherein the variables $Ar_1$, $R_2$, $R_3$, $R_4$, r, q, and t are defined herein. Certain compounds of Formula I described herein possess potent antiviral activity. The invention also provides compounds of Formula I that are potent and/or selective inhibitors of Hepatitis C virus replication. Certain compounds described herein inhibit assembly of the HCV replication complex. The invention also provides pharmaceutical compositions containing one or more compounds of Formula I, or a salt, solvate, or acylated prodrug of such compounds, and one or more pharmaceutically acceptable carriers, excipients, or diluents. The invention further comprises methods of treating patients suffering from certain infectious diseases by administering to such patients an amount of a compound of Formula I effective to reduce signs or symptoms of the disease. These infectious diseases include viral infections, particularly HCV infections. The invention is particularly includes methods of treating human patients suffering from an infectious disease, but also encompasses methods of treating other animals, including livestock and domesticated companion animals, suffering from an infectious disease. Methods of treatment include administering a compound of Formula I as a single active agent or administering a compound of Formula I in combination with on or more other therapeutic agent.

13 Claims, No Drawings

FOREIGN PATENT DOCUMENTS

| | | | |
|---|---|---|---|
| EP | 1525200 B1 | 10/2007 | |
| GB | 1481465 | 7/1977 | |
| GB | 2022085 A | 12/1979 | |
| WO | 9724343 A1 | 7/1997 | |
| WO | 0006575 A2 | 2/2000 | |
| WO | WO 00 33837 | 6/2000 | |
| WO | 0121160 A2 | 3/2001 | |
| WO | 0153267 A1 | 7/2001 | |
| WO | 0164674 A1 | 9/2001 | |
| WO | 0174793 A2 | 10/2001 | |
| WO | 0230357 A2 | 4/2002 | |
| WO | WO 02 051410 | 7/2002 | |
| WO | 02094264 A1 | 11/2002 | |
| WO | 03004467 A2 | 1/2003 | |
| WO | 03015773 A2 | 2/2003 | |
| WO | 03027085 A2 | 4/2003 | |
| WO | 03028729 A2 | 4/2003 | |
| WO | 03066215 A1 | 8/2003 | |
| WO | 03093242 A2 | 11/2003 | |
| WO | 03048140 A1 | 12/2003 | |
| WO | 2004014884 A1 | 2/2004 | |
| WO | 2004071447 A2 | 8/2004 | |
| WO | 2004072070 A1 | 8/2004 | |
| WO | 2004076693 A1 | 9/2004 | |
| WO | 2004085385 A2 | 10/2004 | |
| WO | 2004092145 A1 | 10/2004 | |
| WO | 2004096225 A2 | 11/2004 | |
| WO | 2004096798 A2 | 11/2004 | |
| WO | WO 2004 098612 | 11/2004 | |
| WO | WO 2004 110350 | 12/2004 | |
| WO | 2005007647 A1 | 1/2005 | |
| WO | WO 2005 000298 | 1/2005 | |
| WO | WO 2005 000309 | 1/2005 | |
| WO | 2005016323 A2 | 2/2005 | |
| WO | WO 2005 030194 | 4/2005 | |
| WO | 2005051318 A2 | 6/2005 | |
| WO | WO 2005 051318 | 6/2005 | |
| WO | 2005073225 A1 | 8/2005 | |
| WO | 2005077368 A2 | 8/2005 | |
| WO | 2005082089 A2 | 9/2005 | |
| WO | 2005099673 A1 | 10/2005 | |
| WO | 2005102318 A1 | 11/2005 | |
| WO | 2005102325 A1 | 11/2005 | |
| WO | 2005102326 A2 | 11/2005 | |
| WO | 2005102346 A2 | 11/2005 | |
| WO | 2005102455 A1 | 11/2005 | |
| WO | 2005112920 A1 | 12/2005 | |
| WO | 2005115304 A2 | 12/2005 | |
| WO | 2005115385 A1 | 12/2005 | |
| WO | 2006033005 A2 | 3/2006 | |
| WO | 2006122250 A2 | 11/2006 | |
| WO | 03062215 A1 | 7/2007 | |
| WO | 2007095603 A2 | 8/2007 | |
| WO | WO-2007/103550 A2 * | 9/2007 | |

OTHER PUBLICATIONS

Bailey, N. et al. "A Convenient Procedure for the Solution Phase Preparation of 2-Aminothiazole Combinatorial Libraries," Bioorganic & Medicinal Chemistry Letters (1996) 6(12): 1409-1414.

Misra, R. N. et al. "Synthesis and Biological Activity of N-Aryl-2-Aminothiazoles: Potent Pan Inhibitors of Cyclin-Dependent Kinases," Bioorganic & Medicinal Chemistry Letters (2004) 14(11): 2973-2977.

Mozziconacci, J-C et al. "Optimization and Validation of a Docking-Scoring Protocol; Application to Virtual Screening for COX-2 Inhibitors," Journal of Medicinal Chemistry (2005) 48(4): 1055-1068.

Shipps, G. W. et al. "Anninothiazole Inhibitors of HVC RNA Polymerase," Bioorganic & Medicinal Chemistry Letters (2005) 15(1): 115-119.

Harode, R. et al. "Synthesis of 2,2'-Imino-bis-arylthiazole Derivatives and their Antimicrobial Activity," Journal of the Indian Chemical Society (1990) 67(3): 262-263. Database Beilstein Crossfire. Citation No. 5525052. (Abstract Only).

Fioravanti, R. et al. "Synthesis and Microbiological Evaluations of (N-heteroaryl) Arylnnethanamines and their Schiff Bases," Farmaco (1996) 51(10): 643-652. Database Beilstein Crossfire. Citation No. 6022277. (Abstract Only).

Pathak, V. N. "Synthesis and Biological Activities of Some New 2-(N-arylamino)-4-(fluoroaryl) thiazoles," Journal of the Indian Chemical Society (1979) 56(10): 1010-1012. (Abstract Only).

Beilstein Registry No. 14269. Chemical Name: (5-bromo-4-methyl-thiazol-2-yl)-p-tolyl-amine. Database Beilstein. (Abstract Only), 1931.

Beilstein Registry No. 14823. Chemical Name: (4-ethoxy-phenyl)-(4-methyl-thiazol-2-yl)-amine. Database Beilstein. (Abstract Only), 1934.

Beilstein Registry No. 155628. Chemical Name: (4-methyl-thiazol-2-yl)-p-tolyl-amine. Database Beilstein. (Abstract Only), 1887.

Beilstein Registry No. 989080. Chemical Name: (5-phenyl-thiazol-2-yl)-pyridin-2-yl-amine. Database Beilstein. (Abstract Only), 1976.

Invitation to Pay Additional Fees with International Search Report for International Application No. PCT/US2006/017692. Mailed Jan. 19, 2007.

Shipps, G.W. Jr., et al. "Aminothiazole Inhibitors of HCV Polymerase," Bioorganic and Medicinal Chemistry Letters (2005) 15: 115.

Kuleshova, L.N. et al., "Conformational Polymorphism of N-(4-Butoxyphenyl)-4-(4'-Nitrophenyl)-2-Thiazolamine," Crystallography Reports, (2003) 49(5): 798-806.

Parvate, J.A. "Synthesis of substituted 4,2'-bis thiazoles," Indian Drugs (1989) 26(5): 222-226.

Truce, W.E, et al. "The Stereochemistry of the Reaction of Tetrachloroethylene with p-toluene-thiolate reagent," Tetrahedron 21: 2899-2905 (1965).

Search Report for International Application No. PCT/US2006/017692 dated Mar. 19, 2007.

Written Opinion for International Application No. PCT/US2006/017692 dated Mar. 19, 2007.

* cited by examiner

THIAZOLE COMPOUNDS AND METHODS OF USE

PRIORITY INFORMATION

This application claims priority from U.S. Provisional Application Ser. No. 60/679,133, filed May 9, 2005, which is hereby incorporated by reference in its entirety.

FIELD OF THE INVENTION

The present invention relates to thiazole compounds and the preparation of such compounds. The present invention further relates to methods for use of such compounds, including for the treatment of hepatitis C virus.

BACKGROUND OF THE INVENTION

Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. It has been estimated that almost 4 million Americans, or about 1.8 percent of the U.S. population, have antibodies to HCV (i.e., anti-HCV antibodies), indicating previous or ongoing infection with the virus. Hepatitis C causes an estimated 8,000 to 10,000 deaths annually in the United States. While the acute phase of HCV infection is usually associated with mild symptoms, some evidence suggests that only about 15% to 20% of infected people will clear HCV.

It has been reported that HCV is an enveloped, single-stranded RNA virus that contains a positive-stranded genome of about 9.6 kb. HCV is classified as a member of the *Hepacivirus* genus of the family Flaviviridae.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

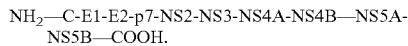

NH$_2$—C-E1-E2-p7-NS2-NS3-NS4A-NS4B—NS5A-NS5B—COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B—NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at 3 downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. Provisional application docket no. A&P 18477.047, "Pharmaceutical compositions for and Methods of Inhibiting HCV Replication," inventor Mingjun Huang, filed Apr. 11, 2005 is hereby incorporated by reference for in its entirety for its disclosure related to assembly of the replicase complex.

While previously known HCV inhibitors are suitable for their intended purposes, there nonetheless remains a need for additional HCV inhibitors. In addition, there remains a need for additional methods of treatment for HCV patients. Thus, there remains a need to develop, characterize and optimize molecules for the development of anti-hepatitis C drugs. Accordingly, it is an object of the present invention to provide such compounds, compositions and methods of treatment.

SUMMARY OF THE INVENTION

In accordance with the present invention, compounds that inhibit hepatitis C virus replication have been identified, and methods for use of such compounds are provided.

In one aspect, the present invention includes and provides compounds of Formulas (I) and pharmaceutically acceptable salts thereof, which compounds are useful in the inhibition of hepatitis C virus replication and the treatment of hepatitis C viral infection. Within this aspect, the invention includes compounds of Formula I

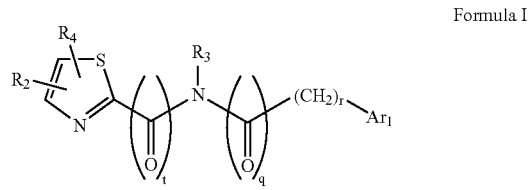

Formula I and pharmaceutically acceptable salt or hydrate thereof, wherein the variables Ar$_1$, R$_2$, R$_3$, R$_4$, q, r, and t carry definitions set forth below.

Ar$_1$ is fluorenyl, or Ar$_1$ is phenyl, naphthyl, a 5- or 6-membered monocyclic heteroaryl group, or a 9- or 10-membered bicyclic heteroaryl group, wherein Ar$_1$ is substituted with R and R$_1$.

R is 0 or one or more substituents independently chosen from halogen, hydroxyl, amino, cyano, nitro, C$_1$-C$_2$alkyl, C$_1$-C$_2$alkoxy, C$_1$-C$_2$haloalkyl, and C$_1$-C$_2$haloalkoxy.

R$_1$ is one or two substituents independently chosen from (a) and (b), where (a) is halogen, hydroxyl, amino, cyano, nitro, —COOH, —SO$_2$NH$_2$C$_1$-C$_2$haloalkyl, and C$_1$-C$_2$haloalkoxy, and (b) C$_1$-C$_{10}$ alkyl, C$_2$-C$_{10}$ alkenyl, C$_2$-C$_{10}$ alkynyl, C$_2$-C$_{10}$alkanoyl, C$_2$-C$_{10}$alkylester, C$_1$-C$_{10}$ alkoxy, mono- or di-C$_1$-C$_{10}$alkylcarboxamide, or a group —YZ.

Y is bond, or Y is C$_1$-C$_{10}$alkyl, a C$_2$C$_{10}$alkenyl, or C$_2$-C$_{10}$alkynyl, each optionally having 1 or 2 oxygen or nitrogen atoms within the alkyl, alkenyl, or alkynyl chain.

Z is hydrogen, C$_3$-C$_7$cycloalkyl, C$_3$-C$_7$cycloalkenyl, heterocycloalkyl, phenyl, naphthyl, indanyl, (C$_3$-C$_7$cycloalkyl)C$_0$-C$_{10}$alkoxy, or 5- to 6-membered heteroaryl containing 1, 2, 3, or 4 heteroatoms independently chosen from N, O, and S, wherein each (b) is substituted with 0 or one or more substituents independently chosen from: halogen, hydroxyl, amino, cyano, nitro, oxo, $C_1$-$C_4$alkyl, $C_1$-$C_4$alkoxy, $C_1$-$C_2$haloalkyl, and $C_1$-$C_2$haloalkoxy;

Any R and $R_1$ which are covalently bound to adjacent carbon atoms may be joined to form an aromatic or partially saturated carbocyclic ring system having 1 or 2 rings, each ring having 5 or 6 ring carbon atoms.

$R_2$ is halogen, —COOH, —CONH$_2$, —C(O)OCH$_3$, —C(O)CH$_3$, —NHC(O)OH, or amino, or $R_2$ is —CH$_2$R$_a$, —NH—S(O)$_2$R$_a$, —CH$_2$—NH—S(O)$_2$R$_a$, —S(O)$_2$R$_a$, —C(O)—NH—R$_a$, —C(O)—NH—CH$_2$R$_a$, —NH—C(O)—R$_a$, —NH—C(O)—R$_b$, —C(O)O—R$_a$, —C(O)—O—R$_b$, —OR$_a$, —C(O)—R$_a$, or —C(O)—R$_b$, each of which is substituted with 0 or one or more substituents independently chosen from (c), (d), and (e), or $R_2$ is $C_1$-$C_6$alkyl, phenyl, a 5- to 6-membered heteroaryl, phenyl fused to a 5 or 6 membered cycloalkyl or heterocycloalkyl ring, or a bicyclic 8- to 10-membered heteroaryl, each of which is substituted with 0 or one or more substituents independently chosen from (c), (d), and (e); where (c) is halogen, hydroxyl, oxo, cyano, amino, nitro, —C(O)NH$_2$, —C(O)OH, —S(O)NH$_2$, $C_1$-$C_2$haloalkyl, and $C_1$-$C_2$haloalkoxy, (d) is $C_1$-$C_4$alkyl, $C_1$-$C_4$alkoxy, $C_2$-$C_4$alkenyl, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester, each of which is substituted with 0 or one ore more substituents independently chosen from oxo, halogen, hydroxyl, oxo, cyano, amino, nitro, —C(O)NH$_2$, —C(O)OH, —S(O)NH2, $C_1$-$C_4$alkoxy, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester $C_1$-$C_2$haloalkyl, and $C_1$-$C_2$haloalkoxy; and (e) ($C_3$-$C_7$cycloalkyl)$C_0$-$C_4$alkyl, (heterocycloalkyl)$C_0$-$C_4$alkyl, (phenyl)$C_0$-$C_4$alkyl, each of which is substituted with oxo, halogen, hydroxyl, oxo, cyano, amino, nitro, —C(O)NH$_2$, —C(O)OH, —S(O)NH$_2$, $C_1$-$C_2$haloalkyl, and $C_1$-$C_2$haloalkoxy.

$R_2$ and $R_4$ are taken together with the carbon atoms of the thiazole ring to which they are attached to form a $C_5$-$C_7$ carbocyclic ring, which is aromatic or partially unsaturated;

$R_3$ is hydrogen, $C_1$-$C_4$alkyl, or —C(O)—R$_d$.

$R_4$ is hydrogen, halogen, hydroxyl, amino, cyano, nitro, $C_1$-$C_2$alkyl, $C_1$-$C_2$alkoxy, $C_1$-$C_2$haloalkyl, $C_1$-$C_2$haloalkoxy or phenyl; or $R_4$ is taken together with $R_2$ to form a ring;

$R_a$ is independently chosen at each occurrence from: heterocycloalkyl, phenyl, and 5- and 6-membered heteroaryl, each of which is substituted with 0 or one or more substituents independently chosen from halogen, hydroxyl, amino, cyano, $C_1$-$C_4$ alkyl, and $C_1$-$C_4$ alkoxy.

$R_b$ is $C_1$-$C_6$ alkyl, wherein the alkyl is optionally substituted with a halogen, hydroxyl, —C(O)OH, phenyl, or 4-(NH$_2$S(O)$_2$)-phenyl.

$R_d$ is $C_1$-$C_6$alkyl, phenyl, or 5- to 6-membered heteroaryl; r is 0, 1, or 2; q is 0 or 1; t is 0 or 1; and q and t are not both 1.

In another aspect, the present invention includes and provides pharmaceutical compositions comprising compounds of the present invention.

In another aspect, the present invention includes and provides methods for the inhibition of hepatitis C virus replication using compounds of the present invention.

In a further aspect, the present invention includes and provides methods for the treatment or prevention of hepatitis C viral infection.

In an aspect, the present invention includes and provides a method for treating or preventing hepatitis C virus in a subject in need thereof, said method comprising: administering to the subject an amount of a compound of formula (I), including compounds of formula (I-a), (I-b), (I-c), (I-d), (I-e), (I-f), and (I-g), or a pharmaceutically acceptable salt, hydrate, prodrug or metabolite thereof, where hepatitis C virus is treated or prevented. The compound of formula I may be administered to the subject alone or may be administered to the subject in combination with one or more other active agents, such as one or more other anti-viral agents.

These and other aspects of the invention will be more clearly understood with reference to the following detailed description, examples and claims.

DETAILED DESCRIPTION OF THE INVENTION

Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

Formula I includes all subformulae thereof. For example Formula I includes compounds of Formulas (I-a), (I-a), (I-b), (I-c), (I-d), (I-e), (I-f), (I-g), (I-h), and (I-i) and the pharmaceutically acceptable salts, prodrugs, hydrates, polymorphs, and thereof.

The term Formula I encompasses all compounds that satisfy Formula I, including any enantiomers, racemates and stereoisomers, as well as all pharmaceutically acceptable salts of such compounds. The phrase "a compound of Formula I" includes all forms of such compounds, including salts and hydrates, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

In certain situations, the compounds of Formula I may contain one or more asymmetric elements such as stereogenic centers, including chiral centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention.

The term "chiral" refers to molecules, which have the property of non-superimposability of the mirror image partner.

The term "stereoisomers" refers to compounds, which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Where a compound exists in various tautomeric forms, the invention is not limited to any one of the specific tautomers, but rather includes all tautomeric forms.

The invention includes compounds of Formula I having all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. R, $R_1$, $R_2$, $R_3$, $R_4$, t, q, and r. Unless otherwise specified, each variable within such a Formula I is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —$(CH_2)C_3$-$C_8$cycloalkyl is attached through carbon of the methylene ($CH_2$) group.

"Alkanoyl" indicates an alkyl group as defined herein, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3$(C=O)—.

As used herein, the term "alkyl" "includes both branched and straight chain saturated aliphatic hydrocarbon groups, having the specified number of carbon atoms, generally from 1 to about 18 carbon atoms, though in some embodiments alkyl groups having from 1 to 10, 1 to 8, 1 to 6, 1 to 4, or 1 to 2 carbon atoms are preferred.

"Alkenyl" as used herein, includes straight and branched hydrocarbon chains comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. C2-C8, C2-C6, and C2-C4 alkenyl groups. Examples of alkenyl groups include ethenyl, propenyl, and butenyl groups.

"Alkynyl" as used herein, includes straight or branched hydrocarbon chain comprising one or more triple carbon-carbon bonds that may occur in any stable point along the chain, such as ethynyl and propynyl. Alkynyl groups described herein typically have from 2 to about 12 carbons atoms. Preferred alkynyl groups are lower alkynyl groups, those alkynyl groups having from 2 to about 8 carbon atoms, e.g. $C_2$-$C_{10}$, $C_2$-$C_6$, and $C_2$-$C_4$ alkynyl groups.

The term "alkylester" indicates an alkyl group as defined herein attached through an ester linkage. The ester linkage may be in either orientation, e.g. a group of the formula —O(C=O)alkyl or a group of the formula —(C=O)Oalkyl.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. $C_4$-$C_{10}$alkoxy group As used herein, the term "aryl" includes radicals of an aromatic group obtained by removal of one hydrogen atom from a single carbon atom of a parent aromatic ring system and containing only carbon in the aromatic ring or rings. Aromatic rings have 4n+2 p electrons in a cyclic arrangement.

Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

A "carbocyclic ring" may have 1 to 3 fused, pendant, or spiro rings, containing only carbon ring members. Typically, a carbocyclic ring comprises contains from 3 to 8 ring members (rings having from 4 or 5 to 7 ring members are recited in certain embodiments) and carbocycles comprising fused, pendant, or spiro rings typically contain from 9 to 14 ring members. Unless otherwise specified, a carbocycle may be a cycloalkyl group (i.e., each ring is saturated), a partially saturated group, or an aryl group (i.e., at least one ring within the group is aromatic). A carbocyclic group may generally be linked via any ring or substituent atom, provided that a stable compound results. When indicated carbocylic groups, such as 4- to 7-membered or 5- to 7-membered groups, may be substituted. Representative aromatic carbocycles are phenyl, naphthyl and biphenyl. In certain embodiments preferred carbocycles are carbocycles having a single ring, such as phenyl and 3- to 7-membered cycloalkyl groups.

"Cycloalkyl" as used herein, includes a monocyclic saturated hydrocarbon ring group, having the specified number of carbon atoms. Monocyclic cycloalkyl groups typically have from 3 to about 8 carbon ring atoms or from 3 to about 7 carbon ring atoms. Examples of cycloalkyl groups include cyclopropyl, cyclobutyl, cyclopentyl, and cyclohexyl.

In the term "(cycloalkyl)alkyl", cycloalkyl and alkyl are as defined above, and the point of attachment is on the alkyl group. This term encompasses, but is not limited to, cyclopropylmethyl, cyclohexylmethyl, and cyclohexylmethyl. (Cycloalkyl)$C_0$-$C_2$alkyl" indicates a cycloalkyl group that is directly attached via a single covalent bond (i.e. (cycloalkyl) $C_0$alkyl) or attached through an alkyl group having from 1 to about 2 carbon atoms. Similarly in the term "(cycloalkyl) alkoxy", cycloalkyl and alkoxy are as defined above, and the point of attachment the oxygen of the alkoxy. "(Cycloalkyl) $C_0$alkoxy is a cycloalky group that is attached through an oxygen linker.

As used herein the term "mono- and/or di-alkylcarboxamide" includes groups of formula (alkyl$_1$)-NH—(C=O)— and (alkyl$_1$)(alkyl$_2$)-N—(C=O)— in which the alkyl$_1$ and alkyl$_2$ groups are independently chosen alkyl groups as defined above having the indicated number of carbon atoms.

As used herein "Haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

"Halogen" as used herein includes fluorine, chlorine, bromine, and iodine. In the context of the present invention, a substituent may be a halogen or may be substituted with a halogen.

"Heteroaryl" as used herein includes an aryl group, wherein one or more carbon atoms has been replaced with another atom. For example, in an embodiment, "heteroaryl" includes an aryl group as defined herein, wherein one or more carbon atoms has been replaced with oxygen, nitrogen, or sulfur. Heteroaryl includes stable 5- to 7-membered monocyclic aromatic rings which contains from 1 to 4, or preferably from 1 to 2, heteroatoms chosen from N, O, and S, with remaining ring atoms being carbon. Heteroaryl also includes stable bicyclic or tricyclic systems containing at least one 5- to 7-membered aromatic ring which contains from 1 to 3, or preferably from 1 to 2, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1.

The term "heterocycloalkyl" includes a saturated monocyclic group containing from 1 to about 3 heteroatoms chosen from N, O, and S, with remaining ring atoms being carbon, or a saturated bicyclic ring system having at least one N, O, or S ring atom with remaining atoms being carbon. Monocyclic heterocycloalkyl groups have from 4 to about 8 ring atoms, and more typically have from 5 to 7 ring atoms. Examples of heterocycloalkyl groups include morpholinyl, piperazinyl, piperidinyl, and pyrrolidinyl groups.

"Heterocycle" as used herein includes by way of example and not limitation these heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "cyclic alkyl" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

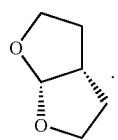

By way of example and not limitation, carbon bonded heterocycles are bonded at position 2, 3, or 4 of a pyridine, position 3 or 4 of a pyridazine, position 2, 4, or 5 of a pyrimidine, position 2 or 3of a pyrazine, position 2 or 3 of a furan, tetrahydrofuran, thiofuran, pyrrole or tetrahydropyrrole, position 2, 4, or 5 of an oxazole, imidazole or thiazole, position 3, 4, or 5 of an isoxazole, pyrazole, or isothiazole, position 2 or 3 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-pyrrolyl, 1-imidazolyl, 1-pyrazolyl, and 1-piperidinyl.

As used herein, the term "mono-and/or di-alkylamino" inincludes secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/ or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

"Phenoxy" means a conjugate base of a phenyl alcohol. "(Phenyl)alkyl is a phenyl group covalently bound to an alkyl radical as described above. Similarly "(phenyl)alkoxy" refers to a phenyl group covalently bound to an alkoxy radical as described above. Non-limiting exemplary phenoxy radicals include:

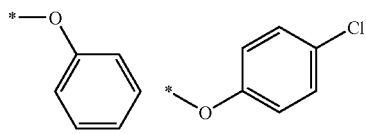

The term "treatment" or "treating" to the extent it relates to a disease or condition includes preventing the desease or condition from occurring; inhibiting the disease or condition, and/or relieving one or more symptoms of the disease or condition.

"Pharmaceutically acceptable salts" includes derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, Mack Publishing Company, Easton, Pa.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exist a wide variety of suitable pharmaceutical formulations of the present invention. The formulations may be prepared by any of the methods known in the art of pharmacy. For example, exemplary techniques and formulations are found in *Remington's Pharmaceutical Sciences* (Mack Publishing Co., Easton, Pa.). In a preferred aspect, formulations of the present invention are prepared by uniformly and intimately bringing into association the active ingredient, e.g., a compound of the present invention, with liquid carriers or finely divided solid carriers or both, and then, optionally shaping the product.

The term "prodrugs" includes any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "therapeutically effective amount" of a compound of this invention means an amount effective, when administered to a human or non-human patient, to provide a therapeutic benefit such as an amelioration of symptoms, e.g., an amount effective to decrease the symptoms of a viral infection, and preferably an amount sufficient to reduce the symptoms of an HCV infection. In certain circumstances a patient suffering from a viral infection may not present symptoms of being infected. Thus a therapeutically effective amount of a compound is also an amount sufficient to prevent a significant increase or significantly reduce the detectable level of virus or viral antibodies in the patient's blood, serum, or tissues. A significant increase or reduction in the detectable level of virus or viral antibodies is any detectable change that is statistically significant in a standard parametric test of statistical significance such as Student's T-test, where $p<0.05$.

A "replicon" as used herein includes any genetic element, for example, a plasmid, cosmid, bacmid, phage or virus, that is capable of replication largely under its own control. A replicon may be either RNA or DNA and may be single or double stranded.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule can be described herein according to the normal convention of providing the sequence in the 5' to 3' direction.

By "viral inhibitory amount" it is meant an amount sufficient to inhibit viral replication or infectivity. Optionally, the pharmaceutical formulations of the invention may comprise a combination of compounds of the present invention, or may include a second active ingredient useful in the treatment of viral infections, such as anti-viral agents that include, but are not limited to: pegylated alpha interferon; un-pegylated alpha interferon; ribavirin; protease inhibitors; polyermase inhibitors; p7 inhibitors; entry inhibitors, including fusion inhibitors such as Fuzeon™ (Trimeris); helicase inhibitors; anti-fibrotics; drugs that target IMPDH (inosine monophosphate dehydrogenase inhibitors), such as Merimepadib™ (Vertex Pharmaceuticals Inc.); synthetic thymosin alpha 1 (ZADAXIN™, SciClone Pharmaceuticals Inc.); therapeutic viral vaccines, such as those produced by Chiron and Immunogenics; and immunomodulators, such as histamine.

Chemical Description

In accordance with the present invention, compounds that inhibit HCV replication have been identified and methods of using these compounds for preventing or treating HCV infection are provided. Without being limited to a particular theory, it is believed that the compounds of the present invention act as replicase complex defect inducers, inhibiting the formation of a functional replicase complex.

In an aspect of the present invention, compounds are provided that are useful for treating or preventing hepatitis C virus infection. In another aspect of the present invention, compounds are provided that are useful for inhibiting replication of hepatitis C virus.

The invention includes methods of treatment using compounds of the Formula (I-a)

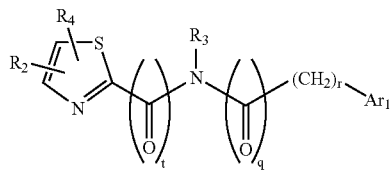

(I-a)

or pharmaceutically acceptable salt, hydrate or prodrug thereof.

Within formula (I-a) the variables $Ar_1$, $R_2$, $R_3$, R4, t, q, and r, carry the values set forth below, wherein:

$Ar_1$ is fluorenyl.

Or, $Ar_1$ is phenyl, naphthyl, a 5- or 6-membered monocyclic heteroaryl group, or a 9- or 10-membered bicyclic heteroaryl group, wherein $Ar_1$ is substituted with R and $R_1$.

R is 0 or one or more substituents independently chosen from halogen, hydroxyl, amino, cyano, nitro, $C_1$-$C_2$alkyl, $C_1$-$C_2$alkoxy, $C_1$-$C_2$haloalkyl, and $C_1$-$C_2$haloalkoxy.

$R_1$ is one or two substituents independently chosen from (a) and (b)

(a) halogen, hydroxyl, amino, cyano, nitro, —COOH, —$SO_2NH_2C_1$-$C_2$haloalkyl, and $C_1$-$C_2$haloalkoxy, and (b) $C_1$-$C_{10}$alkyl, $C_2$-$C_{10}$alkenyl, $C_2$-$C_{10}$alkynyl, $C_2$-$C_{10}$alkanoyl, $C_2$-$C_{10}$alkylester, $C_1$-$C_{10}$alkoxy, mono- or di-$C_1$-$C_{10}$alkylcarboxamide, or a group —YZ, where Y is bond, or Y is $C_1$-$C_{10}$alkyl, a $C_2C_{10}$alkenyl, or $C_2$-$C_{10}$alkynyl, each optionally having 1 or 2 oxygen or nitrogen atoms within the alkyl, alkenyl, or alkynyl chain; and Z is hydrogen, $C_3$-$C_7$cycloalkyl, $C_3$-$C_7$cycloalkenyl, heterocycloalkyl, phenyl, naphthyl, indanyl, ($C_3$-$C_7$cycloalkyl)$C_0$-$C_{10}$alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, $C_1$-$C_4$alkyl, $C_1$-$C_4$alkoxy, $C_1$-$C_2$haloalkyl, and $C_1$-$C_2$haloalkoxy.

Any R and $R_1$ which are covalently bound to adjacent carbon atoms may be joined to form an aromatic or partially saturated carbocyclic ring system having 1 or 2 rings, each ring having 5 or 6 ring carbon atoms.

$R_2$ is halogen, —COOH, —$CONH_2$, —C(O)O$CH_3$, —C(O)$CH_3$, —NHC(O)OH, or amino.

Or, $R_2$ is —$CH_2R_a$, —NH—S(O)$_2R_a$, —$CH_2$—NH—S(O)$_2R_a$, —S(O)$_2R_a$, —C(O)—NH—$R_a$, —C(O)—NH—$CH_2R_a$, —NH—C(O)—$R_a$, —NH—C(O)—$R_b$, —C(O)O—$R_a$, —C(O)—O—$R_b$, —O$R_a$, —C(O)—$R_a$, or —C(O)—$R_b$, each of which is substituted with 0 or one or more substituents independently chosen from (c), (d), and (e).

Or, $R_2$ is $C_1$-$C_6$alkyl, phenyl, a 5- to 6-membered heteroaryl, phenyl fused to a 5 or 6 membered cycloalkyl or heterocycloalkyl ring, or a bicyclic 8- to 10-membered heteroaryl, each of which is substituted with 0 or one or more substituents independently chosen from (c), (d), and (e);

(c) halogen, hydroxyl, oxo, cyano, amino, nitro, —C(O)$NH_2$, —C(O)OH, —S(O)$NH_2$, $C_1$-$C_2$haloalkyl, and $C_1$-$C_2$haloalkoxy, (d) $C_1$-$C_4$alkyl, $C_1$-$C_4$alkoxy, $C_2$-$C_4$alkenyl, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester, each of which is substituted with 0 or one ore more substituents independently chosen from oxo, halogen, hydroxyl, oxo, cyano, amino, nitro, —C(O)$NH_2$, —C(O)OH, —S(O)$NH_2$, $C_1$-$C_4$alkoxy, mono- and di-$C_1$-$C_6$alkylamino, mono- and di-($C_1$-$C_4$alkyl)carboxamide, mono- or di($C_1$-$C_4$alkyl)sulfonamide, $C_1$-$C_4$alkylester $C_1$-$C_2$haloalkyl, and $C_1$-$C_2$haloalkoxy (e) ($C_3$-$C_7$cycloalkyl)$C_0$-$C_4$alkyl, (heterocycloalkyl)$C_0$-$C_4$alkyl, (phenyl)$C_0$-$C_4$alkyl, each of which is substituted with oxo, halogen, hydroxyl, oxo, cyano, amino, nitro, —C(O)$NH_2$, —C(O)OH, —S(O)$NH_2$, $C_1$-$C_2$haloalkyl, and $C_1$-$C_2$haloalkoxy.

$R_2$ and $R_4$ may be taken together with the carbon atoms of the thiazole ring to which they are attached to form a $C_5$-$C_7$ carbocyclic ring, which is aromatic or partially unsaturated.

$R_3$ is hydrogen, $C_1$-$C_4$alkyl, or —C(O)—$R_d$.

$R_4$ is hydrogen, halogen, hydroxyl, amino, cyano, nitro, $C_1$-$C_2$alkyl, $C_1$-$C_2$alkoxy, $C_1$-$C_2$haloalkyl, $C_1$-$C_2$haloalkoxy or phenyl; or $R_4$ is taken together with $R_2$ to form a ring.

$R_a$ is heterocycloalkyl, phenyl, or 5- or 6-membered heteroaryl, each of which is substituted with 0 or one or more substituents independently chosen from halogen, hydroxyl, amino, cyano, $C_1$-$C_4$ alkyl, and $C_1$-$C_4$ alkoxy.

$R_b$ is $C_1$-$C_6$ alkyl, wherein the alkyl is optionally substituted with a halogen, hydroxyl, —C(O)OH, phenyl, or 4-($NH_2S(O)_2$)-phenyl.

$R_d$ is $C_1$-$C_6$alkyl, phenyl, or 5- to 6-membered heteroaryl.

And r is 0, 1,or 2.

q is 0 or 1;

t is 0 or 1; and q and t are not both 1;

Wherein at least one of the following conditions are met:

(i) $R_4$ is not hydrogen; or (ii) at least one $R_1$ is other than halogen, unsubstituted alkyl, unsubstituted alkoxy, amino, —C(O)$NH_2$, —S(O)$_2NH_2$, unsubstituted alkanoyl, unsubstituted alkylester, or —S(O)$_2$NH(heteroaryl); or (iii) $R_2$ is other than aryl or heteroaryl; or (iv) $R_2$ is aryl or heteroaryl, substituted with at least one group other than halogen, unsubstituted alkyl, unsubstituted alkoxy, amino, —C(O)$NH_2$, —S(O)$_2NH_2$, unsubstituted alkanoyl, unsubstituted alkylester, or —S(O)$_2$NH(heteroaryl).

The invention includes compounds, salts and hydrates of Formula I-a, in which one or more of the following conditions are met. The invention includes compounds of Formula I in which the variables $Ar_1$, $R_1$, $R_2$, $R_3$, $R_4$, t, q, carry any combination of the definitions set forth below for these variables that results in a stable compound.

The t, q, and r Variables (a) t is 0, e.g the invention provides compounds and salts of Formula (I-b).

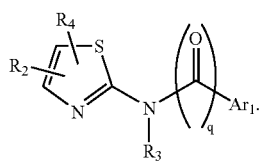

(b) q is 0, e.g. the invention provides compounds, salts, and hydrates of formula (I-c).

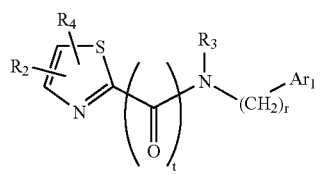

(c) r is 0, i.e. the invention provides compounds and salts of Formula (I-d).

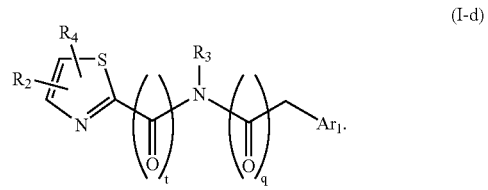

(d) r is 0 and t is 1, i.e. the invention provides compounds and salts of Formula (I-e)

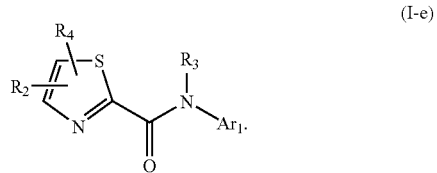

(e) t and q are 0 and r is 1 or 2, e.g. the invention provides compounds and salts of Formula (I-f).

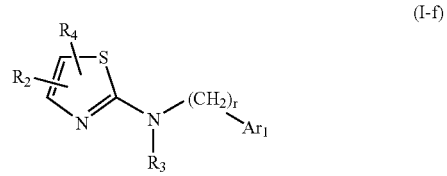

(f) t, q, and r are all 0, e.g. the invention provides compounds and salts of Formula (I-g).

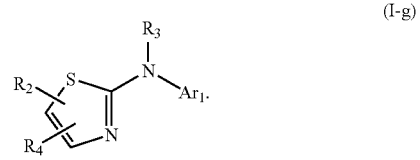

The $Ar_1$ Variable (a) $Ar_1$ is phenyl substituted with R and $R_1$.

(b) $Ar_1$ is pyridyl substituted with R and $R_1$.

(c) $Ar_1$ is phenyl, pyridyl, benzofuranyl, benzimidazolyl, benzothiazolyl, furanyl, imidazolyl, isoxazolyl, pyrrolyl, thienyl, thiazolyl, or tetrahydroisoquinolinyl, each substituted with R and $R_1$.

(d) $Ar_1$ is fluorenyl.

(e) $Ar_1$ is phenyl or pyridyl, each substituted with R and $R_1$; and t, q, and r are all 0.

(f) t and q are both 0 and r is 0 or 1; and $Ar_1$ is phenyl, naphthyl, a 5- or 6-membered monocyclic heteroaryl group, or a 9- or 10-membered bicyclic heteroaryl group, wherein $Ar_1$ is substituted with R and $R_1$.

R is 0 or one or more substituents independently chosen from halogen, hydroxyl, amino, cyano, nitro, $C_1$-$C_2$alkyl, $C_1$-$C_2$alkoxy, $C_1$-$C_2$haloalkyl, and $C_1$-$C_2$haloalkoxy.

R₁ is one or two substituents independently chosen from (a) and (b); (a) halogen, hydroxyl, amino, cyano, nitro, —COOH, —SO₂NH₂C₁-C₂haloalkyl, and C₁-C₂haloalkoxy, and (b) C₁-C₁₀ alkyl, C₂-C₁₀ alkenyl, C₂-C₁₀ alkynyl, C₂-C₁₀alkanoyl, C₂-C₁₀alkylester, C₁-C₁₀ alkoxy, mono- or di-C₁-C₁₀alkylcarboxamide, or a group —YZ.

Where Y is bond, or Y is C₁-C₁₀alkyl, a C₂C₁₀alkenyl, or C₂-C₁₀alkynyl, each optionally having 1 or 2 oxygen or nitrogen atoms within the alkyl, alkenyl, or alkynyl chain; and Z is hydrogen, C₃-C₇cycloalkyl, C₃-C₇cycloalkenyl, heterocycloalkyl, phenyl, naphthyl, indanyl, (C₃-C₇cycloalkyl)C₀-C₁₀alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, C₁-C₄alkyl, C₁-C₄alkoxy, C₁-C₂haloalkyl, and C₁-C₂haloalkoxy.

For certain compounds of this embodiment Ar₁ is phenyl or a 6-membered heteroaryl group substituted with an R₁ in the meta position.

In certain other compounds of this embodiment Ar₁ is phenyl or a 6-membered heteroaryl group substituted with an R₁ in the para position.

(g) Ar₁ is phenyl or a 6-membered heteroaryl group substituted with independently chosen R₁ substituents in the meta and para positions.

(h) Ar₁ is phenyl or a 6-membered heteroaryl group substituted with independently chosen R₁ substituents in the meta and para positions and R is 0 substituents.

(i) Ar₁ is phenyl or a 6-membered heteroaryl group substituted with an R₁ substituent in either the meta and para positions; and at least one R₁ is C₄-C₁₀ alkyl, C₄-C₁₀ alkenyl, C₄-C₁₀ alkynyl, C₄-C₁₀alkanoyl, C₄-C₁₀alkylester, C₄-C₁₀ alkoxy, mono- or di-C₄-C₁₀alkylcarboxamide, or a group —YZ. Where Y is bond, or Y is C₄-C₁₀alkyl, a C₄C₁₀alkenyl, or C₄-C₁₀alkynyl, each optionally having 1 or 2 oxygen or nitrogen atoms within the alkyl, alkenyl, or alkynyl chain; and Z is hydrogen, C₃-C₇cycloalkyl, C₃-C₇cycloalkenyl, heterocycloalkyl, phenyl, naphthyl, indanyl, (C₃-C₇cycloalkyl)C₀-C₁₀alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, C₁-C₄alkyl, C₁-C₄alkoxy, C₁-C₂haloalkyl, and C₁-C₂haloalkoxy.

In certain compounds of this embodiment a second R₁ is halogen, trifluoromethyl, or trifluoromethoxy.

(j) Ar₁ is phenyl or a 6-membered heteroaryl group substituted with R₁ substituents in either the meta and para positions; and one R₁ is C₄-C₁₀ alkyl, C₄-C₁₀ alkenyl, C₄-C₁₀ alkynyl, C₄-C₁₀ alkanoyl, C₄-C₁₀alkylester, C₄-C₁₀ alkoxy, mono- or di-C₄-C₁₀alkylcarboxamide, or a group —YZ. Where Y is bond, or Y is C₄-C₁₀alkyl, a C₄C₁₀alkenyl, or C₄-C₁₀alkynyl, each optionally having 1 or 2 oxygen or nitrogen atoms within the alkyl, alkenyl, or alkynyl chain; and Z is hydrogen, C₃-C₇cycloalkyl, C₃-C₇cycloalkenyl, heterocycloalkyl, phenyl, naphthyl, indanyl, (C₃-C₇cycloalkyl)C₀-C₁₀alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, C₁-C₄alkyl, C₁-C₄alkoxy, C₁-C₂haloalkyl, and C₁-C₂haloalkoxy; and the other R₁ is halogen, trifluormethyl, or trifluoromethoxy.

(k) Ar₁ is phenyl or a 6-membered heteroaryl group substituted with R₁ substituents in either the meta and para positions; and one R₁ is a group —YZ. Where Y is bond, or Y is C₄-C₁₀alkyl, a C₄-C₁₀alkenyl, or C₄-C₁₀alkynyl, each optionally having 1 or 2 oxygen or nitrogen atoms within the alkyl, alkenyl, or alkynyl chain; and Z is hydrogen, C₃-C₇cycloalkyl, C₃-C₇cycloalkenyl, heterocycloalkyl, phenyl, naphthyl, indanyl, (C₃-C₇cycloalkyl)C₀-C₁₀alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, C₁-C₄alkyl, C₁-C₄alkoxy, C₁-C₂haloalkyl, and C₁-C₂haloalkoxy; and the other R₁ is halogen, trifluormethyl, or trifluoromethoxy.

(l) Ar₁ is phenyl or a 6-membered heteroaryl group substituted with R₁ substituents in either the meta and para positions; and one R₁ is a group —YZ. Where Y is C₆-C₁₀alkyl, a C₆C₁₀alkenyl, or C₆-C₁₀alkynyl, each optionally having 1 or 2 oxygen or nitrogen atoms within the alkyl, alkenyl, or alkynyl chain; and Z is C₃-C₇cycloalkyl, heterocycloalkyl, phenyl, naphthyl, indanyl, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, C₁-C₄alkyl, C₁-C₄alkoxy, C₁-C₂haloalkyl, and C₁-C₂haloalkoxy; and the other R₁ is halogen, trifluormethyl, or trifluoromethoxy.

The R and R₁ Variables (a) R is 1 or 2 substituents independently chosen from halogen, hydroxyl, amino, cyano, nitro, C₁-C₂alkyl, C₁-C₂alkoxy, C₁-C₂haloalkyl, and C₁-C₂haloalkoxy.

(b) R is 1 or 2 substituents independently chosen from hydroxyl, cyano, C₁-C₂alkyl, C₁-C₂alkoxy, trifluoromethyl, and trifluoromethoxy.

(c) R is one or more substituents independently chosen from halogen, phenyl, and cyano.

(d) R is one or more substituents independently chosen from fluorine and chlorine.

(e) At least one R₁ is C₁-C₁₀ alkyl, C₂-C₁₀ alkenyl, C₂-C₁₀ alkynyl, C₂-C₁₀ alkanoyl, C₂-C₁₀alkylester, C₁-C₁₀alkoxy, mono- or di-C₁-C₁₀alkylcarboxamide, or a group —YZ. Where Y is bond, or Y is C₁-C₁₀alkyl, a C₂C₁₀alkenyl, or C₂-C₁₀alkynyl, each optionally having 1 or 2 oxygen or nitrogen atoms within the alkyl, alkenyl, or alkynyl chain; and Z is hydrogen, C₃-C₇cycloalkyl, C₃-C₇cycloalkenyl, heterocycloalkyl, phenyl, naphthyl, indanyl, (C₃-C₇cycloalkyl)C₀-C₁₀alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from: halogen, hydroxyl, amino, cyano, nitro, oxo, C₁-C₄alkyl, C₁-C₄alkoxy, C₁-C₂haloalkyl, and C₁-C₂haloalkoxy.

(f) At least one R₁ is:

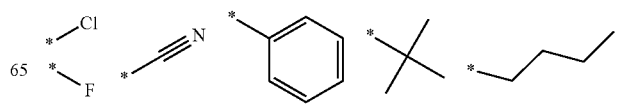

(g) $R_1$ is one or two substituents independently chosen from (a) and (b), (a) halogen, hydroxyl, amino, cyano, nitro, $C_1$-$C_2$haloalkyl, and $C_1$-$C_2$haloalkoxy, and (b) $C_1$-$C_8$ alkyl, $C_2$-$C_8$ alkenyl, $C_2$-$C_8$ alkynyl, $C_1$-$C_{10}$alkoxy, ($C_3$-$C_7$cycloalkyl)$C_0$-$C_2$alkyl, ($C_3$-$C_7$cycloalkyl)$C_0$-$C_2$alkoxy, mono- and di-$C_1$-$C_6$alkylamino, (phenyl)$C_0$-$C_2$alkyl, (phenyl)$C_0$-$C_2$alkoxy, (indanyl)$C_0$-$C_2$alkyl, (indanyl)$C_0$-$C_2$alkoxy, and (heterocycloalkyl)$C_0$-$C_2$alkyl, wherein each (b) is substituted with 0 or more substituents independently chosen from: halogen, hydroxyl, cyano, methyl, methoxy, trifluoromethyl, trifluoromethoxy, difluoromethoxy, and phenyl.

(h) At least one $R_1$ is (a) halogen, hydroxyl, amino, cyano, nitro, $C_1$-$C_2$haloalkyl, $C_1$-$C_2$haloalkoxy, (b) $C_1$-$C_8$alkyl, $C_1$-$C_{10}$alkoxy, or (phenyl)$C_0$-$C_2$alkoxy, each of which is substituted with 0 or more substituents independently chosen from: halogen, hydroxyl, cyano, methyl, methoxy, trifluoromethyl, trifluoromethoxy, difluoromethoxy, and phenyl.

(i) At least one $R_1$ is t-butyl, trifluoromethyl, n-pentoxy, benzyloxy, or para-chlorophenoxy.

(j) At least one $R_1$ is n-butoxy, trifluomethoxy, phenoxy, n-butyl, or phenyl.

(k) At least one $R_1$ is $C_1$-$C_{10}$ alkyl, $C_1$-$C_{10}$ alkoxy, (phenyl)$C_0$-$C_2$alkyl, indanyl-oxy, or phenoxy, each of which is substituted with 0 or 1 or more independently chosen halogen substituents.

(l) At least one $R_1$ is $C_1$-$C_{10}$alkoxy, phenyl, indanyloxy, or phenoxy, each of which is substituted with 0 or 1 or more independently chosen halogen substituents.

(m) At least one $R_1$ is methoxy, phenoxy, n-butoxy, n-pentyloxy, n-hexyloxy, n-heptanyloxy, n-octanyloxy, phenyl($CH_2$)$_2$O—benzyloxy, cycloalkylmethyloxy, indanyloxy, or trifluoromethoxy.

(n) At least one $R_1$ is an independently chosen $C_1$-$C_{10}$alkoxy substituent, substituted with 0 or one or more fluorine substituents.

(o) At least one $R_1$ is an independently chosen $C_1$-$C_{10}$alkoxy substituent, which is substituted with 0 or one or more substituents independently chosen from phenyl, indanyl, and naphthyl.

(p) At least one $R_1$ is a $C_1$-$C_{10}$alkoxy substituent, substituted with a phenyl substituent or $C_3$-$C_7$cycloalkyl substituent.

(q) At least one $R_1$ is a $C_1$-$C_{10}$ alkyl, substituted with 0 or one or more substituents independently chosen from halogen, phenyl, $C_3$-$C_7$cycloalkyl, and 5- to 6-membered heterocyloalkyl.

(r) At least one $R_1$ is methyl, n-butyl, n-pentyl, t-butyl, benzyl, trifluoromethyl, or piperidin-1-ylmethyl.

(s) At least one $R_1$ is heterocycloalkyl or 5- to 6-membered heteroaryl containing 1, 2, 3, or 4 heteroatoms independently chosen from N, O, and S, each of which is substituted with 0 or more substituents independently chosen from: halogen, hydroxyl, amino, cyano, nitro, $C_1$-$C_4$alkyl, $C_1$-$C_4$alkoxy, $C_1$-$C_2$haloalkyl, $C_1$-$C_2$haloalkoxy, phenyl, and naphthyl.

(t) At least one $R_1$ is morpholin-1-yl, 4-phenyl-piperidin-1-yl, 1,2,3-thiazol-4-yl, or 2-methylpyrimidin-6-yl.

(u) At least one $R_1$ is $C_1$-$C_2$haloalkyl, $C_1$-$C_8$alkyl, (phenyl)$C_1$-$C_2$alkyl, or (heterocycloalkyl)$C_1$-$C_2$alkyl.

(v) At least one $R_1$ is (5- and 6-membered heterocycloalkyl)$C_0$-$C_{10}$alkoxy, each of which is substituted with 0 or one or more substituents independently chosen from $C_1$-$C_4$ alkyl and phenyl. In certain compounds of this embodiment the 5- and 6-membered heterocycloalkyl, comprise nitrogen or oxygen or both.

(w) $R_1$ is morpholinyl or piperidinyl.

(x) $R_1$ is a 5- to 6-membered heterocycloalkyl, substituted with a phenyl.

(y) At least one $R_1$ is 5- to 6-membered heteroaryl containing 1, 2, 3, or 4 heteroatoms independently chosen from N, O, and S, substituted with 0 or one or more substituents independently chosen from $C_1$-$C_4$alkyl and phenyl.

(z) $R_1$ is thiadiazolyl.

(aa) $R_1$ is 4-methyl-1,2,3 thiadiazolyl.

(bb) $R_1$ is pyrimidinyl.

(cc) $R_1$ is 4-methyl-pyrimidinyl.

(dd) $R_1$ is a $C_1$-$C_{10}$alkoxy.

(ee) R is halogen or trifluoromethyl, t, q, and r are all 0 and $R_4$ is hydrogen, halogen, methyl, or phenyl.

The $R_3$ Variable (a) $R_3$ is hydrogen.

The $R_2$ and $R_4$ Variables (a) The invention includes compounds Formula (I-h) and (I-i) in which the positions of $R_2$ and $R_4$ are fixed. Compounds of Formula (I-h) and (I-i) in which q ant t are 0 and r is 0 or are preferred. The invention includes:

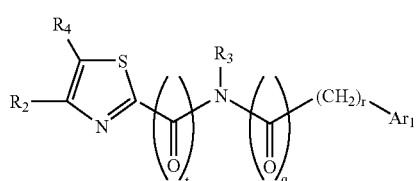

(I-h)

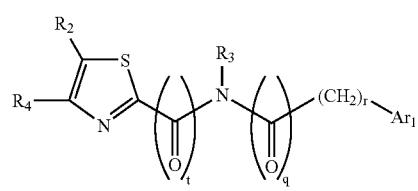

(I-i)

(b) The invention includes compounds of formula (I-h) or (I-i) in which t and q are 0 and r is 0 or 1.
(c) For compounds of formula (I-h) or (I-i) in which t and q are 0 and r is 0.
(d) $R_2$ is phenyl, substituted with 0 or 1 or more independently chosen halogen substituents.
(e) $R_2$ is phenyl substituted with one or more chlorine or fluorine substituents.
(f) $R_2$ is phenyl substituted with fluoro at the para position.
(g) $R_2$ is a 5- to 6-membered heteroaryl.
(h) $R_2$ is a 6-membered heteroaryl.
(i) $R_2$ is a 5- to 6-membered heteroaryl comprising nitrogen.
(j) $R_2$ is 5- to 6-membered heteroaryl group comprises sulfur.
(k) $R_2$ is pyridyl.
(l) $R_2$ is phenyl.
(m) $R_2$ is phenyl, substituted with 0 or one or more substituents independently chosen from halogen, cyano, 5- to 6-membered heterocycloalkyl, and alkoxy, wherein the alkoxy is substituted with 0 or one or more substituents independently chosen from halogen, $R_a$, —C(O)OH, and —C(O)—O—$R_b$.
(n) $R_2$ is

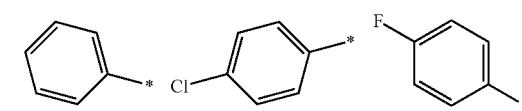

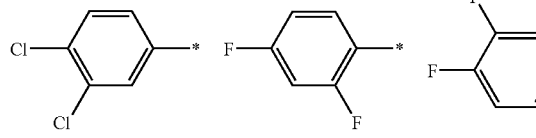

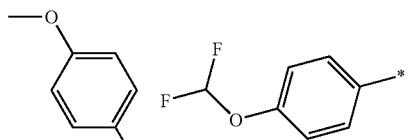

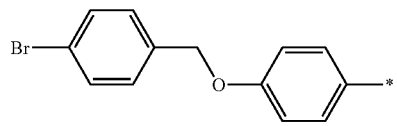

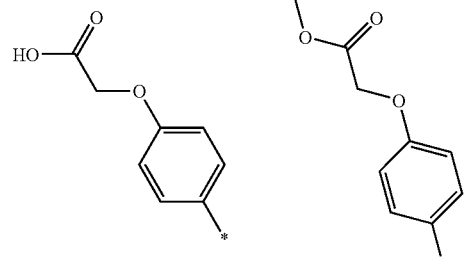

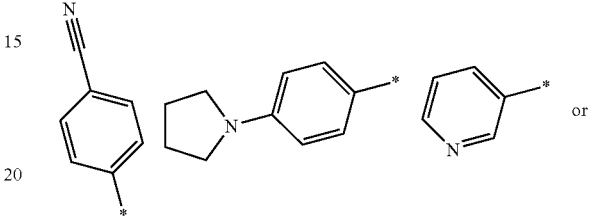

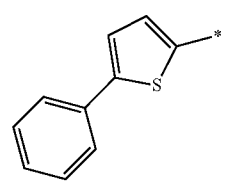

(o) $R_2$ is a 5- to 6-membered heteroaryl group, which is substituted with 0 or one phenyl.
(p) $R_2$ is —C(O)—NH—$R_a$, —C(O)—, —C(O)—O—H, or —C(O)—O—$R_b$.
(q) $R_2$ is —COOH, $C_1$-$C_4$alkylester or

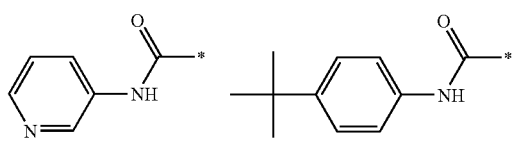

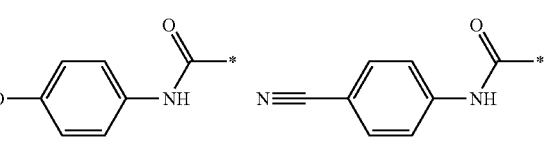

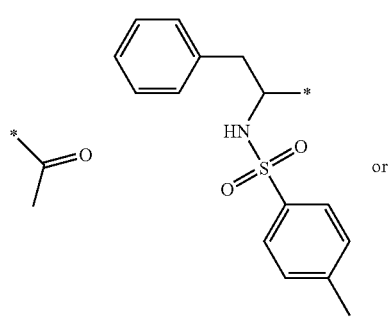

or

-continued

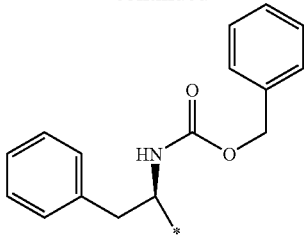

(r) $R_2$ is $C_1$-$C_6$ alkyl substituted with 0 or 1 or more phenyl or amino substituents, wherein the amino is substituted with 0 or one or more substituents independently chosen from —C(O)—O—$R_b$ and or —S(O)$_2R_a$; or $R_2$ and $R_4$ are taken together with the carbon atoms of the thiazole ring to which they are attached to form an aryl ring.

(s) $R_2$ is halogen, or amino substituted with 0 or 1 —C(O)—$R_a$.

(t) $R_2$ is bromine.

(u) $R_4$ is hydrogen or halogen; and $R_2$ is —CH$_2R_a$, —C(O)—NH—$R_a$, —C(O)—NH—CH$_2R_a$, —NH—C(O)—$R_a$, —C(O)O—$R_a$, —O$R_a$, —C(O)—$R_a$, or —C(O)—$R_b$, each of which is substituted with 0 or one or more substituents independently chosen from (c), (d), and (e). Where $R_a$ is heterocycloalkyl, phenyl, or 5- and 6-membered heteroaryl, each of which is substituted with 0 or one or more substituents independently chosen from halogen, hydroxyl, amino, cyano, $C_1$-$C_4$ alkyl, and $C_1$-$C_4$ alkoxy. In certain of these embodiments $R_a$ is piperidinyl, morpholinyl, piperazinyl, thiomorpholinyl, or pyrrolidinyl.

(v) $R_4$ is hydrogen or halogen; and $R_2$ is phenyl, a 5- to 6-membered heteroaryl, phenyl fused to a 5 or 6 membered cycloalkyl or heterocycloalkyl ring, or a bicyclic 8- to 10-membered heteroaryl, each of which is substituted with 0 or one or more substituents independently chosen from (c), (d), and (e). Where (c) is chosen from halogen, hydroxyl, oxo, cyano, amino, nitro, —C(O)NH$_2$, —C(O)OH, —S(O)NH$_2$, $C_1$-$C_2$haloalkyl, and $C_1$-$C_2$haloalkoxy, (d) is chosen from $C_1$-$C_4$alkyl, $C_1$-$C_4$alkoxy, $C_2$-$C_4$alkenyl, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester, each of which is substituted with 0 or one ore more substituents independently chosen from oxo, halogen, hydroxyl, oxo, cyano, amino, nitro, —C(O)NH$_2$, —C(O)OH, —S(O)NH$_2$, $C_1$-$C_4$alkoxy, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester $C_1$-$C_2$haloalkyl, and $C_1$-$C_2$haloalkoxy, and (e) is chosen from ($C_3$-$C_7$cycloalkyl)$C_0$-$C_4$alkyl, (heterocycloalkyl)$C_0$-$C_4$alkyl, (phenyl)$C_0$-$C_4$alkyl, each of which is substituted with oxo, halogen, hydroxyl, oxo, cyano, amino, nitro, —C(O)NH$_2$, —C(O)OH, —S(O)NH$_2$, $C_1$-$C_2$haloalkyl, and $C_1$-$C_2$haloalkoxy.

(w) $R_2$ is phenyl or pyridyl, each of which is substituted with 0 or 1 or 2 substituents independently chosen from (c), (d), and (e).

(x) $R_2$ is piperidinyl, morpholinyl, piperazinyl, thiomorpholinyl, or pyrrolidinyl, each of which is substituted with 0 or 1 or 2 substituents independently chosen from (c), (d), and (e).

(y) $R_2$ is a 5- to 6-membered heteroaryl, phenyl fused to a 5 or 6 membered cycloalkyl or heterocycloalkyl ring, or a bicyclic 8- to 10-membered heteroaryl chosen from imidazo[2,1-b]thiazol-5-yl, pyrazinyl, 1H-imidazo[1,2-a]pyridin-3-yl, thiazolo[3,2-b][1,2,4]triazol-5-yl, isoxazol-3-yl, imidazo[1,2-a]pyridin-2-yl, thiazolyl, 2H-benzo[b][1,4]oxazin-3(4H)-one, benzo[d]thiazol-2-yl, thienyl, benzofuran-2-yl, benzo[d]oxazol-2(3H)-one, pyrimidinyl, imidazolyl, pyridizinyl, furanyl, benzo[d][1,3]dioxol-5-yl, naphthyl, quinolinyl, isobenzofuran-1(3H)-one, isobenzofuran-1(3H)-one, 2H-benzo[b][1,4]thiazin-3(4H)-one, 1,2,3-thiadiazol-4-yl, each of which is substituted with 0 or 1 or more substituents independently chosen from halogen, oxo hydroxyl, amino, cyano, $C_1$-$C_4$ alkyl, and $C_1$-$C_4$ alkoxy.

(z) $R_4$ is fluorine.

The invention also provides compounds of Formula I-a

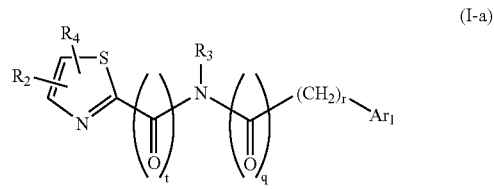

(I-a)

and pharmaceutically acceptable salts, and hydrates thereof, as well as pharmaceutical compositions containing one or more such compounds and a pharmaceutically acceptable excipient.

For such compounds, salts and hydrates $Ar_1$, R, $R_1$, $R_2$, $R_3$, $R_4$, t, q, and r are defined as follows:

wherein:

$Ar_1$ is phenyl, naphthyl, a 5- or 6-membered monocyclic heteroaryl group, or a 9- or 10-membered bicyclic heteroaryl group, wherein $Ar_1$ is substituted with R and $R_1$.

R is 0 or one or more substituents independently chosen from halogen, hydroxyl, amino, cyano, nitro, $C_1$-$C_2$alkyl, $C_1$-$C_2$alkoxy, $C_1$-$C_2$haloalkyl, and $C_1$-$C_2$haloalkoxy.

$R_1$ is one or two substituents independently chosen from (a) and (b):

(a) halogen, hydroxyl, amino, cyano, nitro, —COOH, —SO$_2$NH$_2C_1$-$C_2$haloalkyl, and $C_1$-$C_2$haloalkoxy, and (b) $C_1$-$C_{10}$alkyl, $C_2$-$C_{10}$alkenyl, $C_2$-$C_{10}$alkynyl, $C_2$-$C_{10}$alkanoyl, $C_2$-$C_{10}$alkylester, $C_1$-$C_{10}$ alkoxy, mono- or di-$C_1$-$C_{10}$alkylcarboxamide, or a group —YZ.

Were Y is bond, or Y is $C_1$-$C_{10}$alkyl, a $C_2C_{10}$alkenyl, or $C_2$-$C_{10}$alkynyl, each optionally having 1 or 2 oxygen or nitrogen atoms within the alkyl, alkenyl, or alkynyl chain; and Z is hydrogen, $C_3$-$C_7$cycloalkyl, $C_3$-$C_7$cycloalkenyl, heterocycloalkyl, phenyl, naphthyl, indanyl, ($C_3$-$C_7$cycloalkyl)$C_0$-$C_{10}$alkoxy, or 5- to 6-membered heteroaryl containing 1, 2, 3, or 4 heteroatoms independently chosen from N, O, and S, and at least one $R_1$ is a group —YZ in which Y is $C_6$-$C_{10}$alkyl, a $C_6C_{10}$alkenyl, or $C_6$-$C_{10}$alkynyl, each optionally having 1 or 2 oxygen or nitrogen atoms within the alkyl, alkenyl, or alkynyl chain; and C3-$C_7$cycloalkyl, $C_3$-$C_7$cycloalkenyl, heterocycloalkyl, phenyl, naphthyl, indanyl, ($C_3$-$C_7$cycloalkyl)$C_0$-$C_{10}$alkoxy, or 5- to 6-membered heteroaryl containing 1, 2, 3, or 4 heteroatoms independently chosen from N, O, and S, wherein each (b) other than hydrogen, is substituted with 0 or one or more substituents independently chosen from:

halogen, hydroxyl, amino, cyano, nitro, oxo, $C_1$-$C_4$alkyl, $C_1$-$C_4$alkoxy, $C_1$-$C_2$haloalkyl, and $C_1$-$C_2$haloalkoxy; and the other $R_1$ is halogen, trifluoromethyl, or trifluoromethoxy.

$R_2$ is halogen, —COOH, —CONH$_2$, —C(O)OCH$_3$, —C(O)CH$_3$, —NHC(O)OH, or amino, or $R_2$ is —CH$_2$R$_a$, —NH—S(O)$_2$R$_a$, —CH$_2$—NH—S(O)$_2$R$_a$, —S(O)$_2$R$_a$, —C(O)—NH—R$_a$, —C(O)—NH—CH$_2$R$_a$, —NH—C(O)—R$_a$, —NH—C(O)—R$_b$, —C(O)O—R$_a$, —C(O)—O—R$_b$, —OR$_a$, —C(O)—R$_a$, or —C(O)—R$_b$, each of which is substituted with 0 or one or more substituents independently chosen from (c), (d), and (e), or $R_2$ is $C_1$-$C_6$alkyl, phenyl, a 5- to 6-membered heteroaryl, phenyl fused to a 5 or 6 membered cycloalkyl or heterocycloalkyl ring, or a bicyclic 8- to 10-membered heteroaryl, each of which is substituted with 0 or one or more substituents independently chosen from (c), (d), and (e);

(c) halogen, hydroxyl, oxo, cyano, amino, nitro, —C(O)NH$_2$, —C(O)OH, —S(O)NH$_2$, $C_1$-$C_2$haloalkyl, and $C_1$-$C_2$haloalkoxy, (d) $C_1$-$C_4$alkyl, $C_1$-$C_4$alkoxy, $C_2$-$C_4$alkenyl, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester, each of which is substituted with 0 or one ore more substituents independently chosen from oxo, halogen, hydroxyl, oxo, cyano, amino, nitro, —C(O)NH$_2$, —C(O)OH, —S(O)NH$_2$, $C_1$-$C_4$alkoxy, mono- and di-$C_1$-$C_6$alkylamino, mono- and di-($C_1$-$C_4$alkyl)carboxamide, mono- or di($C_1$-$C_4$alkyl)sulfonamide, $C_1C_4$alkylester $C_1$-$C_2$haloalkyl, and $C_1$-$C_2$haloalkoxy (e) ($C_3$-$C_7$cycloalkyl)$C_0$-$C_4$alkyl, (heterocycloalkyl)$C_0$-$C_4$alkyl, (phenyl)$C_0$-$C_4$alkyl, each of which is substituted with oxo, halogen, hydroxyl, oxo, cyano, amino, nitro, —C(O)NH$_2$, —C(O)OH, —S(O)NH$_2$, $C_1$-$C_2$haloalkyl, and $C_1$-$C_2$haloalkoxy.

$R_2$ and $R_4$ are taken together with the carbon atoms of the thiazole ring to which they are attached to form a $C_5$-$C_7$ carbocyclic ring, which is aromatic or partially unsaturated.

$R_3$ is hydrogen, $C_1$-$C_4$alkyl, or —C(O)—R$_d$.

$R_4$ is hydrogen, halogen, hydroxyl, amino, cyano, nitro, $C_1$-$C_2$alkyl, $C_1$-$C_2$alkoxy, $C_1$-$C_2$haloalkyl, $C_1$-$C_2$haloalkoxy or phenyl; or $R_4$ is taken together with $R_2$ to form a ring.

$R_a$ is heterocycloalkyl, phenyl, or 5- or 6-membered heteroaryl, each of which is substituted with 0 or one or more substituents independently chosen from halogen, hydroxyl, amino, cyano, $C_1$-$C_4$ alkyl, and $C_1$-$C_4$ alkoxy.

$R_b$ is $C_1$-$C_6$ alkyl, wherein the alkyl is optionally substituted with a halogen, hydroxyl, —C(O)OH, phenyl, or 4-(NH$_2$S(O)$_2$)-phenyl; $R_d$ is $C_1$-$C_6$alkyl, phenyl, or 5- to 6-membered heteroaryl; r is 0, 1, or 2; q is 0 or 1; and t is 0 or 1; and q and t are not both 1.

Methods of Treatment

The methods of the invention generally comprise administering a therapeutically effective amount of at least one compound of the present invention to a subject in need of treatment. In a particularly preferred embodiment, the methods of the invention comprise administering a therapeutically effective amount of at least one compound of the present invention to a subject in need of treatment for HCV infection.

In an embodiment, the present invention provides a method for treating or preventing hepatitis C virus infection in a subject in need thereof, said method comprising: administering to the subject an amount of a compound of formula (I), (I-a), (I-b), (I-c), (I-d), (I-e), (I-f), (I-g), (I-h) or (I-i) or a pharmaceutically acceptable salt thereof, or a prodrug or metabolite thereof, wherein hepatitis C virus infection is treated or prevented. The present invention further includes a method for treating or preventing hepatitis C virus infection in a subject in need thereof, said method comprising: administering to said subject an amount of at least one, at least two, at least three, or at least four compounds of formula (I), (I-a), (I-b), (I-c), (I-d), (I-e), (I-f), (I-g), (I-h), or (I-i), or pharmaceutically acceptable salts thereof, or prodrugs or metabolites thereof, wherein hepatitis C virus is treated or prevented. In a further embodiment, the present invention provides a method for treating or preventing hepatitis C virus in a subject in need thereof, said method comprising: administering to said subject both an amount of an additional anti-HCV agent and an amount of one or more compounds of formula (I), (I-a), (I-b), (I-c), (I-d), (I-e), (I-f), (I-g), (I-h), or (I-i), or a pharmaceutically acceptable salt thereof, or a prodrug or metabolite thereof, wherein hepatitis C virus is treated or prevented.

Anti-HCV agents are those agents, including for example, compounds of the present invention, that are believed to inhibit hepatitis C virus. Anti-HCV agents may believed to inhibit HCV as indicated by, for example, any clinical observations or laboratory experiments. Anti-HCV agents may act by any mechanism. Without being limited by any theory, a compound of the present invention that is an anti-HCV agent may inhibit HCV by causing miscleavage of the HCV polyprotein and leading to formation of miscleavage products. In another embodiment, a compound of the present invention that is an anti-HCV agent may lead to formation of defective replication complexes.

Generally, RNA synthesis proceeds as a two-step process: initiation and elongation. In initiation, an initiated template RNA is formed in which only a portion of the newly synthesized positive or negative strand RNA is made using a minus or plus strand template. Upon initiation, the partial transcripts may be unable to dissociate from the RNA polymerase. In elongation, the remainder of the positive or negative strand RNA transcript is synthesized. In an embodiment, a compound of the present invention blocks replication prior to initiation. In another embodiment, a compound of the present invention blocks replication after initiation. In an embodiment, a compound of the present invention blocks replication prior to elongation. In another embodiment, a compound of the present invention blocks replication after elongation. In an embodiment, a compound of the present invention blocks replication prior to both initiation and elongation. In another embodiment, a compound of the invention blocks replication after both initiation and elongation.

Additional anti-HCV agents (i.e., anti-HCV agents in addition to those provided by the present invention) may optionally be formulated together with compounds of the invention in a single pharmaceutical formulation or may be administered as separate formulations. Exemplary additional anti-HCV agents include pegylated alpha interferon, un-pegylated alpha interferon, ribavirin, protease inhibitors, polymerase inhibitors, p7 inhibitors, entry inhibitors, a fusion inhibitors, an anti-fibrotics, drugs which targets inosine monophosphate dehydrogenase inhibitors (IMPDH), synthetic thymosin alpha 1, therapeutic vaccines, immunomodulators, and helicase inhibitors.

The degree to which hepatitis C virus is treated or prevented by administration of a compound of the present invention may be evaluated by any techniques available to the skilled artisan. For example, treatment of hepatitis C virus may be evaluated by analyzing RNA levels of hepatitis C virus, anti-HCV antibodies, and hepatocellular damage. In another embodiment, treatment or prevention of HCV may be monitored by observing the levels of serum alanine amino transferase (ALT) and aspartate aminotransferase (AST).

In an embodiment, the present invention provides a method for treating a subject that has liver disease, comprising administering an effective amount of a compound of the present invention, where the subject that has liver disease is treated. In the context of the present invention, a subject is any living organism that may benefit from treatment for a disease or condition. For example, a subject includes without limitation mammals such as dogs, cats, cows, horses, rabbits, monkeys, and humans. In a preferred embodiment, a subject is a human. Subjects that may benefit from treatment include those that have been diagnosed with a disease or condition, those that are suspected of having a disease or condition, or those that may be susceptible to a disease or condition. Benefits of treatment may include prevention of a disease or condition or amelioration of a disease or condition, including elimination of a disease or condition.

A subject that has liver disease includes any subject that has any manifestation of liver dysfunction. In addition, a subject that has liver disease further includes any subject that has a history of any disease that is associated with liver dysfunction. A disease that is associated with liver dysfunction is a disease for which it is known or suspected that the liver may be affected. Liver dysfunction may be determined by clinical evaluation, laboratory testing, pathology report, or any other means available to the skilled artisan. In the context of the present invention, a subject that has liver disease may have, without limitation, acute hepatitis, chronic hepatitis, liver cancer, cirrhosis of the liver, end-stage liver disease, or any combination thereof. A subject that has liver disease includes a liver transplant patient. In a preferred embodiment, a subject that has liver disease includes any subject that has antibodies to hepatitis C virus.

One or more compounds of the present invention may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary. Individuals infected with HCV can be treated with the compounds of the present invention to prevent or reduce further replication of HCV.

The term therapeutically effective amount, as used herein, refers for example to an amount of a compound of the present invention effective to inhibit HCV translation, thereby effectively treating or ameliorating the HCV infection. The precise effective amount for a subject may depend upon factors such as the subject's body weight, size, health, age, other medications, for example. Therapeutically effective amounts for a given patient can be determined by routine experimentation that is within the skill and judgment of the clinician.

For any compound, the therapeutically effective amount can be estimated initially either in cell culture assays or in relevant animal models, such as rodents. An animal model may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 1 µg/ml to approximately 100 µg/mL, preferably from approximately 5 µg/mL to approximately 50 µg/mL, more preferably from approximately 10 µg/mL to approximately 50 µg/mL, even more preferably from approximately 10 µg/mL to approximately 25 µg/mL. To achieve such plasma concentrations, the compounds of the invention may be administered at doses that vary from 0.1 µg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In an embodiment, the present invention provides a method for inhibiting hepatitis C virus replication in a subject in need thereof, said method comprising: administering to said subject an amount of a compound of formula (I), (I-a), (I-b), (I-c), (I-d), (I-e), (I-f), (I-g), (I-h), or (I-i), or a pharmaceutically acceptable salt thereof, or a prodrug or metabolite thereof, wherein hepatitis C virus replication is inhibited.

Inhibition of hepatitis C virus replication may be measured by any technique known to the artisan. For example, inhibition may be measured by clinical observation, or laboratory tests such as $EC_{50}$. In another embodiment, inhibition of hepatitis C virus replication may be measured by a decrease in nucleotide or protein production and includes a reduction in HCV replication of at least about 10%, at least about 25%, at least about 35%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% as compared with HCV replication prior to administration of one or more compounds of the invention.

In an embodiment of the present invention, inhibition of hepatitis C virus replication may be measured by a decrease in nucleotide or protein production and includes a reduction in HCV replication of at least about 10%, at least about 25%, at least about 35%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% as compared with HCV replication prior to administration of one or more compounds of the invention.

In another embodiment of the present invention, a method for inhibiting HCV replication is provided, the method comprising contacting a compound of formula (I), (I-a), (I-b), (I-c), (I-d), (I-e), (I-f), (I-g), (I-h), or (I-i) with a hepatitis C virus replicon, replicase complex, or polyprotein or fragment, wherein replication of hepatitis C virus is inhibited.

In a further embodiment, the present invention provides a method for inhibiting HCV replicase complex activity comprising contacting a compound of formula (I), (I-a), (I-b), (I-c), (I-d), (I-e), (I-f), (I-g), (I-h), or (I-i) with a hepatitis C virus replicon, replicase complex, or polyprotein or fragment, wherein hepatitis C virus replicase complex activity is inhibited.

In another embodiment, the compounds of the present invention may also be used in assays, such as for example diagnostic, screening or cell culture assays. A compound of the present invention may be contacted with a cell expressing a hepatitis C virus RNA replicon in any manner that permits the test compound and the cell comprising the replicon to interact. In an embodiment, a test compound may be contacted with a cell expressing a hepatitis C virus RNA replicon by mixing the test compound and the cell together in vivo or in vitro, for example in any container such as a flask, a replicate plate, a tube, or a vial.

A replicon is a genetic element, including by way of non-limiting example, a plasmid, cosmid, bacmid, phage or virus or any portion of the foregoing that is capable of replication largely under its own control. A replicon may be either RNA or DNA and may be single- or double-stranded. A replicon may contain a positive nucleic acid strand, a negative nucleic acid strand or both. In a preferred embodiment, an HCV replicon comprises the NS5B nonstructural protein of an HCV genome. In another preferred embodiment, an HCV replicon comprises the NS3-NS4A nonstructural proteins of an HCV genome. In another preferred embodiment, an HCV replicon comprises the NS3-NS5B nonstructural proteins of an HCV genome. In a further preferred embodiment, one or more HCV nonstructural proteins is operably linked to sequences necessary for efficient replication.

It is contemplated that any HCV replicon may be used in the methods of the present invention. In a preferred embodiment, a hepatitis C virus RNA replicon can be used in the methods of the present invention.

An HCV replicon may be obtained in any manner. For example, RNA molecules encoding an HCV replicon may be produced by in vitro transcription and transfected into cells such as by electroporation. In another embodiment, the HCV replicon may be DNA that is transfected. An HCV replicon may be transfected into any cells known to the skilled artisan. In an embodiment, an HCV replicon is transfected into Huh-7 cells using electroporation. In another embodiment, an HCV replicon is obtained from an accession database such as GenBank or ATCC.

The present invention also contemplates contacting a compound of the invention with a cell that expresses an HCV replicase complex. Any HCV replicase complex may be used in the methods of the present invention. In an embodiment, replicase complexes may be isolated in any manner known to the skilled artisan. Replicase complexes may be isolated for example as described in Lohmann, V. et al., Replication of subgenomic hepatitis C virus RNAs in a hepatoma cell line, Science 285:110-113 (1999); Blight, K. J., et al., Efficient replication of hepatitis C virus genotype 1a RNAs in cell culture, J. Virol. 77(5) 3181-90 (2003); Wolk, B. et al., Subcellular localization stability, and trans-cleavage competence of the hepatitis C virus NS3-NS4A complex expressed in tetracycline-regulated cell lines, J. Virol. 74(5): 2293-2304 (2000).

Exemplary replicase complexes include those that comprise an NS5B protein or fragment thereof, an NS3-NS5B polyprotein or fragment thereof, or an NS3-NS4A polyprotein or fragment thereof. In the context of the present invention, a replicase complex that is isolated includes one that is removed or separated from its natural environment. Any techniques for removing a replicase complex from the location where it is naturally found may be used for isolation, including for example extraction, fractionation, centrifugation, precipitation, etc.

The present invention also contemplates contacting a cell that expresses an isolated HCV polyprotein or fragment thereof. Any isolated HCV polyprotein or fragment thereof may be used in the methods of the present invention. HCV polyproteins may be isolated for example as described in Lohmann, V. et al., Replication of subgenomic hepatitis C virus RNAs in a hepatoma cell line, Science 285:110-113 (1999); Blight, K. J., et al., Efficient replication of hepatitis C virus genotype 1a RNAs in cell culture, J. Virol. 77(5) 3181-90 (2003); Wolk, B. et al., Subcellular localization stability, and trans-cleavage competence of the hepatitis C virus NS3-NS4A complex expressed in tetracycline-regulated cell lines, J. Virol. 74(5): 2293-2304 (2000).

Exemplary hepatitis C virus polyproteins or fragments thereof of the present invention include those that comprise an NS5B protein or fragment thereof, an NS3-NS5B polyprotein or fragment thereof, or an NS3-NS4A polyprotein or fragment thereof. In the context of the present invention, a polyprotein or fragment thereof that is isolated includes one that is removed or separated from its natural environment. An isolated polyprotein or fragment thereof may optionally be purified from other components.

The present invention further provides a method of screening for a compound of the present invention useful for treating hepatitis C virus, the method comprising contacting a cell comprising hepatitis C viral replicon, isolated replicase complex or isolated polypeptide with a compound of the present invention, measuring inhibition of hepatitis C virus replication, and selecting a candidate compound that is capable of inhibiting hepatitis C virus.

Pharmaceutical Formulations

While it is possible for the compounds of the present invention to be administered neat, it may be preferable to formulate the compounds as pharmaceutical formulations. In an aspect of the present invention, pharmaceutical formulations useful in the methods of the invention are provided. The pharmaceutical formulations of the invention may be prepared with pharmaceutically acceptable excipients such as carriers, solvents, stabilizers, adjuvants, diluents, glidants, etc., depending upon the particular mode of administration and dosage form. Formulations optionally contain excipients such as those set forth in the Handbook of Pharmaceutical Excipients (1986). The pharmaceutical formulations should generally be formulated to achieve a physiologically compatible pH, and may range from a pH of about 3 to a pH of about 11, a pH of about 7 to a pH of about 10, a pH of about 5 to a pH of about pH 8, preferably a pH of about pH 3 to a pH of about pH 7, depending on the formulation and route of administration.

More particularly, the pharmaceutical formulations of the invention comprise a therapeutically or prophylactically effective amount of at least one compound of the present invention, together with one or more pharmaceutically acceptable excipients. A therapeutically or prophylactically effective amount of a compound of the present invention includes a viral inhibitory amount of the compound.

One or more compounds of the invention may be administered by any route appropriate to the condition to be treated. Suitable routes include parenteral (including subcutaneous, intramuscular, intravenous, intradermal, intrathecal and epidural), oral, nasal, topical (including buccal and sublingual), rectal, vaginal, and the like. It will be appreciated that the preferred route of administration may vary, depending for example upon the condition of the recipient and the duration of the treatment. In a preferred embodiment, treatment is administered orally or parenterally to a subject who has antibodies to hepatitis C virus.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A pharmaceutical composition of the invention may also be formulated as a lyophilized solid that is reconstituted with a physiologically-compatible solvent prior to administration. Alternative pharmaceutical formulations of the invention may be prepared as syrups, elixirs, creams, ointments, tablets, and the like.

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

Formulations for oral use include, for example, tablets, troches, lozenges, electuaries, aqueous or oil suspensions, non-aqueous solutions, dispersible powders or granules (including micronized particles or nanoparticles), emulsions, hard or soft capsules, syrups or elixirs may be prepared. Formulations intended for oral use may be prepared according to any method known to the art for the manufacture of pharmaceutical formulations, and such formulations may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may optionally be scored. In addition, tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical formulations of the invention may be formulated as suspensions comprising a compound of the present invention in an admixture with at least one pharmaceutically acceptable excipient suitable for the manufacture of a suspension. In yet another embodiment, pharmaceutical formulations of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents and flavoring agents optionally may be added to provide a palatable oral preparation. One or more antioxidant, such as ascorbic acid, for example, may be added as a preservative.

The pharmaceutical formulations of the invention may also be in the form of oil-in-water emulsions. In an aspect, the oily phase of an emulsion may comprise only one or more emulsifiers (otherwise known as emulgents). In a preferred aspect, the oily phase comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

In an aspect of the present invention, the oily phase comprises a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. In an aspect, such formulations may also contain a demulcent, a preservative, a flavoring, a coloring agent, or any combination of these ingredients.

Additionally, in an aspect of the present invention, the pharmaceutical formulations of the invention may be in the form of a sterile injectable preparation. An injectable may be administered for example by injection, infusion, or as a bolus. Injectable preparations include by way of non-limiting example sterile injectable aqueous emulsions and oleaginous suspensions. An emulsion or suspension may be formulated according to the known art using those suitable dispersing or wetting agents and suspending agents such as for example those mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

The compounds of the present invention may be formulated for oral administration in a lipid-based formulation suitable for low solubility compounds. Lipid-based formulations can generally enhance the oral bioavailability of such compounds. As such, a pharmaceutical formulation of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative embodiment, cyclodextrins may be added as aqueous solubility enhancers. Cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-$\beta$-cyclodextrin (HPBC), which may be added to any of the above-described formulations to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

The formulations of the present invention may be provided in unit dosage form or in multi-dose containers, including for example sealed ampoules and vials, and may be stored in a freeze-dried or lyophilized condition, requiring only the addition of the sterile liquid carrier, for example saline for injection, immediately prior to use. In an embodiment, unit dosage formulations contain a daily dose or subdose, or a fraction thereof, of the active ingredient.

The amount of active ingredient that is combined with the carrier material to produce a single dosage form will be determined by the skilled artisan and will vary depending upon considerations including the host, the nature of the condition being treated, the particular mode of administration, the pharmaceutical formulation, and the toxicity. In an embodiment, the dose of active ingredient is determined by the clinician using conventional dose escalation studies. In an embodiment, a formulation intended for administration to humans may contain approximately 0.0001 to 100 mg/kg body weight per day, preferably from about 0.01 to about 10 mg/kg body weight per day, more preferably from about 0.01 to about 5 mg/kg body weight per day, or even more preferably from about 0.5 to about 0.5 mg/kg body weight per day. For example, in an embodiment, the daily candidate dose for an adult human of approximately 70 kg body weight ranges from about 1 mg to about 1000 mg, preferably between about 5 mg and about 500 mg, and may be administered in a single dose or multiple doses.

Compounds of the invention may be formulated with an appropriate and convenient amount of carrier material, which may vary, for example from about 5% to about 95% of the total compositions (weight:weight). The pharmaceutical composition can be prepared to provide easily measurable amounts for administration. For example, by way of non-limiting example, an aqueous solution intended for intravenous infusion may contain from about 3 to 500 µg of the active ingredient per milliliter of solution in order that infusion of a suitable volume at a rate of about 30 mL/hr can occur.

Compounds of the invention may also be formulated to provide controlled release of the compound, allowing for example, less frequent dosing or improved pharmacokinetic or toxicity profiles. In an embodiment, the present invention provides pharmaceutical formulations designed for sustained or controlled release.

In a further embodiment, the present invention also provides veterinary formulations comprising at least one compound of the present invention together with a veterinary carrier. In an embodiment, a veterinary carrier is one that is suitable for administration to an animal other than a human. A veterinary carrier may be a solid, liquid, or gaseous material, which is acceptable in the veterinary art and is not incompatible with the one or more compounds of the invention to be administered. Veterinary formulations may be administered orally, parenterally, or by any other route.

In an embodiment of the present invention, it is also possible to combine any compound of the present invention with one or more other active ingredients. Combinations may be selected on the basis of any considerations available to the skilled art working, including for example, the condition to be treated, cross-reactivity of ingredients, and pharmaco-properties of the combination. In a preferred embodiment, a pharmaceutical formulation may comprise one or more compounds of the invention that are useful in the treatment of HCV infection together with one or more other ingredients that are useful in the treatment of HCV infection.

Compounds may be formulated in a unitary dosage form, or in separate dosage forms intended for simultaneous or sequential administration to a patient in need of treatment. When administered sequentially, the combination may be administered in two or more, three or more, four or more, five or more, or six or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the viral inhibiting activity of the compounds of the invention. Such active ingredients include, but are not limited to, IFN-α, ribavirin, protease inhibitors, polymerase inhibitors, and helicase inhibitors. Furthermore, the compounds of the invention may also be administered in combination with other compounds that affect IRES activity known to one of skill in the art.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

EXAMPLES

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

Compounds provided herein may generally be prepared using standard synthetic methods. Starting materials are generally readily available from commercial sources, such as Sigma-Aldrich Corp. (St. Louis, Mo.). For example, a synthetic route similar to that shown in Example 1 or 2 may be used. It will be apparent that the final product and any intermediate(s) shown in the following schemes may be extracted, dried, filtered and/or concentrated, and may be further purified (e.g., by chromatography). Each variable (e.g., "R") in the following Schemes, refers to any group consistent with the description of the compounds provided herein. An individual skilled in the art may find modifications of one or several of the synthetic steps described herein without diverting significantly from the overall synthetic scheme. Further experimental details for synthesis of representative compounds via these schemes are provided in Examples 1-2, herein.

In the following Schemes and synthetic Examples 1-2, the following abbreviations are used:

Chemical Abbreviations

DCM dichloromethane
DMF dimethyl formamide
DMPA dimethylol propionic acid
Et₃N triethylamine
THF tetrahydrofuran
TMSCHN₂ trimethylsilyl diazomethane Example 1

Synthesis of N-(4-(Pentyloxy)-3-(Trifluoromethyl) Phenyl)-4-(Pyridin-3-yl)Thiazol-2-Amine

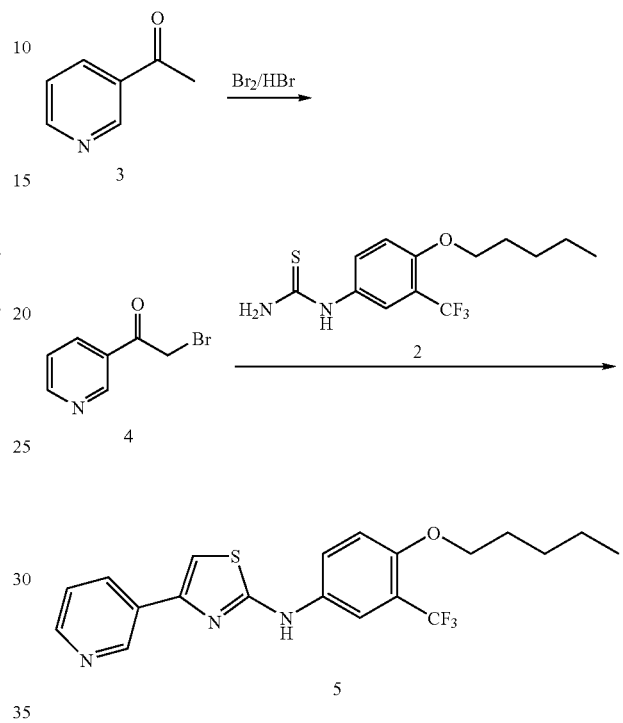

Step 1. Preparation of 2-bromo-1-(pyridin-3-yl)ethanone

Bromine (17.2 g, 0.11 mol) is added dropwise to a cooled solution (0° C.) of 3-acetylpyridine (12.1 g, 0.1 mol) in acetic acid containing 33% HBr with vigorous stirring. The stirring mixture is allowed to warm to 40° C. and maintained at this temperature for 2 hrs and then heated to 75° C. After 2 hrs, the mixture is cooled and diluted with ether (400 ml) to precipitate the product, which is collected by filtration and washed with ether and acetone to give 4 HBr salt as white crystals, which can be used for next step reaction without further purification.

Step 2. Preparation of N-(4-(pentyloxy)-3-(trifluoromethyl) phenyl)-4-(pyridin-3-yl)thiazol-2-amine.

Step 2. Preparation of N-(4-(pentyloxy)-3-(trifluoromethyl) phenyl)-4-(pyridin-3-yl)thiazol-2-amine.

The reaction mixture of 4 HBr salt (2.87 g, 10 mmol) and thiourea 2 (3.07 g, 10 mmol) in ethyl acetate (20 ml) is heated to 70° C. and stirred overnight. The reaction mixture is cooled to ambient temperature, and precipitates form. The product is collected by filtration, washed with ether, dried in air to give the product 5 as light yellow crystals.

NMR (CDCl₃, δ ppm): 10.69 (1H, s), 9.30 (1H, d, J=1.8 Hz), 8.95 (1H, dt, J=1.5, 8.4 Hz), 8.86 (1H, d, J=8.4 Hz), 8.14 (2H, m), 7.93 (1H, s), 7.91 (1H, dd, J=2.7, 7.5 Hz), 7.21 (1H, d, J=7.5 Hz), 4.06 (2H, t, J=6.2 Hz), 1.70 (2H, m), 1.37 (4H, m), 0.88 (3H, t, J=6.9 Hz).

Example 2

Synthesis of 4-(6-((Dimethylamino)Methyl)Pyridin-3-yl)-N-(4-(Pentyloxy)-3-(Trifluoromethyl)Phenyl) Thiazol-2-Amine

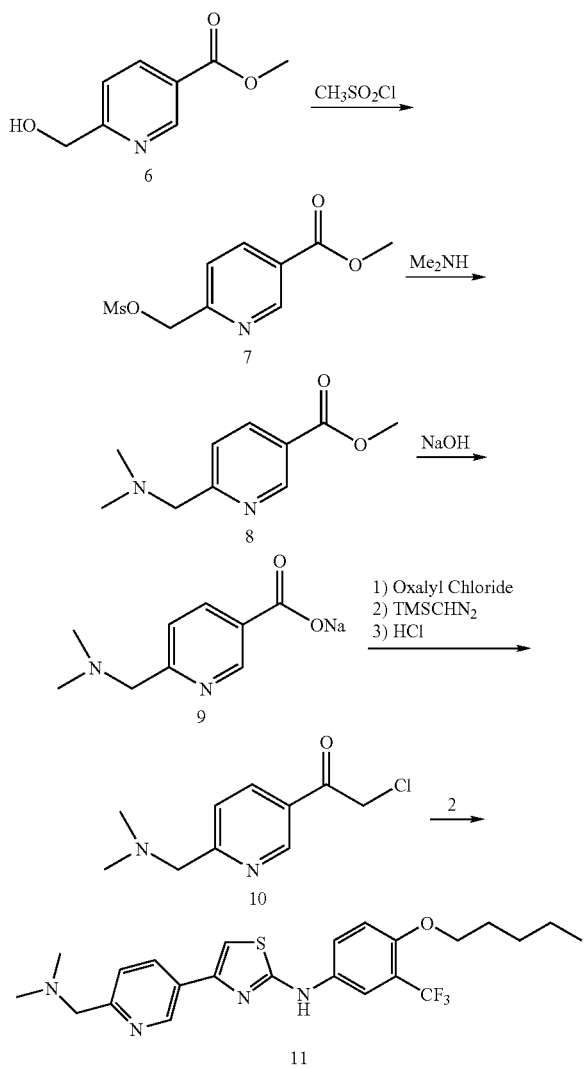

Step 1. Preparation of methyl 6-((methylsulfonyloxy)methyl) nicotinate

A Catalytic amount of DMPA (dimethylol propionic acid), triethylamine (2.0 g, 19.7 mmol) in 20 mL CH2Cl2, and methanesulfonyl chloride (1.95 g, 17.0 mmol) are added dropwise to a solution of 6-hydroxymethyl-nicotinic methyl ester 6 (2.2 g, 13.1 mmol), at −78° C. under argon. The mixture is stirred for 5 hours at −78° C. and then quenched with 30 mL saturated aqueous sodium bicarbonate. The organic layer is collected and the water phase extracted with CH2Cl2 (2×30 mL). The organic phases are combined and washed with water. The CH2Cl2 solution is dried over MgSO4 and concentrated to give compound 7, which is used without further purification.

Step 2. Preparation of 6-dimethylaminomethy-nicotinic methyl ester

Compound 7 is treated with dimethylamine (2M) in methanol at 0° C. for 30 minutes and then raised to room temperature and stirred for 5 hours. The solvent is removed and the residue passed through silical gel (flashed with ethyl acetate-methanol 95:5) to afford 6-dimethylaminomethy-nicotinic methyl ester 8.

1HNMR (CDCl3, ppm) δ 9.13 (1H), 8.24 (1H), 7.48 (1H), 3.93 (3H), 3.66 (2H), 2.28 (6H).

Step 3. Preparation of 6-dimethylaminomethyl-nicotinic Na salt 6-dimethylaminomethy-nicotinic methyl ester 8 (1.75 g, 9.0 mmol) is dissolved in 15 mL methanol; 5 mL 2 N sodium hydroxide is added. The mixture is heated at 90° C. for 1.5 hours and then quickly cooled to room temperature. The solvent is removed under vacuum and the remaining residue is dried by co-evaporated toluene. The solid is used without further purification. A small portion of sample is prepared for analytical use by acidification with 1N HCl, removal of water and drying.

1HNMR (D2O, ppm) δ 8.86 (1H), 8.16 (1H), 7.46 (1H), 4.05 (2H), 2.53 (6H).

Step 4. Preparation of chloroacetyl pyridine 6-dimethylaminomethyl-nicotinic Na salt 9 (202 mg, 1 mmol) is suspended in 8 mL CH2Cl2 and 2 drops of DMF is added. The mixture is treated with oxallyl chloride (1.2 mmol) at 0° C. and then warmed to room temperature and allowed to remain at this temperature 1.5 hours. The solvent is removed and the residue suspended in 10 mL THF. Et3N (2.2 mmol) is added, followed by TMSCHN2 (2.5 mmol, 2M solution in ether) which is added at 0° C. The mixture is warmed to room temperature and stirred overnight. The mixture is then cooled to 0° C. and HCl (4.0 mmol, 2M in ether) is added. The mixture is stirred for 2 hrs at 0° C. and then the solvent is removed. The residue is diluted with CH2Cl2 (30 mL), neutralized with 10% aqueous NaHCO3. The organic phase is collected and washed with water. The solvent is dried over MgSO4 and concentrated to give chloroacetyl pyridine 10, which is used directly in the next step.

Step 5. Preparation of 4-(6-((dimethylamino)methyl)pyridin-3-yl)-N-(4-(pentyloxy)-3-(trifluoromethyl)phenyl)thiazol-2-amine The mixture of 10 with thiourea 2 (0.3 mmol) in 10 mL ethyl alcohol is refluxed for 2 hours and cooled to room temperature. The solvent is removed and the residue purified by HPLC to give the title compound 11.

1HNMR (CDCl3, ppm) δ 8.96 (1H), 8.03 (1H, dd, J=2.2, 8.1 Hz), 7.64 (1H), 7.55 (1H, dd, J=2.7, 8.9 Hz), 7.38 (1H, d, J=8.1 Hz), 7.16 (1H), 6.94 (1H, d, J=8.8 Hz), 6.84 (1H), 3.97 (2H, t, J=6.4 Hz), 3.66 (2H), 2.33 (6H), 1.76 (2H, m), 1.37 (m, 4H), 0.87 (3H, t, J=7.1 Hz).

Example 3

Additional Exemplified Compounds

The compounds shown below in may be synthesized by the methods given in Examples 1 and 2, and by variations in the methods disclosed in Examples 1 and that will be readily apparent to those of skill in the art of synthetic organic synthesis.

The arrays provided below show disclose compounds of the general formula

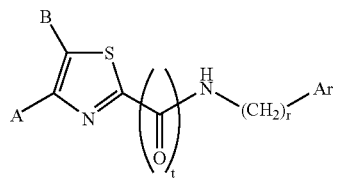

The values "A" in this formula are found in Array A1 and Array A2.

The values for "B" in this formula are found in Array B1 and Array B2; the values for "t" are given in Array t, the values for "r" are given in Array r, and the values for "Ar" are given in Array AR.

Each combination of 1 element from each of Array A1, Array B1, Array t, Array r, and Array Ar specifically discloses a discrete compound of the invention.

Each combination of 1 element from each of Array A2, Array B2, Array t, Array r, and Array Ar also specifically discloses a discrete compound of the invention.

For example [A1-1][B1-2][t0][R0][AR1] is

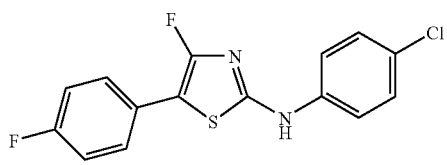

N-(4-chlorophenyl)-4-fluoro-5-(4-fluorophenyl)thiazol-2-amine.

ARRAY A1

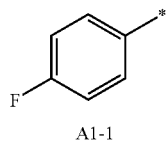

A1-1

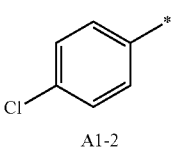

A1-2

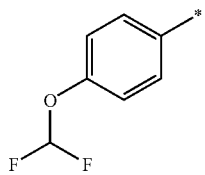

A1-3

ARRAY A1-continued

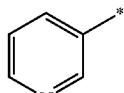

A1-4

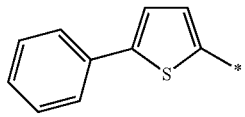

A1-5

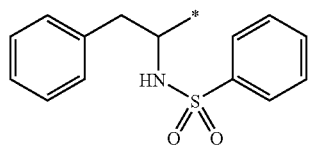

A1-6

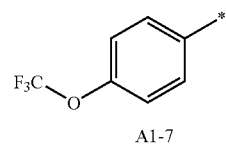

A1-7

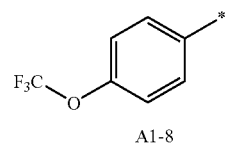

A1-8

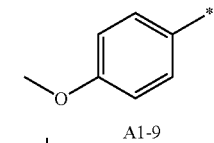

A1-9

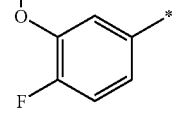

A1-10

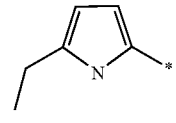

A1-11

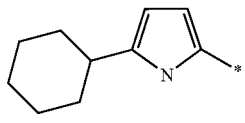

A1-12

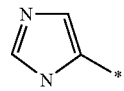

A1-13

ARRAY A1-continued
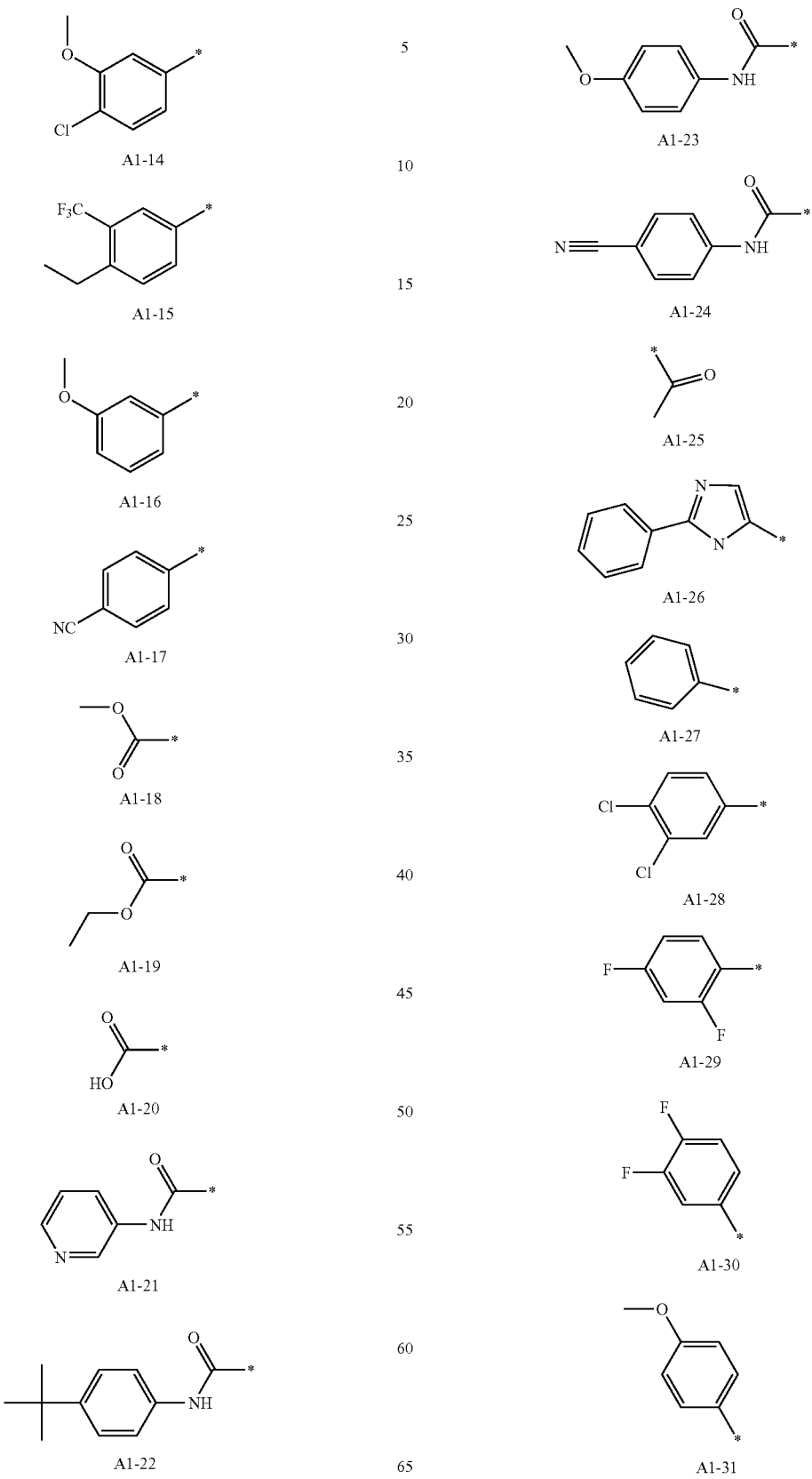

ARRAY A1-continued
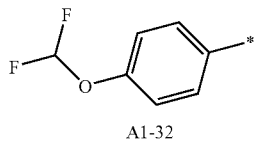
A1-32
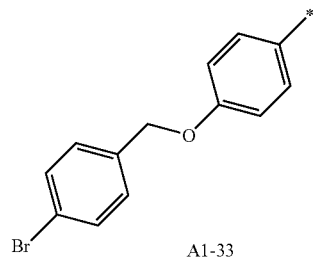
A1-33
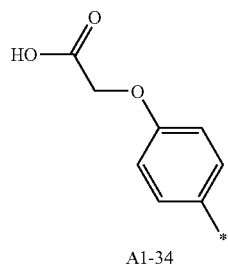
A1-34
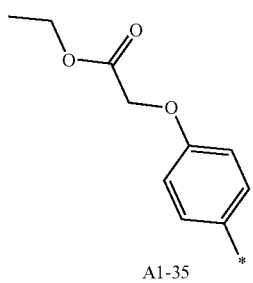
A1-35
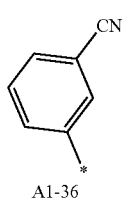
A1-36
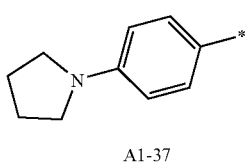
A1-37
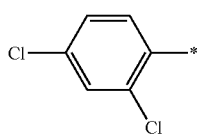
A1-38
ARRAY A1-continued
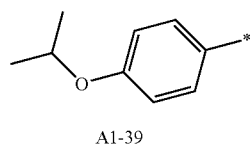
A1-39
ARRAY B1
| | | | | | |
|---|---|---|---|---|---|
| *—OH | B1-1 | *—F | B1-2 | *—Cl | B1-3 |
| *—CN | B1-4 | *—CH$_3$ | B1-5 | *—CH$_2$CH$_3$ | B1-6 |
| *—OCH$_3$ | B1-7 | *—OCH$_2$CH$_3$ | B1-8 | *—CF$_3$ | B1-9 |
| *—OCF$_3$ | B1-10 | *—OCHF$_2$ | B1-11 | *—H | B1-12 |
ARRAY A2
| | | | | | |
|---|---|---|---|---|---|
| *—OH | A2-1 | *—F | A2-2 | *—Cl | A2-3 |
| *—CN | A2-4 | *—CH$_3$ | A2-5 | *—CH$_2$CH$_3$ | A2-6 |
| *—OCH$_3$ | A2-7 | *—OCH$_2$CH$_3$ | A2-8 | *—CF$_3$ | A2-9 |
| *—OCF$_3$ | A2-10 | *—OCHF$_2$ | A2-11 | *—H | A2-12 |
ARRAY B2
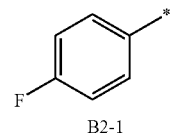
B2-1
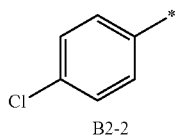
B2-2
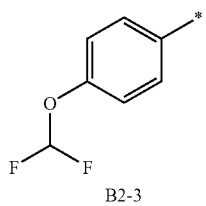
B2-3
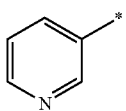
B2-4
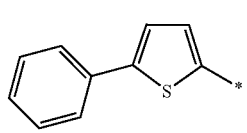
B2-5

ARRAY B2-continued
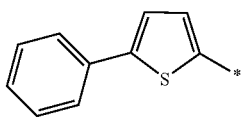
B2-6
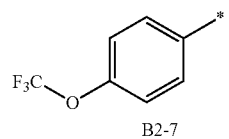
B2-7
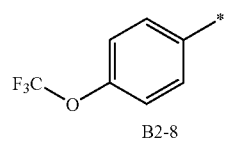
B2-8
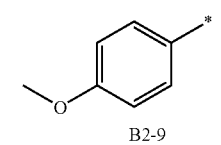
B2-9
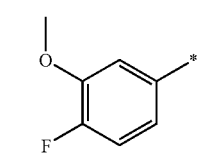
B2-10
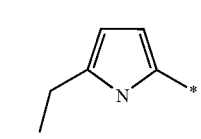
B2-11
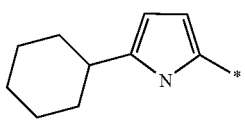
B2-12
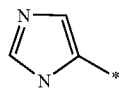
B2-13
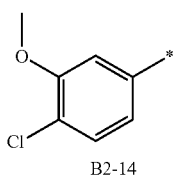
B2-14
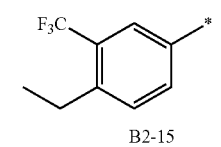
B2-15
ARRAY B2-continued
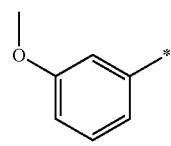
B2-16
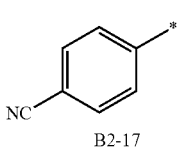
B2-17
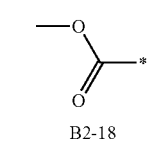
B2-18
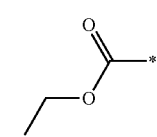
B2-19
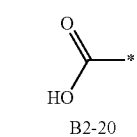
B2-20
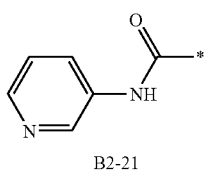
B2-21
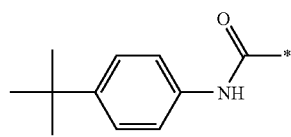
B2-22
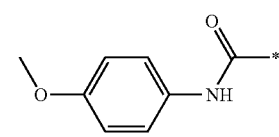
B2-23
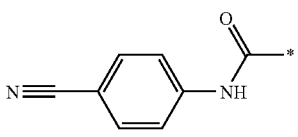
B2-24

ARRAY B2-continued
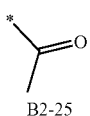
B2-25
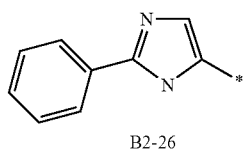
B2-26
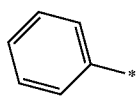
B2-27
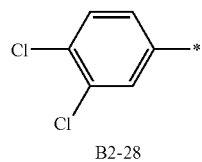
B2-28
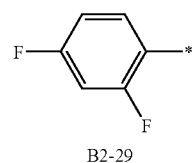
B2-29
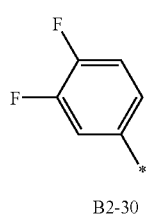
B2-30
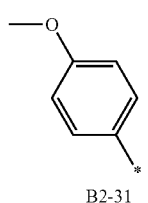
B2-31
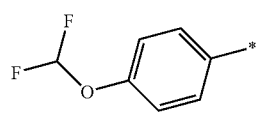
B2-32
ARRAY B2-continued
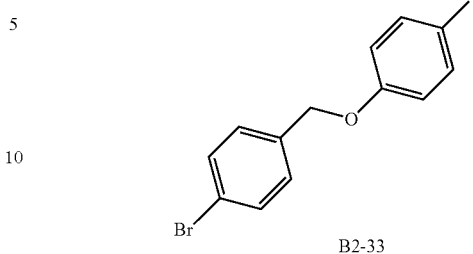
B2-33
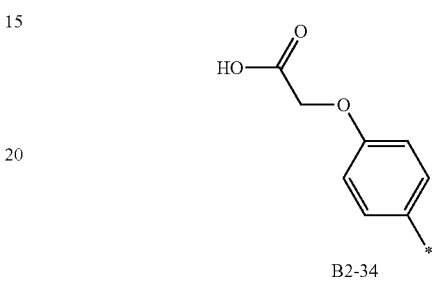
B2-34
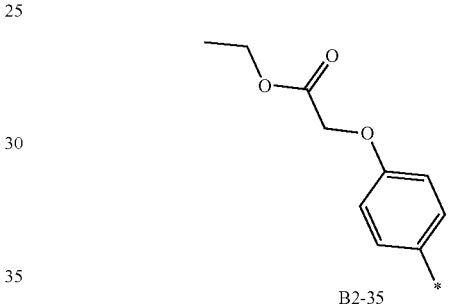
B2-35
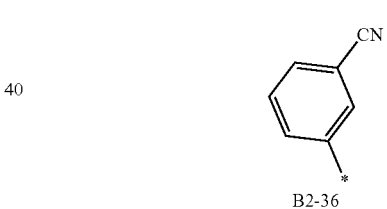
B2-36
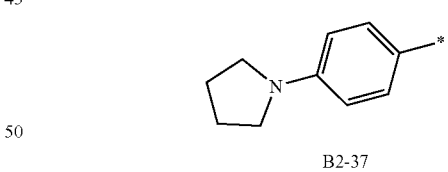
B2-37
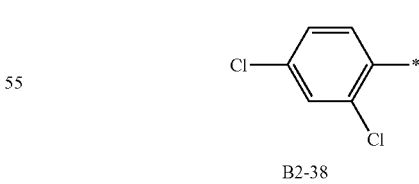
B2-38
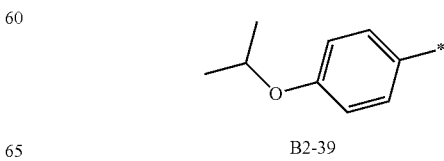
B2-39

| ARRAY t | | | |
|---|---|---|---|
| 0 | t0 | 1 | t1 |
| ARRAY r | | | | | |
|---|---|---|---|---|---|
| 0 | R0 | 1 | R1 | 2 | R2 |
ARRAY AR
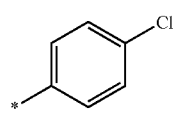
AR1
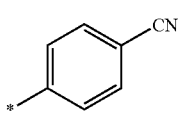
AR2
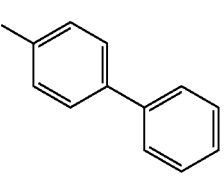
AR3
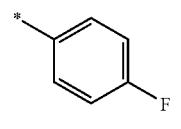
AR4
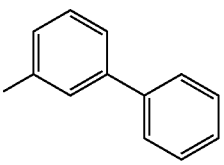
AR5
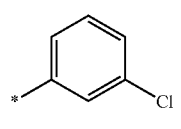
AR6
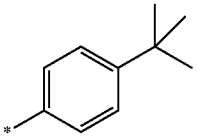
AR7
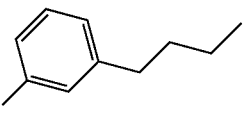
AR8
ARRAY AR-continued
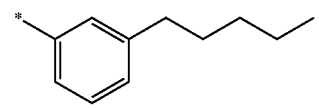
AR9
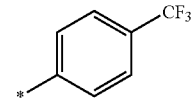
AR10
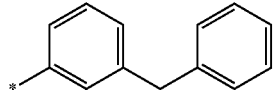
AR11
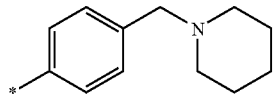
AR12
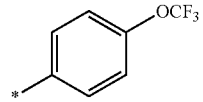
AR13
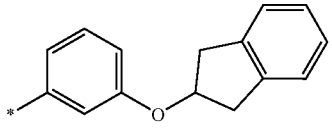
AR14
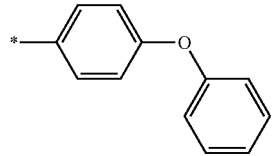
AR15
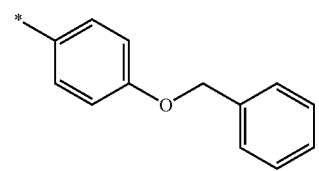
AR16
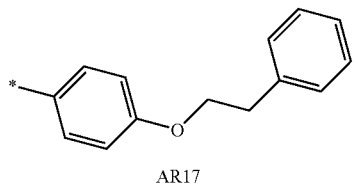
AR17

ARRAY AR-continued
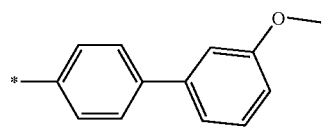
AR18
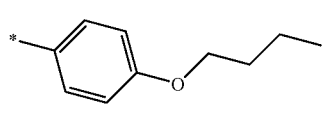
AR19
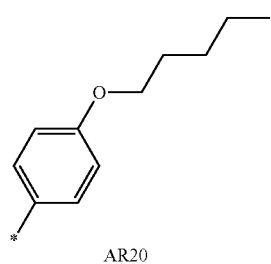
AR20
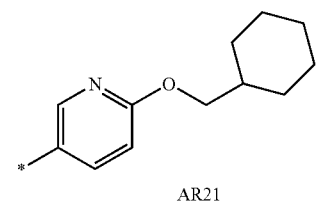
AR21
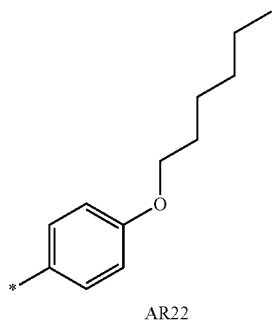
AR22
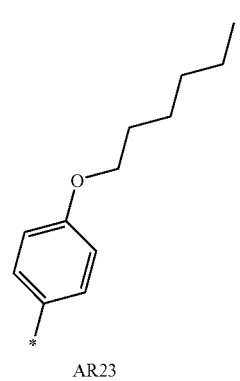
AR23
ARRAY AR-continued
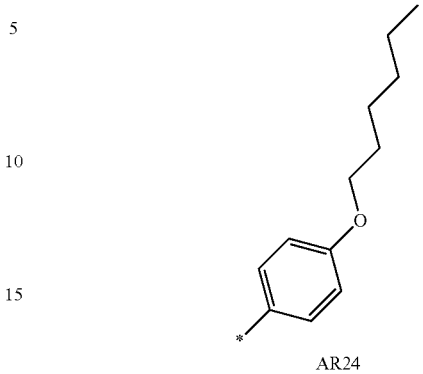
AR24
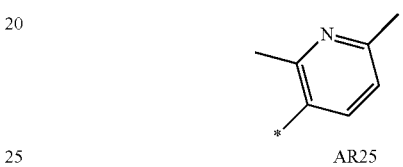
AR25
AR26
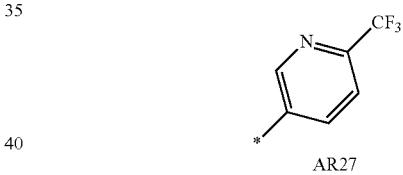
AR27
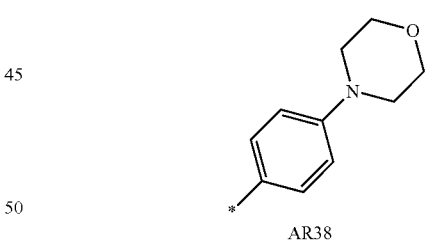
AR38
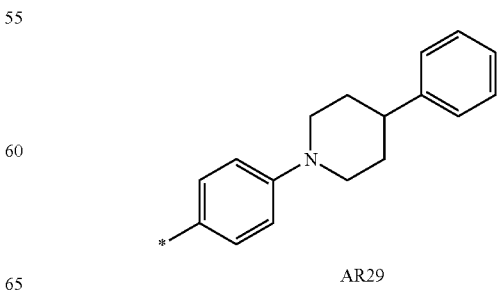
AR29

ARRAY AR-continued
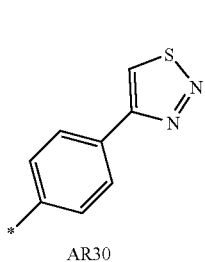
AR30
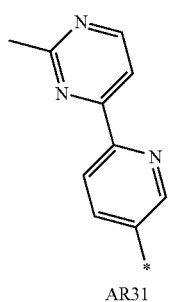
AR31
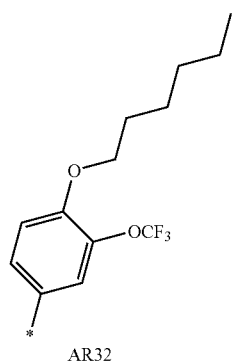
AR32
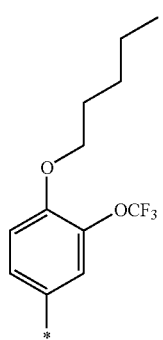
AR33
ARRAY AR-continued
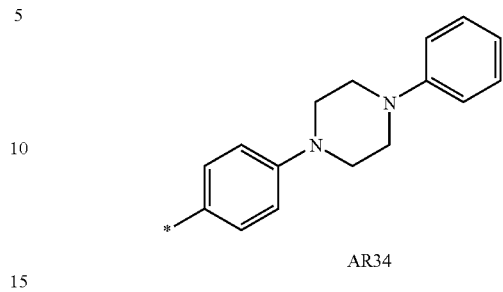
AR34
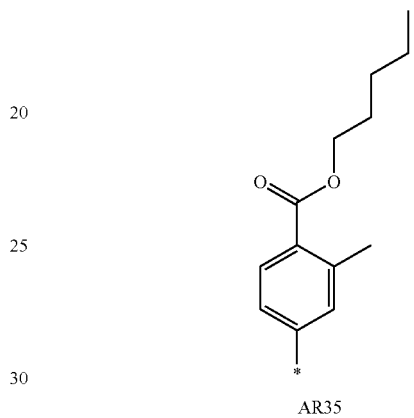
AR35
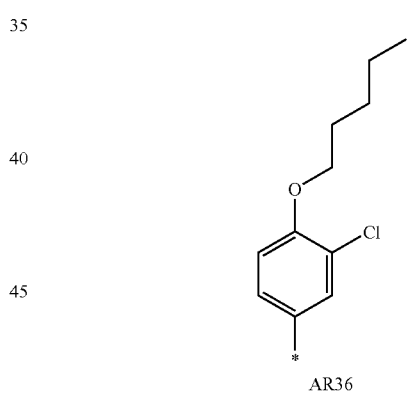
AR36
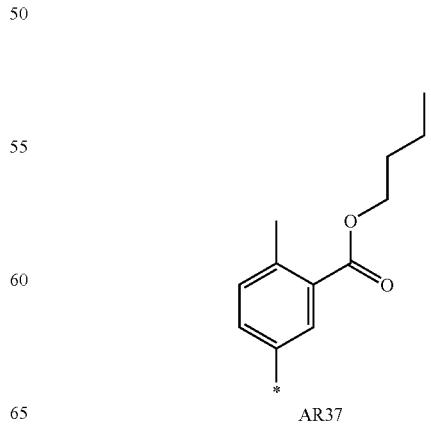
AR37

ARRAY AR-continued

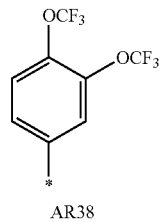

AR38

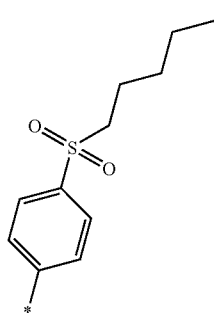

AR39

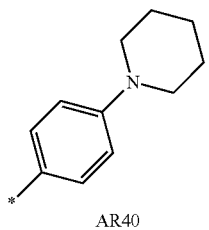

AR40

ARRAY AR-continued

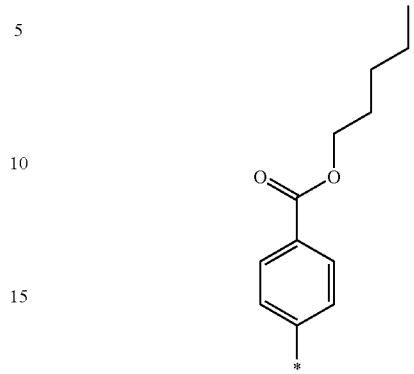

AR41

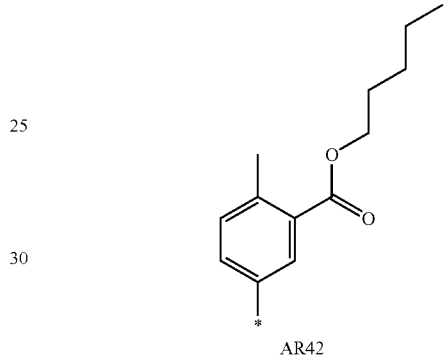

AR42

Compounds listed in Tables I, II, III, and IV have been synthesized and tested in a replicon based assay of HCV replication inhibition. A replicon based assay of HCV replication inhibition is given in Example 4. The activity of each compound in the assay is indicated by +++ ($EC_{50}$<1 micromolar), ++ ($EC_{50}$ between 1 micromolar and 10 micromolar) and + ($EC_{50}$ greater than 10 micromolar).

| Cmp. | Structure | Name | Activity |
|---|---|---|---|
| 1 | 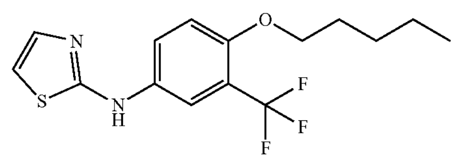 | N-(3-(trifluoromethyl)-4-(pentyloxy)phenyl)thiazol-2-amine | +++ |
| 2 | 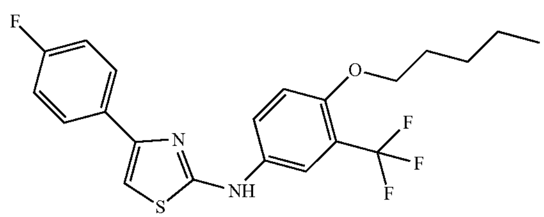 | N-(3-(trifluoromethyl)-4-(pentyloxy)phenyl)-4-(4-fluorophenyl)thiazol-2-amine | +++ |
| 3 | 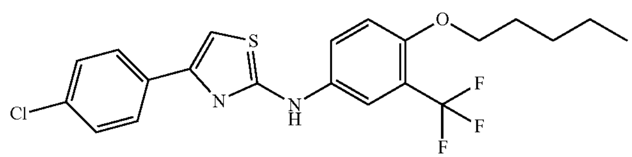 | 4-(4-chlorophenyl-N-(3-(trifluoromethyl)-4-(pentyloxy)phenyl)thiazol-2-amine | +++ |
| 4 | 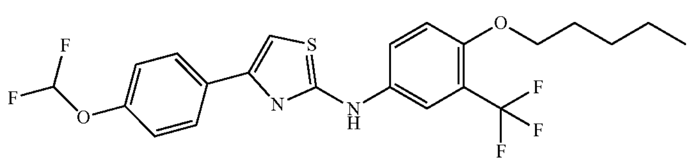 | 4-(4-(difluoromethoxy)phenyl)-N-(3-(trifluoromethyl)-4-(pentyloxy)phenyl)thiazol-2-amine | +++ |
| 5 | 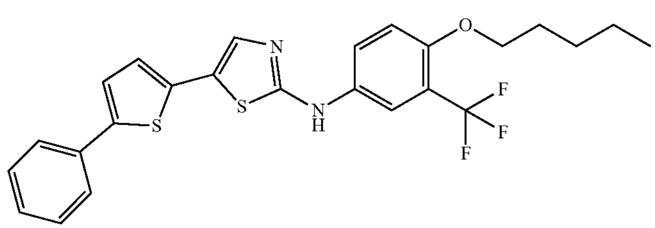 | N-(4-(pentyloxy)-3-(trifluoromethyl)phenyl)-4-(5-phenylthiophen-2-yl)thiazol-2-amine | +++ |

-continued

| Cmp. | Structure | Name | Activity |
|---|---|---|---|
| 6 | 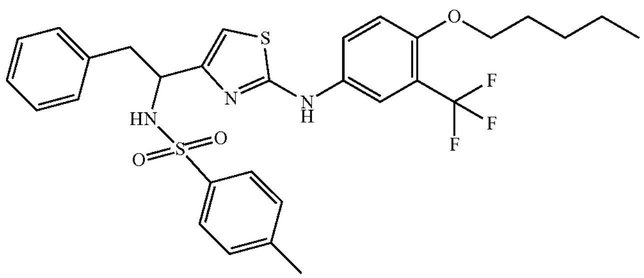 | N-(3-(trifluoromethyl)-4-(pentyloxy)phenyl)-4-(2-phenyl-1-(tosylamino)ethyl)thiazol-2-amine | ++ |
| 7 | 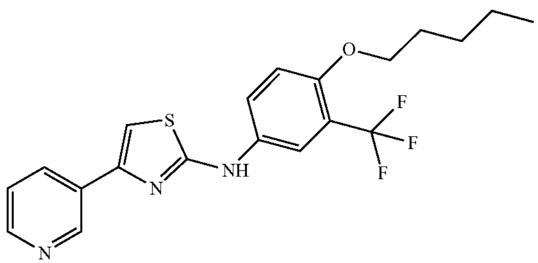 | N-(3-(trifluoromethyl)-4-(pentyloxy)phenyl)-4-(pyridin-3-yl)thiazol-2-amine | +++ |
| 8 | 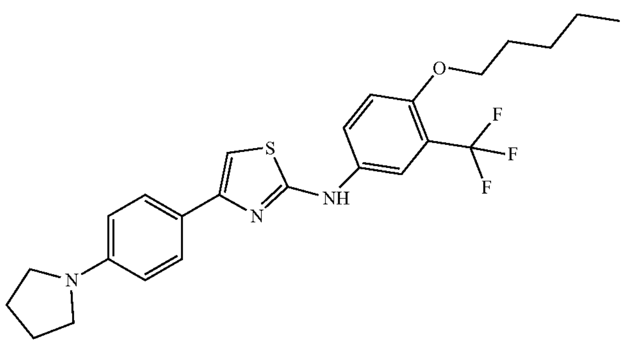 | N-(3-(trifluoromethyl)-4-(pentyloxy)phenyl)-4-(4-(pyrrolidin-1-yl)phenyl)thiazol-2-amine | +++ |
| 9 | 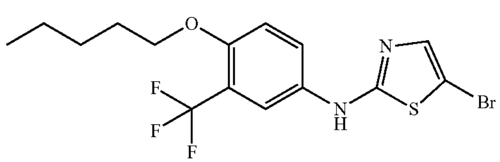 | 5-bromo-N-(3-(trifluoromethyl)-4-(pentyloxy)phenyl)thiazol-2-amine | +++ |

-continued

| Cmp. | Structure | Name | Activity |
|---|---|---|---|
| 10 | 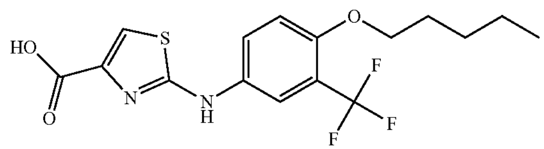 | 2-(3-(trifluoromethyl)-4-(pentyloxy)phenylamino)thiazole-4-carboxylic acid | + |
| 11 | 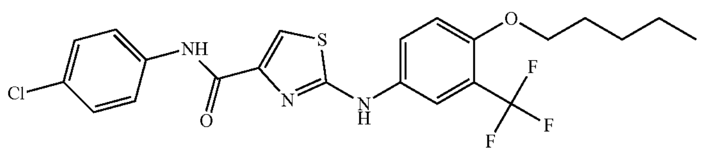 | 2-(3-(trifluoromethyl)-4-(pentyloxy)phenylamino)-N-(4-chlorophenyl)thiazole-4-carboxamide | + |
| 12 | 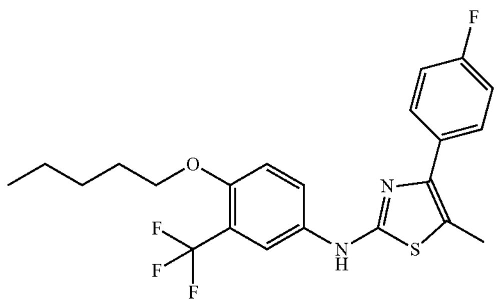 | N-(3-(trifluoromethyl)-4-(pentyloxy)phenyl)-4-(4-fluorophenyl)-5-methylthiazol-2-amine | +++ |
| 13 | 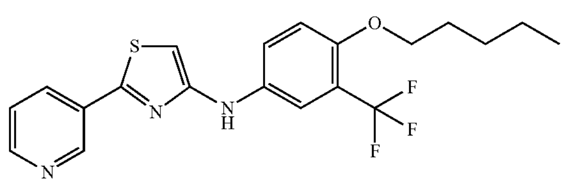 | N-(3-(trifluoromethyl)-4-(pentyloxy)phenyl)-2-(pyridin-3-yl)thiazol-4-amine | + |
| 14 | 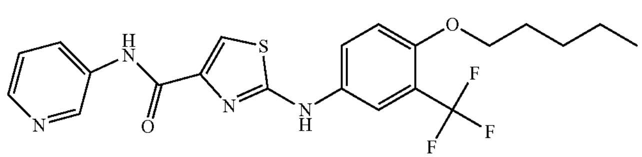 | 2-(3-(trifluoromethyl)-4-(pentyloxy)phenylamino)-N-(pyridin-3-yl)thiazole-4-carboxamide | +++ |

-continued

| Cmp. | Structure | Name | Activity |
|---|---|---|---|
| 15 | 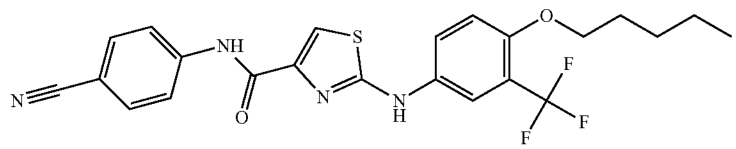 | 2-(3-(trifluoromethyl)-4-(pentyloxy)phenylamino)-N-(4-cyanophenyl)thiazole-4-carboxamide | + |
| 16 | 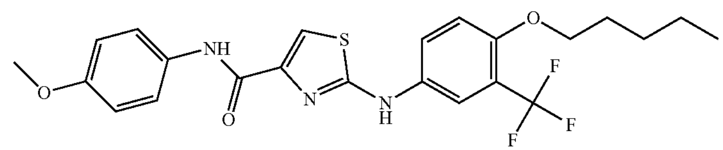 | 2-(3-(trifluoromethyl)-4-(pentyloxy)phenylamino)-N-(4-methoxyphenyl)thiazole-4-carboxamide | + |
| 17 | 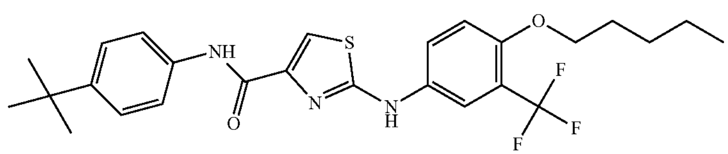 | 2-(3-(trifluoromethyl)-4-(pentyloxy)phenylamino)-N-(4-tert-butylphenyl)thiazole-4-carboxamide | + |
| 18 | 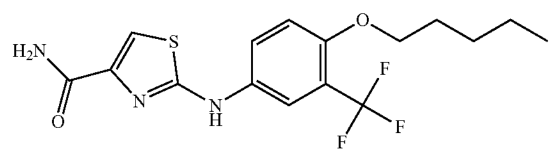 | 2-(3-(trifluoromethyl)-4-(pentyloxy)phenylamino)thiazole-4-carboxamide | +++ |
| 19 | 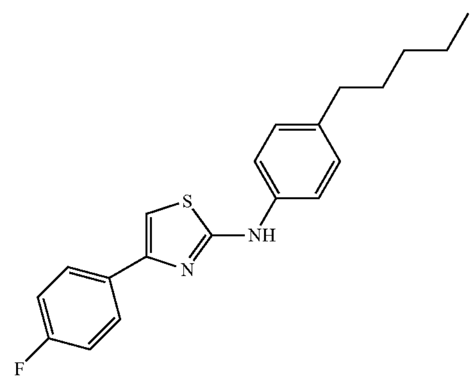 | 4-(4-fluorophenyl)-N-(4-pentylphenyl)thiazol-2-amine | +++ |

-continued

| Cmp. | Structure | Name | Activity |
|---|---|---|---|
| 20 | (structure) | 4-(4-chlorophenyl)-N-(4-pentylphenyl)thiazol-2-amine | +++ |
| 21 | (structure) | 4-(4-fluorophenyl)-N-(4-(pentyloxy)phenyl)thiazol-2-amine | +++ |

-continued

| Cmp. | Structure | Name | Activity |
|---|---|---|---|
| 22 | 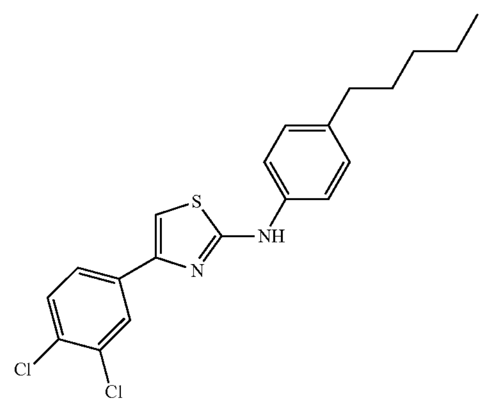 | 4-(3,4-dichlorophenyl)-N-(4-pentylphenyl)thiazol-2-amine | +++ |
| 23 | 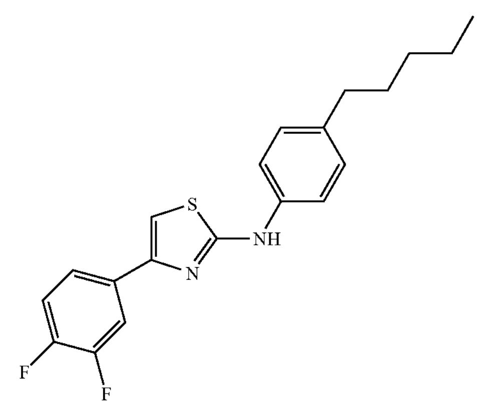 | 4-(2,4-difluorophenyl)-N-(4-pentylphenyl)thiazol-2-amine | + |

| Cmp. | Structure | Name | Activity |
|---|---|---|---|
| 24 | 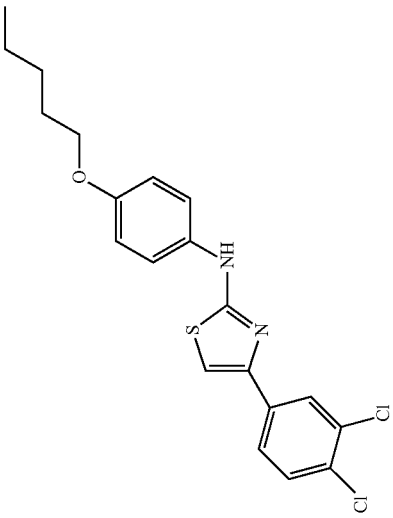 | 4-(3,4-dichlorophenyl)-N-(4-(pentyloxy)phenyl)thiazol-2-amine | +++ |
| 25 | 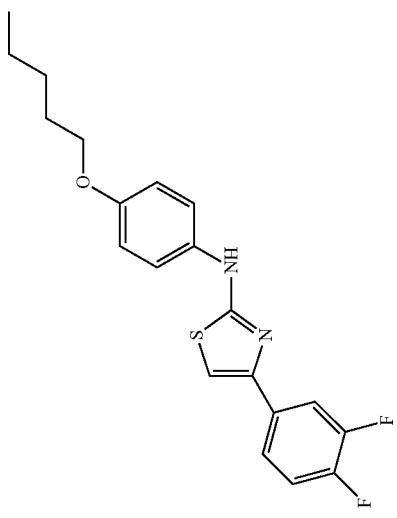 | 4-(2,4-difluorophenyl)-N-(4-(pentyloxy)phenyl)thiazol-2-amine | + |

-continued

| Cmp. | Structure | Name | Activity |
|---|---|---|---|
| 26 | (4-chlorophenyl-thiazole with 4-pentyloxyphenyl-NH) | 4-(4-chlorophenyl)-N-(4-(pentyloxy)phenyl)thiazol-2-amine | +++ |
| 27 | (4-fluorophenyl-thiazole with 3-benzyloxyphenyl-NH) | N-(3-(benzyloxy)phenyl)-4-(4-fluorophenyl)thiazol-2-amine | +++ |
| 28 | (3,4-dichlorophenyl-thiazole with 3-benzyloxyphenyl-NH) | N-(3-(benzyloxy)phenyl)-4-(3,4-dichlorophenyl)thiazol-2-amine | +++ |

-continued

| Cmp. | Structure | Name | Activity |
|---|---|---|---|
| 29 | 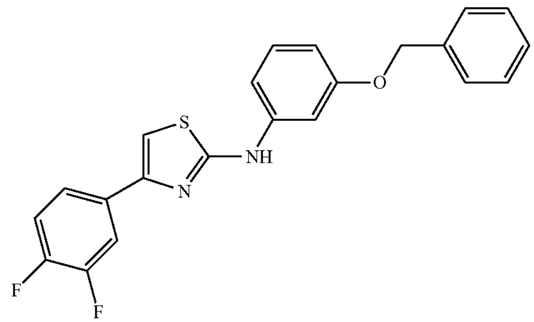 | N-(3-(benzyloxy)phenyl)-4-(2,4-difluorophenyl)thiazol-2-amine | +++ |
| 30 | 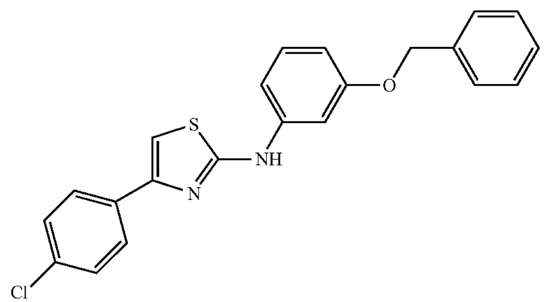 | N-(3-(benzyloxy)phenyl)-4-(4-chlorophenyl)thiazol-2-amine | +++ |
| 31 | 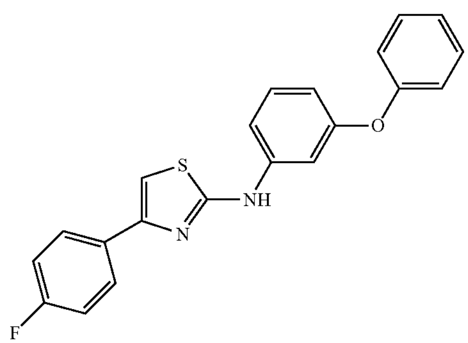 | 4-(4-fluorophenyl)-N-(3-phenoxyphenyl)thiazol-2-amine | +++ |

-continued

| Cmp. | Structure | Name | Activity |
|---|---|---|---|
| 32 | 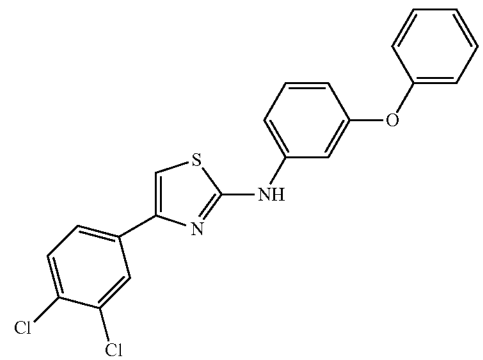 | 4-(3,4-dichlorophenyl)-N-(3-phenoxyphenyl)thiazol-2-amine | +++ |
| 33 | 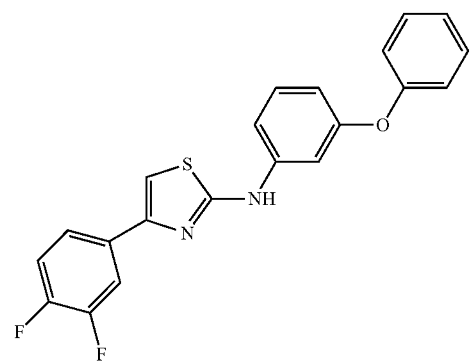 | 4-(2,4-difluorophenyl)-N-(3-phenoxyphenyl)thiazol-2-amine | +++ |
| 34 | 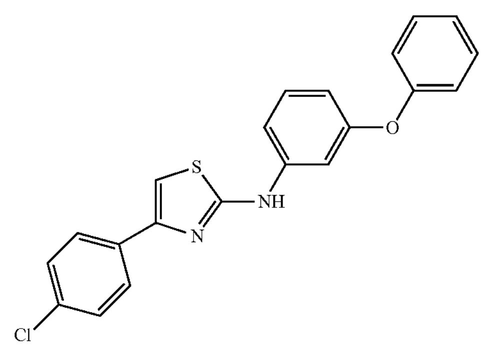 | 4-(4-chlorophenyl)-N-(3-phenoxyphenyl)thiazol-2-amine | +++ |

-continued

| Cmp. | Structure | Name | Activity |
|---|---|---|---|
| 35 | 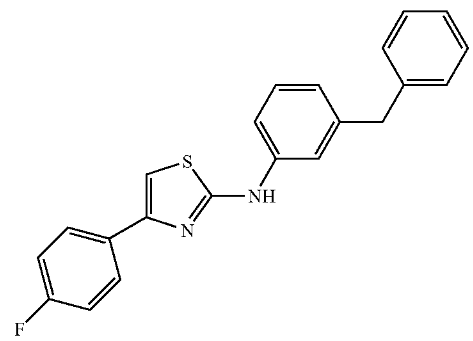 | N-(3-benzylphenyl)-4-(4-fluorophenyl)thiazol-2-amine | + |
| 36 | 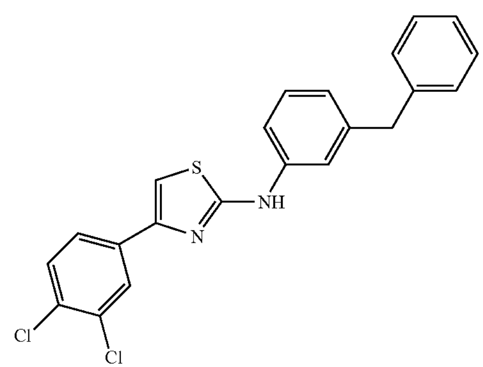 | N-(3-benzylphenyl)-4-(3,4-dichlorophenyl)thiazol-2-amine | +++ |

-continued

| Cmp. | Structure | Name | Activity |
|---|---|---|---|
| 37 | 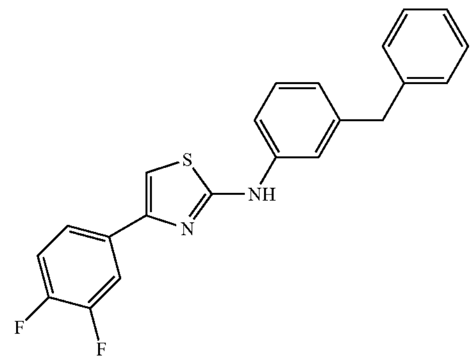 | N-(3-benzylphenyl)-4-(2,4-difluorophenyl)thiazol-2-amine | +++ |
| 38 | 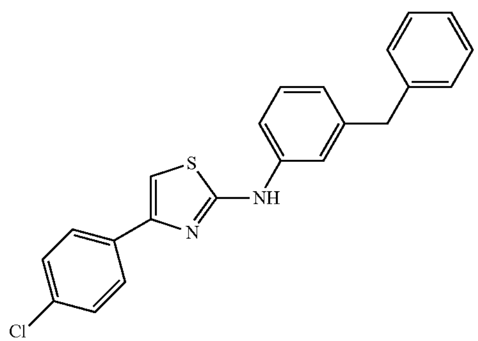 | N-(3-benzylphenyl)-4-(4-chlorophenyl)thiazol-2-amine | +++ |
| 39 | 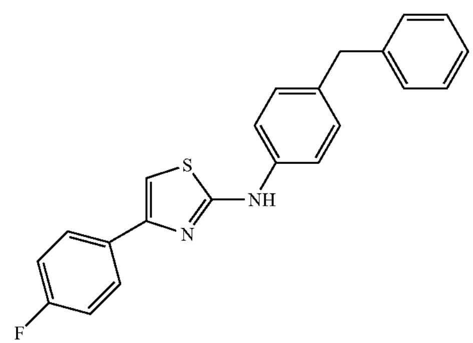 | N-(4-benzylphenyl)-4-(4-fluorophenyl)thiazol-2-amine | + |

-continued

| Cmp. | Structure | Name | Activity |
|---|---|---|---|
| 40 | 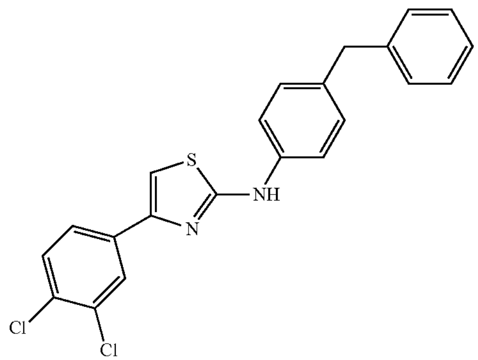 | N-(4-benzylphenyl)-4-(3,4-dichlorophenyl)thiazol-2-amine | + |
| 41 | 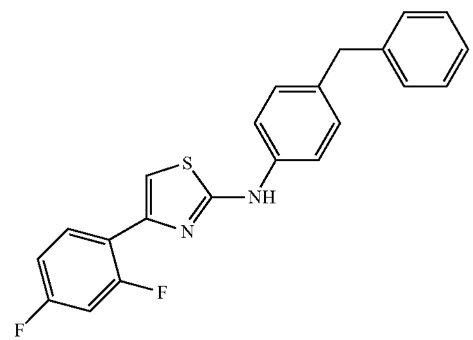 | N-(4-benzylphenyl)-4-(2,4-difluorophenyl)thiazol-2-amine | + |
| 42 | 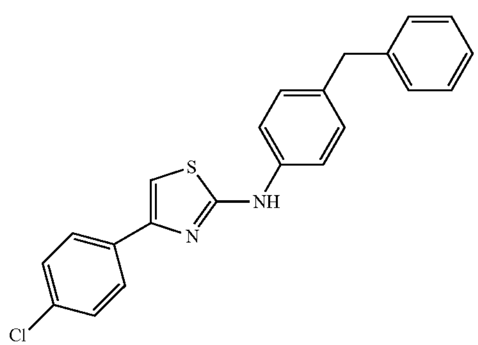 | N-(4-benzylphenyl)-4-(4-chlorophenyl)thiazol-2-amine | + |

-continued

| Cmp. | Structure | Name | Activity |
|---|---|---|---|
| 43 | (structure) | 4-(4-fluorophenyl)-N-(4-(trifluoromethoxy)phenyl)thiazol-2-amine | + |
| 44 | (structure) | 4-(3,4-dichlorophenyl)-N-(4-(trifluoromethoxy)phenyl)thiazol-2-amine | + |
| 45 | (structure) | 4-(2,4-difluorophenyl)-N-(4-(trifluoromethoxy)phenyl)thiazol-2-amine | + |

-continued

| Cmp. | Structure | Name | Activity |
|---|---|---|---|
| 46 | 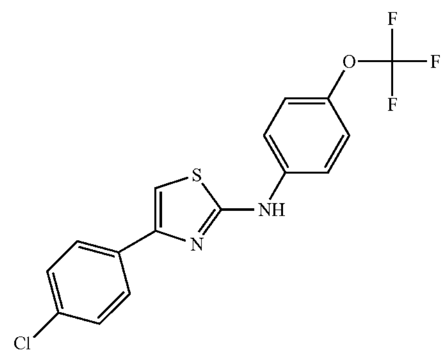 | 4-(4-chlorophenyl)-N-(4-(trifluoromethoxy)phenyl)thiazol-2-amine | + |
| 47 | 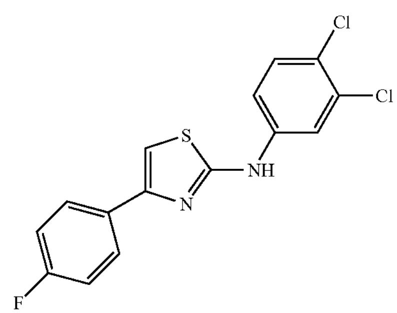 | N-(3,4-dichlorophenyl)-4-(4-fluorophenyl)thiazol-2-amine | +++ |
| 48 | 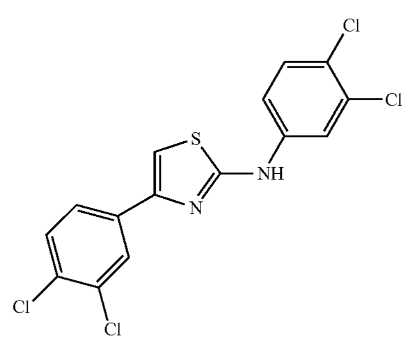 | N,4-bis(3,4-dichlorophenyl)thiazol-2-amine | +++ |

-continued

| Cmp. | Structure | Name | Activity |
|---|---|---|---|
| 49 | 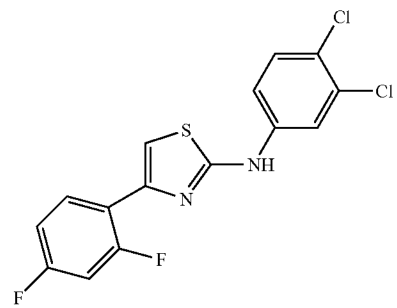 | N-(3,4-dichlorophenyl)-4-(2,4-difluorophenyl)thiazol-2-amine | +++ |
| 50 | 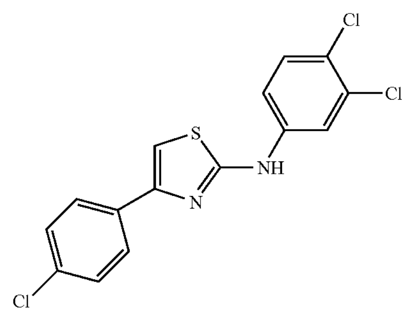 | N-(3,4-dichlorophenyl)-4-(4-chlorophenyl)thiazol-2-amine | + |
| 51 | 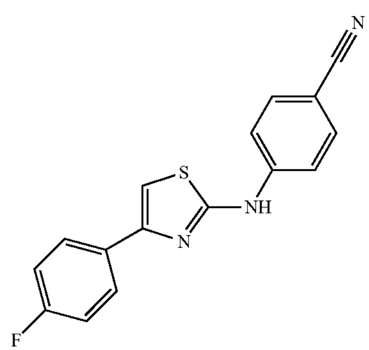 | 4-(4-(4-fluorophenyl)thiazol-2-ylamino)benzonitrile | + |

-continued

| Cmp. | Structure | Name | Activity |
|---|---|---|---|
| 52 | 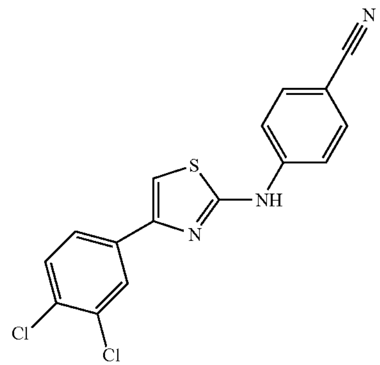 | 4-(4-(3,4-dichlorophenyl)thiazol-2-ylamino)benzonitrile | + |
| 53 | 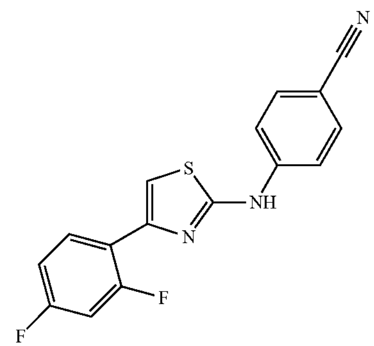 | 4-(4-(2,4-difluorophenyl)thiazol-2-ylamino)benzonitrile | + |
| 54 | 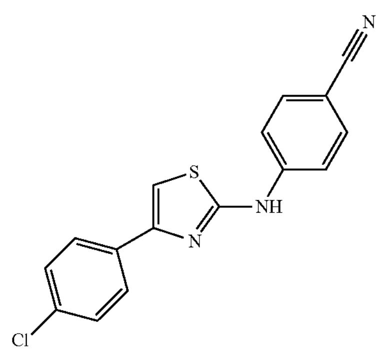 | 4-(4-(4-chlorophenyl)thiazol-2-ylamino)benzonitrile | + |

| Cmp. | Structure | Name | Activity |
|---|---|---|---|
| 55 | (3-cyanophenyl)-NH-thiazole-4-(4-fluorophenyl) | 3-(4-(4-fluorophenyl)thiazol-2-ylamino)benzonitrile | + |
| 56 | (3-cyanophenyl)-NH-thiazole-4-(3,4-dichlorophenyl) | 3-(4-(3,4-dichlorophenyl)thiazol-2-ylamino)benzonitrile | + |
| 57 | (3-cyanophenyl)-NH-thiazole-4-(2,4-difluorophenyl) | 3-(4-(2,4-difluorophenyl)thiazol-2-ylamino)benzonitrile | + |

-continued

| Cmp. | Structure | Name | Activity |
|---|---|---|---|
| 58 | (4-chlorophenyl at thiazole 4-position; 3-cyanophenyl-NH at thiazole 2-position) | 3-(4-(4-chlorophenyl)thiazol-2-ylamino)benzonitrile | + |
| 59 | (4-fluorophenyl at thiazole 4-position; 4-chloro-3-(trifluoromethyl)phenyl-NH at thiazole 2-position) | N-(4-chloro-3-(trifluoromethyl)phenyl)-4-(4-fluorophenyl)thiazol-2-amine | +++ |
| 60 | (3,4-dichlorophenyl at thiazole 4-position; 4-chloro-3-(trifluoromethyl)phenyl-NH at thiazole 2-position) | N-(4-chloro-3-(trifluoromethyl)phenyl)-4-(3,4-dichlorophenyl)thiazol-2-amine | +++ |

-continued

| Cmp. | Structure | Name | Activity |
|---|---|---|---|
| 61 | 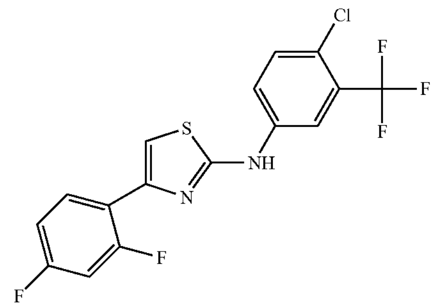 | N-(4-chloro-3-(trifluoromethyl)phenyl)-4-(2,4-difluorophenyl)thiazol-2-amine | +++ |
| 62 | 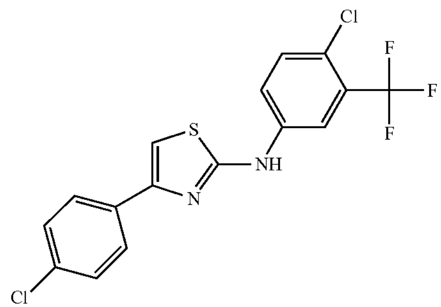 | N-(4-chloro-3-(trifluoromethyl)phenyl)-4-(4-chlorophenyl)thiazol-2-amine | + |
| 63 | 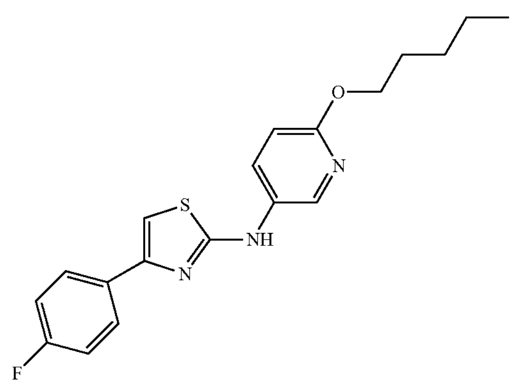 | N-(4-(4-fluorophenyl)thiazol-2-yl)-6-(pentyloxy)pyridin-3-amine | +++ |

-continued

| Cmp. | Structure | Name | Activity |
|---|---|---|---|
| 64 | 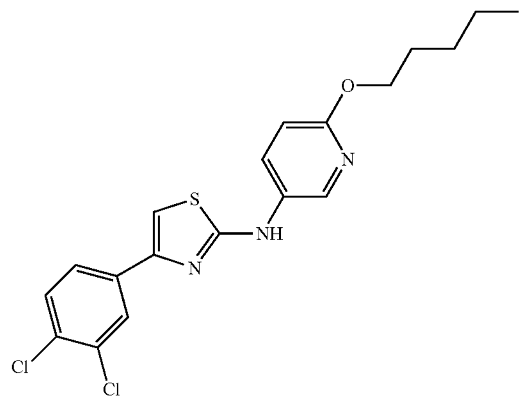 | N-(4-(3,4-dichlorophenyl)thiazol-2-yl)-6-(pentyloxy)pyridin-3-amine | + |
| 65 | 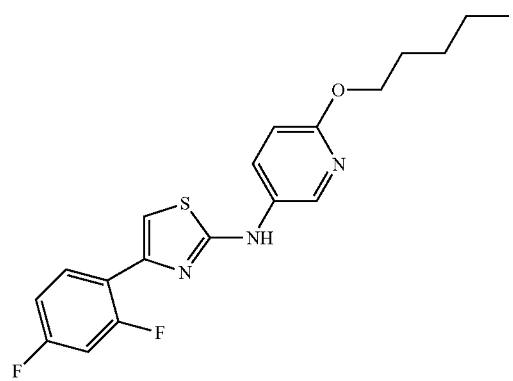 | N-(4-(2,4-difluorophenyl)thiazol-2-yl)-6-(pentyloxy)pyridin-3-amine | + |

| Cmp. | Structure | Name | Activity |
|---|---|---|---|
| 66 | 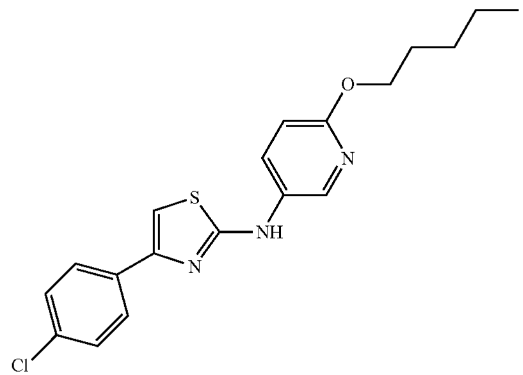 | N-(4-(4-chlorophenyl)thiazol-2-yl)-6-(pentyloxy)pyridin-3-amine | +++ |
| 67 | 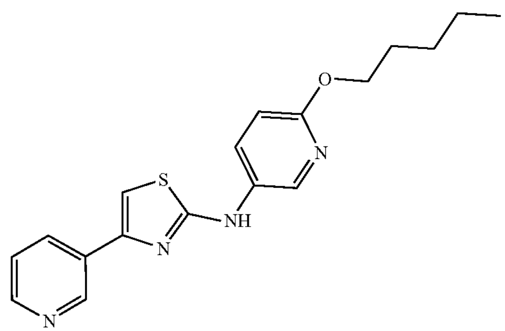 | 6-(pentyloxy)-N-(4-(pyridin-3-yl)thiazol-2-yl)pyridin-3-amine | +++ |
| 68 | 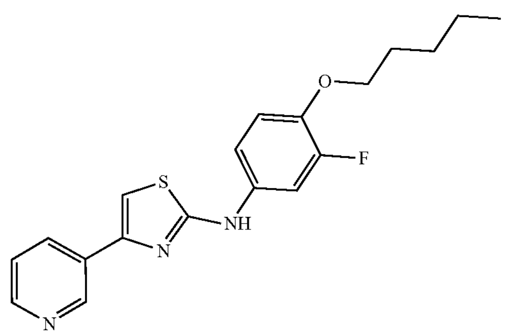 | N-(3-fluoro-4-(pentyloxy)phenyl)-4-(pyridin-3-yl)thiazol-2-amine | +++ |

-continued

| Cmp. | Structure | Name | Activity |
|---|---|---|---|
| 69 | 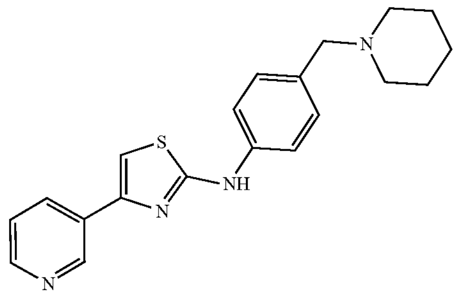 | N-(4-((piperidin-1-yl)methyl)phenyl)-4-(pyridin-3-yl)thiazol-2-amine | + |
| 70 | 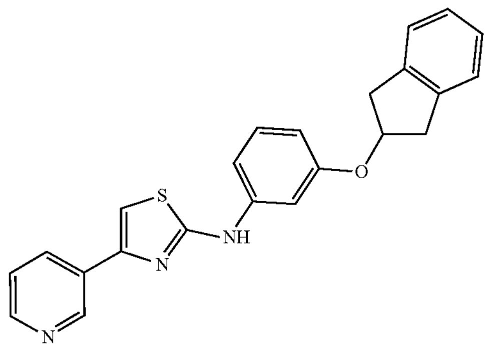 | N-(3-(2,3-dihydro-1H-inden-2-yloxy)phenyl)-4-(pyridin-3-yl)thiazol-2-amine | +++ |
| 71 | 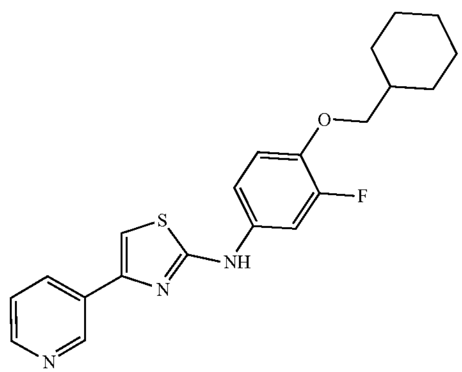 | N-(4-(cyclohexylmethoxy)-3-fluorophenyl)-4-(pyridin-3-yl)thiazol-2-amine | +++ |

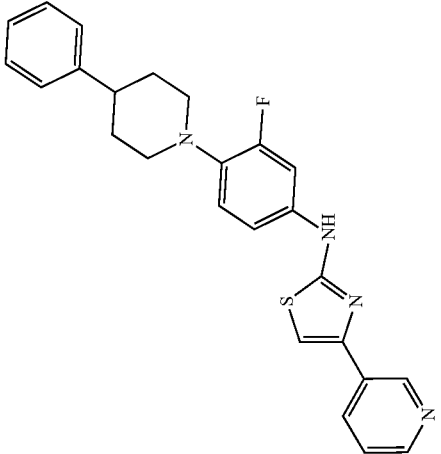
| Cmp. | Structure | Name | Activity |
|---|---|---|---|
| 72 | 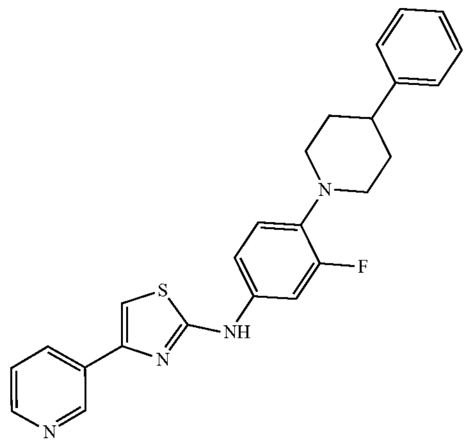 | N-(3-fluoro-4-(4-phenylpiperidin-1-yl)phenyl)-4-(pyridin-3-yl)thiazol-2-amine | +++ |
| 73 | 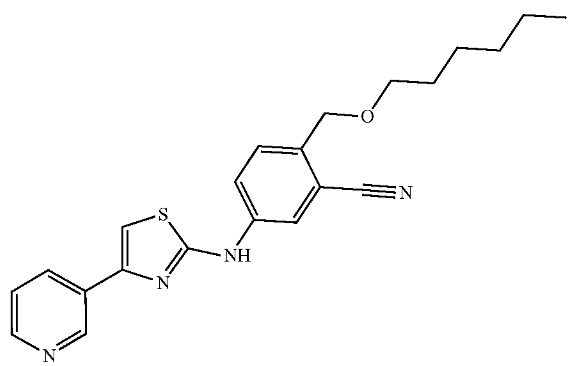 | 5-(4-(pyridin-3-yl)thiazol-2-ylamino)-2-(heptyloxy)benzonitrile | + |

-continued

| Cmp. | Structure | Name | Activity |
|---|---|---|---|
| 74 | 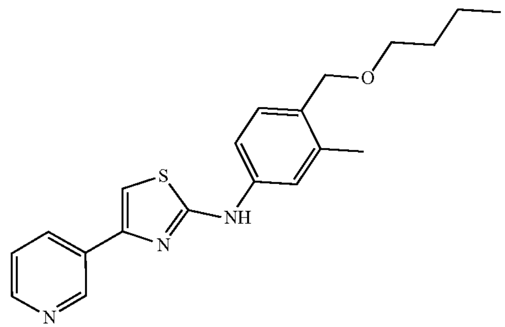 | N-(3-methyl-4-(pentyloxy)phenyl)-4-(pyridin-3-yl)thiazol-2-amine | +++ |
| 75 | 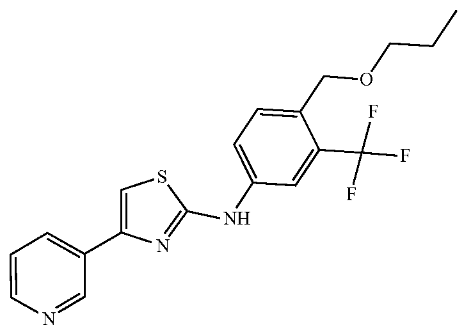 | N-(4-butoxy-3-(trifluoromethyl)phenyl)-4-(pyridin-3-yl)thiazol-2-amine | +++ |
| 76 | 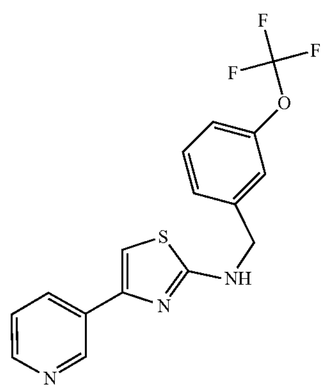 | N-(3-(trifluoromethoxy)benzyl)-4-(pyridin-3-yl)thiazol-2-amine | + |

-continued
| Cmp. | Structure | Name | Activity |
|---|---|---|---|
| 77 | 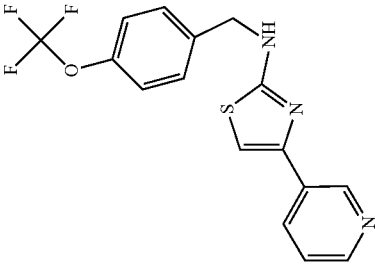 | N-(4-(trifluoromethoxy)benzyl)-4-(pyridin-3-yl)thiazol-2-amine | + |
| 78 | 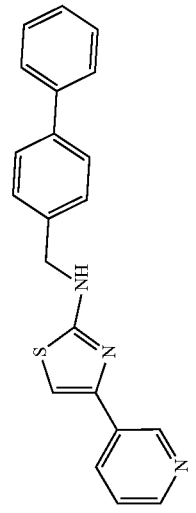 | N-(4-phenyl-benzyl)-4-(pyridin-3-yl)thiazol-2-amine | + |
| 79 | 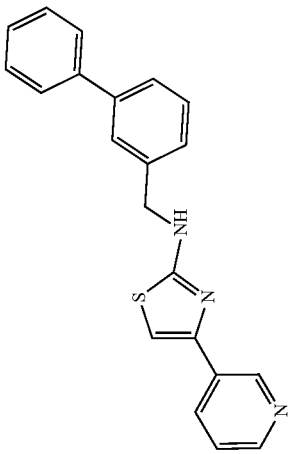 | N-(3-phenyl-benzyl)-4-(pyridin-3-yl)thiazol-2-amine | + |

| Cmp. | Structure | Name | Activity |
|---|---|---|---|
| 80 | 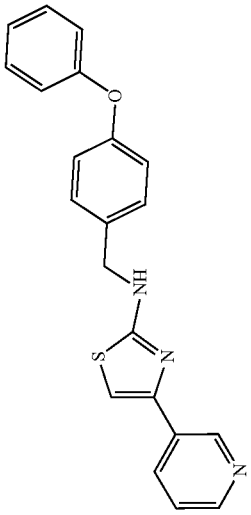 | N-(4-phenoxybenzyl)-4-(pyridin-3-yl)thiazol-2-amine | + |
| 81 | 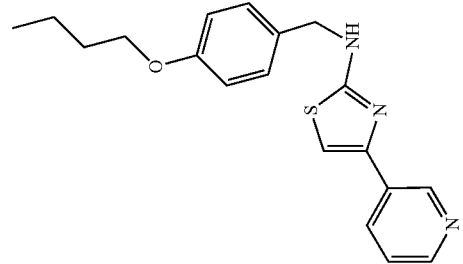 | N-(4-butoxybenzyl)-4-(pyridin-3-yl)thiazol-2-amine | + |

-continued

| Cmp. | Structure | Name | Activity |
|---|---|---|---|
| 82 | 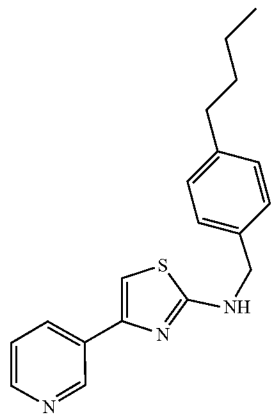 | N-(4-butylbenzyl)-4-(pyridin-3-yl)thiazol-2-amine | + |
| 83 | 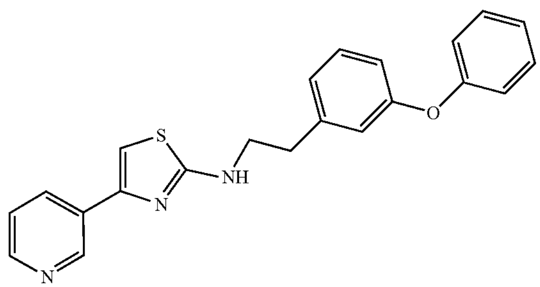 | N-(3-phenoxyphenethyl)-4-(pyridin-3-yl)thiazol-2-amine | + |
| 84 | 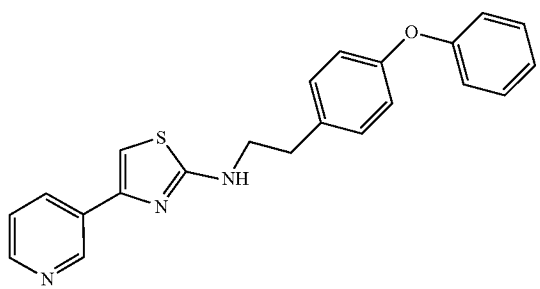 | N-(4-phenoxyphenethyl)-4-(pyridin-3-yl)thiazol-2-amine | + |

-continued
| Cmp. | Structure | Name | Activity |
|---|---|---|---|
| 85 | 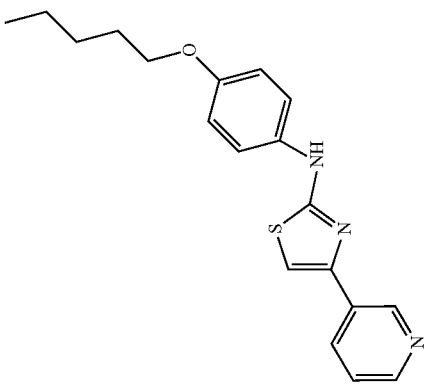 | N-(4-(pentyloxy)phenyl)-4-(pyridin-3-yl)thiazol-2-amine | +++ |
| 86 | 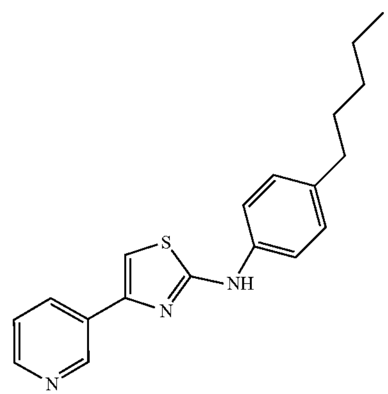 | N-(4-pentylphenyl)-4-(pyridin-3-yl)thiazol-2-amine | +++ |

-continued

| Cmp. | Structure | Name | Activity |
|---|---|---|---|
| 87 | 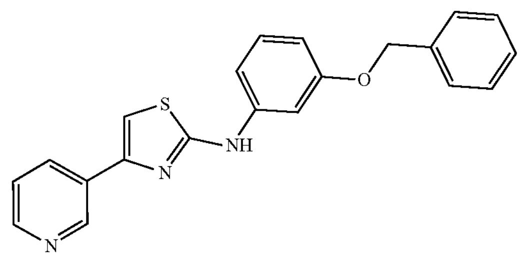 | N-(3-(benzyloxy)phenyl)-4-(pyridin-3-yl)thiazol-2-amine | +++ |
| 88 | 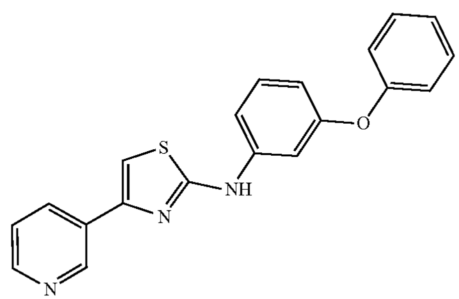 | N-(3-phenoxyphenyl)-4-(pyridin-3-yl)thiazol-2-amine | +++ |
| 89 | 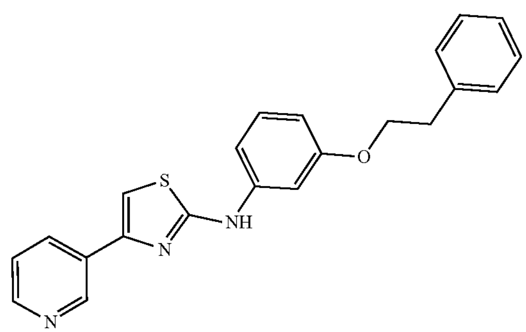 | N-(3-phenethyloxy)phenyl)-4-(pyridin-3-yl)thiazol-2-amine | +++ |

-continued
| Cmp. | Structure | Name | Activity |
|---|---|---|---|
| 90 | 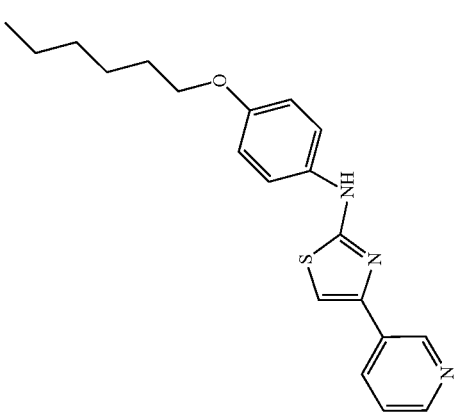 | N-(4-(hexyloxy)phenyl)-4-(pyridin-3-yl)thiazol-2-amine | +++ |
| 91 | 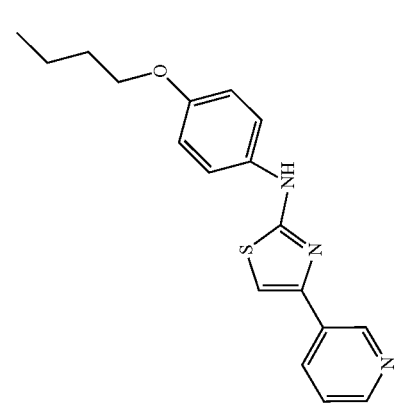 | N-(4-butoxyphenyl)-4-(pyridin-3-yl)thiazol-2-amine | +++ |

| Cmp. | Structure | Name | Activity |
|---|---|---|---|
| 92 | 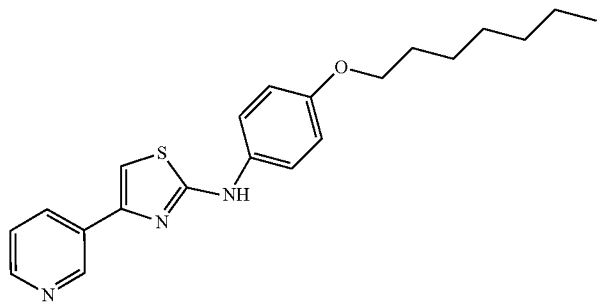 | N-(4-(heptyloxy)phenyl)-4-(pyridin-3-yl)thiazol-2-amine | +++ |
| 93 | 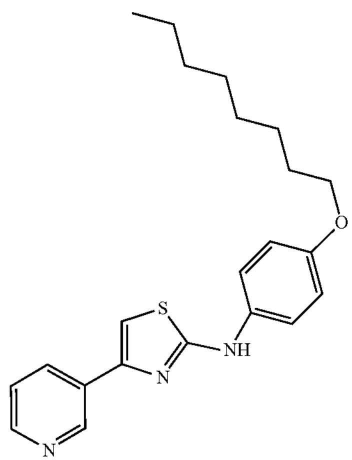 | N-(4-(octyloxy)phenyl)-4-(pyridin-3-yl)thiazol-2-amine | +++ |

-continued
| Cmp. | Structure | Name | Activity |
|---|---|---|---|
| 94 | 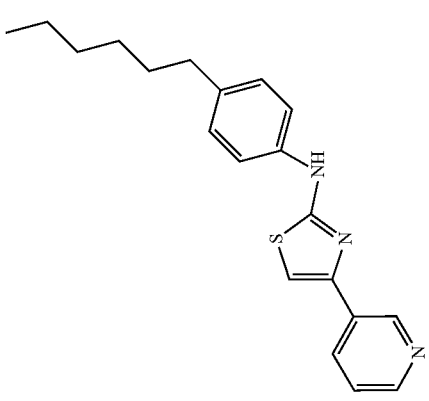 | N-(4-hexylphenyl)-4-(pyridin-3-yl)thiazol-2-amine | |
| 95 | 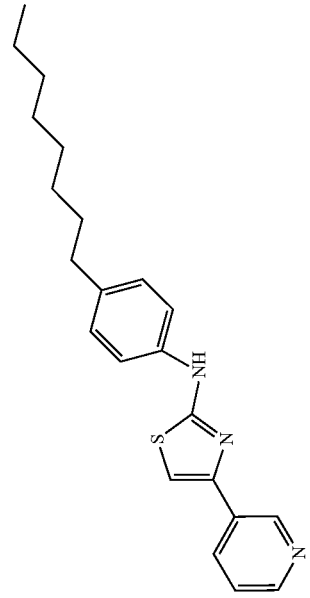 | N-(4-octylphenyl)-4-(pyridin-3-yl)thiazol-2-amine | +++ |
| 96 | 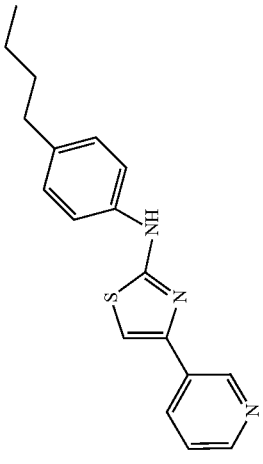 | N-(4-butylphenyl)-4-(pyridin-3-yl)thiazol-2-amine | ++ |

-continued

| Cmp. | Structure | Name | Activity |
|---|---|---|---|
| 97 | 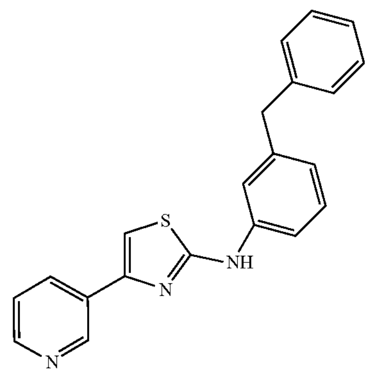 | N-(3-benzylphenyl)-4-(pyridin-3-yl)thiazol-2-amine | +++ |
| 98 | 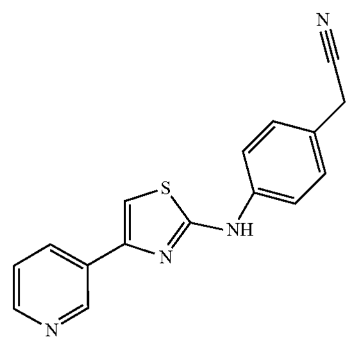 | 2-(4-(4-(pyridin-3-yl)thiazol-2-ylamino)phenyl)acetonitrile | + |
| 99 | 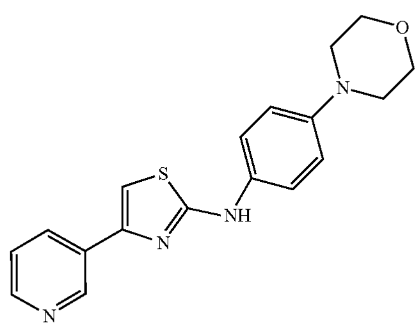 | N-(4-morpholinophenyl)-4-(pyridin-3-yl)thiazol-2-amine | + |

-continued

| Cmp. | Structure | Name | Activity |
|---|---|---|---|
| 100 | 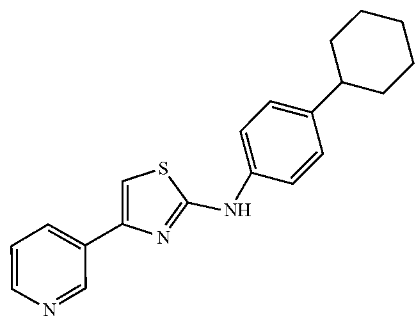 | N-(4-cyclohexylphenyl)-4-(pyridin-3-yl)thiazol-2-amine | +++ |
| 101 | 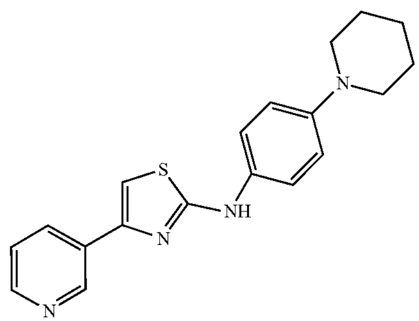 | N-(4-(piperidin-1-yl)phenyl)-4-(pyridin-3-yl)thiazol-2-amine | + |
| 102 | 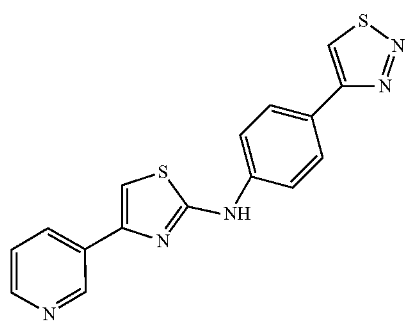 | N-(4-(1,2,3-thiadiazol-4-yl)phenyl)-4-(pyridin-3-yl)thiazol-2-amine | + |

-continued

| Cmp. | Structure | Name | Activity |
|---|---|---|---|
| 103 | 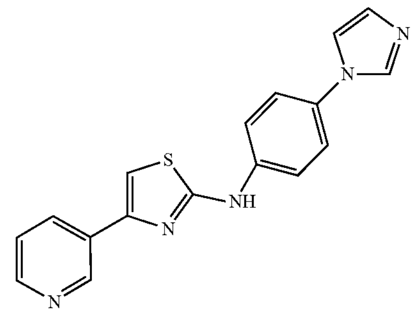 | N-(4-(1H-imidazol-1-yl)phenyl)-4-(pyridin-3-yl)thiazol-2-amine | + |
| 104 | 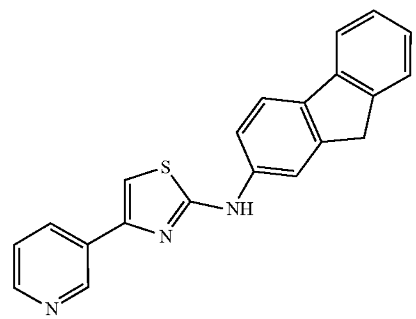 | N-(9H-fluoren-7-yl)-4-(pyridin-3-yl)thiazol-2-amine | ++ |
| 105 | 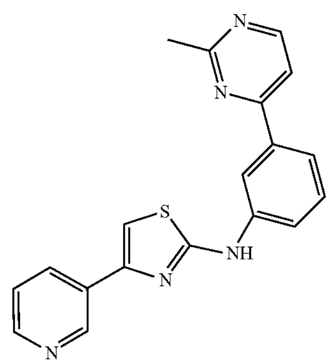 | N-(3-(2-methylpyrimidin-4-yl)phenyl)-4-(pyridin-3-yl)thiazol-2-amine | + |

| Cmp. | Structure | Name | Activity |
|---|---|---|---|
| 106 | 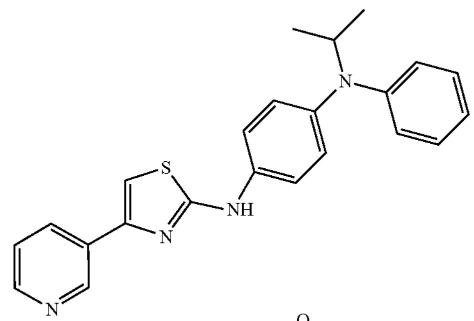 | N1-isopropyl-N1-phenyl-N4-(4-(pyridin-3-yl)thiazol-2-yl)benzene-1,4-diamine | + |
| 107 | 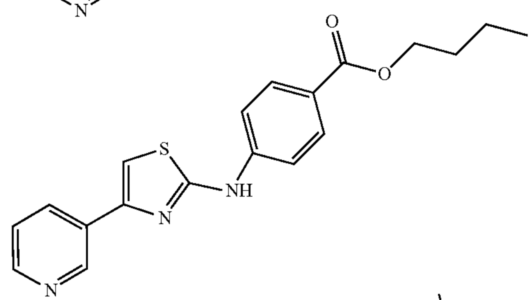 | butyl 4-(4-(pyridin-3-yl)thiazol-2-ylamino)benzoate | + |
| 108 | 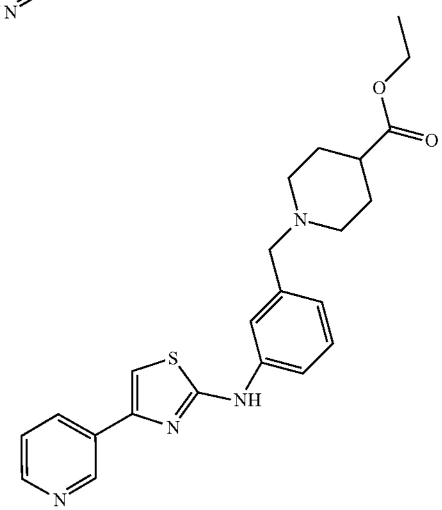 | ethyl 1-(3-(4-(pyridin-3-yl)thiazol-2-ylamino)benzyl)piperidine-4-carboxylate | + |

-continued
| Cmp. | Structure | Name | Activity |
|---|---|---|---|
| 109 | 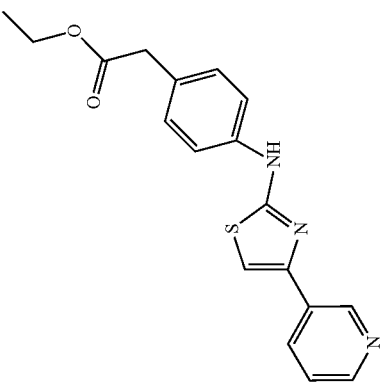 | ethyl 2-(4-(4-(pyridin-3-yl)thiazol-2-ylamino)phenyl)acetate | + |
| 110 | 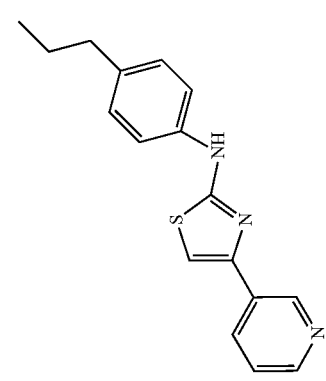 | N-(4-propylphenyl)-4-(pyridin-3-yl)thiazol-2-amine | + |
| 111 | 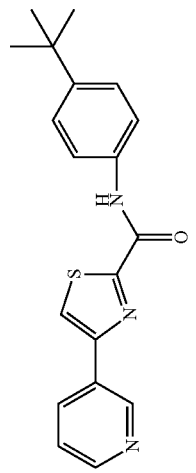 | N-(4-tert-butylphenyl)-4-(pyridin-3-yl)thiazole-2-carboxamide | + |

| Cmp. | Structure | Name | Activity |
|---|---|---|---|
| 112 | 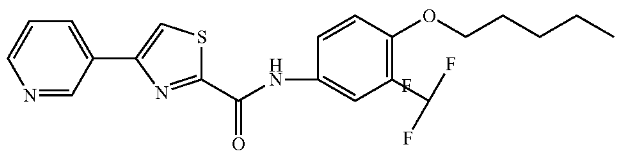 | N-(3-(trifluoromethyl)-4-(pentyloxy)phenyl)-4-(pyridin-3-yl)thiazole-2-carboxamide | + |
| 113 | 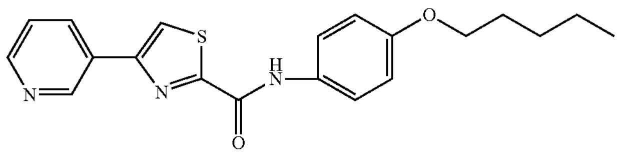 | N-(4-(pentyloxy)phenyl)-4-(pyridin-3-yl)thiazole-2-carboxamide | + |
| 114 | 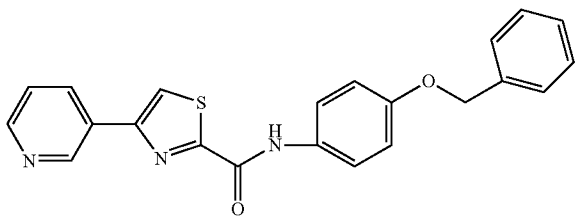 | N-(4-benzyloxy)phenyl)-4-(pyridin-3-yl)thiazole-2-carboxamide | + |
| 115 | 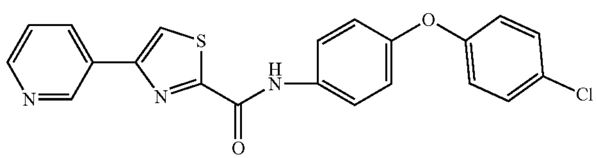 | N-(4-(4-chlorophenoxy)phenyl)-4-(pyridin-3-yl)thiazole-2-carboxamide | + |
| 116 | 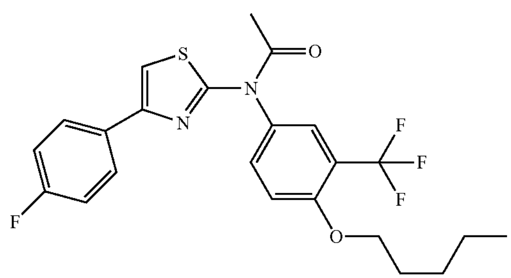 | N-(3-(trifluoromethyl)-4-(pentyloxy)phenyl)-N-(4-(4-fluorophenyl)thiazol-2-yl)acetamide | +++ |

| Cmp. | Structure | Name | Activity |
|---|---|---|---|
| 117 | 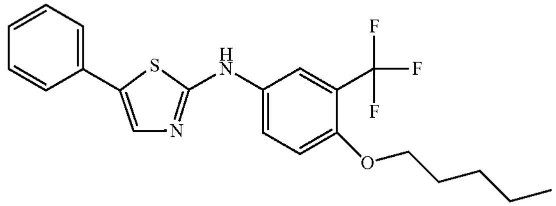 | N-(3-(trifluoromethyl)-4-(pentyloxy)phenyl)-5-phenylthiazol-2-amine | +++ |
| 118 | 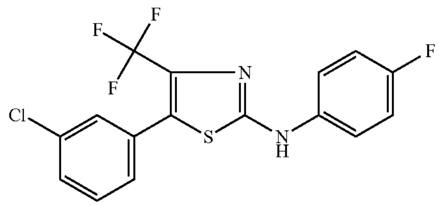 | 5-(3-chlorophenyl)-4-(trifluoromethyl)-N-(4-fluorophenyl)thiazol-2-amine | + |
| 119 | 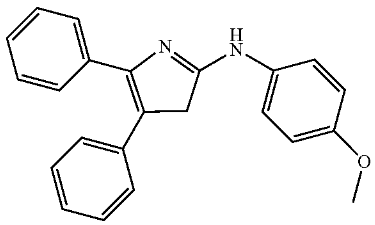 | N-(4-methoxyphenyl)-4,5-diphenylthiazol-2-amine | +++ |
| 120 | 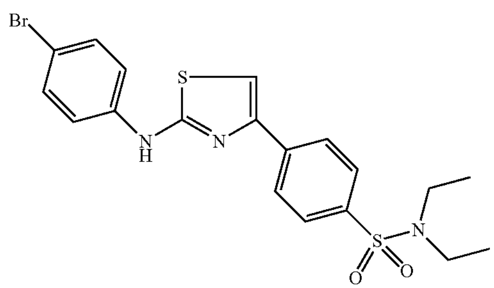 | N-(4-bromophenyl)-4-diethylaminosulfonyl-phenyl-2-amine | + |

-continued

| Cmp. | Structure | Name | Activity |
|---|---|---|---|
| 121 | 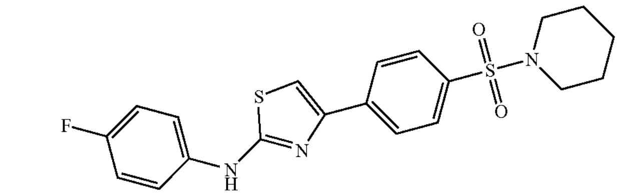 | N-(4-fluorophenyl)-4-piperidin-1-ylsulfonyl-phenyl-2-amine | + |
| 122 | 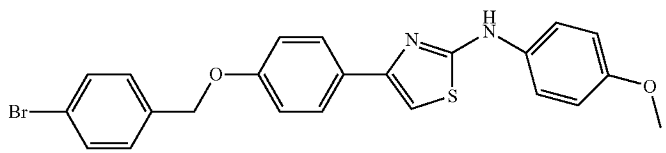 | 4-(4-(4-bromobenzyloxy)phenyl)-N-(4-methoxyphenyl)thiazol-2-amine | + |
| 123 | 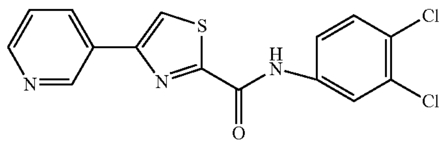 | N-(3,4-dichlorophenyl)-4-(pyridin-3-yl)thiazole-2-carboxamide | + |
| 124 | 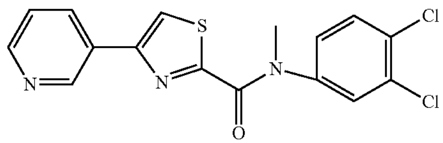 | N-(3,4-dichlorophenyl)-N-methyl-4-(pyridin-3-yl)thiazole-2-carboxamide | + |
| 125 | 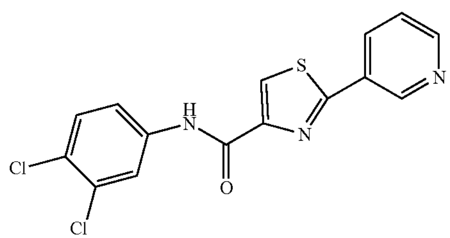 | N-(3,4-dichlorophenyl)-2-(pyridin-3-yl)thiazole-4-carboxamide | + |

| Cmp. | Structure | Name | Activity |
|---|---|---|---|
| 126 | 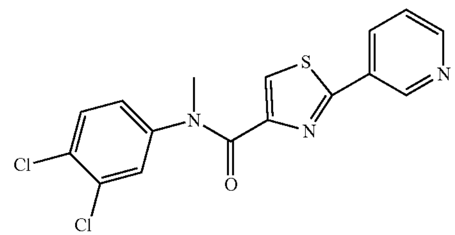 | N-(3,4-dichlorophenyl)-N-methyl-2-(pyridin-3-yl)thiazole-4-carboxamide | + |
| 127 | 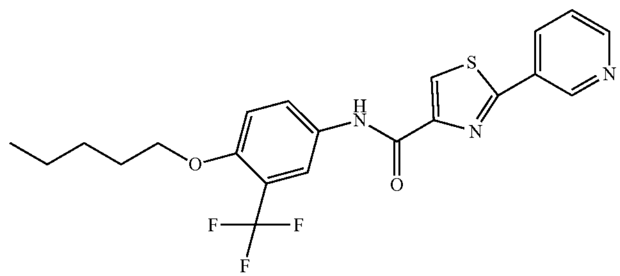 | N-(3-(trifluoromethyl)-4-(pentyloxy)phenyl)-2-(pyridin-3-yl)thiazole-4-carboxamide | + |
| 128 | 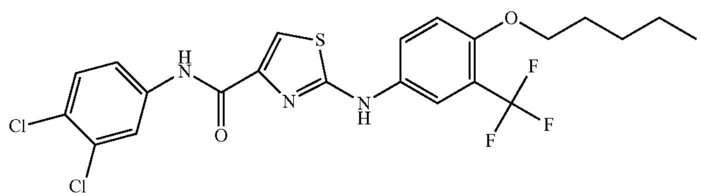 | 2-(3-(trifluoromethyl)-4-(pentyloxy)phenylamino)-N-(3,4-dichlorophenyl)thiazole-4-carboxamide | ++ |
| 129 | 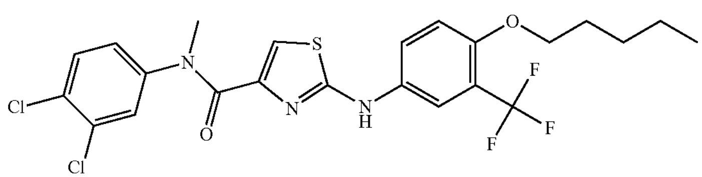 | 2-(3-(trifluoromethyl)-4-(pentyloxy)phenylamino)-N-(3,4-dichlorophenyl)-N-methylthiazole-4-carboxamide | + |

| Cmp. | Structure | Name | Activity |
|---|---|---|---|
| 130 | 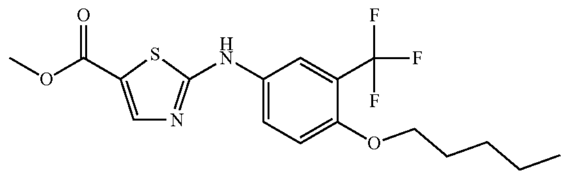 | methyl 2-(3-(trifluoromethyl)-4-(pentyloxy)phenylamino)thiazole-5-carboxylate | + |
| 131 | 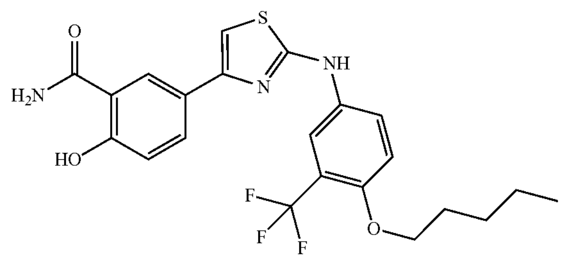 | 5-(2-(3-(trifluoromethyl)-4-(pentyloxy)phenylamino)thiazol-4-yl)-2-hydroxybenzamide | +++ |
| 132 | 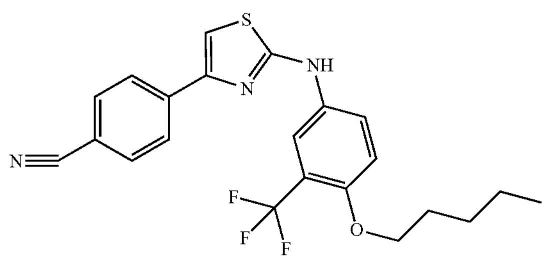 | 4-(2-(3-(trifluoromethyl)-4-(pentyloxy)phenylamino)thiazol-4-yl)benzonitrile | +++ |
| 133 | 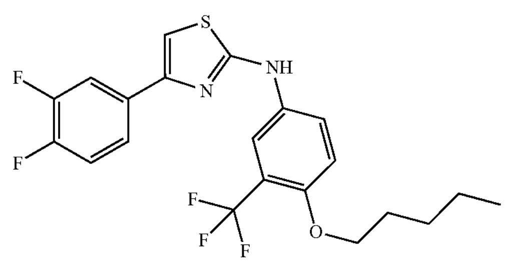 | N-(3-(trifluoromethyl)-4-(pentyloxy)phenyl)-4-(3,4-difluorophenyl)thiazol-2-amine | +++ |

-continued

| Cmp. | Structure | Name | Activity |
|---|---|---|---|
| 134 | 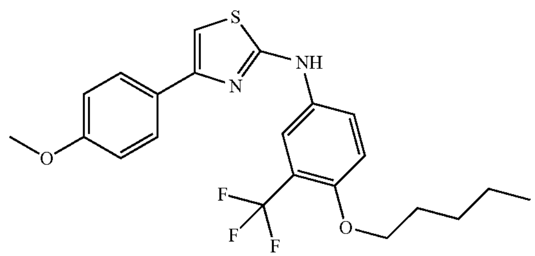 | N-(3-(trifluoromethyl)-4-(pentyloxy)phenyl)-4-(4-methoxyphenyl)thiazol-2-amine | +++ |
| 135 | 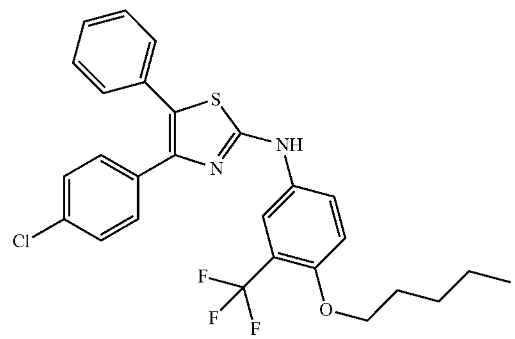 | 4-(4-chlorophenyl)-N-(3-(trifluoromethyl)-4-(pentyloxy)phenyl)-5-phenylthiazol-2-amine | + |
| 136 | 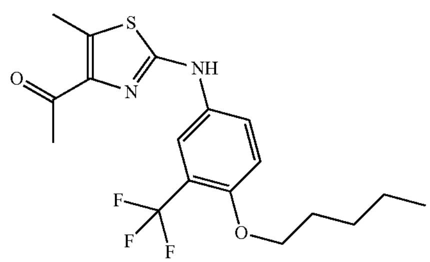 | 1-(2-(3-(trifluoromethyl)-4-(pentyloxy)phenylamino)-5-methylthiazol-4-yl)ethanone | + |

| Cmp. | Structure | Name | Activity |
|---|---|---|---|
| 137 | 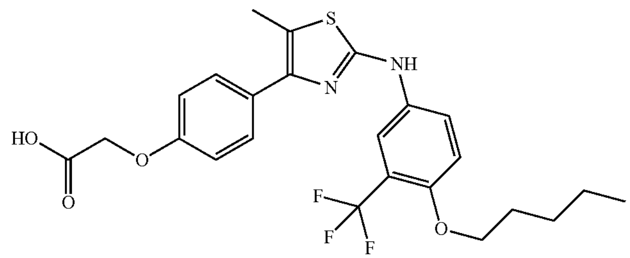 | 2-(4-(2-(3-(trifluoromethyl)-4-(pentyloxy)phenylamino)-5-methylthiazol-4-yl)phenoxy)acetic acid | +++ |
| 138 | 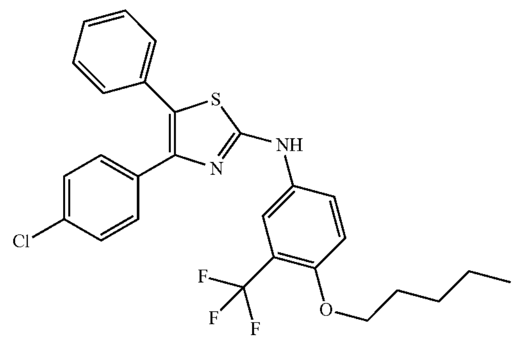 | 4-(4-chlorophenyl)-N-(3-(trifluoromethyl)-4-(pentyloxy)phenyl)-5-phenylthiazol-2-amine | + |
| 139 | 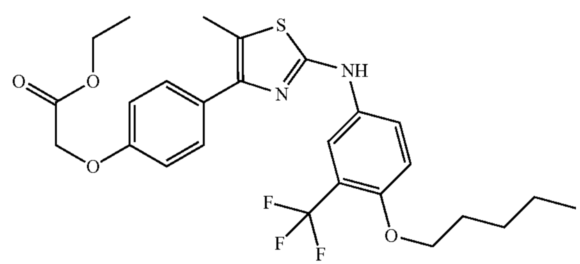 | ethyl 2-(4-(2-(3-(trifluoromethyl)-4-(pentyloxy)phenylamino)-5-methylthiazol-4-yl)phenoxy)acetate | +++ |

-continued

| Cmp. | Structure | Name | Activity |
|---|---|---|---|
| 140 | 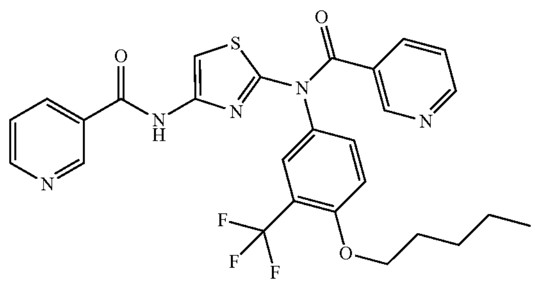 | N-(2-(N-(3-(trifluoromethyl)-4-(pentyloxy)phenyl)nicotinamido)-thiazol-4-yl)nicotinamide | +++ |
| 141 | 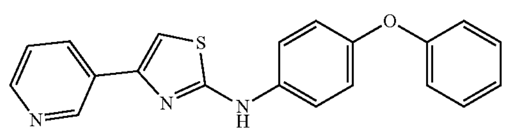 | N-(4-phenoxyphenyl)-4-(pyridin-3-yl)thiazol-2-amine | +++ |
| 142 | 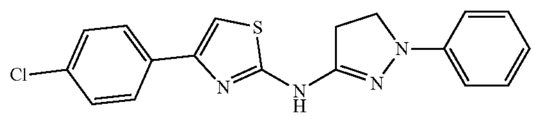 | N-(4-(4-chlorophenyl)thiazol-2-yl)-4,5-dihydro-1-phenyl-1H-pyrazol-3-amine | + |
| 143 | 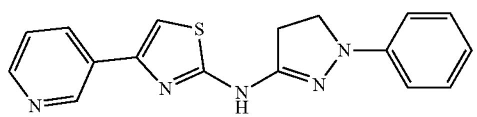 | 4,5-dihydro-1-phenyl-N-(4-(pyridin-3-yl)thiazol-2-yl)-1H-pyrazol-3-amine | + |
| 144 | 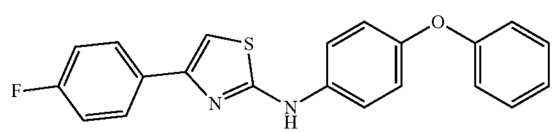 | 4-(4-fluorophenyl)-N-(4-phenoxyphenyl)thiazol-2-amine | +++ |
| 145 | 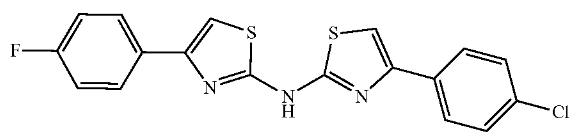 | 4-(4-chlorophenyl)-N-(4-(4-fluorophenyl)thiazol-2-yl)thiazol-2-amine | + |
| 146 | 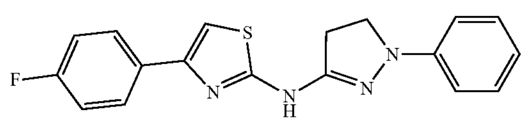 | N-(4-(4-fluorophenyl)thiazol-2-yl)-4,5-dihydro-1-phenyl-1H-pyrazol-amine | + |

-continued

| Cmp. | Structure | Name | Activity |
|---|---|---|---|
| 147 | 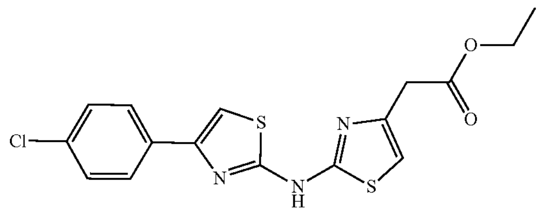 | ethyl 2-(2-(4-chlorophenyl)thiazol-2-ylamino)thiazol-4-yl)acetate | + |
| 148 | 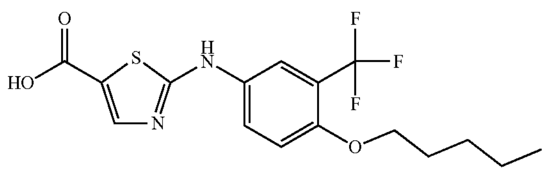 | 2-(3-(trifluoromethyl)-4-(pentyloxy)phenylamino)thiazole-5-carboxylic acid | + |
| 149 | 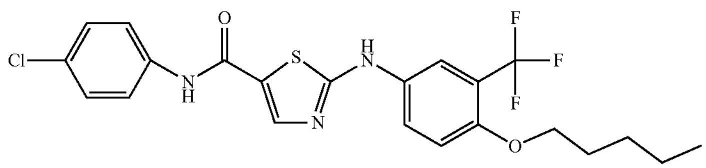 | 2-(3-(trifluoromethyl)-4-(pentyloxy)phenylamino)-N-(4-chlorophenyl)thiazole-5-carboxamide | +++ |
| 150 | 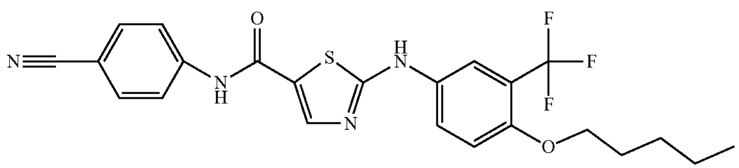 | 2-(3-(trifluoromethyl)-4-(pentyloxy)phenylamino)-N-(4-cyanophenyl)thiazole-5-carboxamide | +++ |
| 151 | 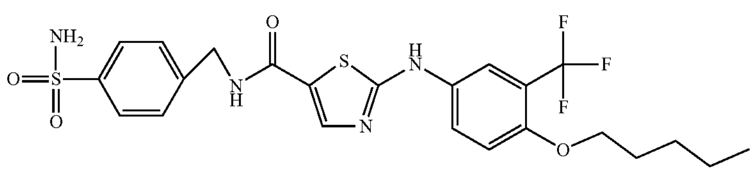 | N-(4-aminosulfonyl-benzyl)-2-(4-(pentyloxy)-3-(trifluoromethyl)phenylamino)-thiazole-5-carboxamide | + |

-continued

| Cmp. | Structure | Name | Activity |
|---|---|---|---|
| 152 | 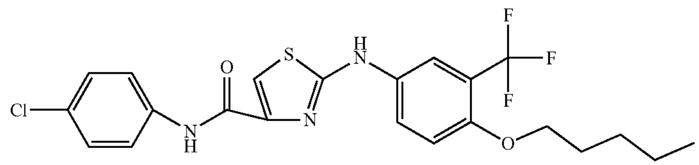 | 2-(4-(pentyloxy)-3-(trifluoromethyl)phenylamino)-N-(4-chlorophenyl)thiazole-4-carboxamide | + |
| 153 | 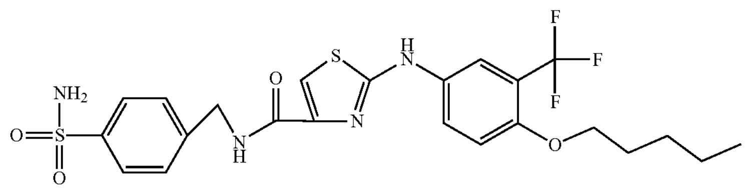 | 2-(4-(pentyloxy)-3-(trifluoromethyl)phenylamino)-N-(4-aminosulfonylbenzyl)thiazole-4-carboxamide | ++ |
| 154 | 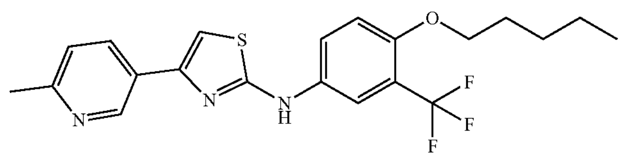 | N-(3-(trifluoromethyl)-4-(pentyloxy)phenyl)-4-(6-methylpyridin-3-yl)thiazol-2-amine | +++ |
| 155 | 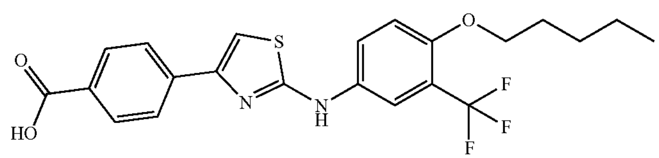 | 4-(2-(3-(trifluoromethyl)-4-(pentyloxy)phenylamino)thiazol-4-yl)benzoic acid | +++ |
| 156 | 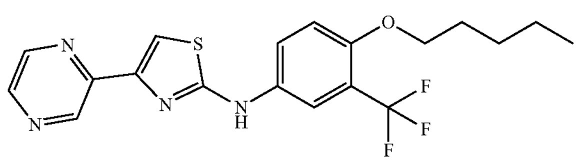 | N-(3-(trifluoromethyl)-4-(pentyloxy)phenyl)-4-(pyrazin-2-yl)thiazol-2-amine | +++ |
| 157 | 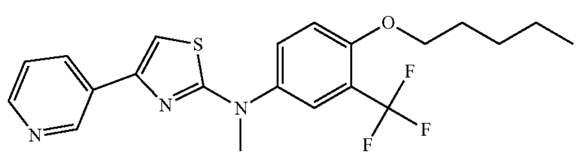 | N-(3-(trifluoromethyl)-4-(pentyloxy)phenyl)-N-methyl-4-(pyridin-3-yl)thiazol-2-amine | +++ |

| Cmp. | Structure | Name | Activity |
|---|---|---|---|
| 158 | 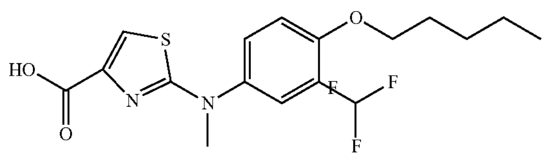 | 2-(N-(3-(trifluoromethyl)-4-(pentyloxy)phenyl)-N-methylamino)thiazole-4-carboxylic acid | + |
| 159 | 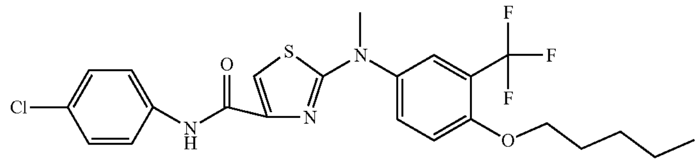 | 2-(N-(3-(trifluoromethyl)-4-(pentyloxy)phenyl)-N-methylamino)-N-(4-chlorophenyl)thiazole-4-carboxamide | + |
| 160 | 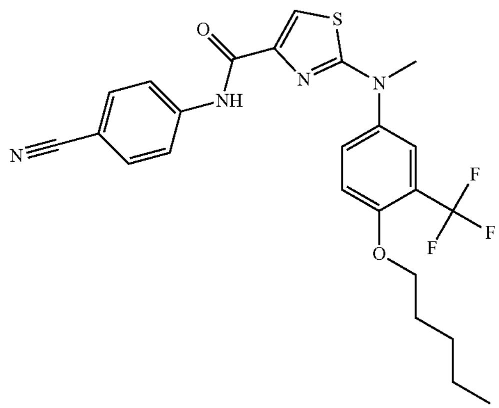 | 2-(N-(3-(trifluoromethyl)-4-(pentyloxy)phenyl)-N-methylamino)-N-(4-cyanophenyl)thiazole-4-carboxamide | + |
| 161 | 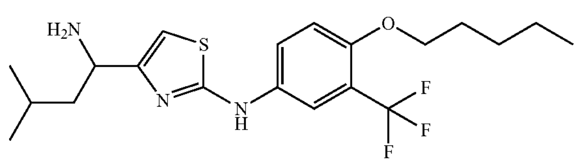 | 4-(1-amino-3-methylbutyl)-N-(3-(trifluoromethyl)-4-(pentyloxy)phenyl)thiazol-2-amine | ++ |

| Cmp. | Structure | Name | Activity |
|---|---|---|---|
| 162 | 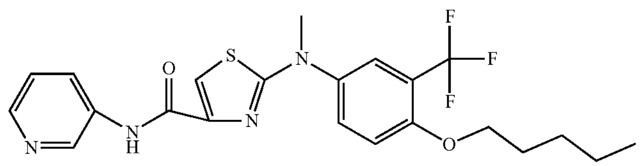 | 2-(N-(3-(trifluoromethyl)-4-(pentyloxy)phenyl)-N-methylamino)-N-(pyridin-3-yl)thiazole-4-carboxamide | + |
| 163 | 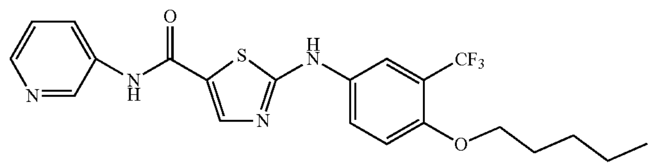 | 2-(3-(trifluoromethyl)-4-(pentyloxy)phenylamino)-N-(pyridin-3-yl)thiazole-5-carboxamide | +++ |
| 164 | 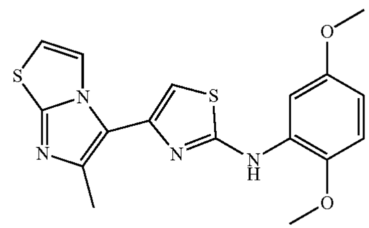 | N-(2,5-dimethoxyphenyl)-4-(6-methylimidazo[2,1-b]thiazol-5-yl)thiazol-2-amine | + |
| 165 | 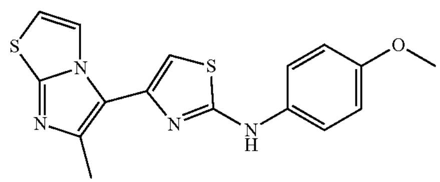 | N-(4-methoxyphenyl)-4-(6-methylimidazo[2,1-b]thiazol-5-yl)thiazol-2-amine | +++ |
| 166 | 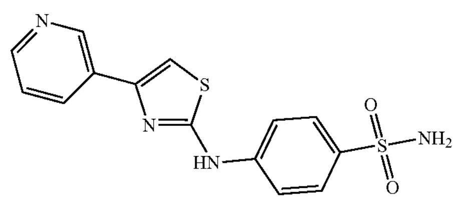 | N-(4-aminosulfonyl phenyl)-4-(pyridin-3-yl)thiazole-2-carboxamide | + |

| Cmp. | Structure | Name | Activity |
|---|---|---|---|
| 167 | 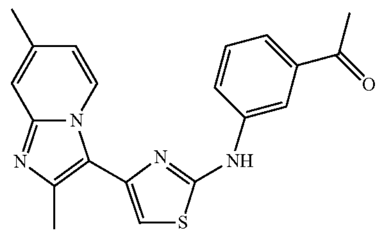 | 1-(3-(4-(2,7-dimethylH-imidazo[1,2-a]pyridin-3-yl)thiazol-2-ylamino)phenyl)ethanone | + |
| 168 | 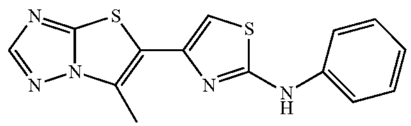 | 4-(6-methylthiazolo[3,2-b][1,2,4]triazol-5-yl)-N-phenylthiazol-2-amine | ++ |
| 169 | 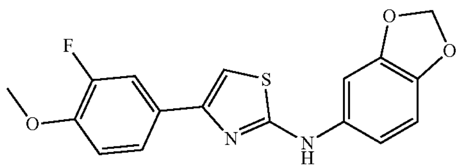 | N-(benzo[d][1,3]dioxol-5-yl)-4-(3-fluoro-4-methoxyphenyl)thiazol-2-amine | + |
| 170 | 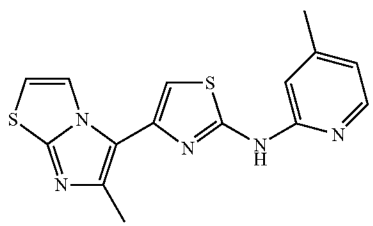 | 4-methyl-N-(4-(6-methylimidazo[2,1-b]thiazol-5-yl)thiazol-2-yl)pyridin-2-amine | + |
| 171 | 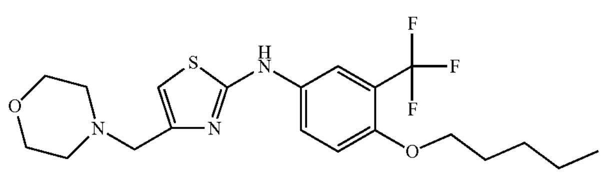 | N-(3-(trifluoromethyl)-4-(pentyloxy)phenyl)-4-(morpholinomethyl)thiazol-2-amine | +++ |

-continued

| Cmp. | Structure | Name | Activity |
|---|---|---|---|
| 172 | 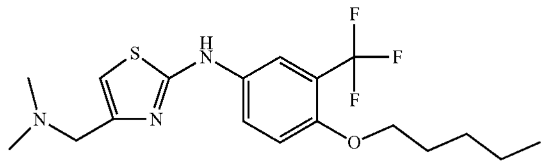 | 4-((dimethylamino)methyl)-N-(3-(trifluoromethyl)-4-(pentyloxy)phenyl)thiazol-2-amine | +++ |
| 173 | 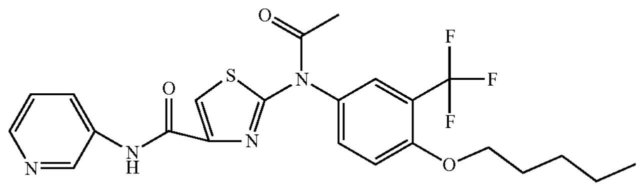 | 2-(N-(3-(trifluoromethyl)-4-(pentyloxy)phenyl)acetamido)-N-(pyridin-3-yl)thiazole-4-carboxamide | + |
| 174 | 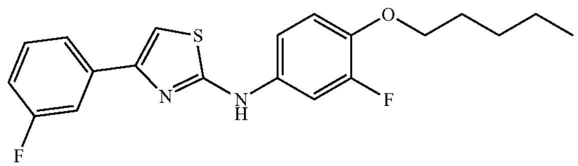 | N-(3-fluoro-4-(pentyloxy)phenyl)-4-(3-fluorophenyl)thiazol-2-amine | +++ |
| 175 | 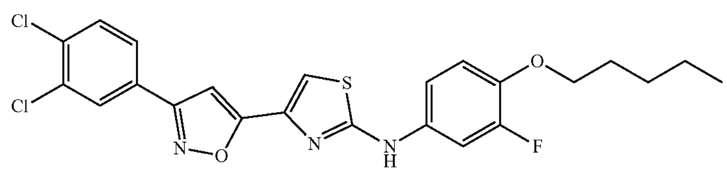 | 4-(3,4-dichlorophenyl)isoxazol-5-yl)-N-(3-fluoro-4-(pentyloxy)phenyl)thiazole-2-amine | + |
| 176 | 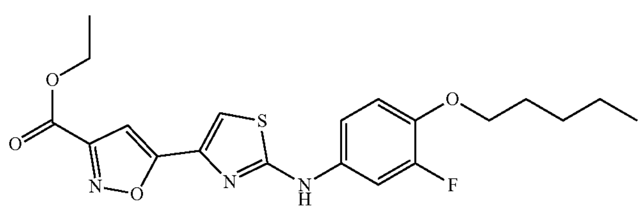 | ethyl 5-(2-(3-fluoro-4-(pentyloxy)phenylamino)thiazol-4-yl)isoxazole-3-carboxylate | + |

| Cmp. | Structure | Name | Activity |
|---|---|---|---|
| 177 | 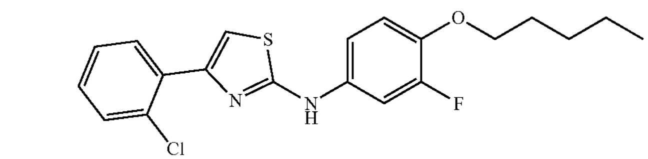 | 4-(2-chlorophenyl)-N-(3-fluoro-4-(pentyloxy)phenyl)thiazol-2-amine | +++ |
| 178 | 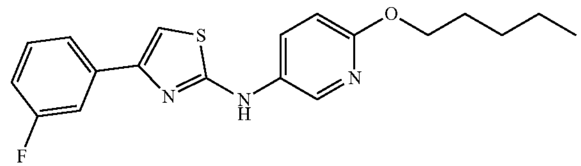 | N-(4-(3-fluorophenyl)thiazol-2-yl)-6-(pentyloxy)pyridin-3-amine | +++ |
| 179 | 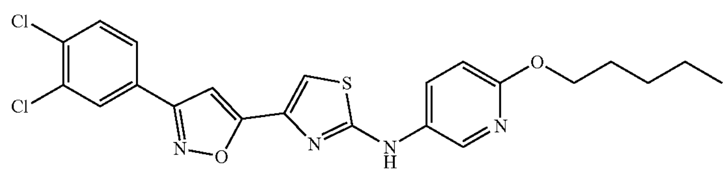 | N-(4-(3-(3,4-dichlorophenyl)isoxazol-5-yl)thiazol-2-yl)-6-(pentyloxy)pyridin-3-amine | + |
| 180 | 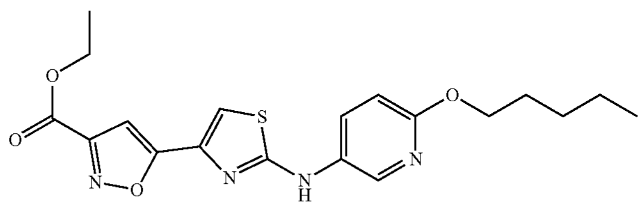 | ethyl 5-(2-(6-(pentyloxy)pyridin-3-ylamino)thiazol-4-yl)isoxazole-3-carboxylate | + |
| 181 | 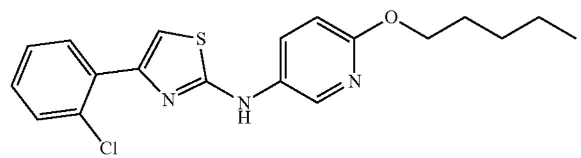 | N-(4-(2-chlorophenyl)thiazol-2-yl)-6-(pentyloxy)pyridin-3-amine | +++ |
| 182 | 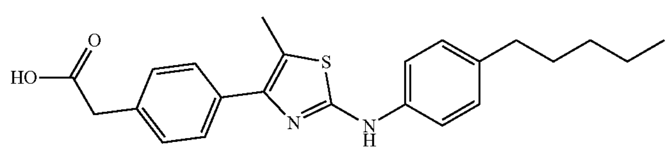 | 2-(4-(2-(4-pentylphenylamino)-5-methylthiazol-4-yl)phenyl)acetic acid | +++ |

-continued

| Cmp. | Structure | Name | Activity |
|---|---|---|---|
| 183 | 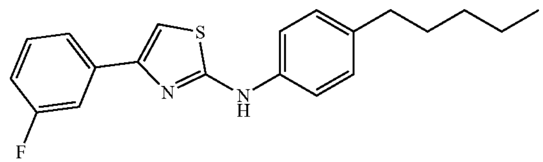 | 4-(3-fluorophenyl)-N-(4-pentylphenyl)thiazol-2-amine | +++ |
| 184 | 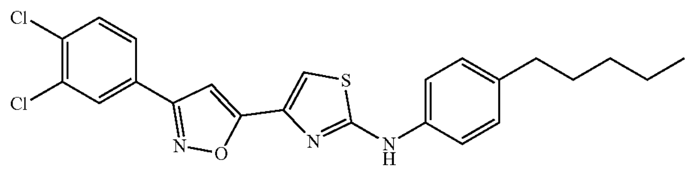 | 4-(3,4-dichlorophenyl)isoxazol-5-yl)-N-(4-pentylphenyl)thiazol-2-amine | + |
| 185 | 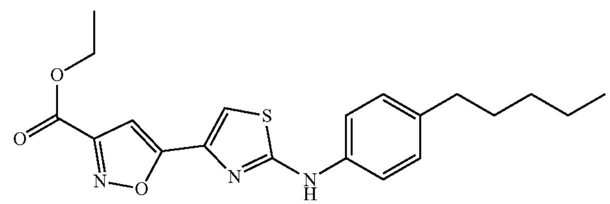 | ethyl 5-(2-(4-pentylphenylamino)thiazol-4-yl)isoxazole-3-carboxylate | + |
| 186 | 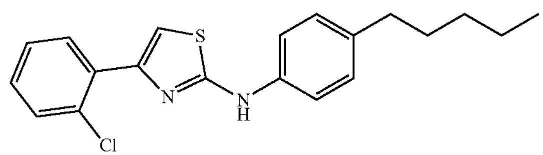 | 4-(2-chlorophenyl)-N-(4-pentylphenyl)thiazol-2-amine | + |
| 187 | 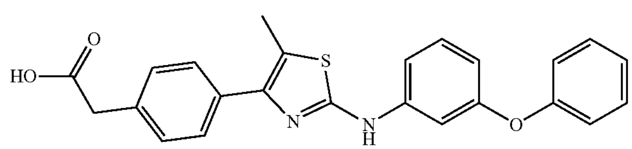 | 2-(4-(2-(3-phenoxyphenylamino)-5-methylthiazol-4-yl)phenyl)acetic acid | +++ |
| 188 | 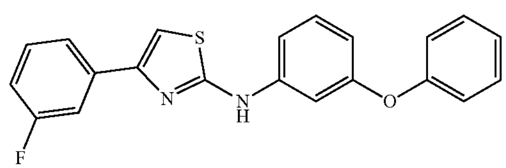 | 4-(3-fluorophenyl)-N-(3-phenoxyphenyl)thiazol-2-amine | +++ |

| Cmp. | Structure | Name | Activity |
|---|---|---|---|
| 189 | 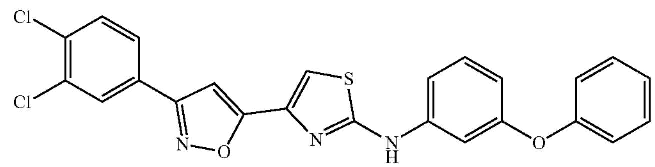 | 4-(3,4-dichlorophenyl)isoxazol-5-yl)-N-(3-phenoxyphenyl)thiazol-2-amine | + |
| 190 | 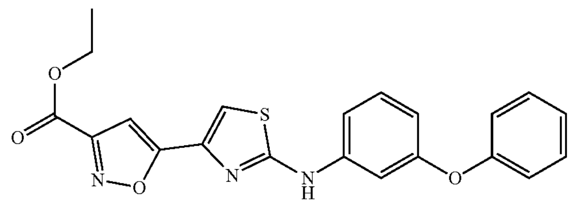 | ethyl 5-(2-(3-phenoxyphenylamino)thiazol-4-yl)isoxazole-3-carboxylate | + |
| 191 | 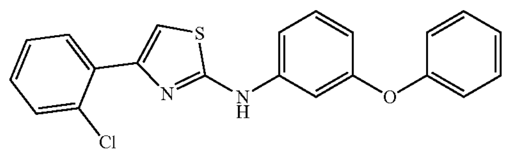 | 4-(2-chlorophenyl)-N-(3-phenoxyphenyl)thiazol-2-amine | +++ |
| 192 | 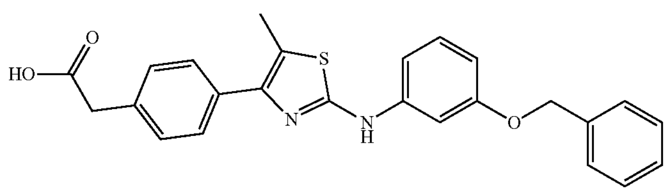 | 2-(4-(2-(3-(benzyloxy)phenylamino)-5-methylthiazol-4-yl)phenyl)acetic acid | +++ |
| 193 | 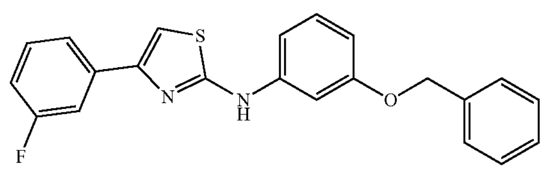 | N-(3-(benzyloxy)phenyl)-4-(3-fluorophenyl)thiazol-2-amine | +++ |

| Cmp. | Structure | Name | Activity |
|---|---|---|---|
| 194 | 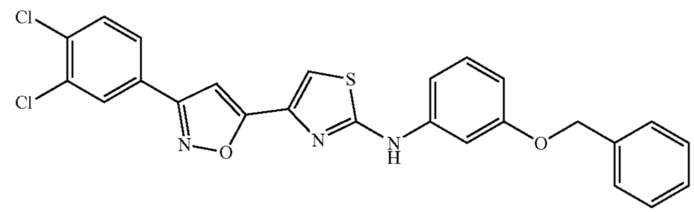 | N-(3-(benzyloxy)phenyl)-4-(3-(3,4-dichlorophenyl)isoxazol-5-yl)thiazol-2-amine | + |
| 195 | 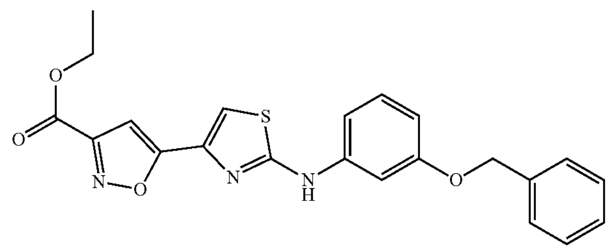 | ethyl 5-(2-(3-(benzyloxy)phenylamino)thiazol-4-yl)isoxazole-3-carboxylate | + |
| 196 | 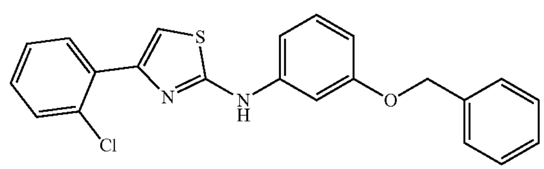 | N-(3-(benzyloxy)phenyl)-4-(2-chlorophenyl)thiazol-2-amine | +++ |
| 197 | 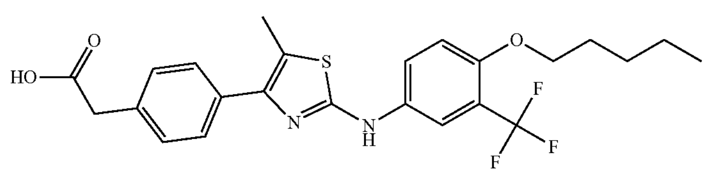 | 2-(4-(2-(3-(trifluoromethyl)-4-(pentyloxy)phenylamino)-5-methylthiazol-4-yl)phenyl)acetic acid | +++ |
| 198 | 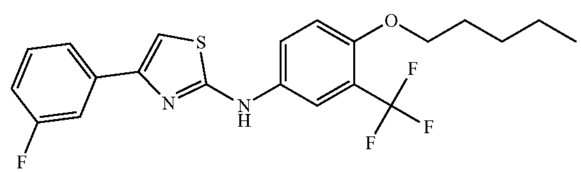 | N-(3-(trifluoromethyl)-4-(pentyloxy)phenyl)-4-(3-fluorophenyl)thiazol-2-amine | +++ |

| Cmp. | Structure | Name | Activity |
|---|---|---|---|
| 199 | 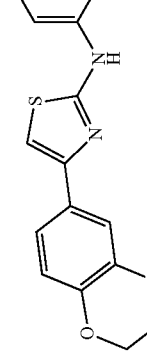 | 6-(2-(3-(trifluoromethyl)-4-(pentyloxy)phenylamino)thiazol-4-yl)-2H-benzo[b][1,4]oxazin-3(4H)-one | +++ |
| 200 | 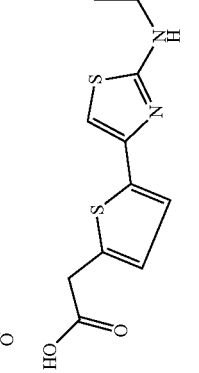 | 2-(5-(2-(3-(trifluoromethyl)-4-(pentyloxy)phenylamino)thiazol-4-yl)thiophen-2-yl)acetic acid | +++ |
| 201 | 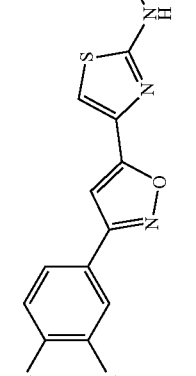 | 4-(3,4-dichlorophenyl)isoxazol-5-yl)-N-(3-(trifluoromethyl)-4-(pentyloxy)phenyl)thiazol-2-amine | + |
| 202 | 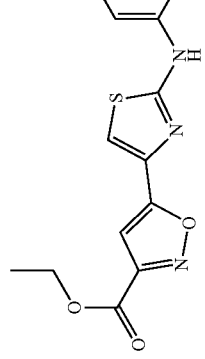 | ethyl 5-(2-(3-(trifluoromethyl)-4-(pentyloxy)phenylamino)thiazol-4-yl)isoxazole-3-carboxylate | +++ |
| 203 | 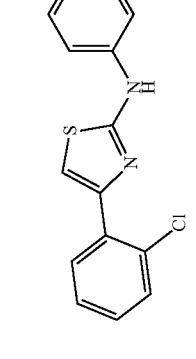 | 4-(2-chlorophenyl)-N-(3-(trifluoromethyl)-4-(pentyloxy)phenyl)thiazol-2-amine | +++ |

| Cmp. | Structure | Name | Activity |
|---|---|---|---|
| 204 | 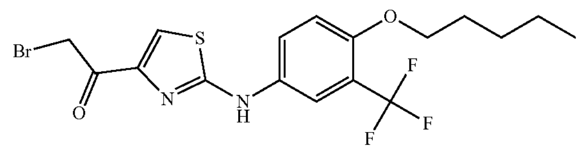 | 1-(2-(3-(trifluoromethyl)-4-(pentyloxy)phenylamino)thiazol-4-yl)-2-bromoethanone | +++ |
| 205 | 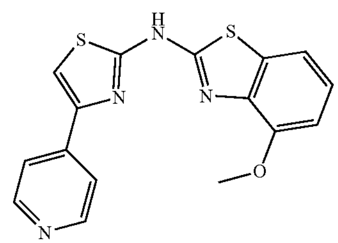 | 4-methoxy-N-(4-(pyridin-4-yl)thiazol-2-yl)benzo[d]thiazol-2-amine | +++ |
| 206 | 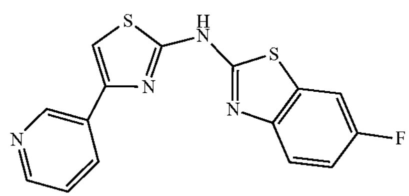 | 6-fluoro-N-(4-(pyridin-3-yl)thiazol-2-yl)benzo[d]thiazol-2-amine | ++ |
| 207 | 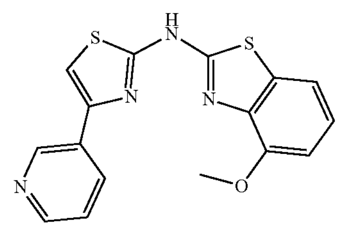 | 4-methoxy-N-(4-(pyridin-3-yl)thiazol-2-yl)benzo[d]thiazol-2-amine | ++ |
| 208 | 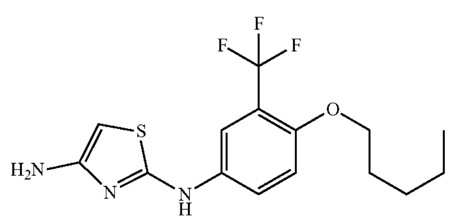 | N2-(3-(trifluoromethyl)-4-(pentyloxy)phenyl)thiazole-2,4-diamine | ++ |

-continued

| Cmp. | Structure | Name | Activity |
|---|---|---|---|
| 209 | 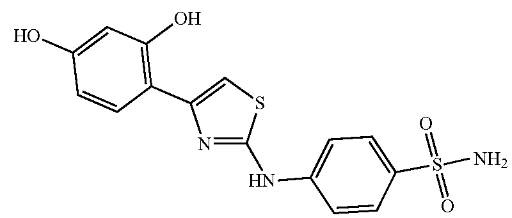 | 4-(2,5-dihydroxyphenyl)-N-(4-aminosulfonyl phenyl)thiazol-2-amine | + |
| 210 | 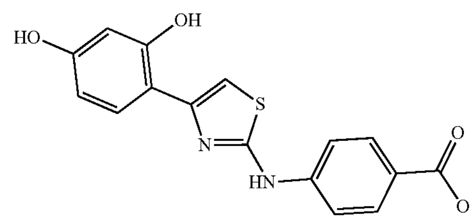 | 4-(2,5-dihydroxyphenyl)-N-(4-carboxylic acid phenyl)thiazol-2-amine | + |
| 211 | 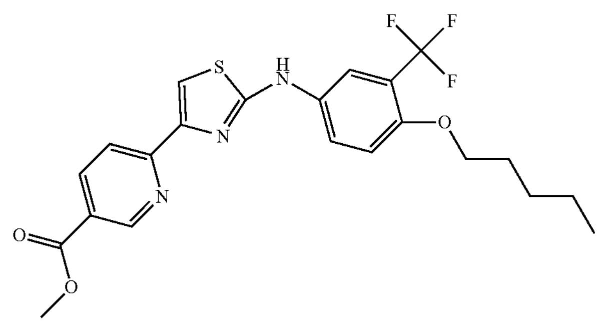 | methyl 6-(2-(3-(trifluoromethyl)-4-(pentyloxy)phenylamino)thiazol-4-yl)pyridine-3-carboxylate | +++ |

| Cmp. | Structure | Name | Activity |
|---|---|---|---|
| 212 | 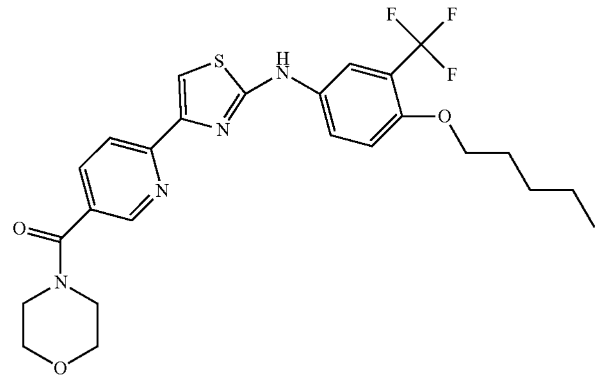 | (5-(2-(3-(trifluoromethyl)-4-(pentyloxy)phenylamino)thiazol-4-yl)pyridin-2-yl)(morpholino)methanone | +++ |
| 213 | 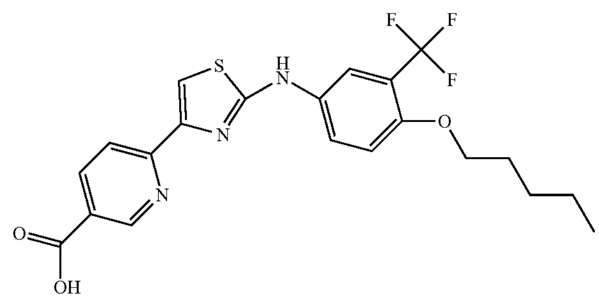 | 6-(2-(3-(trifluoromethyl)-4-(pentyloxy)phenylamino)thiazol-4-yl)pyridine-3-carboxylic acid | +++ |
| 214 | 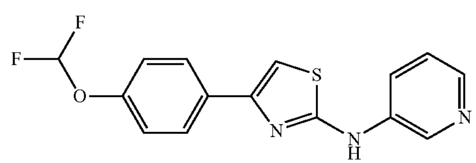 | N-(4-(4-(difluoromethoxy)phenyl)thiazol-2-yl)pyridin-3-amine | + |

| Cmp. | Structure | Name | Activity |
|---|---|---|---|
| 215 | 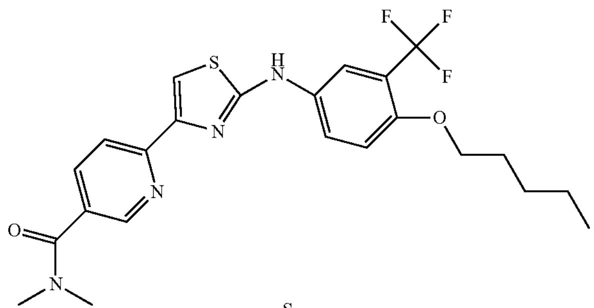 | 6-(2-(3-(trifluoromethyl)-4-(pentyloxy)phenylamino)thiazol-4-yl)-N,N-dimethylpyridine-3-carboxamide | +++ |
| 216 | 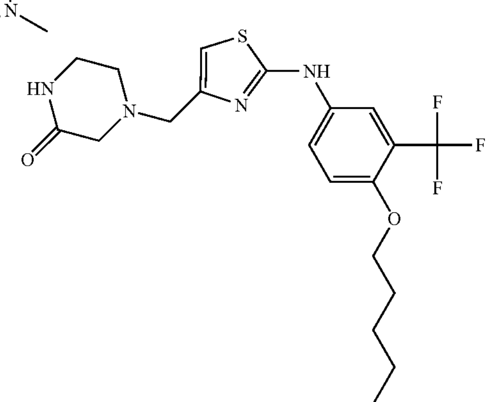 | 4-((2-(3-(trifluoromethyl)-4-(pentyloxy)phenylamino)thiazol-4-yl)methyl)piperazin-2-one | +++ |
| 217 | 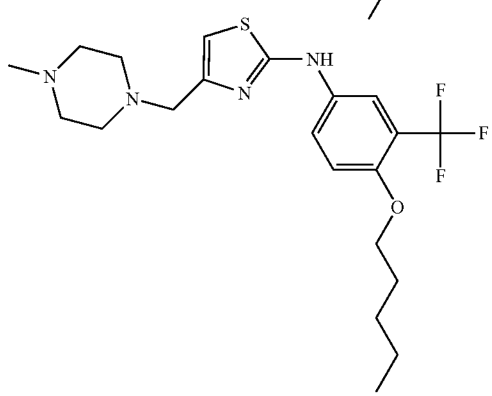 | N-(3-(trifluoromethyl)-4-(pentyloxy)phenyl)-4-((4-methylpiperazin-1-yl)methyl)thiazol-2-amine | +++ |

| Cmp. | Structure | Name | Activity |
|---|---|---|---|
| 218 | 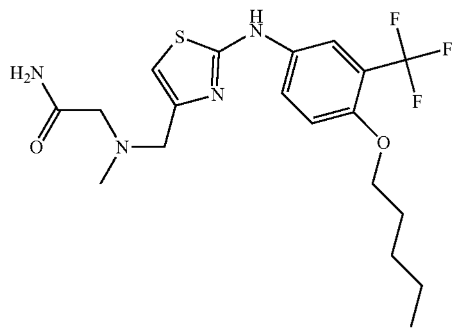 | 2-(N-((2-(3-(trifluoromethyl)-4-(pentyloxy)phenylamino)thiazol-4-yl)methyl)-N-methylamino)acetamide | +++ |
| 219 | 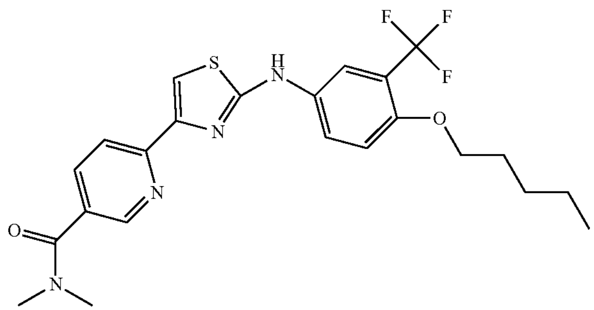 | 5-(2-(3-(trifluoromethyl)-4-(pentyloxy)phenylamino)thiazol-4-yl)-N,N-dimethylpyridine-2-carboxamide | +++ |
| 220 | 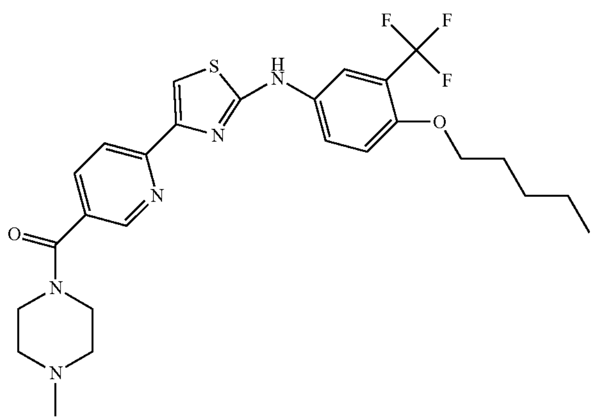 | (5-(2-(3-(trifluoromethyl)-4-(pentyloxy)phenylamino)thiazol-4-yl)pyridin-2-yl)(4-methylpiperazin-1-yl)methanone | +++ |

| Cmp. | Structure | Name | Activity |
|---|---|---|---|
| 221 | 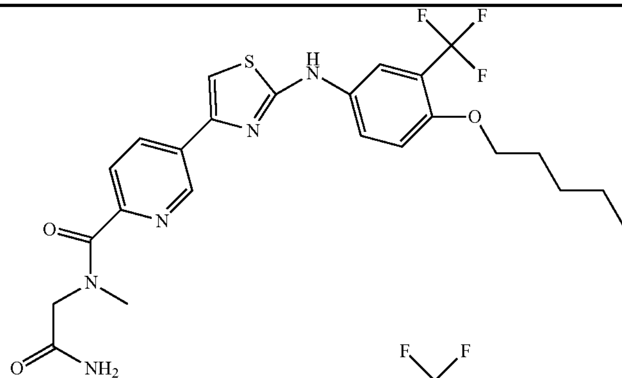 | 5-(2-(3-(trifluoromethyl)-4-(pentyloxy)phenylamino)thiazol-4-yl)-N-(carbamoylmethyl)-N-methylpyridine-2-carboxamide | +++ |
| 222 | 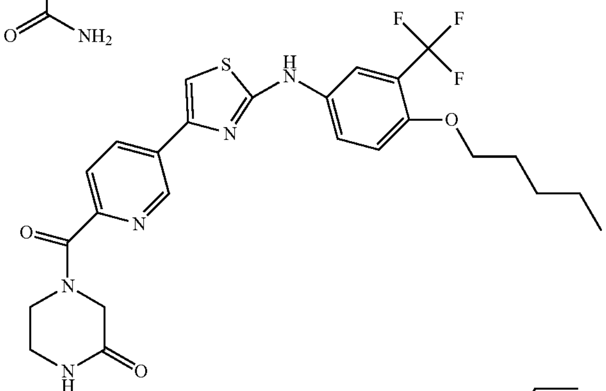 | | +++ |
| 223 | 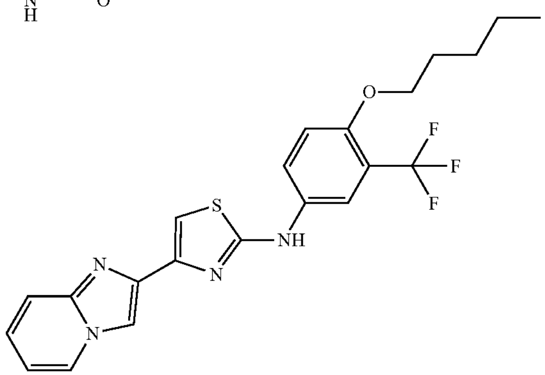 | N-(3-(trifluoromethyl)-4-(pentyloxy)phenyl)-4-(H-imidazo[1,2-a]pyridin-2-yl)thiazol-2-amine | +++ |

TABLE II

| Cpd | Structure | Name | Activity |
|-----|-----------|------|----------|
| 224 | 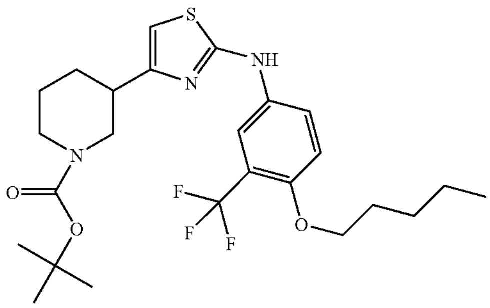 | tert-butyl 3-(2-(4-(pentyloxy)-3-(trifluoromethyl)phenyl-amino)thiazol-4-yl)piperidine-1-carboxylate | +++ |
| 225 | 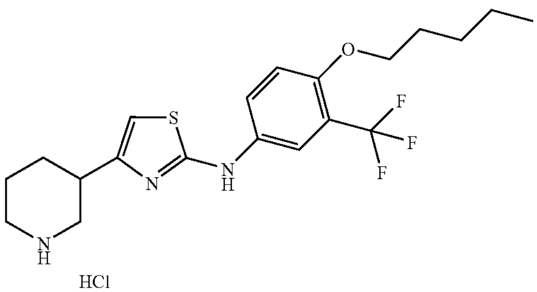 | N-(4-(pentyloxy)-3-(trifluoromethyl)phenyl)-4-(piperidin-3-yl)thiazol-2-amine hydrochloride | ++ |
| 226 | 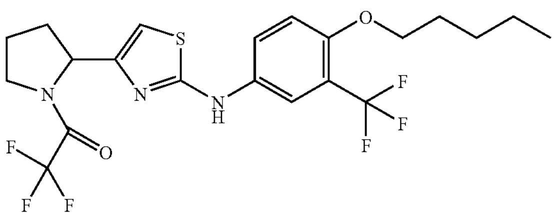 | 2,2,2-trifluoro-1-(2-(2-(4-(pentyloxy)-3(trifluoromethyl)phenyl-amino)thiazol-4-yl)pyrrolidin-1-yl)ethanone | ++ |
| 227 | 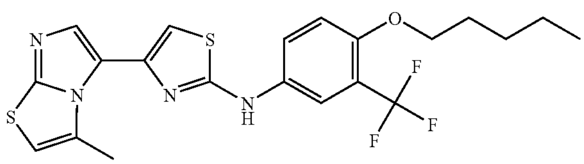 | 4-(3-methylimidazo[1,2-b]thiazol-5-yl)-N-(4-(pentyloxy)-3-(trifluoromethyl)phenyl)thiazol-2-amine | +++ |
| 228 | 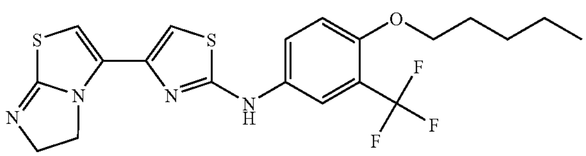 | 4-(5,6-dihydroimidazo[2,1-b]thiazol-3-yl)-N-(4-(pentyloxy)-3-(trifluoromethyl)phenyl)thiazol-2-amine | +++ |
| 229 | 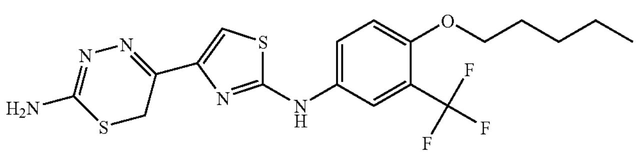 | 5-(2-(4-(pentyloxy)-3-(trifluoromethyl)phenyl-amino)thiazol-4-yl)-6H-1,3,4-thiazdiazin-2-amine | +++ |
| 230 | 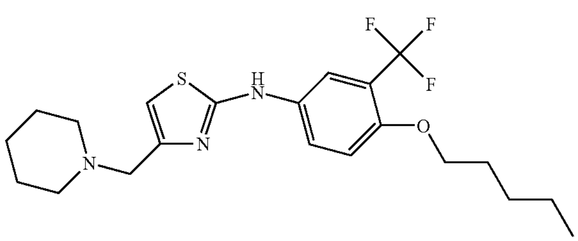 | N-(4-(pentyloxy)-3-(trifluoromethyl)phenyl)-4-(piperidin-1-ylmethyl)thiazol-2-amine | ++ |

TABLE II-continued

| Cpd | Structure | Name | Activity |
|---|---|---|---|
| 231 | 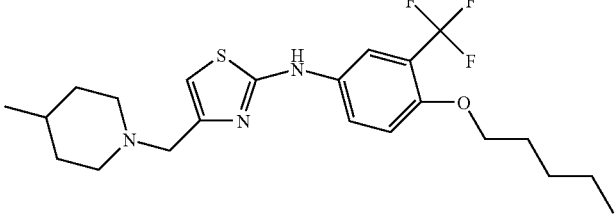 | 4-((4-methylpiperidin-1-yl)methyl)-N-(4-(pentyloxy)-3-(trifluoromethyl)phenyl)thiazol-2-amine | +++ |
| 232 | 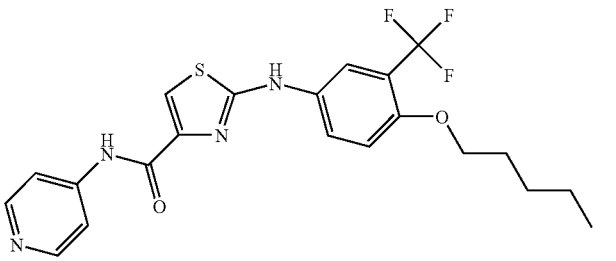 | 2-(4-(pentyloxy)-3-(trifluoromethyl)phenylamino)-N-(pyridin-4-yl)thiazole-4-carboxamide | ++ |
| 233 | 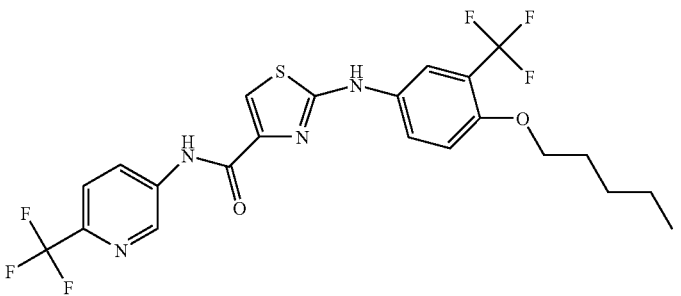 | 2-(4-(pentyloxy)-3-(trifluoromethyl)phenylamino)-N-(6-(trifluoromethyl)pyridin-3-yl)thiazole-4-carboxamide | + |
| 234 | 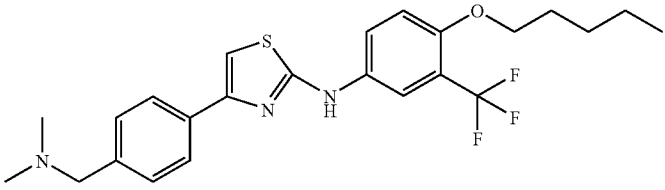 | 4-(4-((dimethylamino)methyl)phenyl)-N-(4-(pentyloxy)-3-(trifluoromethyl)phenyl)thiazol-2-amine | +++ |
| 235 | 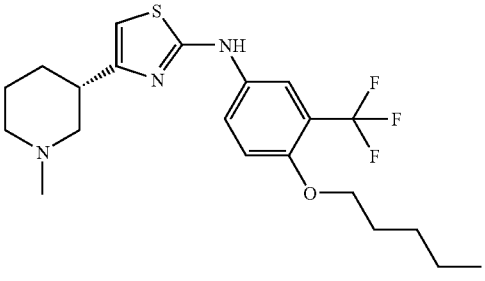 | (S)-4-(1-methylpiperidin-3-yl)-N-(4-(pentyloxy)-3-(trifluoromethyl)phenyl)thiazol-2-amine | +++ |
| 236 | 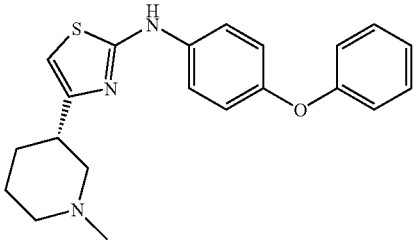 | (S)-4-(1-methylpiperidin-3-yl)-N-(4-phenoxyphenyl)thiazol-2-amine | ++ |

TABLE II-continued

| Cpd | Structure | Name | Activity |
|---|---|---|---|
| 237 | 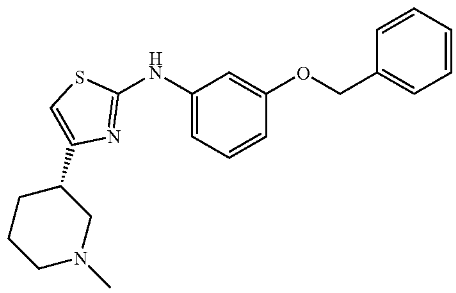 | (S)-N-(3-(benzyloxy)phenyl)-4-(1-methylpiperidin-3-yl)thiazol-2-amine | ++ |
| 238 | 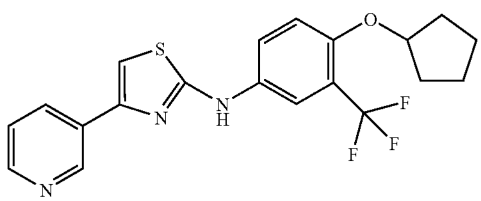 | N-(4-(cyclopentyloxy)-3-(trifluoromethyl)phenyl)-4-(pyridin-3-yl)thiazol-2-amine | +++ |
| 239 | 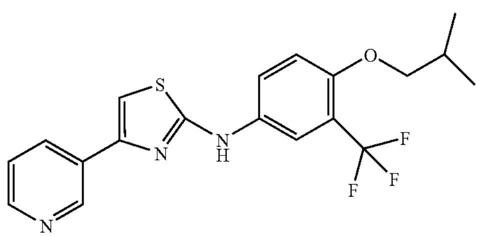 | N-(4-isobutoxy-3-(trifluoromethyl)phenyl)-4-(pyridin-3-yl)thiazol-2-amine | +++ |
| 240 | 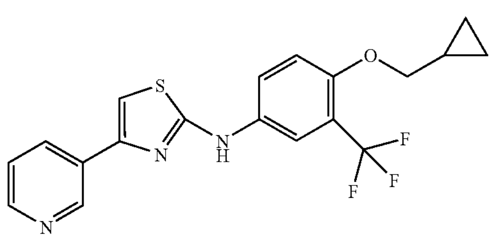 | N-(4-(cyclopropylmethoxy)-3-(trifluoromeethyl)phenyl)-4-(pyridin-3-yl)thiazol-2-amine | +++ |
| 241 | 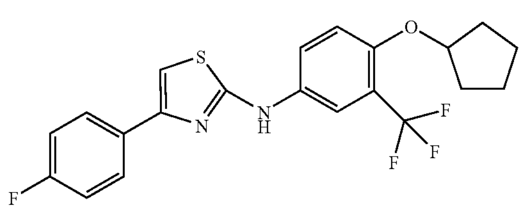 | N-(4-(cyclopentyloxy)-3-(trifluoromethyl)phenyl)-4-(4-fluorophenyl)thiazol-2-amine | +++ |
| 242 | 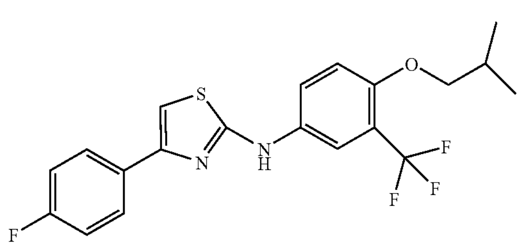 | 4-(4-fluorophenyl)-N-(4-isobutoxy-3-(trifluoromethyl)phenyl)thiazol-2-amine | +++ |

TABLE II-continued

| Cpd | Structure | Name | Activity |
|---|---|---|---|
| 243 | 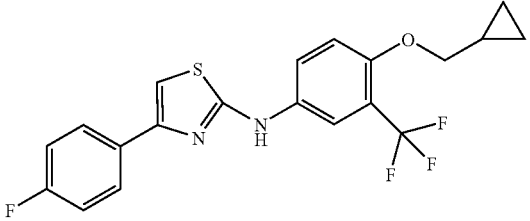 | N-(4-(cyclopropylmethoxy)-3-(trifluoromethyl)phenyl)-4-(4-fluorophenyl)thiazol-2-amine | +++ |
| 244 | 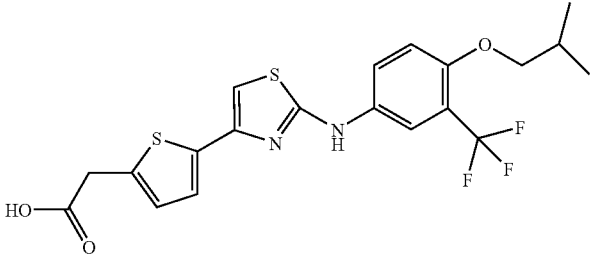 | 2-(5-(2-(4-isobutoxy-3-(trifluoromethyl)phenyl-amino)thiazol-4-yl)thiophen-2-yl)acetic acid | +++ |
| 245 | 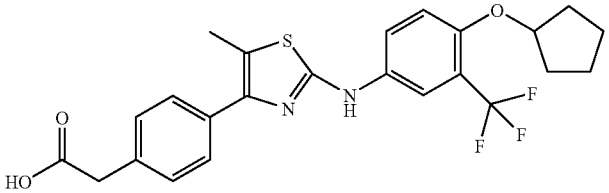 | 2-(4-(2-(4-(cyclopentyloxy)-3-(trifluoromethyl)phenyl-amino)-5-methylthiazol-4-yl)phenyl)acetic acid | +++ |
| 246 | 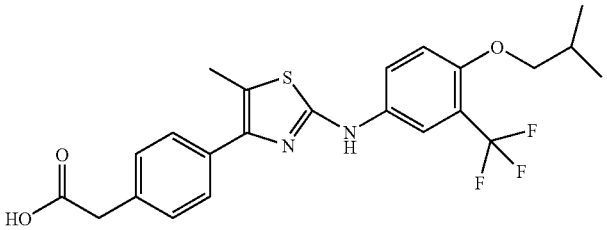 | 2-(4-(2-(4-isobutoxy-3-(trifluoromethyl)phenyl-amino)-5-methylthiazol-4-yl)phenyl)acetic acid | ++ |
| 247 | 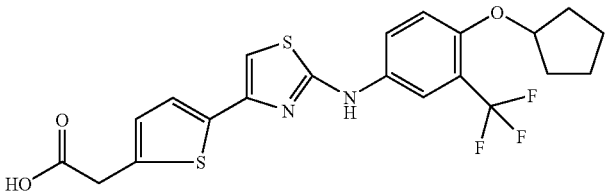 | 2-(5-(2-(4-(cyclopentyloxy)-3-(trifluoromethyl)phenyl-amino)-thiazol-4-yl)thiophen-2-yl)acetic acid | +++ |
| 248 | 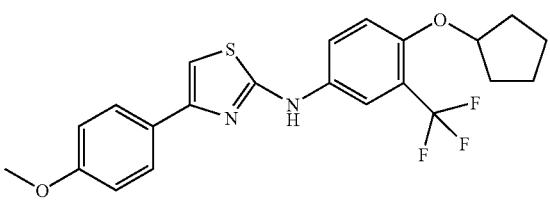 | N-(4-(cyclopentyloxy)-3-(trifluoromethyl)phenyl)-4-(4-methoxyphenyl)thiazol-2-amine | +++ |
| 249 | 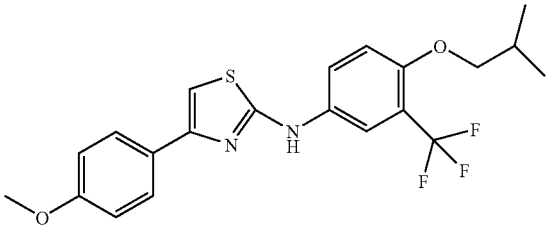 | N-(4-isobutoxy-3-(trifluoromethyl)phenyl)-4-(4-methoxyphenyl)thiazol-2-amine | +++ |

TABLE II-continued

| Cpd | Structure | Name | Activity |
|---|---|---|---|
| 250 | 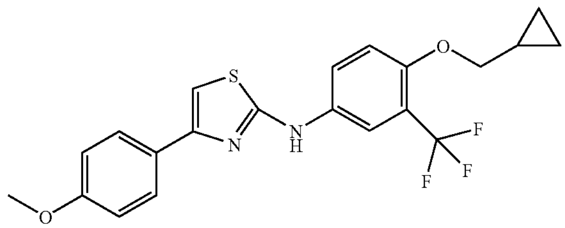 | N-(4-(cyclopropylmethoxy)-3-(trifluoromethyl)phenyl)-4-(4-methoxyphenyl)thiazol-2-amine | +++ |
| 251 | 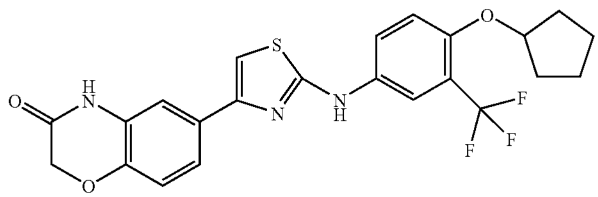 | 6-(2-(4-(cyclopentyloxy)-3-(trifluoromethyl)phenyl-amino)thiazol-4-yl)-2H-benzo[b][1,4]oxazin-3(4H)-one | +++ |
| 252 | 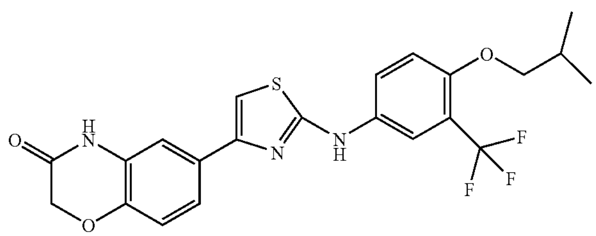 | 6-(2-(4-isobutoxy-3-(trifluoromethyl)phenyl-amino)thiazol-4-yl)-2H-benzo[b][1,4]oxazin-3(4H)-one | +++ |
| 253 | 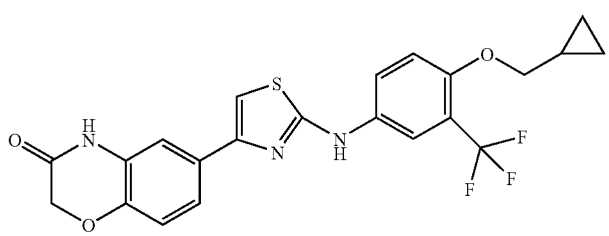 | 6-(2-(4-(cyclopropylmethoxy)-3-(trifluoromthyl)phenyl-amino)thiazol-4-yl)-2H-benzo[b][1,4]oxazin-3(4H)-one | ++ |
| 254 | 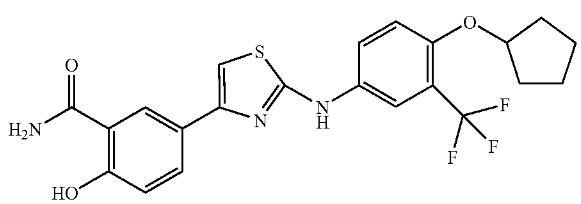 | 5-(2-(4-(cyclopentyloxy)-3-(trifluoromethyl)phenyl-amino)thiazol-4-yl)-2-hydroxybenzamide | +++ |
| 255 | 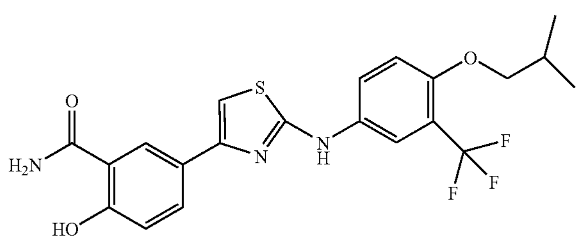 | 2-hydroxy-5-(2-(4-isobutoxy-3-(trifluoromethyl)phenyl-amino)thiazol-4-yl)benzamide | +++ |

TABLE II-continued

| Cpd | Structure | Name | Activity |
|---|---|---|---|
| 256 | 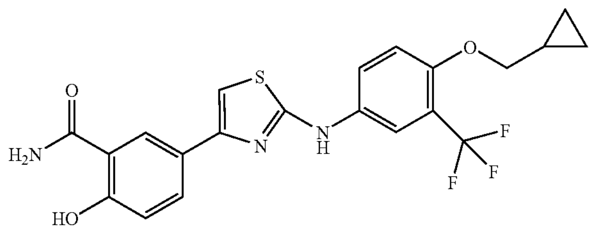 | 5-(2-(4-(cyclopropylmethoxy)-3-(trifluoromethyl)phenyl-amino)thiazol-4-yl)-2-hydroxybenzamide | +++ |
| 257 | 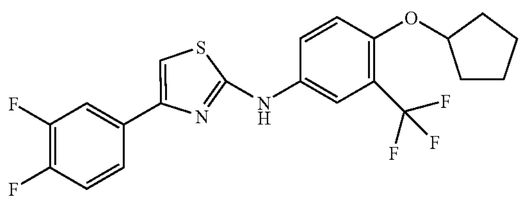 | N-(4-(cyclopentyloxy)-3-(trifluoromethyl)phenyl)-4-(3,4-difluorophenyl)thiazol-2-amine | +++ |
| 258 | 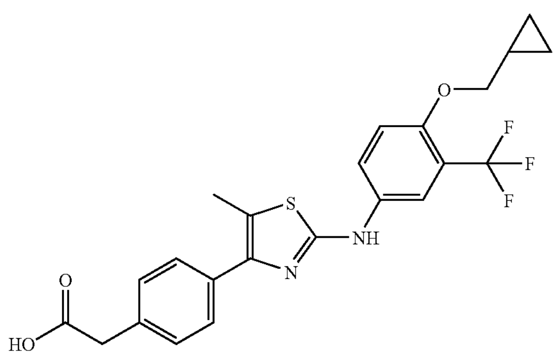 | 2-(4-(2-(4-(cyclopropylmethoxy)-3-(trifluoromethyl)phenyl-amino)-5-methylthiazol-4-yl)phenyl)acetic acid | +++ |
| 259 | 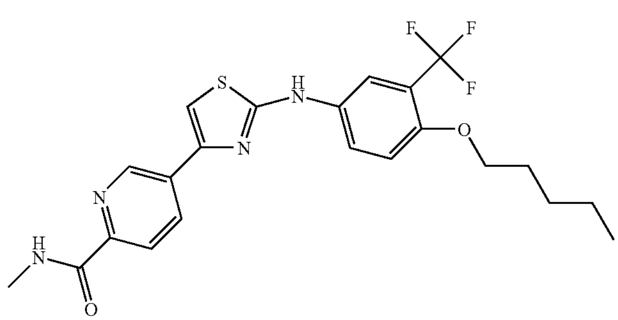 | N-methyl-5-(2-(4-(pentyloxy)-3-(trifluoromethyl)phenyl-amino)thiazol-4-yl)picolinamide | +++ |
| 260 | 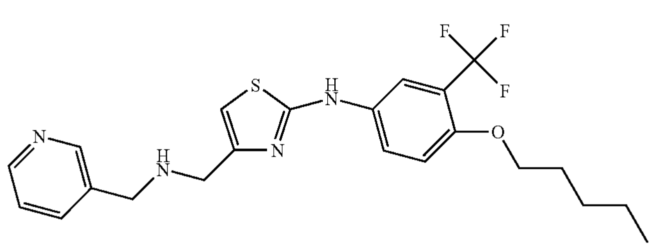 | N-(4-(pentyloxy)-3-(trifluoromethyl)phenyl)-4-((pyridin-3-ylmethylamino)methyl)thiazol-2-amine | +++ |

TABLE II-continued

| Cpd | Structure | Name | Activity |
|---|---|---|---|
| 261 | 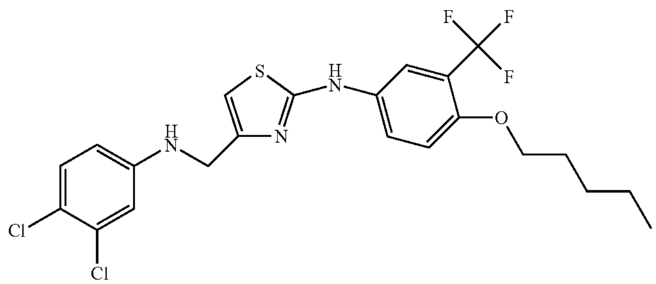 | 4-((3,4-dichlorophenylamino)methyl)-N-(4-pentyloxy)-3-(trifluoromethyl)phenyl)thiazol-2-amine | ++ |
| 262 | 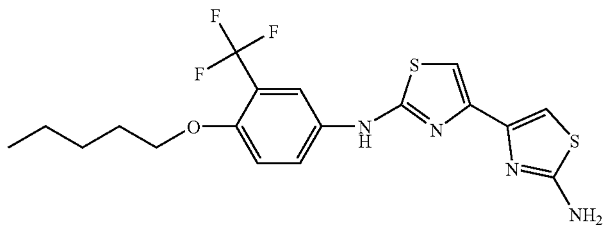 | 4-(2-aminothiazol-4-yl)-N-(4-(pentyloxy)-3-(trifluoromethyl)phenyl)thiazol-2-amine | +++ |
| 263 | 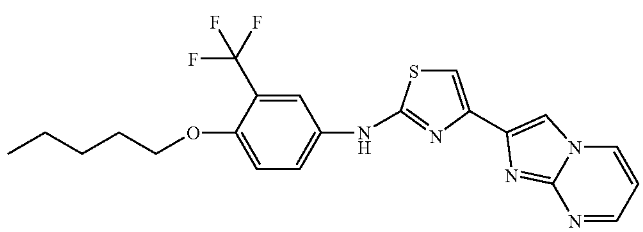 | 4-(imidazo[1,2-a]pyrimidin-2-yl)-N-(4-(pentyloxy)-3-(trifluoromethyl)phenyl)thiazol-2-amine | +++ |
| 264 | 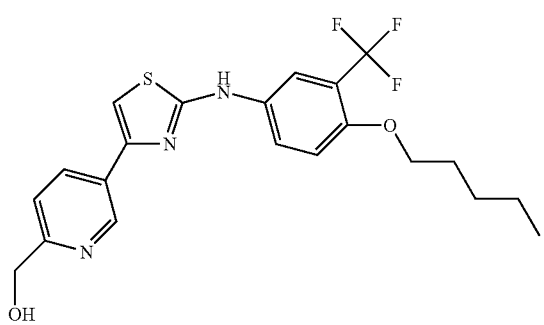 | (5-(2-(4-(pentyloxy)-3-(trifluoromethyl)phenylamino)thiazol-4-yl)pyridin-2-yl)methanol | +++ |
| 265 | 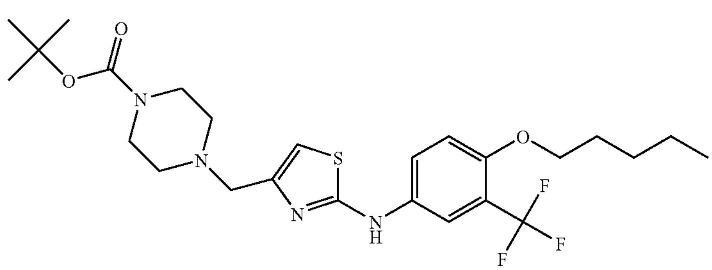 | tert-butyl 4-((2-(4-(pentyloxy)-3-(trifluoromethyl)phenylamino)thiazol-4-yl)methyl)piperazine-1-carboxylate | +++ |

TABLE II-continued

| Cpd | Structure | Name | Activity |
|---|---|---|---|
| 266 | 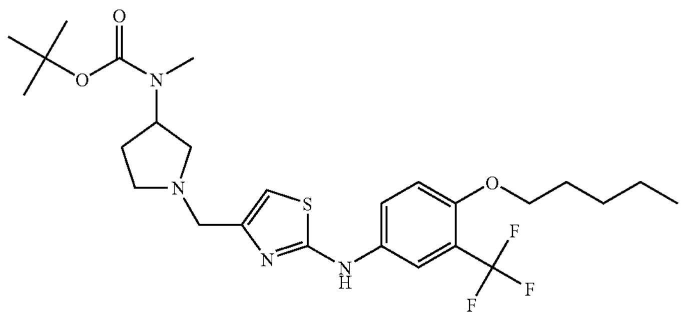 | tert-butyl methyl(1-((2-(4-(pentyloxy)-3-(trifluoromethyl)phenyl-amino)thiazol-4-yl)methyl)pyrrolidin-3-yl)carbamate | +++ |
| 267 | 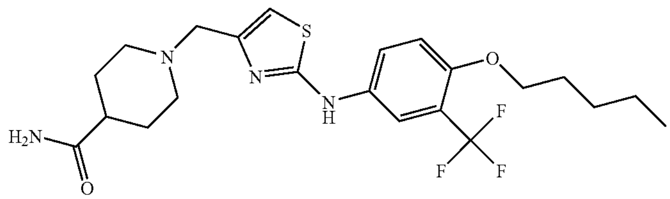 | 1-((2-(4-(pentyloxy)-3-(trifluoromethyl)phenyl-amino)thiazol-4-yl)methyl)piperidine-4-carboxamide | +++ |
| 268 | 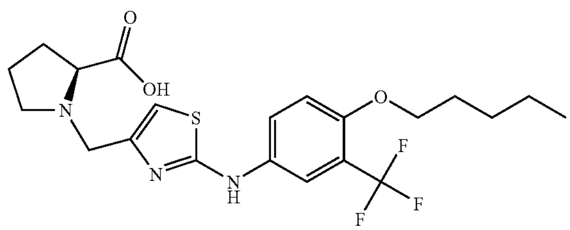 | (S)-1-((2-(4-(pentyloxy)-3-(trifluoromethyl)phenyl-amino)thiazol-4-yl)methyl)pyrrolidine-2-carboxylic acid | +++ |
| 269 | 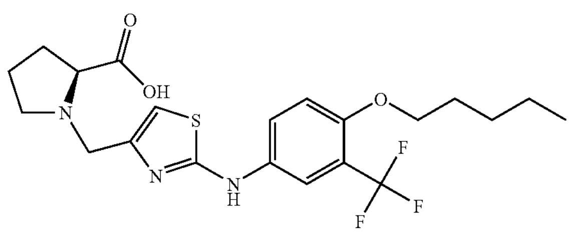 | (S)-1-((2-(4-(pentyloxy)-3-(trifluoromethyl)phenyl-amino)thiazol-4-yl)methyl)pyrrolidin-2-carboxylic acid | +++ |
| 270 | 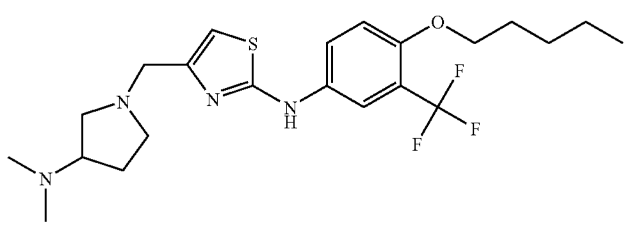 | 4-((3-(dimethylamino)pyrrolidin-1-yl)methyl))-N-(4-(pentyloxy)-3-(trifluoromethyl)phenyl)thia-zol-2-amine | |
| 271 | 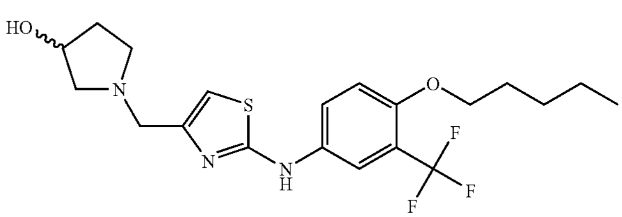 | 1-((2-(4-(pentyloxy)-3-(trifluoromethyl)phenyl-amino)thiazol-4-yl)methyl)pyrrolidin-3-ol | |

TABLE II-continued

| Cpd | Structure | Name | Activity |
|---|---|---|---|
| 272 | 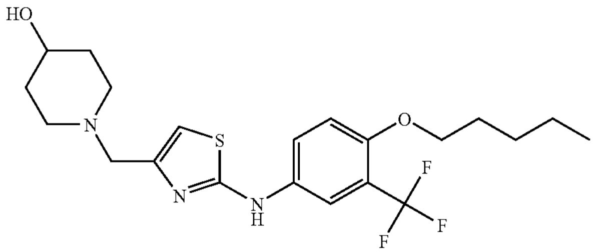 | 1-((2-(4-(pentyloxy)-3-(trifluoromethyl)phenyl-amino)thiazol-4-yl)methyl)piperidin-4-ol | +++ |
| 273 | 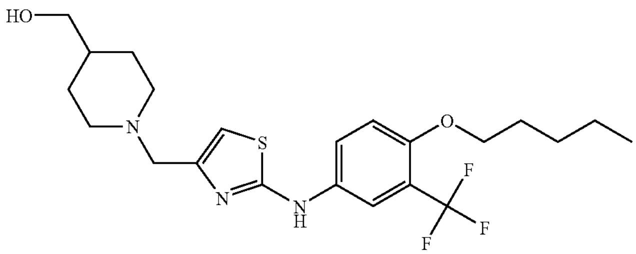 | (1-((2-(4-(pentyloxy)-3-(trifluoromethyl)phenyl-amino)thiazol-4-yl)methyl)piperidin-4-yl)methanol | +++ |
| 274 | 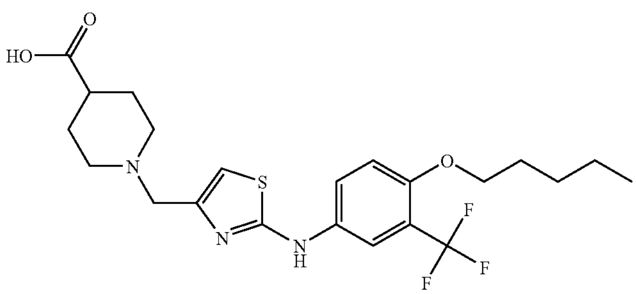 | 1-((2-(4-(pentyloxy)-3-(trifluoromethyl)phenyl-amino)thiazol-4-yl)methyl)piperidine-4-carboxylic acid | +++ |
| 275 | 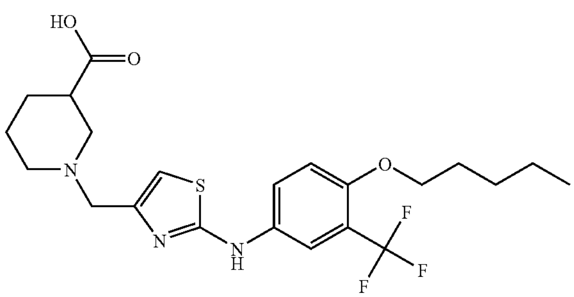 | 1-((2-(4-(pentyloxy)-3-(trifluoromethyl)phenyl-amino)thiazol-4-yl)methyl)piperidin-3-carboxylic acid | +++ |
| 276 | 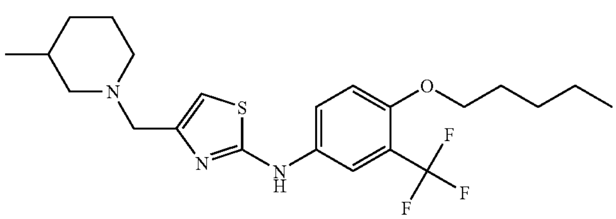 | 4-((3-methylpiperidin-1-yl)methyl)-N-(4-(pentyloxy)-3-(trifluoromethyl)phenyl)thiazol-2-amine | +++ |
| 277 | 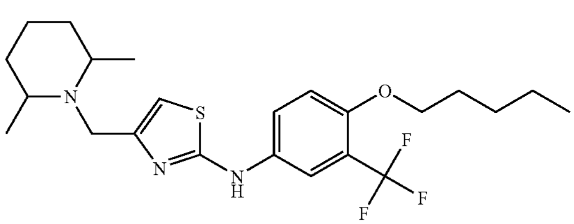 | 4-((2,6-dimethylpiperidin-1-yl)methyl)-N-(4-(pentyloxy)-3-(trifluoromthyl)phenyl)thiazol-2-amine | +++ |

TABLE II-continued

| Cpd | Structure | Name | Activity |
|---|---|---|---|
| 278 | 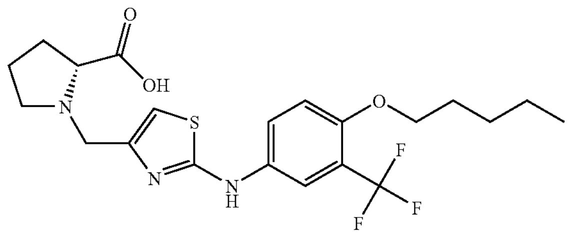 | (R)-1-((2-(4-(pentyloxy)-3-(trifluoromethyl)phenyl-amino)thiazol-4-yl)methyl)pyrrolidine-2-carboxylic acid | +++ |
| 279 | 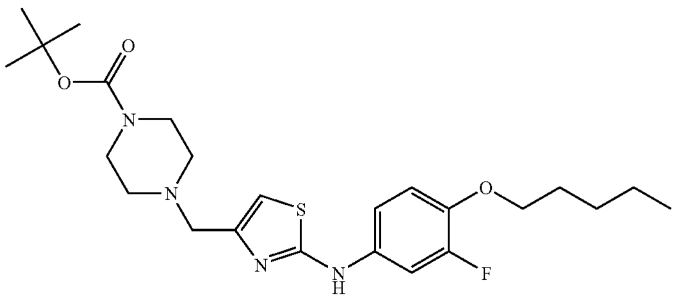 | tert-butyl 4-((2-(3-fluoro-4-(pentyloxy)phenylamino)thiazol-4-yl)methyl)piperiazine-1-carboxylate | ++ |
| 280 | 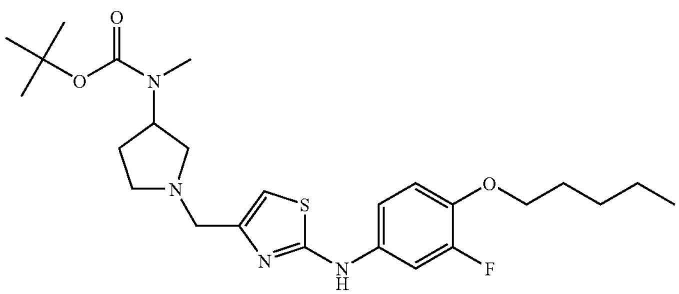 | tert-butyl 1-((2-(3-fluoro-4-(pentyloxy)phenylamino)thiazol-4-yl)m,ethyl)pyrrolidin-3-yl(methyl)carbamate | ++ |
| 281 | 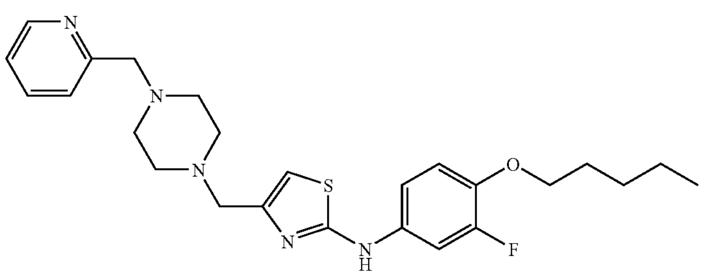 | N-(3-fluoro-4-(pentyloxy)phenyl)-4-((4-(pyridin-2-ylmethyl)piperiazin-1-yl)methyl)thiazol-2-amine | +++ |
| 282 | 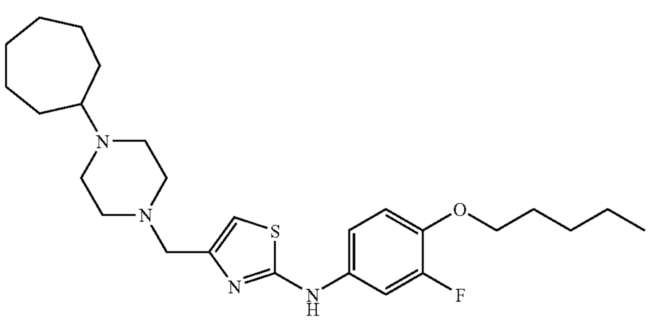 | 4-((4-cycloheptylpiperazin-1-yl)methyl)-N-(3-fluoro-4-(pentyloxy)phenyl)thiazol-2-amine | +++ |

TABLE II-continued

| Cpd | Structure | Name | Activity |
|---|---|---|---|
| 283 | 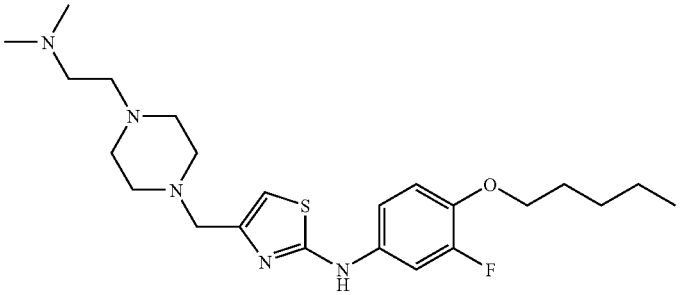 | 4-((4-(2-(dimeethylamino)ethyl)piper-azin-1-yl)methyl)-N-(3-fluoro-4-(pentyloxy)phenyl)thiazol-2-amine | ++ |
| 284 | 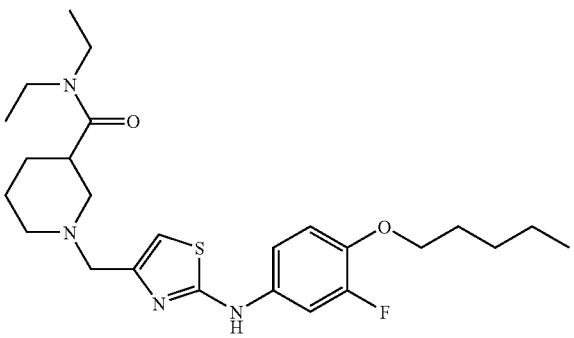 | N,N-diethyl-1-((2-(3-fluoro-4-(pentyloxy)phenylamino)thia-zol-4-yl)methyl)piperidine-3-carboxamide | ++ |
| 285 | 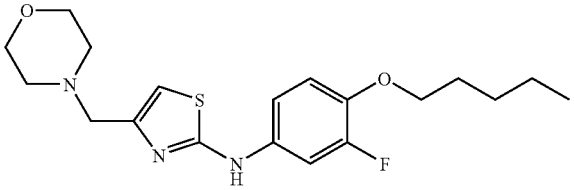 | N-(3-fluoro-4-(pentyloxy)phenyl)-4-(morpholinomethyl)thiazol-2-amine | ++ |
| 286 | 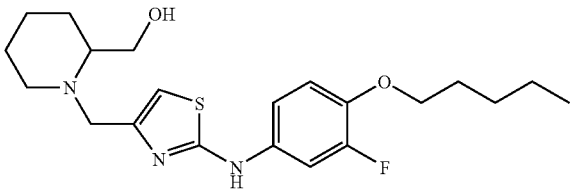 | (1-((2-(3-fluoro-4-(pentyloxy)phenylamino)thia-zol-4-yl)methyl)piperidin-2-yl)methanol | ++ |
| 287 | 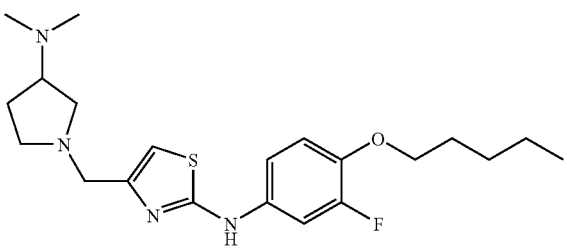 | 4-((3-(dimethylamino)pyrrolidin-1-yl)methyl)-N-(3-fluoro-4-(pentyloxy)pheenyl)thiazol-2-amine | +++ |
| 288 | 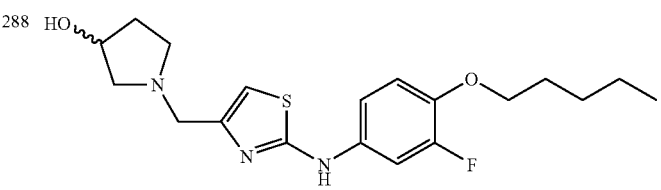 | 1-((2-(3-fluoro-4-(pentyloxy)phenylamino)thia-zzol-4-yl)methyl)pyrrolidin-3-ol | +++ |

TABLE II-continued

| Cpd | Structure | Name | Activity |
|---|---|---|---|
| 289 | 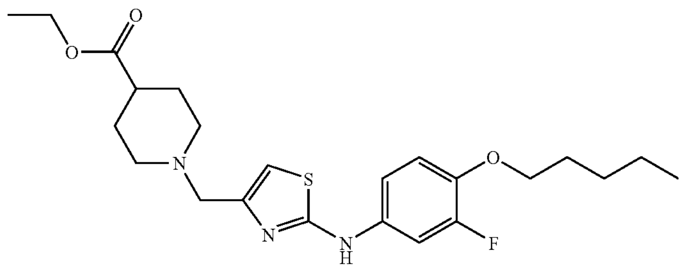 | ethyl 1-((2-(3-fluoro-4-(pentyloxy)phenylamino)thiazol-4-yl)methyl)piperidine-4-carboxylate | ++ |
| 290 | 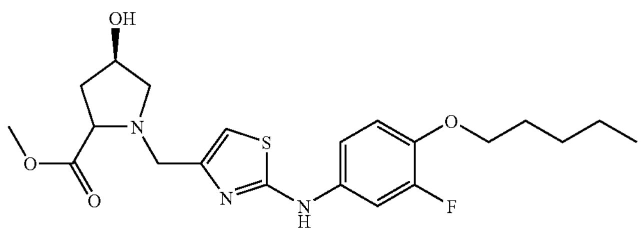 | (4R)-methyl 1-((2-(3-fluoro-4-(pentyloxy)phenylamino)thiazol-4-yl)methyl)-4-hydroxypyrrolidine-2-carboxylate | +++ |
| 291 | 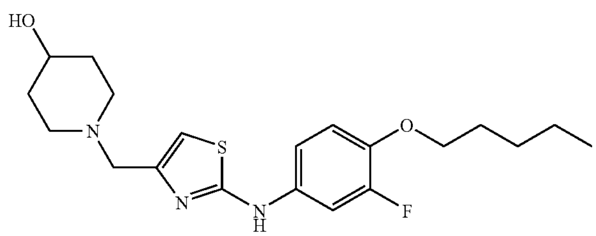 | 1-((2-(3-fluoro-4-(pentyloxy)phenylamino)thiazol-4-yl)methyl)piperidin-4-ol | ++ |
| 292 | 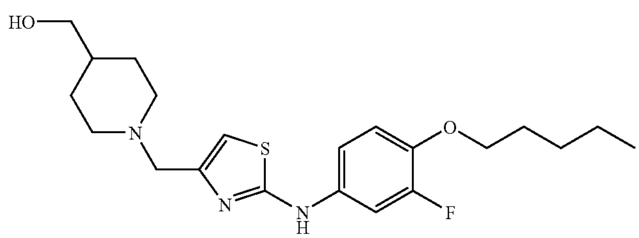 | (1-((2-(3-fluoro-4-(pentyloxy)phenylamino)thiazol-4-yl)methyl)piperidin-4-yl)methanol | ++ |
| 293 | 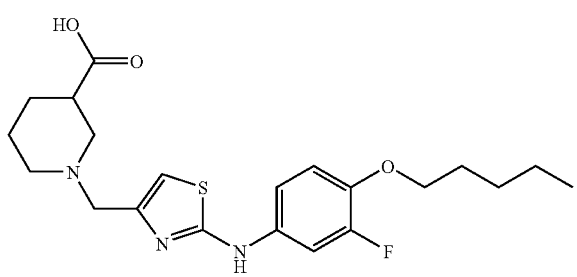 | 1-((2-(3-fluoro-4-(pentyloxy)phenylamino)thiazol-4-yl)methyl)piperidine-3-carboxylic acid | ++ |
| 294 | 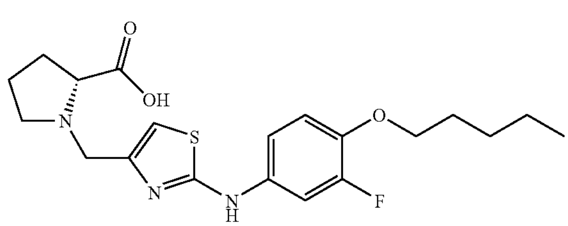 | (R)-1-((2-(3-fluoro-4-(pentyloxy)phenylamino)thiazol-4-yl)methyl)pyrrolidine-2-carboxylic acid | ++ |

TABLE II-continued

| Cpd | Structure | Name | Activity |
|---|---|---|---|
| 295 | 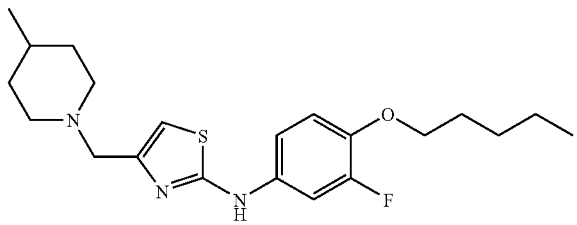 | N-(3-fluoro-4-(pentyloxy)pheenyl)-4-((4-methylpiperidin-1-yl)methyl)thiazol-2-amine | ++ |
| 296 | 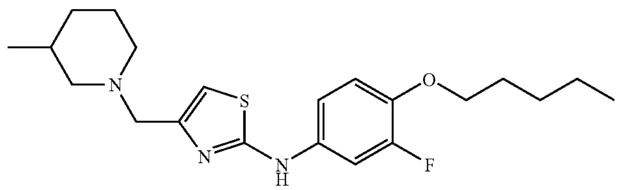 | N-(3-fluoro-4-(pentyloxy)phenyl)-4-((3-methylpiperidin-1-yl)methyl)thiazol-2-amine | ++ |
| 297 | 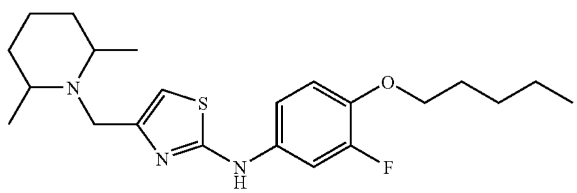 | 4-((2,6-dimethylpiperidin-1-yl)methyl)-N-(3-fluoro-4-(pentyloxy)phenyl)thiazol-2-amine | ++ |
| 298 | 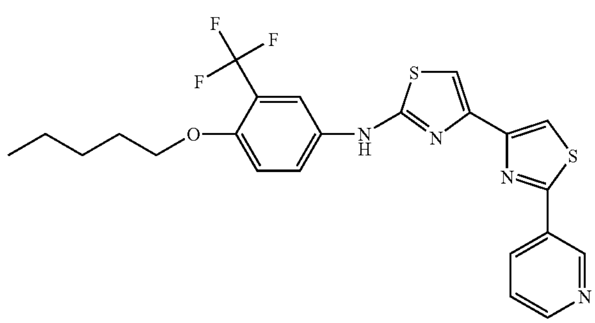 | N-(4-(pentyloxy)-3-(trifluoromethyl)phenyl)-4-(2-(pyridin-3-yl)thiazol-4-yl)thiazol-2-amine | +++ |
| 299 | 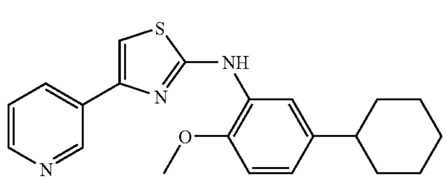 | N-(5-cyclohexyl-2-methoxyphenyl)-4-(pyridin-3-yl)thiazol-2-amine | ++ |
| 300 | 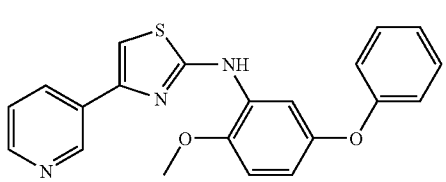 | N-(2-methoxy-5-phenoxyphenyl)-4-(pyridin-3-yl)thiazol-2-amine | ++ |

TABLE II-continued

| Cpd | Structure | Name | Activity |
|---|---|---|---|
| 301 | 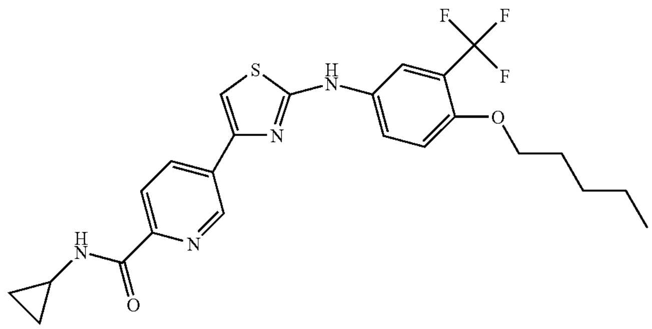 | N-cyclopropyl-5-(2-(4-(pentyloxy)-3-(trifluoromethyl)phenylamino)thiazolo-4-yl)picolinamide | +++ |
| 302 | | | +++ |
| 303 | 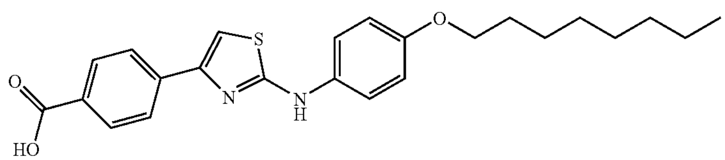 | 4-(2-(4-(octyloxy)phenylamino)thiazol-4-yl)benzoic acid | ++ |
| 304 | 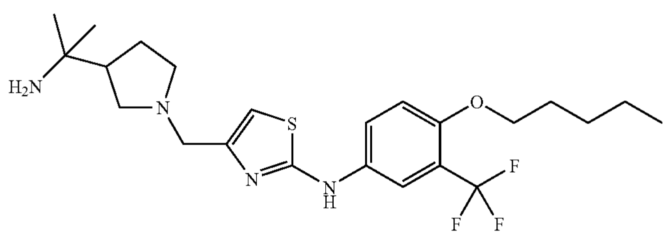 | 4-((3-(2-aminopropan-2-yl)pyrrolidin-1-yl)methyl)-N-(4-(pentyloxy)-3-(trifluoromethyl)phenyl)thiazol-2-amine | ++ |
| 305 | 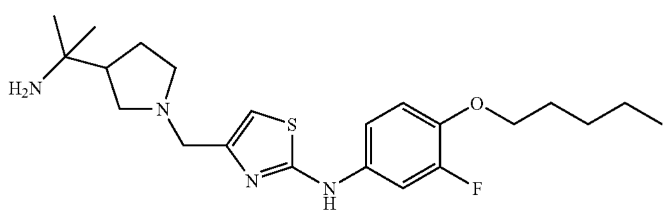 | 4-((3-(2-aminopropan-2-yl)pyrrolidin-1-yl)methyl)-N-(3-fluoro-4-(pentyloxy)phenyl)thiazol-2-amine | ++ |
| 306 | 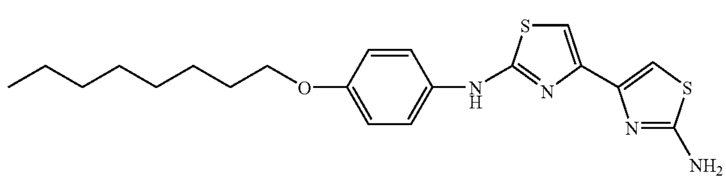 | 4-(2-aminothiazol-4-yl)-N-(4-(octyloxy)phenyl)thiazol-2-amine | +++ |
| 307 | 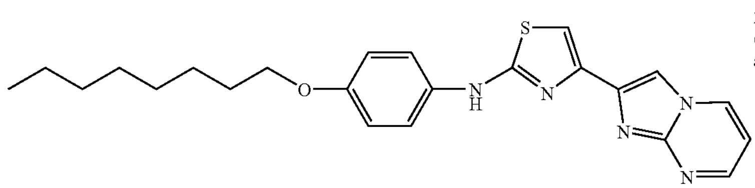 | 4-(imidazo[1,2-a]pyrimidin-2-yl)-N-(4-(octyloxy)phenyl)thiazol-2-amine | +++ |

TABLE II-continued

| Cpd | Structure | Name | Activity |
|---|---|---|---|
| 308 | 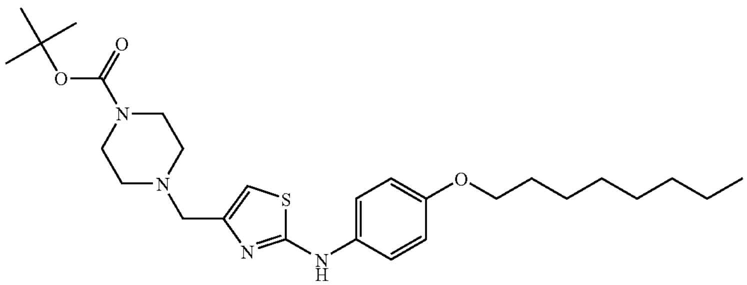 | tert-butyl 4-((2-(4-(octyloxy)phenylamino)thiazol-4-yl)methyl)piperazine-1-carboxylate | ++ |
| 309 | 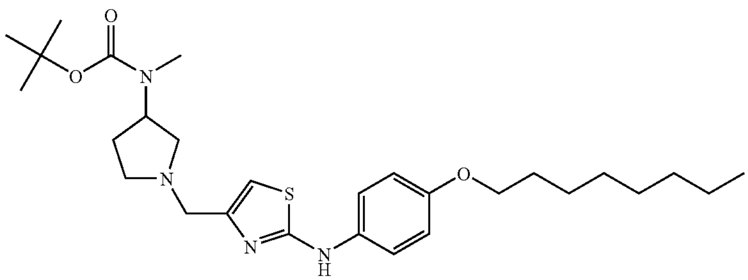 | tert-butyl methyl(1-((2-(4-(octyloxy)phenylamino)thiazol-4-yl)methyl)pyrrolidin-3-yl)carbamate | ++ |
| 310 | 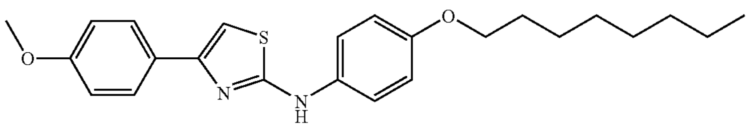 | 4-(4-methoxyphenyl)-N-(4-(octyloxy)phenyl)thiazol-2-amine | +++ |
| 311 | 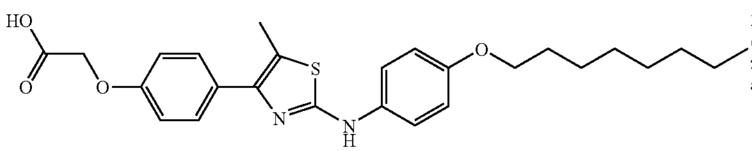 | 2-(4-(5-methyl-2-(4-(octyloxy)phenyl)thiazol-4-yl)phenoxy)acetic acid | +++ |
| 312 | 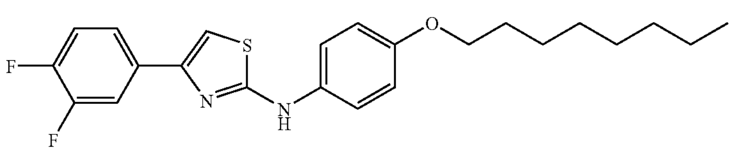 | 4-(3,4-difluorophenyl)-N-(4-(octyloxy)phenyl)thiazol-2-amine | +++ |
| 313 | 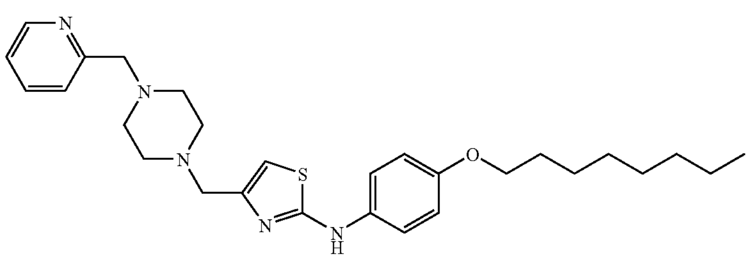 | N-(4-(octyloxy)phenyl)-4-((4-pyridin-2-ylmethyl)piperazin-1-yl)methyl)thiazol-2-amine | ++ |
| 314 | 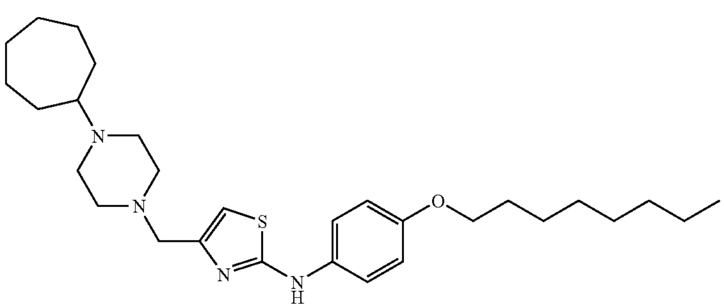 | 4-((4-cycloheptylpiperazin-1-yl)methyl)-N-(4-(octyloxy)phenyl)thiazol-2-amine | +++ |

TABLE II-continued

| Cpd | Structure | Name | Activity |
|---|---|---|---|
| 315 | 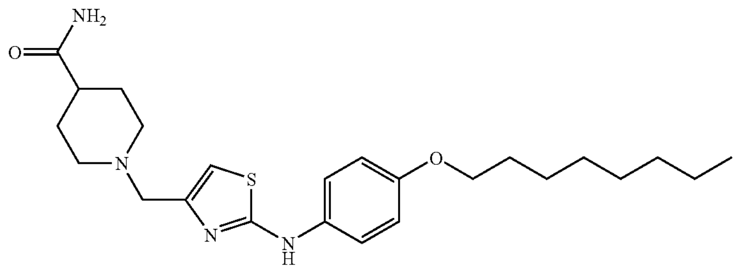 | 1-((2-(4-(octyloxy)phenylamino)thiazol-4-yl)methyl)piperidine-4-carboxammide | ++ |
| 316 | 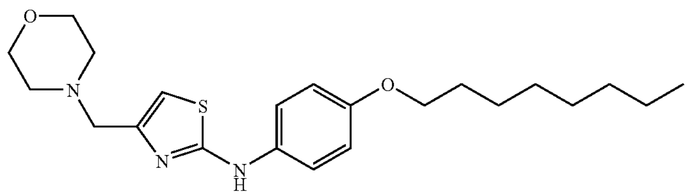 | 4-(morpholinomethyl)-N-(4-(octyloxy)phenyl)thiazol-2-amine | ++ |
| 317 | 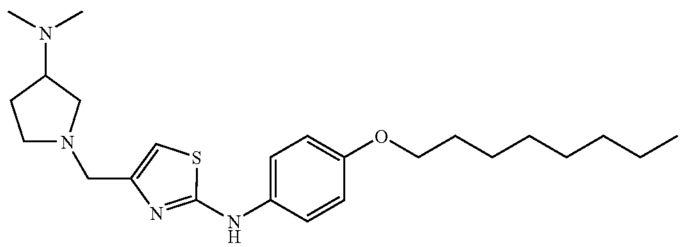 | 4-((3-(dimethylamino)pyrrolidin-1-yl)methyl)-N-(4-(octyloxy)phenyl)thiazol-2-amine | +++ |
| 318 | 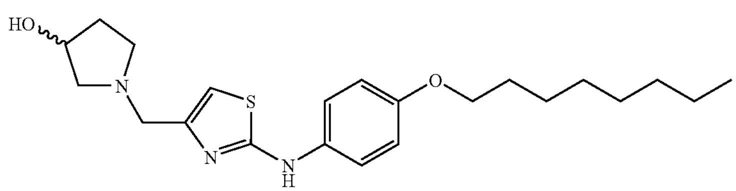 | 1-((2-(4-(octyloxy)phenylamino)thiazol-4-yl)methyl)pyrrolidin-3-ol | +++ |
| 319 | 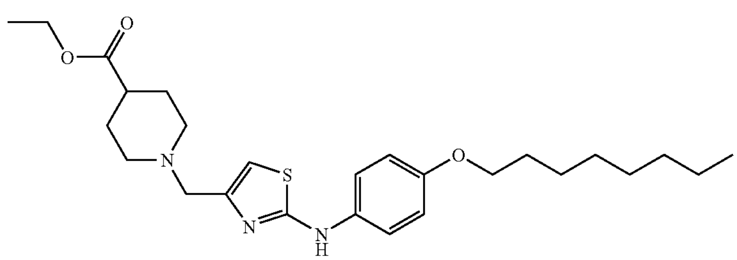 | ethyl 1-((2-(4-(octyloxy)phenylamino)thiazol-4-yl)methyl)piperidine-4-carboxylate | ++ |
| 320 | 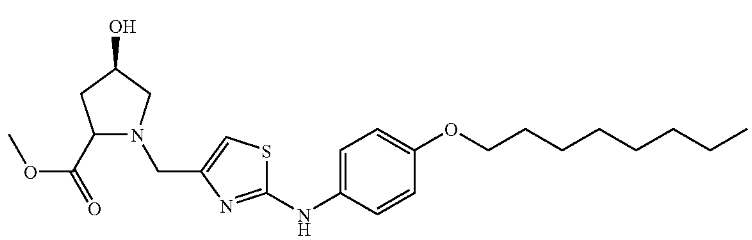 | (4R)-methyl 4-hydroxy-1-((2-(4-(octyloxy)pheenylamino)thiazol-4-yl)methyl)pyrrolidine-2-carboxylate | +++ |

TABLE II-continued

| Cpd | Structure | Name | Activity |
|---|---|---|---|
| 321 | 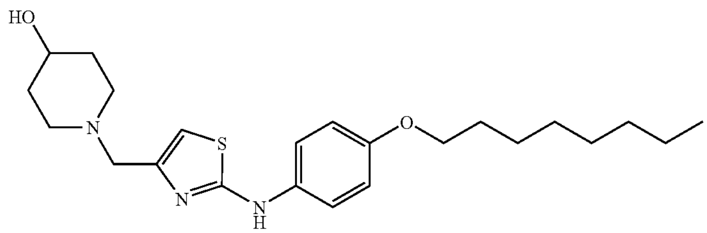 | 1-((2-(4-(octyloxy)phenylamino)thiazol-4-yl)methyl)piperidin-4-ol | ++ |
| 322 | 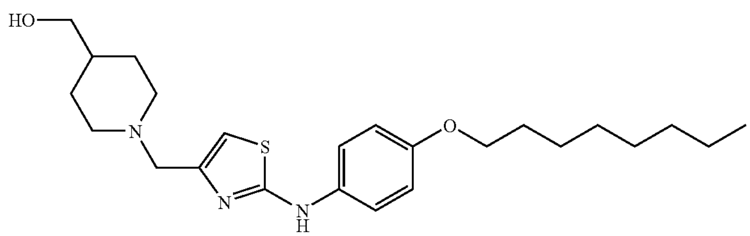 | (1-((2-(4-(octyloxy)phenylamino)thiazol-4-yl)methyl)piperidin-4-yl)methanol | ++ |
| 323 | 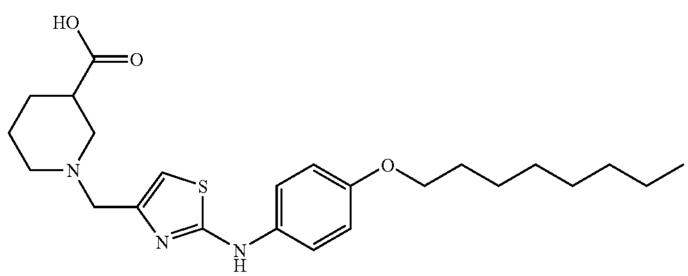 | 1-((2-(4-(octyloxy)phenylamino)thiazol-4-yl)methyl)piperidine-3-carboxylic acid | ++ |
| 324 | 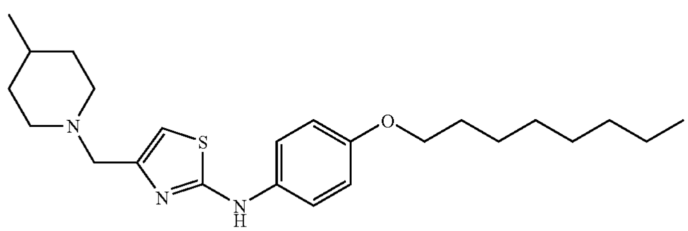 | 4-((4-methylpiperidin-1-yl)methyl)-N-(4-(octyloxy)phenyl)thiazol-2-amine | ++ |
| 325 | 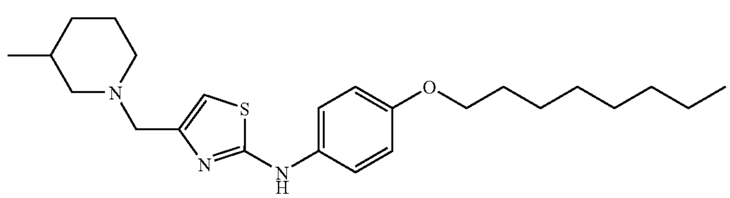 | 4-((3-methylpiperidin-1-yl)methyl)-N-(4-(octyloxy)phenyl)thiazol-2-amine | ++ |
| 326 | 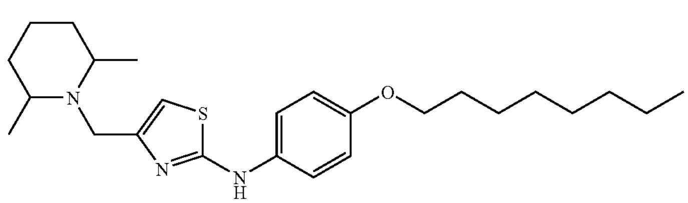 | 4-((2,6-dimethylpiperidin-1-yl)methyl)-N-(4-(octyloxy)phenyl)thiazol-2-amine | ++ |
| 327 | 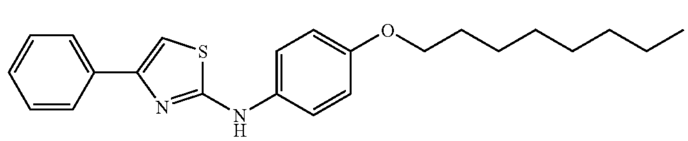 | N-(4-(octyloxy)phenyl)-4-phenylthiazol-2-amine | +++ |

TABLE II-continued

| Cpd | Name | Activity |
|---|---|---|
| 328 | 4-(4-fluorophenyl)-N-(4-(octyloxy)phenyl)thiazol-2-amine | +++ |
| 329 | 4-(3,4-ddichlorophenyl)-N-(4-(octyloxy)phenyl)thiazol-2-amine | ++ |
| 330 | 4-(2,4-difluorophenyl)-N-(4-(octyloxy)phenyl)thiazol-2-amine | ++ |
| 331 | 4-(2-(4-(octyloxy)phenylamino)thiazol-4-yl)-1H-imidazol-2(5H)-one | ++ |
| 332 | N-(4-(octyloxy)phenyl)-4-(2-phenylthiazol-4-yl)thiazol-2-amine | ++ |
| 333 | 4,5-bis(4-methoxyphenyl)-N-(3-(trifluoromethyl)phenyl)thiazol-2-amine | ++ |
| 334 | ethyl 4-(4,5-bis(4-methoxyphenyl)thiazol-2-ylamino)benzoate | ++ |

TABLE II-continued

| Cpd | Structure | Name | Activity |
|-----|-----------|------|----------|
| 335 | 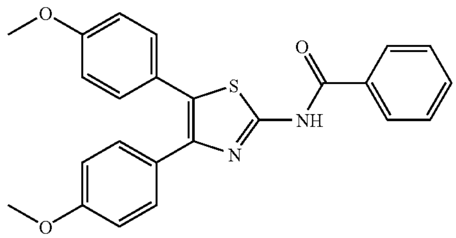 | N-(4,5-bis(4-methoxyphenyl)thiazol-2-yl)benzamide | ++ |
| 336 | 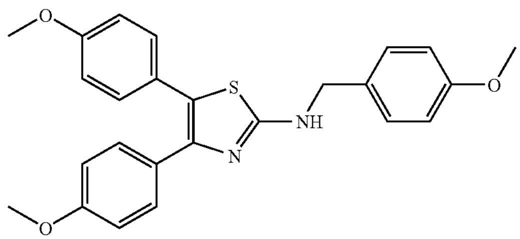 | N-(4-methoxybenzyl)-4,5-bis(4-methoxypheenyl)thiazol-2-amine | + |
| 337 | 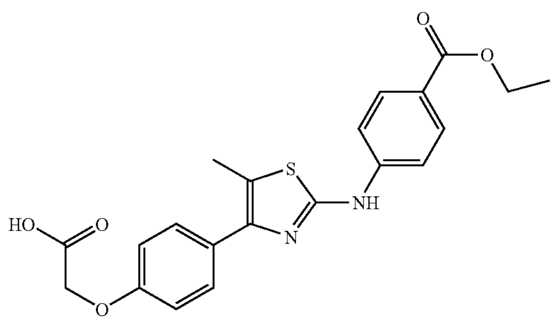 | 2-(4-(2-(4-(ethoxycarbonyl)phenylamino)-5-methylthiazol-4-yl)phenoxy)acetic acid | + |
| 338 | 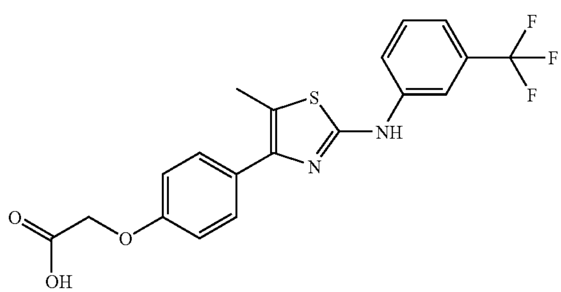 | 2-(4-(5-methyl-2-(3-(trifluoromthyl)phenylamino)thiazol-4-yl)phenoxy)acetic acid | + |
| 339 | 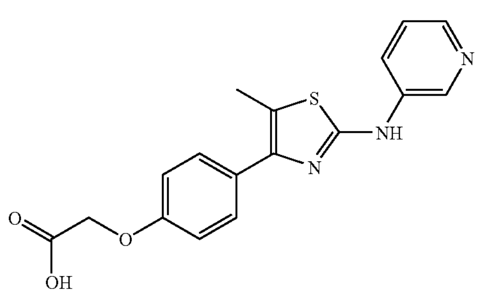 | 2-(4-(5-methyl-2-(pyridin-4-ylamino)thiazol-4-yl)phenoxy)acetic acid | + |
| 340 | 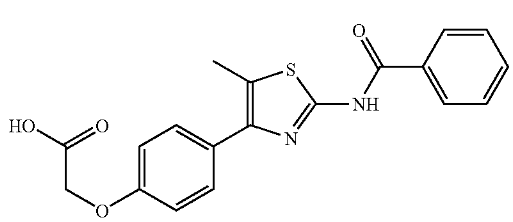 | 2-(4-(2-benzamido-5-methylthiazol-4-yl)phenoxy)acetic acid | + |

TABLE II-continued

| Cpd | Structure | Name | Activity |
|---|---|---|---|
| 341 | 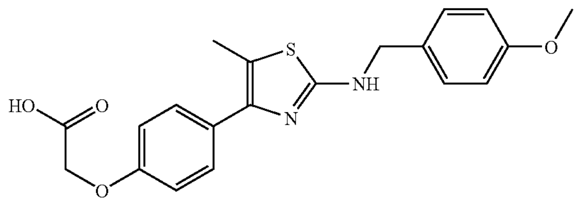 | 2-(4-(2-(4-methoxybenzylamino)-5-methylthiazol-4-yl)phenoxy)acetic acid | + |
| 342 | 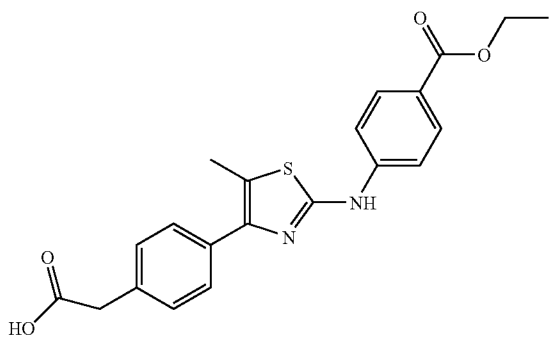 | 2-(4-(2-(4-(ethoxycarbonyl)phenylamino)-5-methylthiazol-4-yl)phenyl)acetic acid | + |
| 343 | 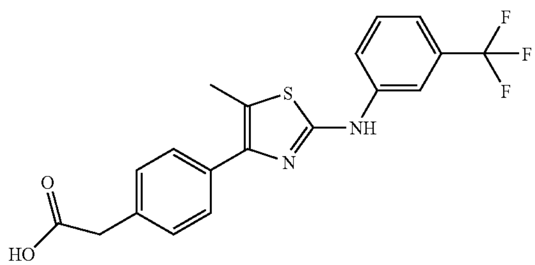 | 2-(4-(5-methyl-2-(3-(trifluoromethyl)phenylamino)thiazol-4-yl)phenyl)acetic acid | + |
| 344 | 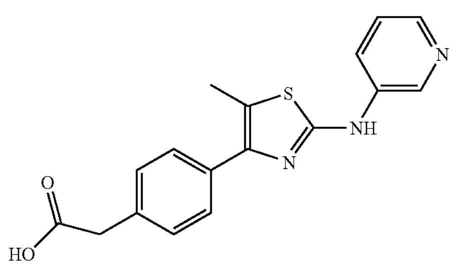 | 2-(4-(5-methyl-2-(pyridin-3-ylamino)thiazol-4-yl)phenyl)acetic acid | + |
| 345 | 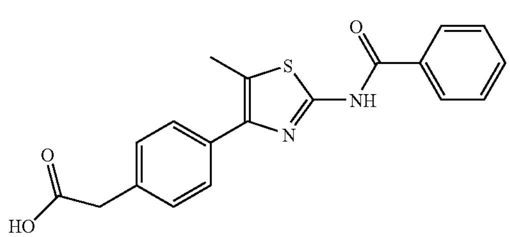 | 2-(4-(2-benzamido-5-methylthiazol-4-yl)phenyl)acetic acid | + |
| 346 | 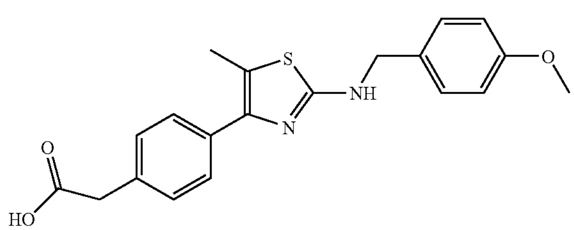 | 2-(4-(2-(4-methoxybenzylamino)-5-methylthiazol-4-yl)phenyl)acetic acid | + |

TABLE II-continued

| Cpd | Structure | Name | Activity |
|---|---|---|---|
| 347 | 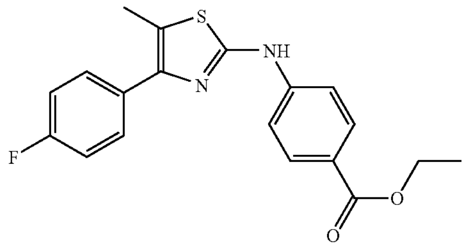 | ethyl 4-(4-(4-fluorophenyl)-5-mthylthiazol-2-ylamino)benzoate | + |
| 348 | 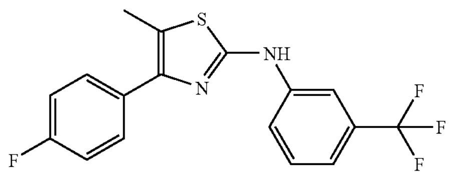 | 4-(4-fluorophenyl)-5-methyl-N-(3-(trifluoromethyl)phenyl)thiazol-2-amine | ++ |
| 349 | 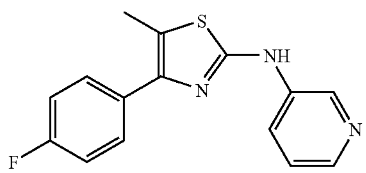 | N-(4-(4-fluorophenyl)-5-methylthiazol-2-yl)pyridin-3-amine | + |
| 350 | 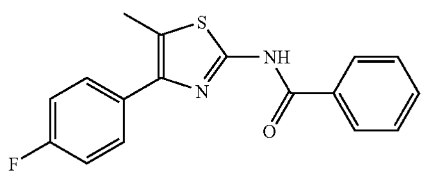 | N-(4-(4-fluorophenyl)-5-methylthiazol-2-yl)benzamide | + |
| 351 | 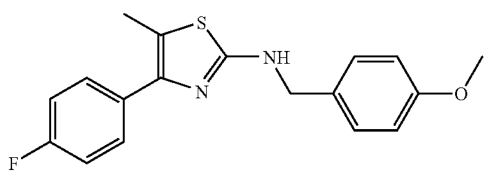 | N-(4-methoxybenzyl)-4-(4-fluorophenyl)-5-methylthiazol-2-amine | + |
| 352 | 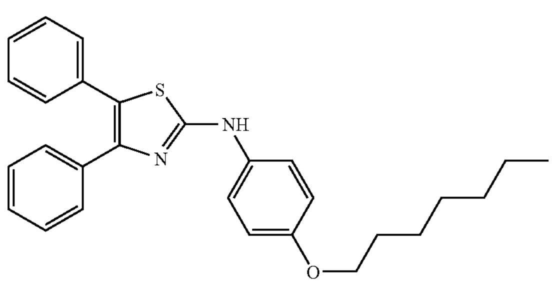 | N-(4-(heptyloxy)phenyl)-4,5-diphenylthiazol-2-amine | + |
| 353 | 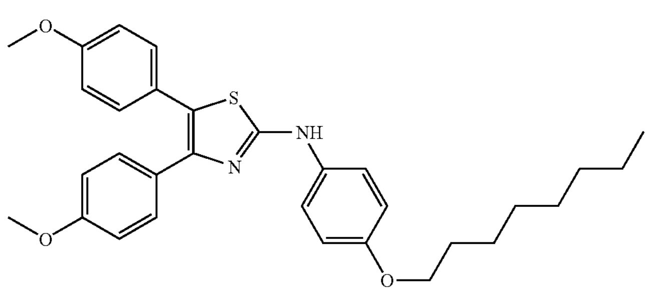 | 4,5-bis(4-methoxyphenyl)-N-(4-(octyloxy)phenyl)thiazol-2-amine | ++ |

TABLE II-continued

| Cpd | Structure | Name | Activity |
|---|---|---|---|
| 354 | 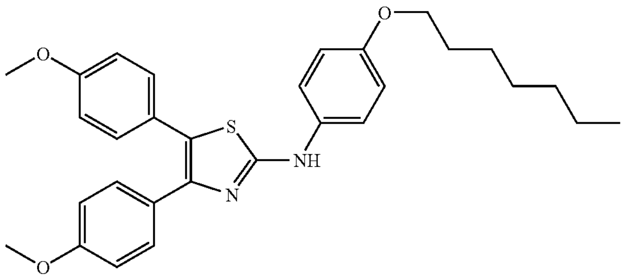 | N-(4-(heptyl)phenyl)-4,5-bis(4-methoxyphenyl)thiazol-2-amine | +++ |
| 355 | 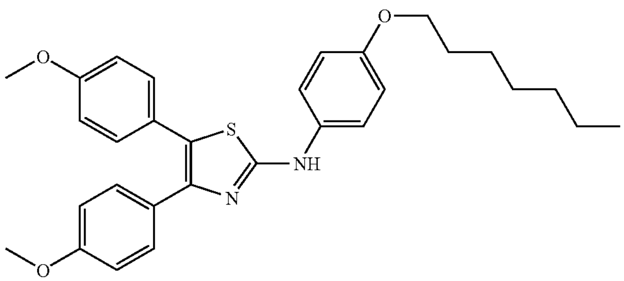 | N-(4-(heptyloxy)phenyl)-4,5-bis(4-methoxyphenyl)thiazol-2-amine | + |
| 356 | 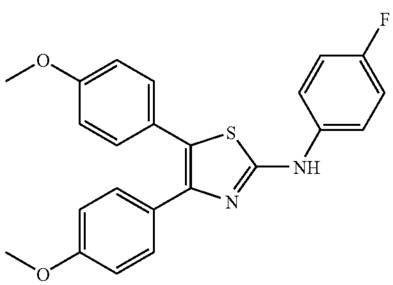 | N-(4-fluorophenyl)-4,5-bis(4-methoxyphenyl)thiazol-2-amine | ++ |
| 357 | 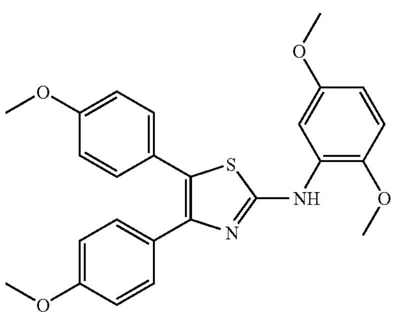 | N-(2,5-dimthoxyphenyl)-4,5-bis(4-methoxyphenyl)thiazol-2-amine | + |
| 358 | 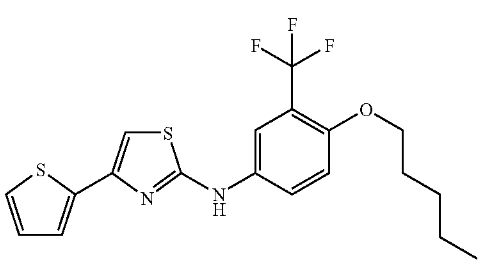 | N-(4-(pentyloxy)-3-(trifluoromethyl)phenyl)-4-(thiophen-2-yl)thiazol-2-amine | +++ |
| 359 | 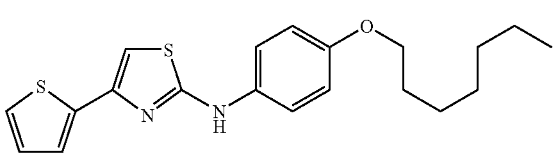 | N-(4-(heptyloxy)phenyl)-4-(thiophen-2-yl)thiazol-2-amine | +++ |

TABLE II-continued

| Cpd | Structure | Name | Activity |
|---|---|---|---|
| 360 | 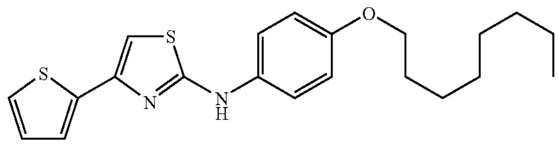 | N-(4-(octyloxy)phenyl)-4-(thiophen-2-yl)thiazol-2-amine | +++ |
| 361 | 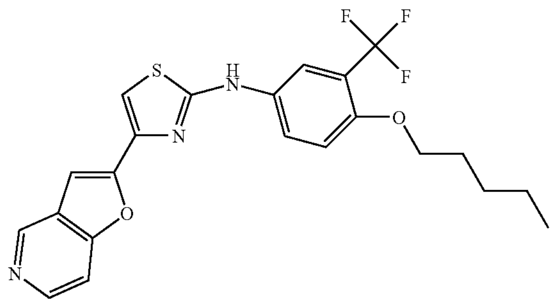 | 4-(furo[3,2-c]pyridin-2-yl)-N-(4-(pentyloxy)-3-(trifluoromethyl)phenyl)thiazol-2-amine | +++ |
| 362 | 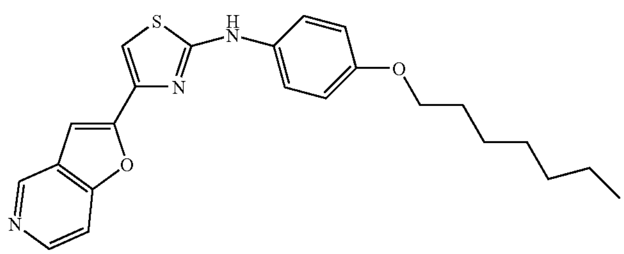 | 4-(furo[3,2-c]pyridin-2-yl)-N-(4-(heptyloxy)phenyl)thiazol-2-amine | ++ |
| 363 | 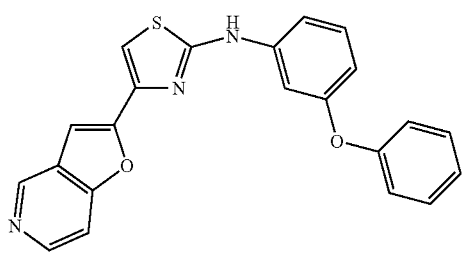 | 4-(furo[3,2-c]pyridin-2-yl)-N-(3-phenoxyphenyl)thiazol-2-amine | + |
| 364 | 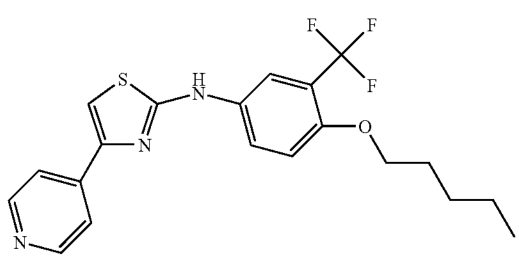 | N-(4-(pentyloxy)-3-(trifluoromethyl)phenyl)-4-(pyridin-4-yl)thiazol-2-amine | +++ |
| 365 | 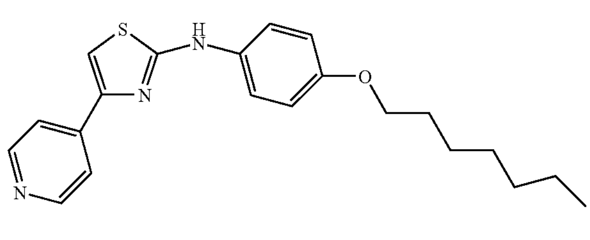 | N-(4-(heptyloxy)phenyl)-4-(pyridin-4-yl)thiazol-2-amine | +++ |

TABLE II-continued

| Cpd | Structure | Name | Activity |
|---|---|---|---|
| 366 | 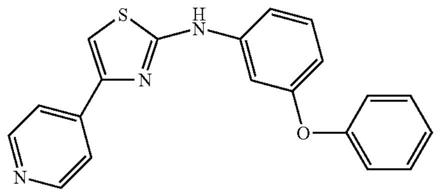 | N-(3-phenoxyphenyl)-4-(pyridin-4-yl)thiazol-2-amine | +++ |
| 367 | 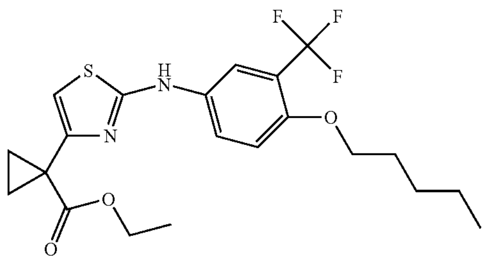 | ethyl 1-(2-(4-(pentyloxy)-3-(trifluoromethyl)pheenyl-amino)thiazol-4-yl)cyclopropanecarboxylate | + |
| 368 | 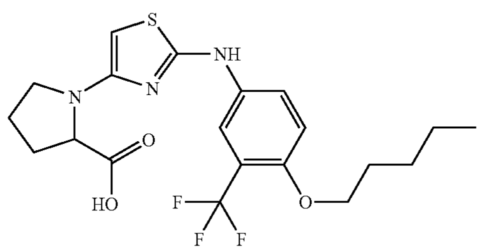 | 1-(2-(4-(pentyloxy)-3-(trifluoromethyl)phenyl-amino)thiazol-4-yl)pyrrolidine-2-carboxylic acid | ++ |
| 369 | 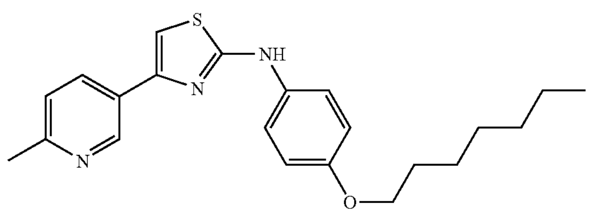 | N-(4-(heptyloxy)phenyl)-4-(6-methylpyridin-3-yl)thiazol-2-amine | +++ |
| 370 | 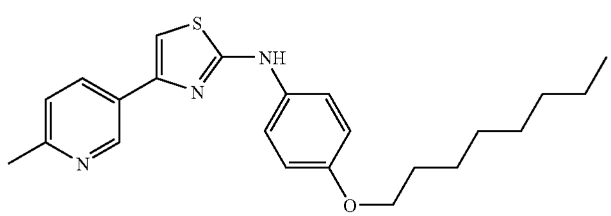 | 4-(6-methylpyridin-3-yl)-N-(4-(octyloxy)phenyl)thiazol-2-amine | +++ |
| 371 | 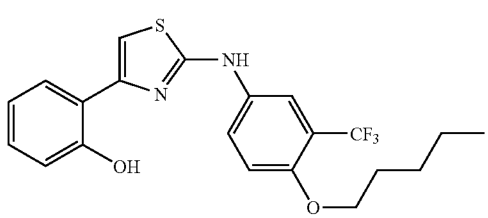 | 2-(2-(4-(pentyloxy)-3-(trifluoromeethyl)phenyl-amino)thiazol-4-yl)phenol | ++ |
| 372 | 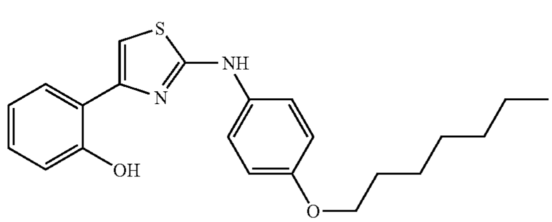 | 2-(2-(4-(heptyloxy)phenylamino)thia-zol-4-yl)phenol | +++ |

TABLE II-continued

| Cpd | Structure | Name | Activity |
|---|---|---|---|
| 373 | 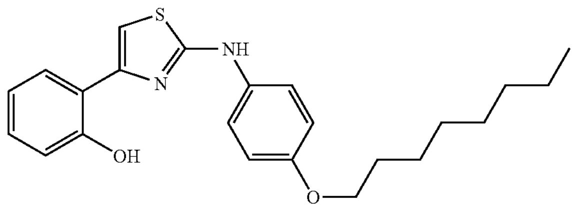 | 2-(2-(4-(octyloxy)phenylamino)thiazol-4-yl)phenol | +++ |
| 374 | 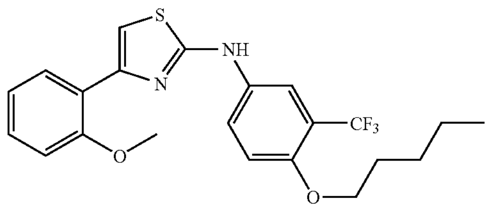 | 4-(2-methoxyphenyl)-N-(4-(pentyloxy)-3-(trifluoromethyl)phenyl)thiazol-2-amine | ++ |
| 375 | 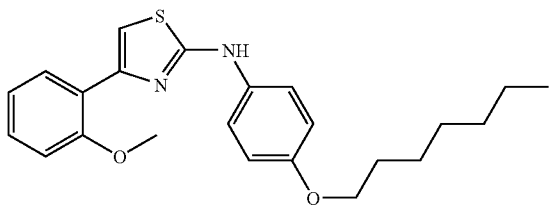 | N-(4-(heptyloxy)phenyl)-4-(2-methoxyphenyl)thiazol-2-amine | +++ |
| 376 | 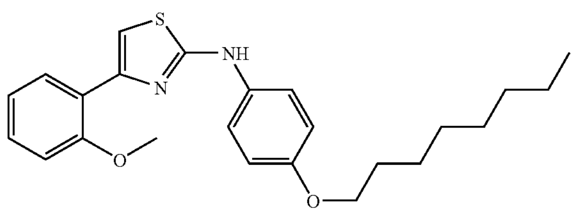 | 4-(2-methoxyphenyl)-N-(4-(octyloxy)phenyl)thiazol-2-amine | +++ |
| 377 | 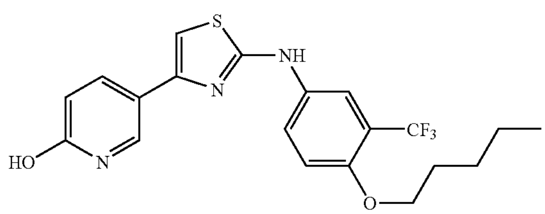 | 5-(2-(4-(pentyloxy)-3-(trifluoromethyl)phenylamino)thiazol-4-yl)pyridin-2-ol | +++ |
| 378 | 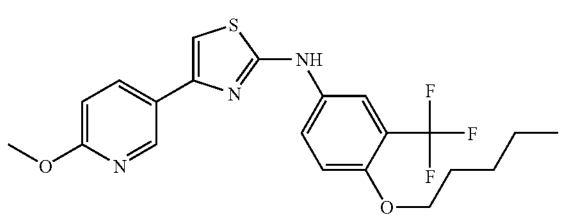 | 4-(6-methoxypyridin-3-yl)-N-(4-(pentyloxy)-3-(trifluoromethyl)phenyl)thiazol-2-amine | +++ |
| 379 | 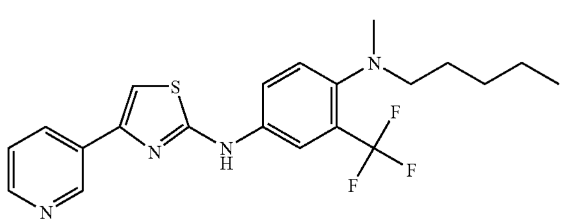 | $N^1$-methyl-$N^1$-pentyl-$N^4$-(4-(pyridin-3-yl)thiazol-2-yl)-2-(trifluoromethyl)benzene-1,4-diamine | +++ |

TABLE II-continued
| Cpd | Structure | Name | Activity |
|---|---|---|---|
| 380 | 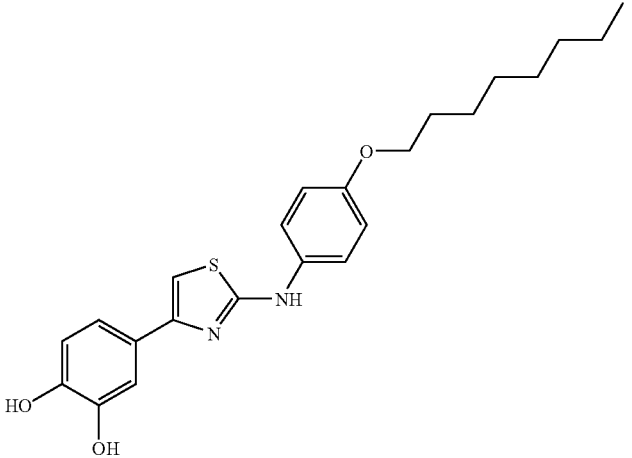 | 4-(2-(4-(octyloxy)phenylamino)thiazol-4-yl)benzene-1,2-diol | |
| 381 | 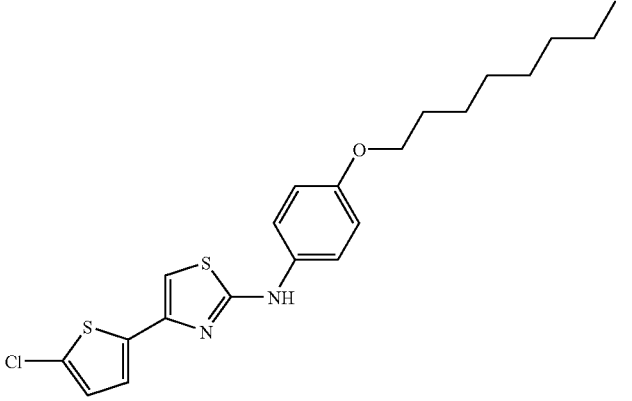 | 4-(5-chlorothiophen-2-yl)-N-(4-(octyloxy)phenyl)thiazol-2-amine | |
| 382 | 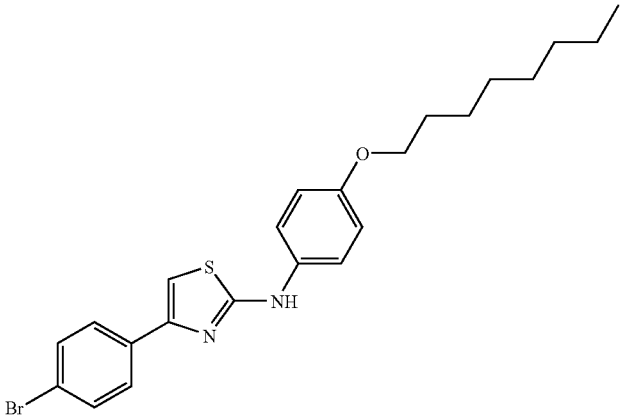 | 4-(4-bromophenyl)-N-(4-(octyloxy)phenyl)thiazol-2-amine | +++ |

TABLE II-continued
| Cpd | Structure | Name | Activity |
|---|---|---|---|
| 383 | 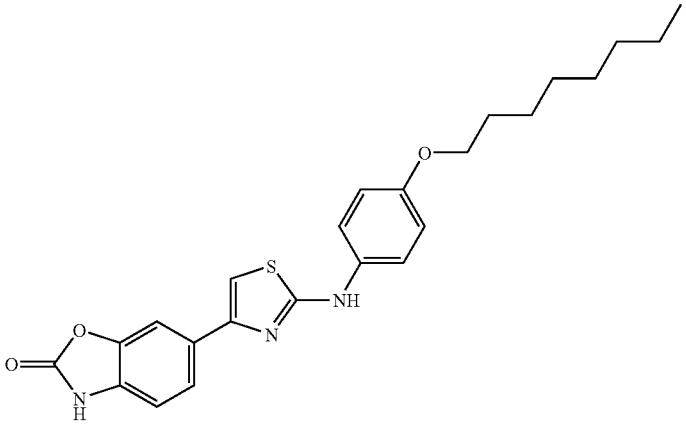 | 6-(2-(4-(octyloxy)phenylamino)thiazol-4-yl)benzo[d]oxazol-2(3H)-one | +++ |
| 384 | 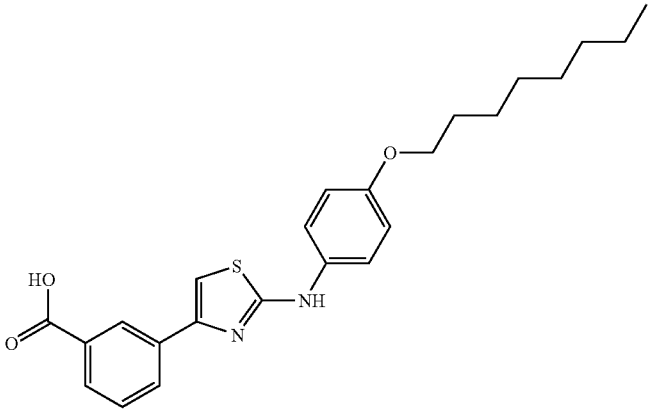 | 3-(2-(4-(octyloxy)phenylamino)thiazol-4-yl)benzoic acid | +++ |
| 385 | 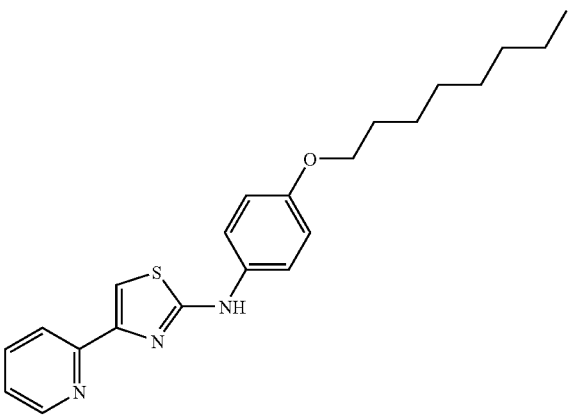 | N-(4-(octyloxy)phenyl)-4-(pyridin-2-yl)thiazol-2-amine | +++ |

TABLE II-continued

| Cpd | Structure | Name | Activity |
|---|---|---|---|
| 386 | 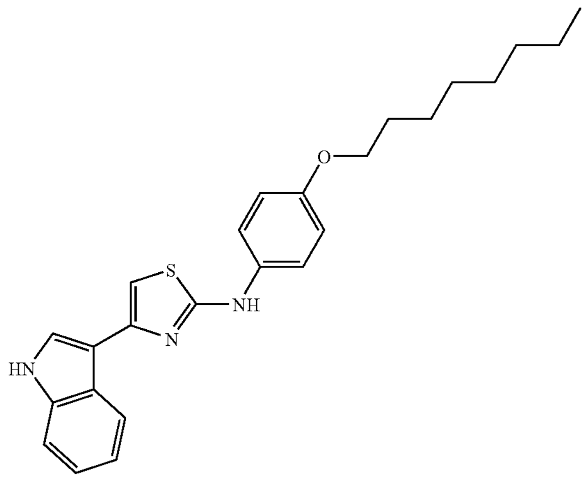 | 4-(1H-indol-3-yl)-N-(4-(octyloxy)pheenyl)thiazol-2-amine | +++ |
| 387 | 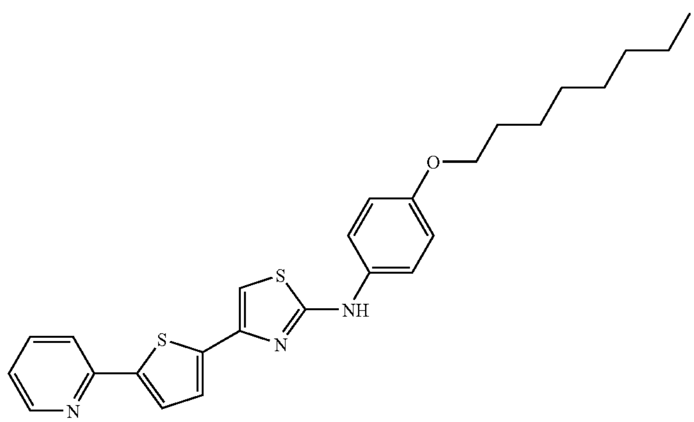 | N-(4-(octyloxy)phenyl)-4-(5-(pyridin-2-yl)thiophen-2-yl)thiazol-2-amine | +++ |
| 388 | 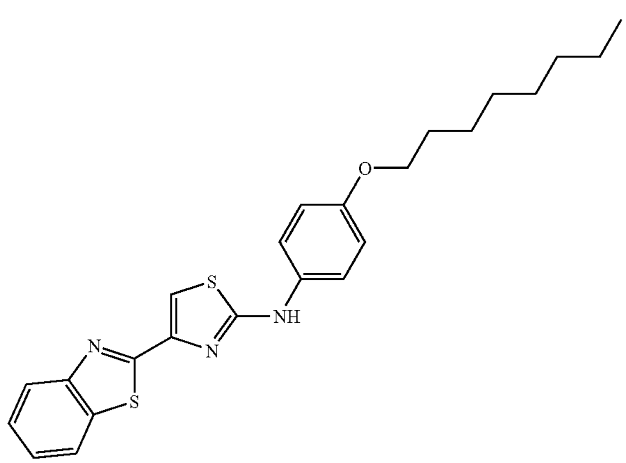 | 4-(benzo[d]thiazol-2-yl)-N-(4-(octyloxy)phenyl)thiazol-2-amine | +++ |

TABLE II-continued
| Cpd | Structure | Name | Activity |
|---|---|---|---|
| 389 | 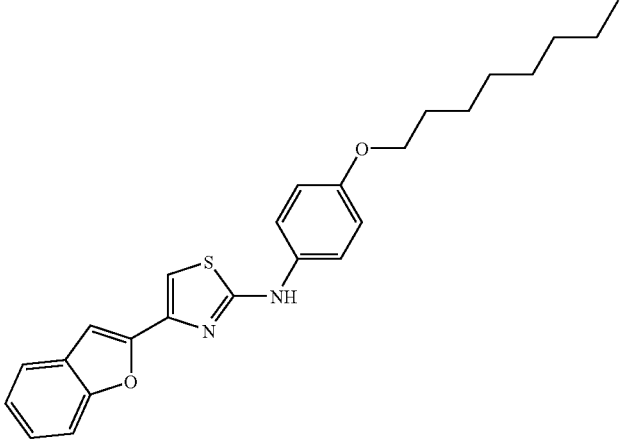 | 4-(benzofuran-2-yl)-N-94-(octyloxy)phenyl)thiazol-2-amine | +++ |
| 390 | 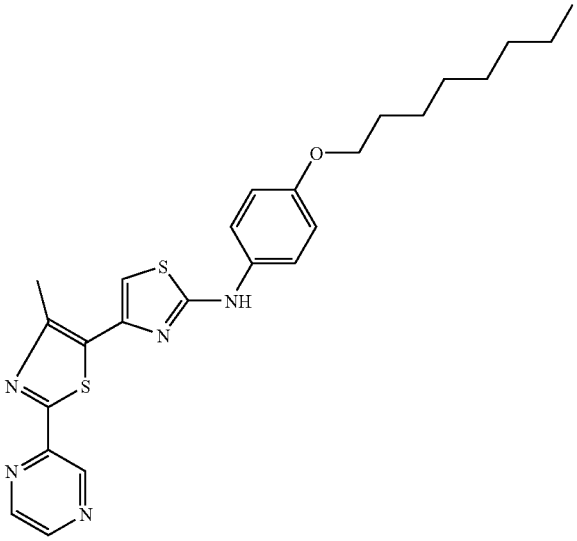 | 4-(4-methyl-2-(pyrazin-2-yl)thiazol-5-yl)-N-(4-(octyloxy)phenyl)thiazol-2-amine | +++ |
| 391 | 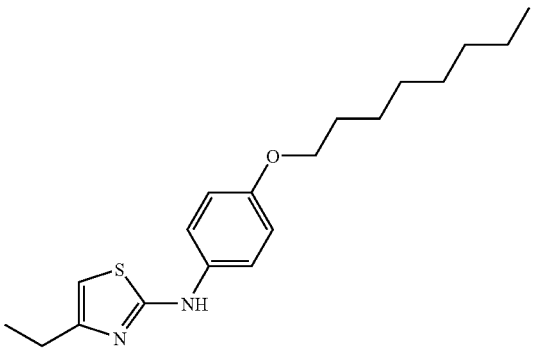 | 4-ethyl-N-(4-(octyloxy)phenyl)thiazol-2-amine | +++ |

TABLE II-continued

| Cpd | Structure | Name | Activity |
|---|---|---|---|
| 392 | 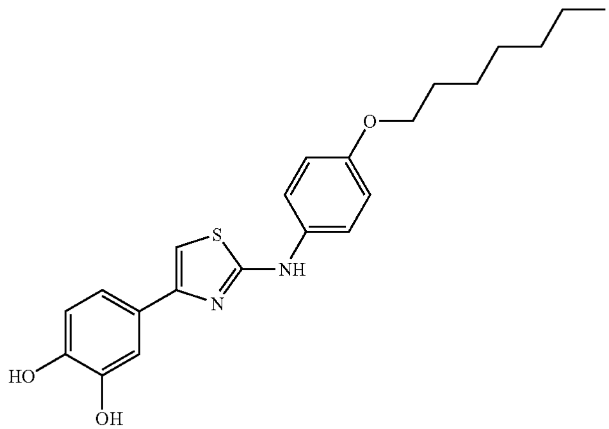 | 4-(2-(4-(heptyloxy)phenylamino)thiazol-4-yl)benzene-1,2-diol | +++ |
| 393 | 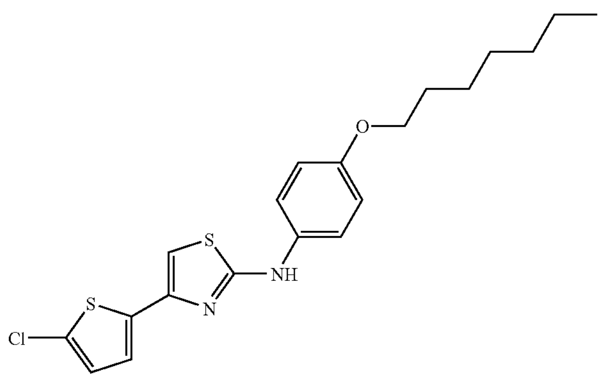 | 4-(5-chlorothiophen-2-yl)-N-(4-(heptyloxy)phenyl)thiazol-2-amine | +++ |
| 394 | 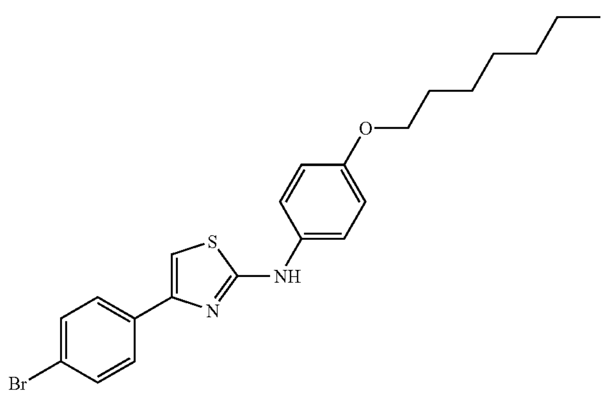 | 4-(4-bromophenyl)-N-(4-(heptyloxy)phenyl)thiazol-2-amine | +++ |
| 395 | 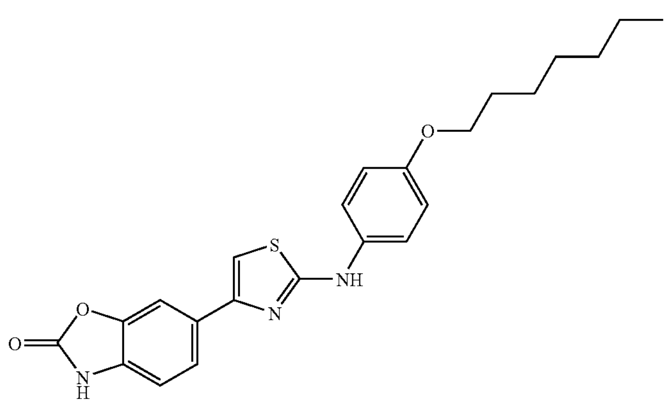 | 6-(2-(4-(heptyloxy)phenylamino)thiazol-4-yl)benzo[d]exazol-2(3H)-one | +++ |

TABLE II-continued
| Cpd | Structure | Name | Activity |
|---|---|---|---|
| 396 | 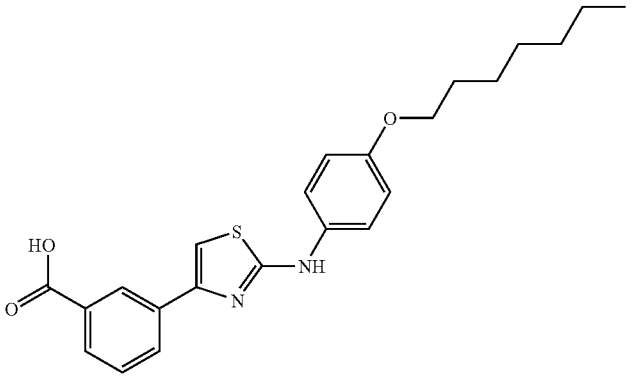 | 3-(2-(4-(heptyloxy)phenylamino)thiazol-4-yl)benzoic acid | +++ |
| 397 | 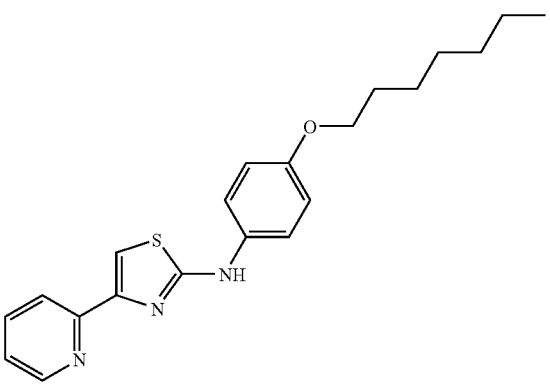 | N-(4-(heptyloxy)phenyl)-4-(pyridin-2-yl)thiazol-2-amine | +++ |
| 398 | 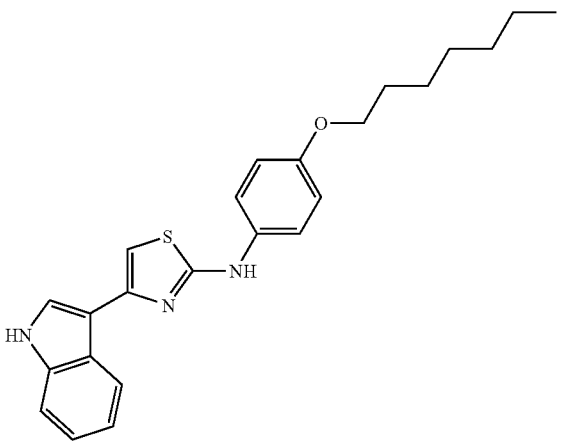 | N-(4-(heptyloxy)phenyl)-4-(1H-indol-3-yl)thiazol-2-amine | +++ |
| 399 | 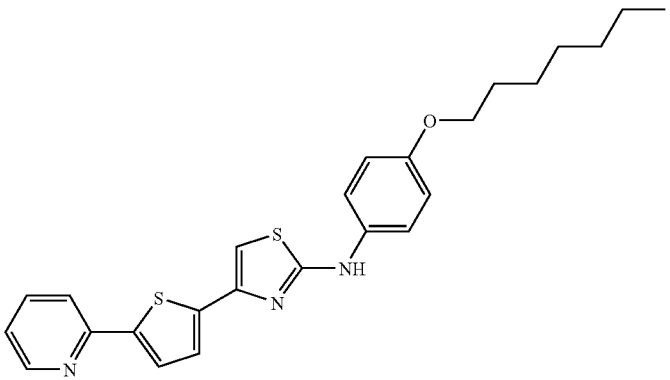 | N-(4-(heptyloxy)phenyl)-4-(5-(pyridin-2-yl)thiophen-2-yl)thiazol-2-amine | +++ |

TABLE II-continued

| Cpd | Structure | Name | Activity |
|---|---|---|---|
| 400 | 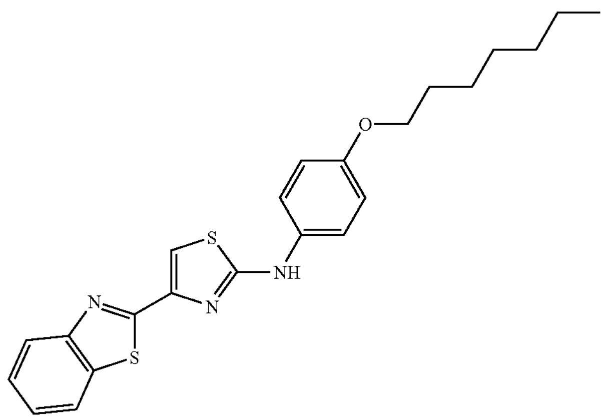 | 4-(benzo[d]thiazol-2-yl)-N-(4-(heptyloxy)phenyl)thiazol-2-amine | ++ |
| 401 | 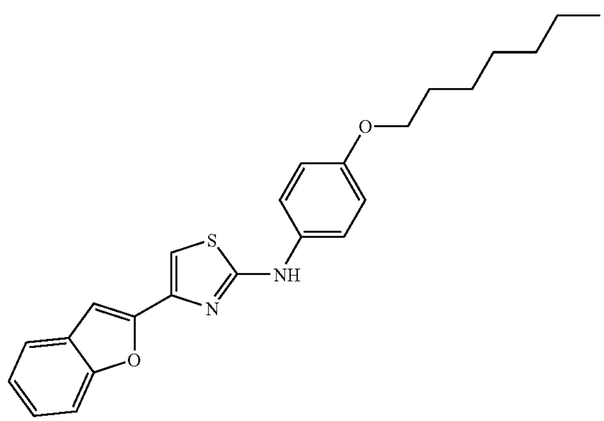 | 4-(benzofuran-2-yl)-N-(4-(heptyloxy)phenyl)thiazol-2-amine | ++ |
| 402 | 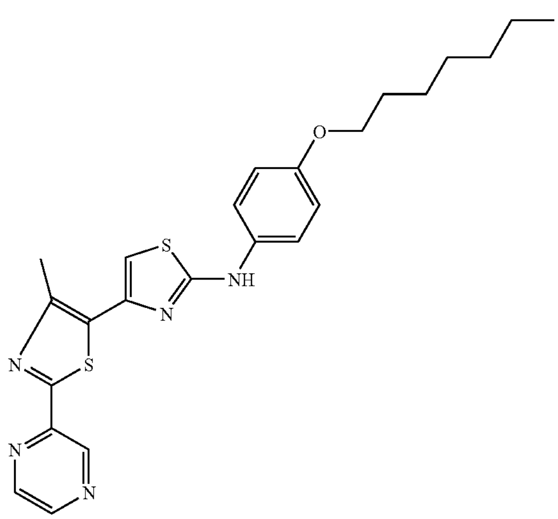 | N-(4-heptyloxy)phenyl)-4-(4-methyl-2-(pyrazin-2-yl)thiazol-5-yl)thiazol-2-amine | +++ |

TABLE II-continued

| Cpd | Structure | Name | Activity |
|---|---|---|---|
| 403 | 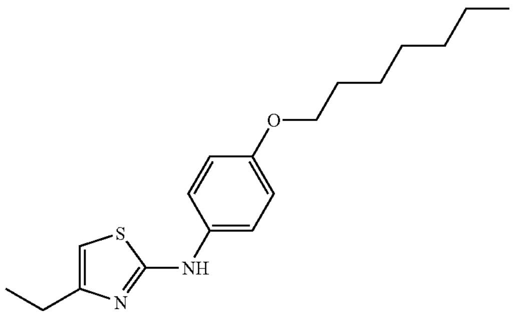 | 4-ethyl-N-(4-(heptyloxy)phenyl)thiazol-2-amine | +++ |
| 404 | 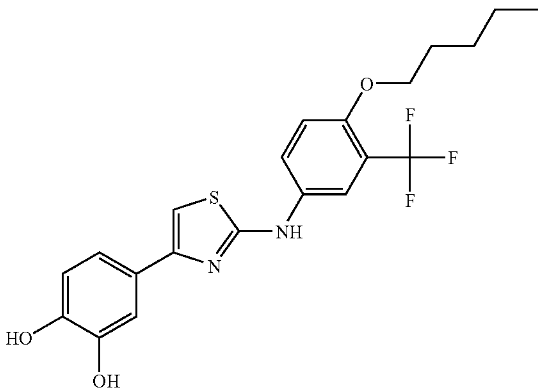 | 4-(2-(3-(trifluoromethyl)-4-(pentyloxy)phenylamino)thiazol-4-yl)benzene-1,2-diol | +++ |
| 405 | 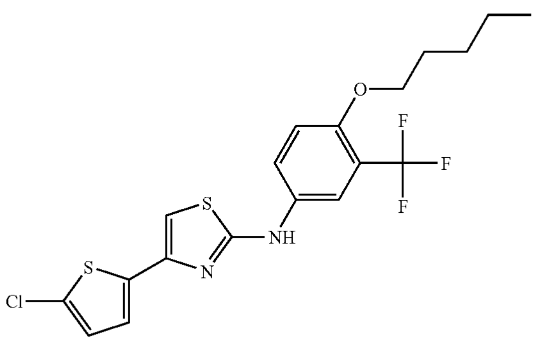 | 4-(5-chlorothiophen-2-yl)-N-(3-trifluoromethyl)-4-(pentyloxy)phenyl)thiazol-2-amine | +++ |
| 406 | 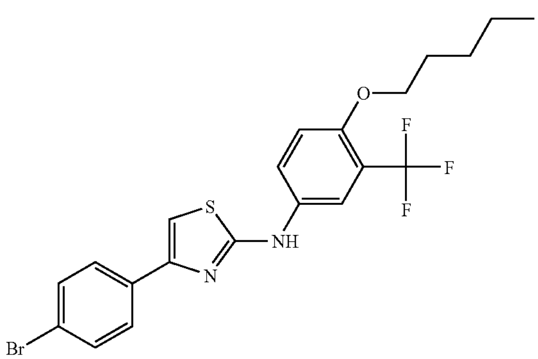 | 4-(4-bromophenyl)-N-(3-(trifluoromethyl)-4-(pentyloxy)phenyl)thiazol-2-amine | +++ |

TABLE II-continued

| Cpd | Structure | Name | Activity |
|---|---|---|---|
| 407 | 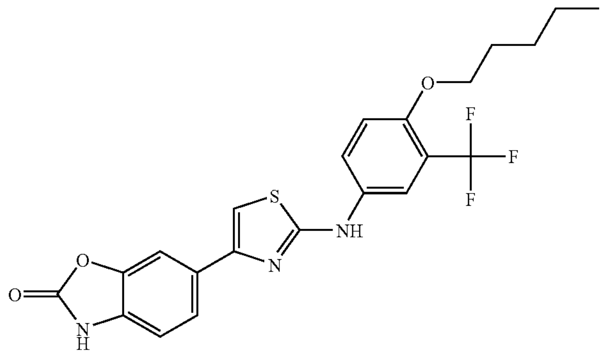 | 6-(2-(3-(trifluoromethyl)-4-(pentyloxy)phenylamino)thiazol-4-yl)benzo[d]oxazol-2(3H)-one | +++ |
| 408 | 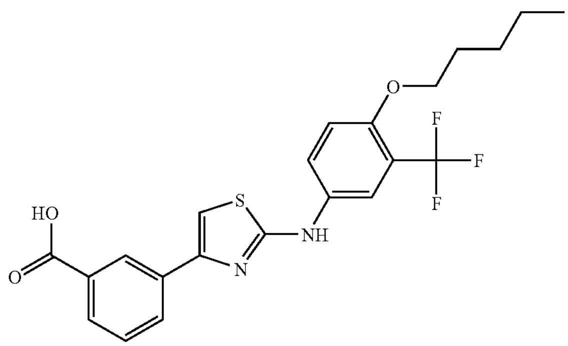 | 3-(2-(3-(trifluoromethyl)-4-(pentyloxy)phenylamino)thiazol-4-yl)benzoic acid | +++ |
| 409 | 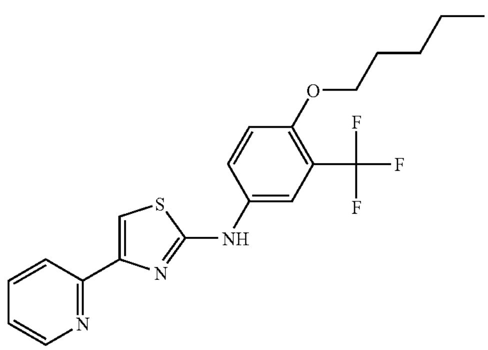 | N-(3-(trifluoromethyl)-4-(pentyloxy)phenyl)-4-(pyridin-2-yl)thiazol-2-amine | +++ |
| 410 | 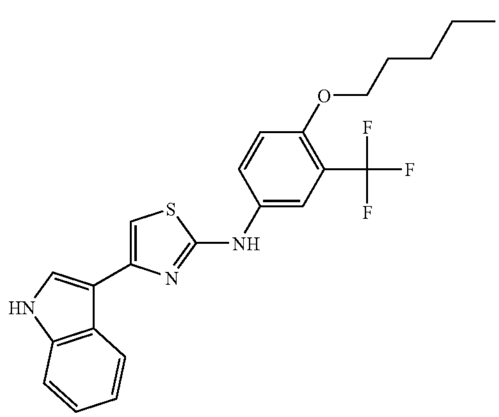 | N-(3-(trifluoromethyl)-4-(pentyloxy)phenyl)-4-(1H-indol-3-yl)thiazol-2-amine | +++ |

TABLE II-continued

| Cpd | Structure | Name | Activity |
|---|---|---|---|
| 411 | 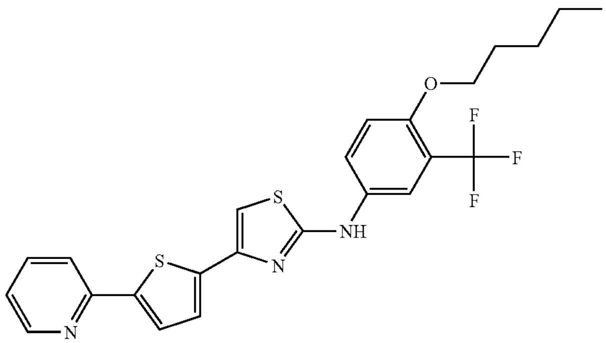 | N-(3-(trifluoromethyl)-4-(pentyloxy)phenyl)-4-(5-(pyridin-2-yl)thiophen-2-yl)thiazol-2-amine | +++ |
| 412 | 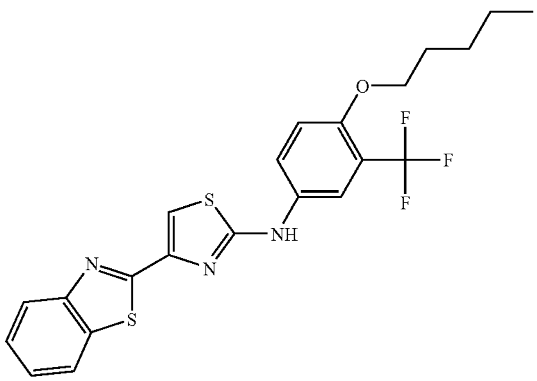 | 4-(benzo[d]thiazol-2-yl)-N-(3-(trifluoromethyl)-4-(pentyloxy)phenyl)thiazol-2-amine | +++ |
| 413 | 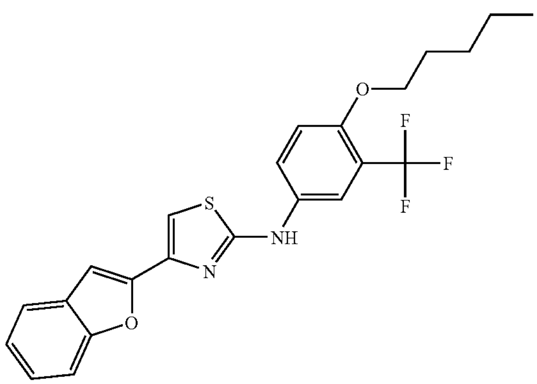 | 4-(benzofuran-2-yl)-N-(3-(trifluoromethyl)-4-(pentyloxy)phenyl)thiazol-2-amine | +++ |
| 414 | 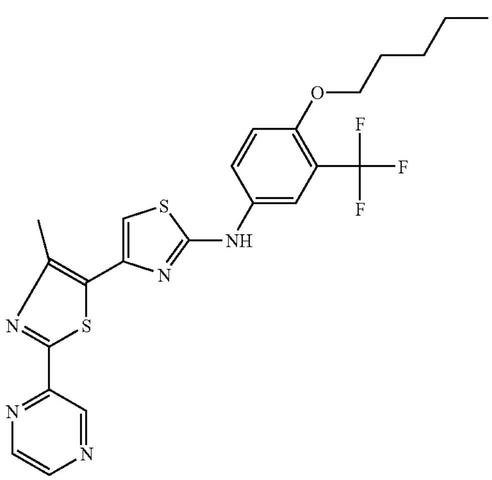 | N-(3-(trifluoromethyl)-4-(pentyloxy)phenyl)-4-(4-methyl-2-(pyrazin-2-yl)thiazol-5-yl)thiazol-2-amine | +++ |

TABLE II-continued

| Cpd | Structure | Name | Activity |
|---|---|---|---|
| 415 | 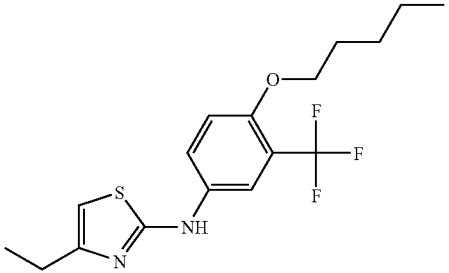 | 4-ethyl-N-(3-(trifluoromethyl)-4-(pentyloxy)phenyl)thiazol-2-amine | +++ |
| 416 | 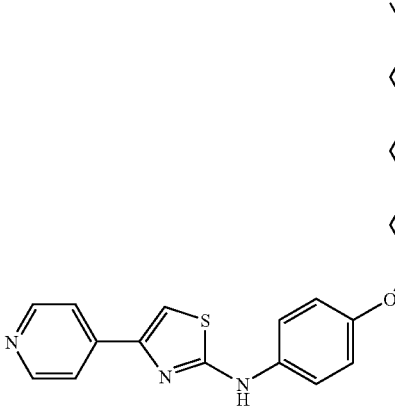 | N-(4-(octyloxy)phenyl)-4-(pyridin-4-yl)thiazol-2-amine | +++ |
| 417 | 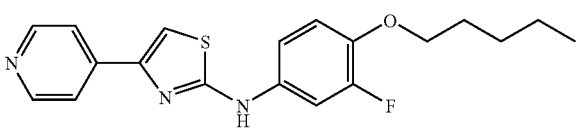 | N-(3-fluoro-4-(pentyloxy)phenyl)-4-(pyridin-4-yl)thiazol-2-amine | ++ |
| 418 | 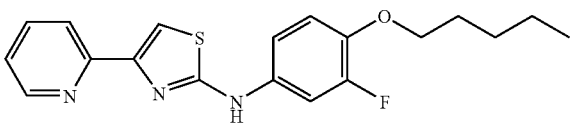 | N-(3-fluoro-4-(pentyloxy)phenyl)-4-(pyridin-2-yl)thiazol-2-amine | +++ |
| 419 | 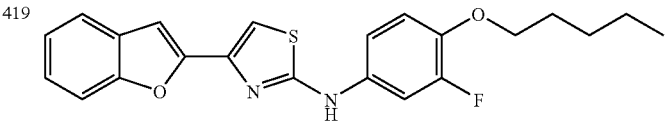 | 4-(benzofuran-2-yl)-N-(3-fluoro-4-(pentyloxy)phenyl)thiazol-2-amine | ++ |
| 420 | 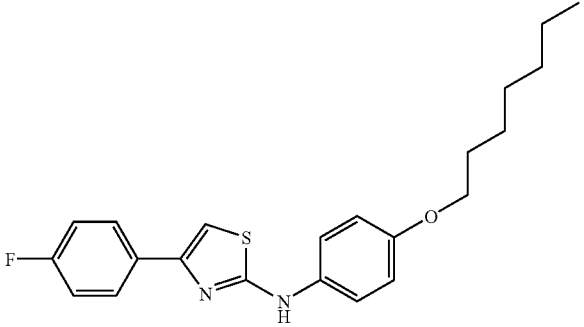 | 4-(4-fluorophenyl)-N-(4-(heptyloxy)phenyl)thiazol-2-amine | +++ |

TABLE II-continued

| Cpd | Structure | Name | Activity |
|---|---|---|---|
| 421 | 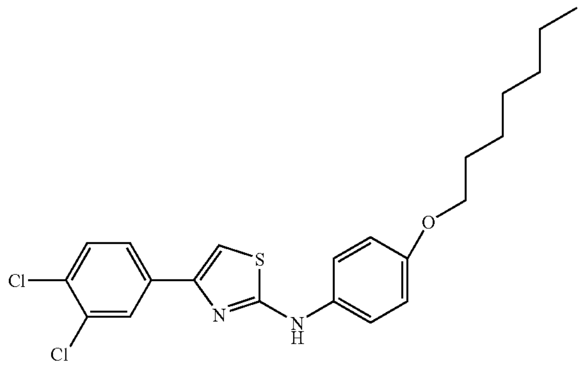 | 4-(3,4-dichlorophenyl)-N-(4-(heptyloxy)phenyl)thiazol-2-amine | +++ |
| 422 | 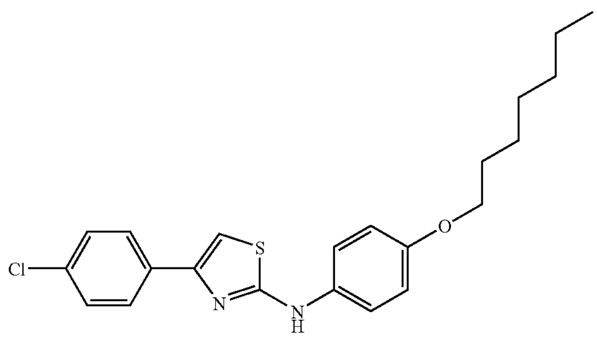 | 4-(4-chlorophenyl)-N-(4-(heptyloxy)phenyl)thiazol-2-amine | +++ |
| 423 | 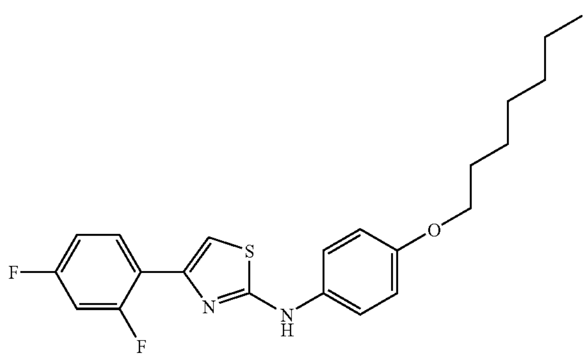 | 4-(2,4-difluorophenyl)-N-(4-(heptyloxy)phenyl)thiazol-2-amine | +++ |
| 424 | 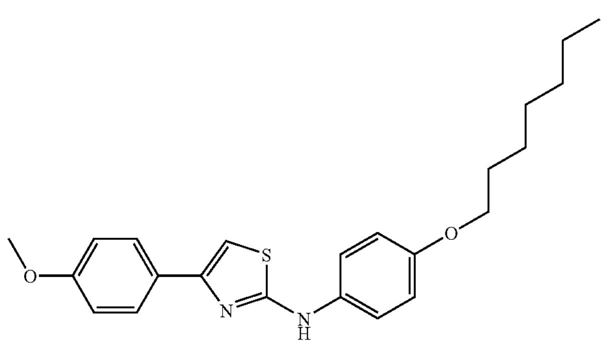 | N-(4-(heptyloxy)phenyl)-4-(4-methoxyphenyl)thiazol-2-amine | +++ |

TABLE II-continued

| Cpd | Structure | Name | Activity |
|---|---|---|---|
| 425 | 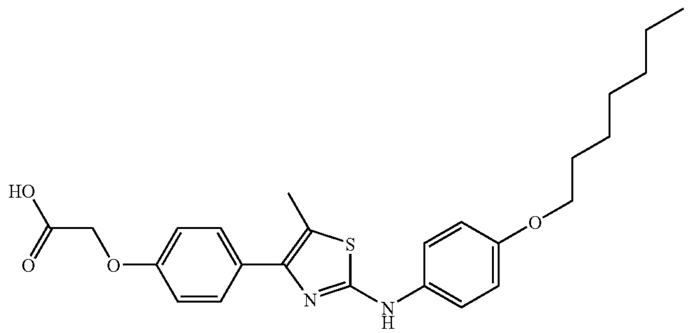 | 2-(4-(2-(4-(heptyloxy)phenylamino)-5-methylthiazol-4-yl)phenoxy)acetic acid | +++ |
| 426 | 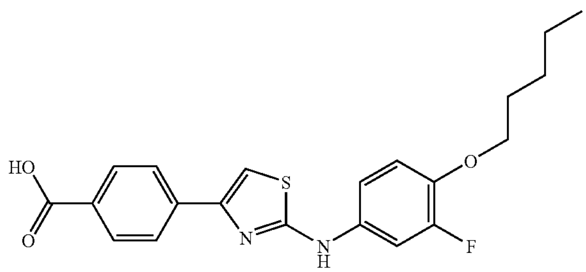 | 4-(2-(3-fluoro-4-(pentyloxy)phenylamino)thiazol-4-yl)benzoic acid | ++ |
| 427 | 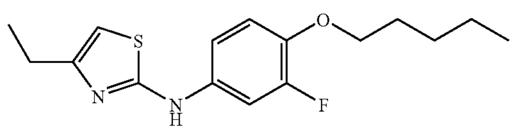 | 4-ethyl-N-(3-fluoro-4-(pentyloxy)phenyl)thiazol-2-amine | ++ |
| 428 | 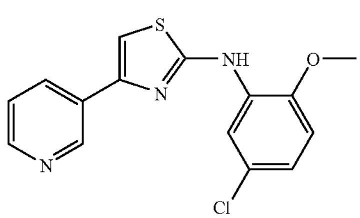 | N-(5-chloro-2-methoxyphenyl)-4-(pyridin-3-yl)thiazol-2-amine | ++ |
| 429 | 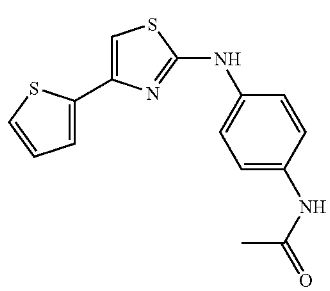 | N-(4-(4-(thiophen-2-yl)thiazol-2-ylamino)phenyl)acetamide | + |
| 430 | 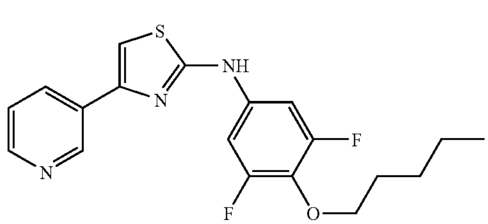 | N-(3,5-difluoro-4-(pentyloxy)phenyl)-4-(pyridin-3-yl)thiazol-2-amine | +++ |

TABLE II-continued

| Cpd | Structure | Name | Activity |
|---|---|---|---|
| 431 | 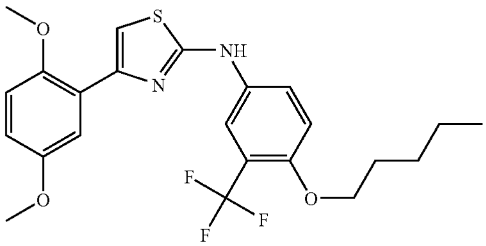 | N-(3-(trifluoromethyl)-4-(pentyloxy)phenyl)-4-(2,5-dimethoxyphenyl)thiazol-2-amine | ++ |
| 432 | 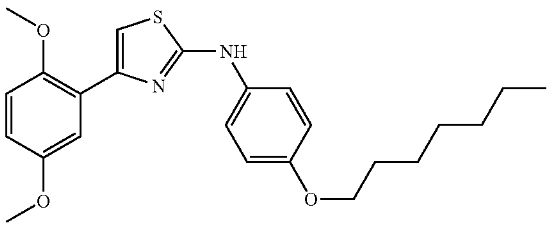 | N-(4-(heptyloxy)phenyl)-4-(2,5-dimethoxyphenyl)thiazol-2-amine | +++ |
| 433 | 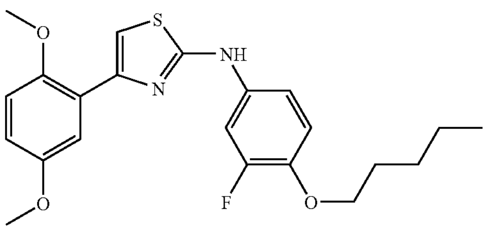 | N-(3-fluoro-4-(pentyloxy)phenyl)-4-(2,5-dimethoxyphenyl)thiazol-2-amine | +++ |
| 434 | 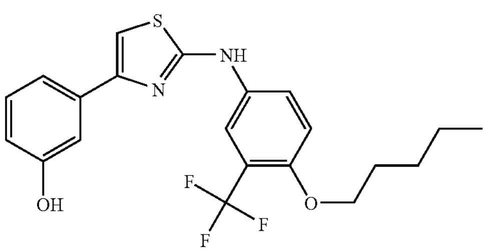 | 3-(2-(3-(trifluoromethyl)-4-(pentyloxy)phenylmino)thiazol-4-yl)phenol | ++ |
| 435 | 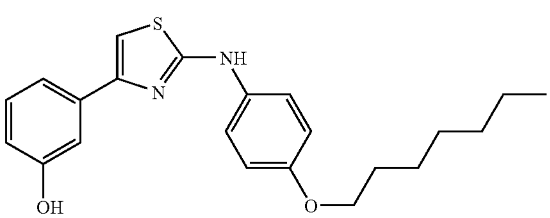 | 3-(2-(4-(heptyloxy)phenylamino)thiazol-4-yl)phenol | +++ |
| 436 | 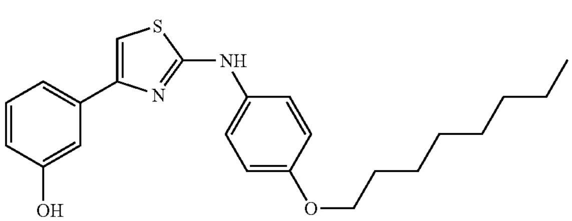 | 3-(2-(4-(octyloxy)phenylamino)thiazol-4-yl)phenol | +++ |
| 437 | 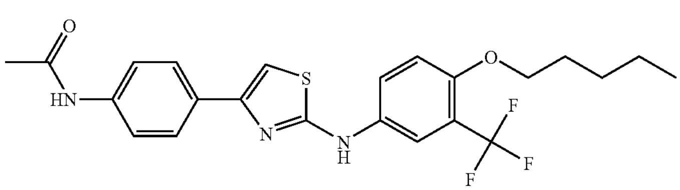 | N-(4-(2-(3-(trifluoromethyl)-4-(pentyloxy)phenylamino)thiazol-4-yl)phenyl)acetamide | ++ |

TABLE II-continued

| Cpd | Structure | Name | Activity |
|---|---|---|---|
| 438 | 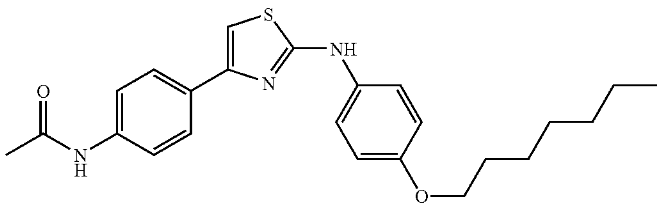 | N-(4-(2-(4-(heptyloxy)phenylamino)thiazol-4-yl)phenyl)acetamide | +++ |
| 439 | 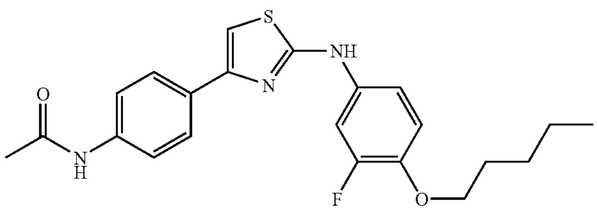 | N-(4-(2-(3-fluoro-4-(pentyloxy)phenylamino)thiazol-4-yl)phenyl)acetamide | +++ |
| 440 | 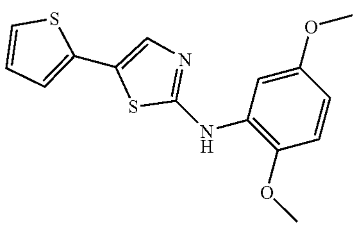 | N-(2,5-dimethoxyphenyl)-5-(thiophen-2-yl)thiazol-2-amine | ++ |
| 441 | 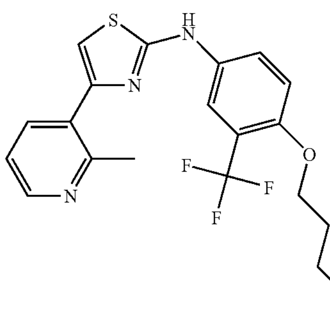 | N-(3-(trifluoromethyl)-4-(pentyloxy)phenyl)-4-(2-methylpyridin-3-yl)thiazol-2-amine | +++ |
| 442 | 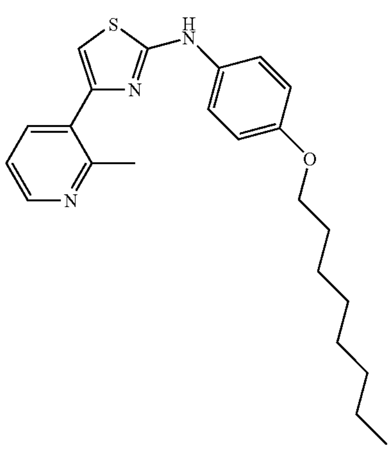 | 4-(2-methylpyridin-3-yl)-N-(4-(octyloxy)phenyl)thiazol-2-amine | +++ |

TABLE II-continued

| Cpd | Structure | Name | Activity |
|---|---|---|---|
| 443 | 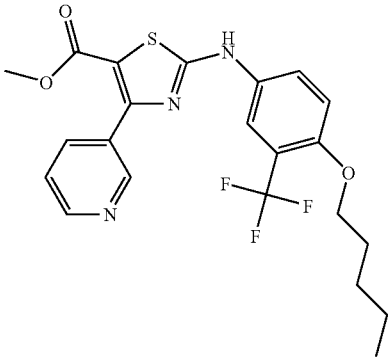 | methyl 2-(3-(trifluoromethyl)-4-(pentyloxy)phenylamino)-4-(pyridin-3-yl)thiazol-5-carboxylate | +++ |
| 444 | 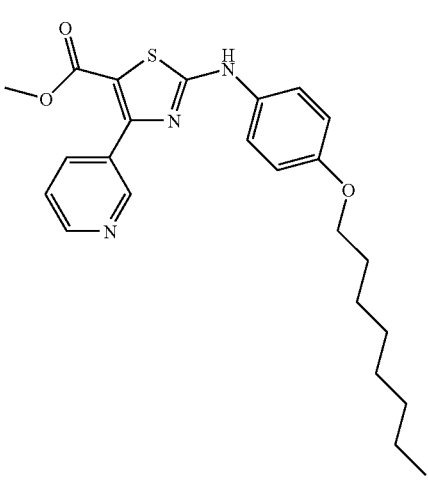 | meethyl 2-(4-(octyloxy)pheenylamino)-4-(pyridin-3-yl)thiazol-5-carboxylate | ++ |
| 445 | 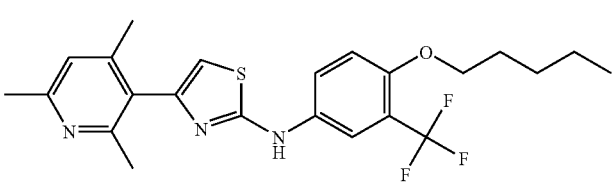 | N-(3-(trifluoromethyl)-4-(pentyloxy)phenyl)-4-(2,4,6-trimethylpyridin-3-yl)thiazol-2-amine | + |
| 446 | 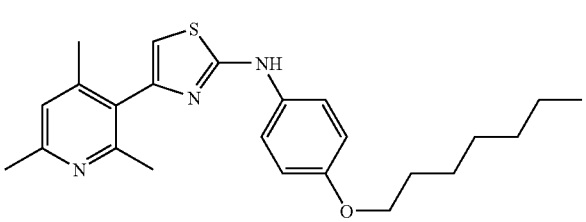 | N-(4-(heptyloxy)phenyl)-4-(2,4,6-trimethylpyridin-3-yl)thiazol-2-amine | + |
| 447 | 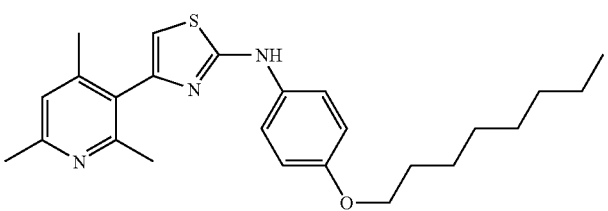 | 4-(2,4,6-trimethylpyridin-3-yl)-N-(4-(octyloxy)phenyl)thiazol-2-amine | + |

TABLE II-continued

| Cpd | Structure | Name | Activity |
|---|---|---|---|
| 448 | 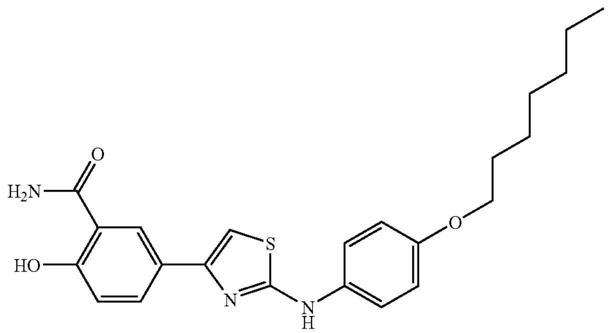 | 5-(2-(4-(heptyloxy)phenylamino)thiazol-4-yl)-2-hydroxybenzamide | +++ |
| 449 | 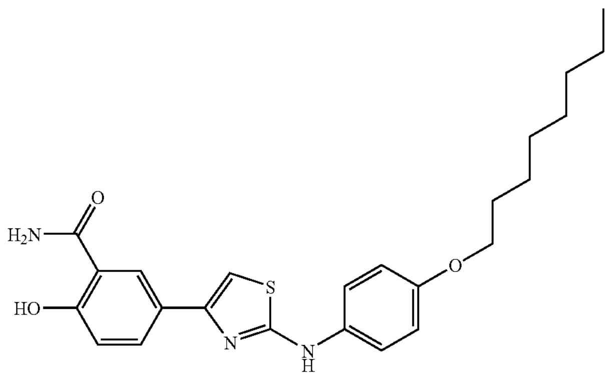 | 5-(2-(4-(octyloxy)phenylamino)thiazol-4-yl)-2-hydroxybenzamide | +++ |
| 450 | 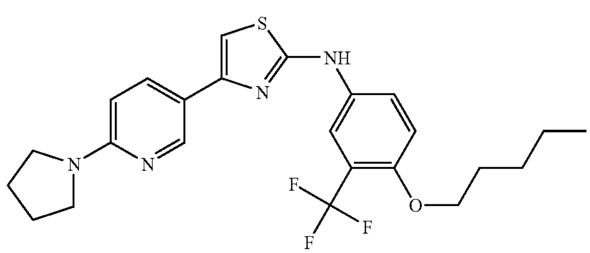 | N-(3-(trifluoromethyl)-4-(pentyloxy)phenyl-4-(6-(pyrrolidin-1-yl)pyridin-3-yl)thiazol-2-amine | +++ |
| 451 | 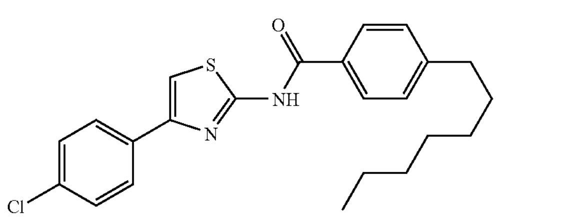 | N-(4-(4-chlorophenyl)thiazol-2-yl)-4-heptylbenzamide | +++ |
| 452 | 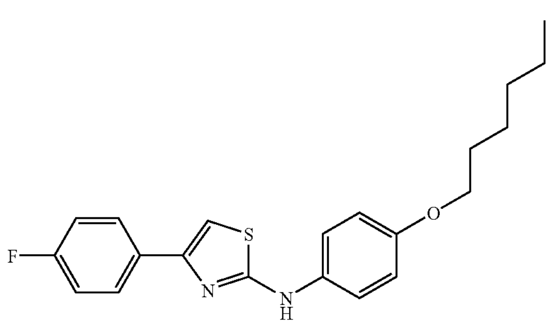 | 4-(4-fluorophenyl)-N-(4-(hexyloxy)phenyl)thiazol-2-amine | +++ |

TABLE II-continued

| Cpd | Structure | Name | Activity |
|---|---|---|---|
| 453 | 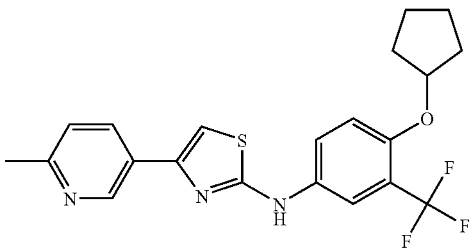 | N-(4-(cyclopentyloxy)-3-(trifluoromethyl)phenyl)-4-(6-methylpyridin-3-yl)thiazol-2-amine | +++ |
| 454 | 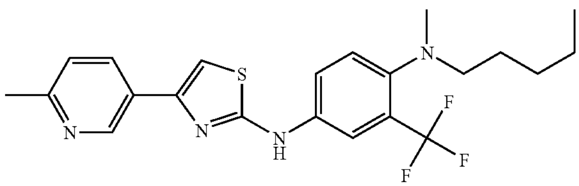 | 2-(trifluoromethyl)-$N^1$-methyl-$N^4$-(4-(6-methylpyridin-3-yl)thiazol-2-yl)-$N^1$-pentylbenzene-1,4-diamine | +++ |
| 455 | 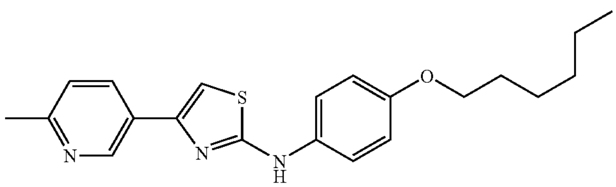 | N-(4-(hexyloxy)phenyl)-4-(6-methylpyridin-3-yl)thiazol-2-amine | +++ |
| 456 | 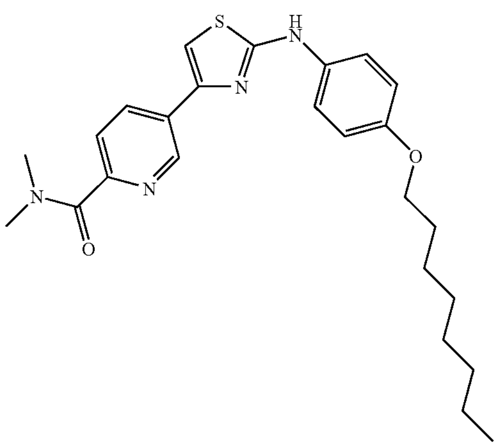 | 5-(2-(4-(octyloxy)phenylamino)thiazol-4-yl)-N,N-dimethylpyridine-2-carboxamide | ++ |
| 457 | 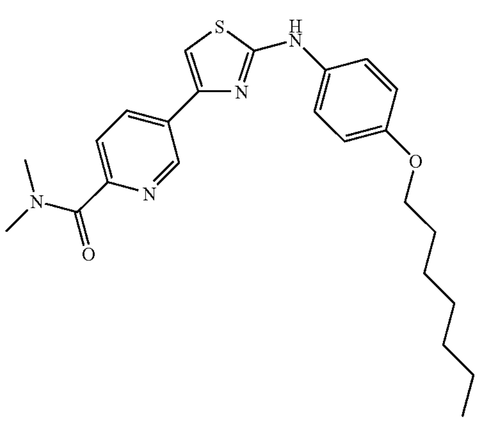 | 5-(2-(4-(heptyloxy)phenylamino)thiazol-4-yl)-N,N-dimethylpyridine-2-carboxamide | ++ |

TABLE II-continued

| Cpd | Structure | Name | Activity |
|---|---|---|---|
| 458 | 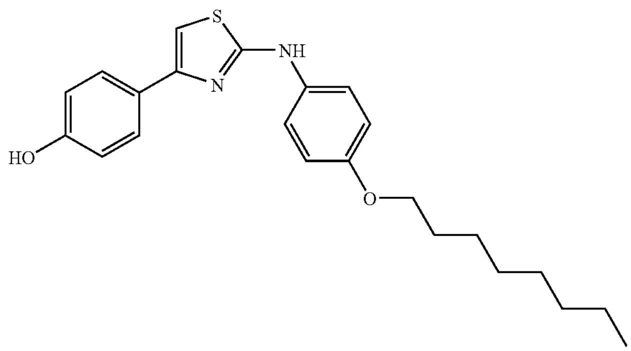 | 4-(2-(4-(octyloxy)phenylamino)thiazol-4-yl)phenol | +++ |
| 459 | 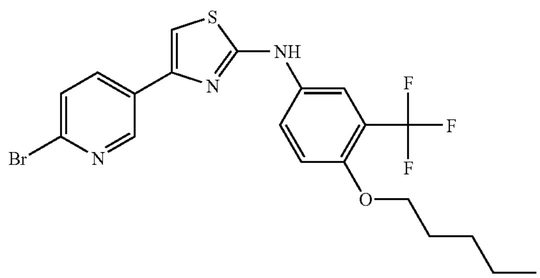 | 4-(6-bromopyridin-3-yl)-N-(3-(trifluoromethyl)-4-(pentyloxy)phenyl)thiazol-2-amine | +++ |
| 460 | 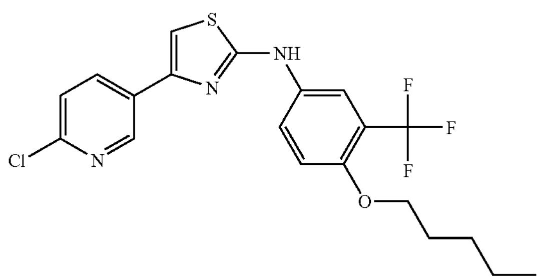 | 4-(6-chloropyridin-3-yl)-N-(3-(trifluoromethyl)-4-(pentyloxy)phenyl)thiazol-2-amine | +++ |
| 461 | 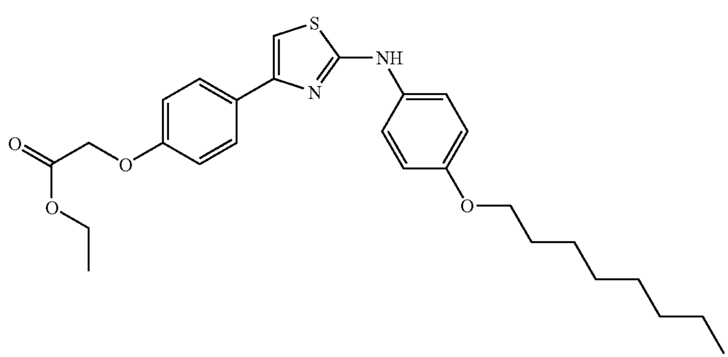 | ethyl 2-(4-(2-(4-(octyloxy)phenylamino)thiazol-4-yl)phenoxy)acetate | +++ |
| 462 | 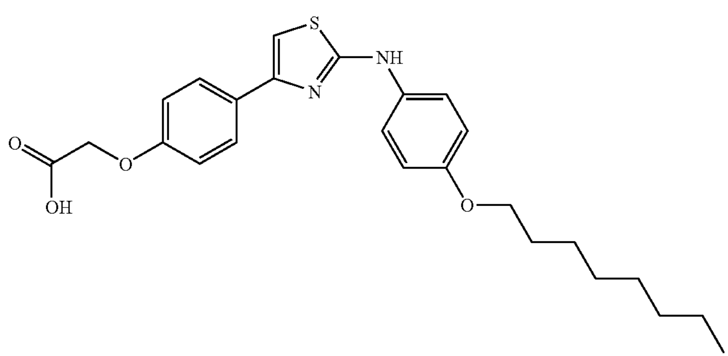 | 2-(4-(2-(4-(octyloxy)phenylamino)thiazol-4-yl)phenoxy)acetic acid | +++ |

TABLE II-continued

| Cpd | Structure | Name | Activity |
|---|---|---|---|
| 463 | 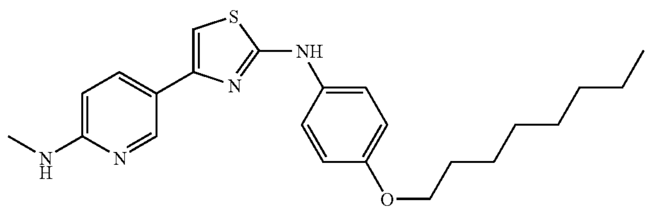 | 5-(2-(4-(octyloxy)phenylamino)thiazol-4-yl)-N-meethylpyridin-2-amine | +++ |
| 464 | 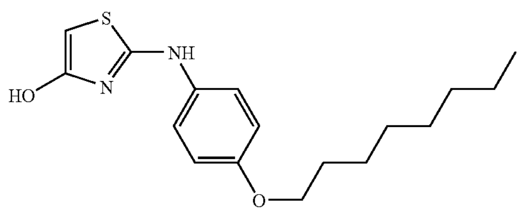 | 2-(4-(octyloxy)phenylamino)thiazol-4-ol | ++ |
| 465 | 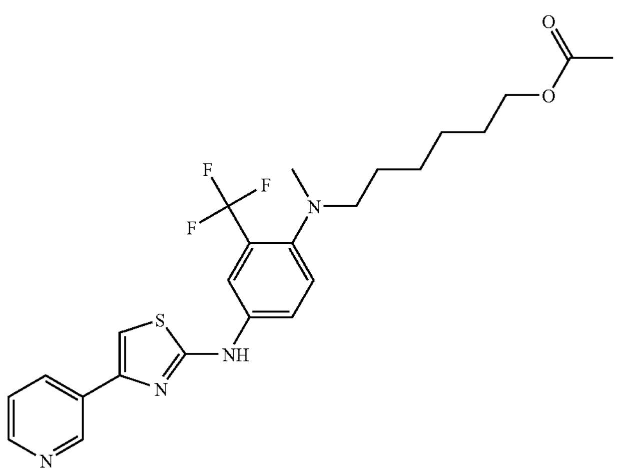 | CHEMDRAW COULD NOT NAME STRUCTURE | ++ |
| 466 | 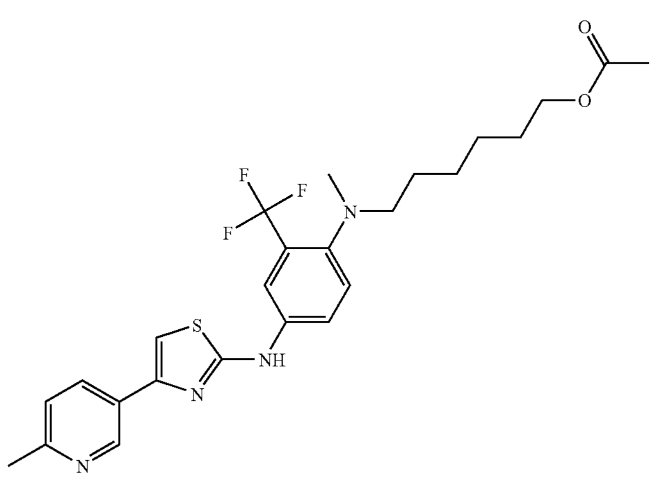 | CHEMDRAW COULD NOT NAME STRUCTURE | ++ |

TABLE II-continued

| Cpd | Structure | Name | Activity |
|-----|-----------|------|----------|
| 467 | 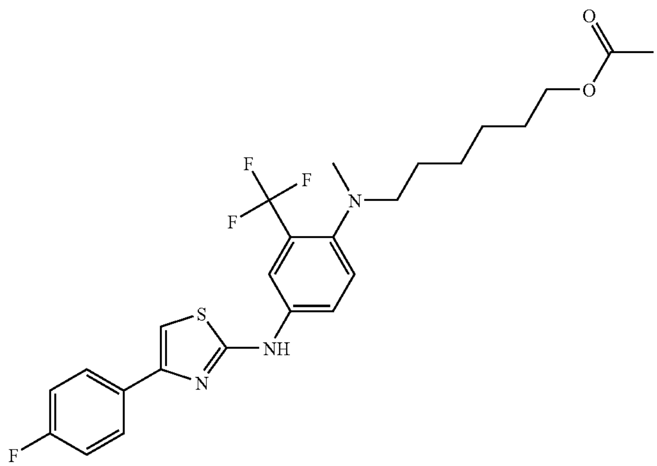 | | + |
| 468 | 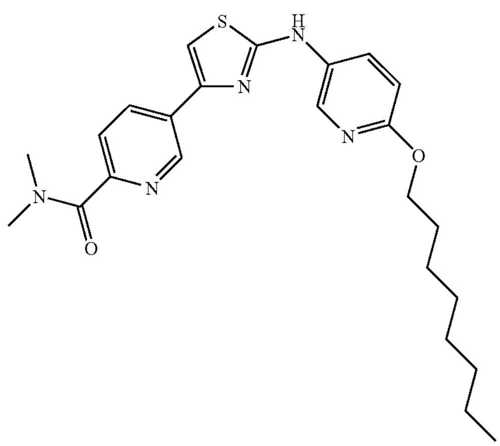 | 5-(2-(6-(octyloxy)pyridin-3-ylamino)thiazol-4-yl)-N,N-dimethylpyridine-2-carboxamide | ++ |
| 469 | 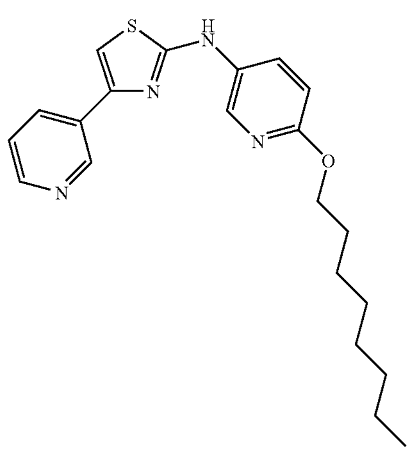 | 6-(octyloxy)-N-0(4-(pyridin-3-yl)thiazol-2-yl)pyridin-3-amine | ++ |

TABLE II-continued

| Cpd | Structure | Name | Activity |
|---|---|---|---|
| 470 | 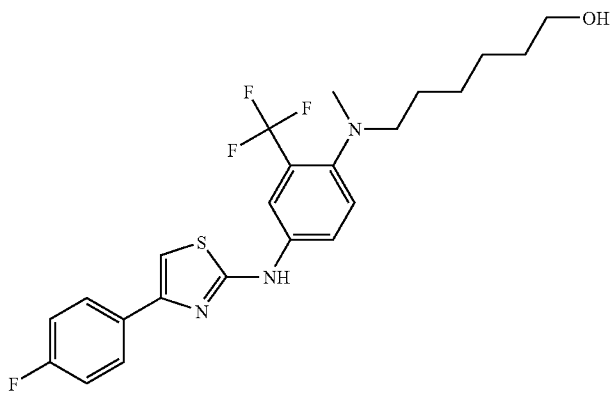 | 6-(N-(4-(4-(4-fluorophenyl)thiazol-2-ylamino)-2-(trifluoromethyl)phenyl)-N-methylamino)hexan-1-ol | ++ |
| 471 | 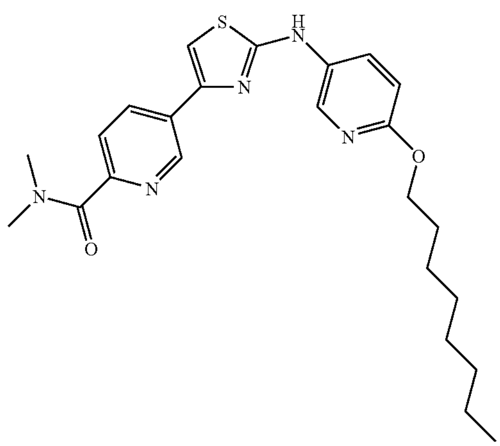 | 5-(2-(6-(octyloxy)pyridin-3-ylamino)thiazol-4-yl)-N,N-dimethylpyridine-2-carboxamide | +++ |
| 472 | 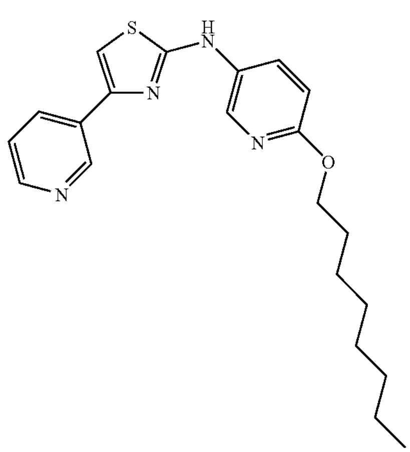 | 6-(octyloxy)-N-(4-(pyridin-3-yl)thiazol-2-yl)pyridin-3-amine | +++ |

TABLE II-continued

| Cpd | Structure | Name | Activity |
|---|---|---|---|
| 473 | 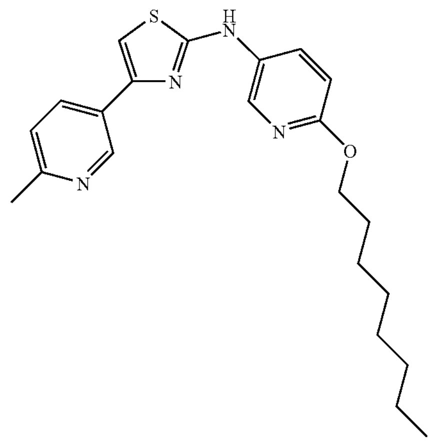 | N-(4-(6-methylpyridin-3-yl)thiazol-2-yl)-6-(octyloxy)pyridin-3-amine | +++ |
| 474 | 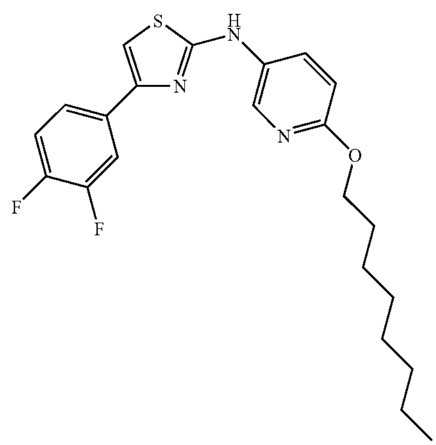 | N-(4-(3,4-difluorophenyl)thiazol-2-yl)-6-(octyloxy)pyridin-3-amine | +++ |
| 475 | 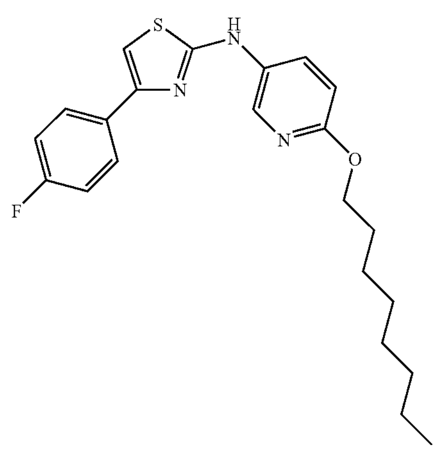 | N-(4-(4-fluorophenyl)thiazol-2-yl)-6-(octyloxy)pyridin-3-amine | +++ |

TABLE II-continued

| Cpd | Structure | Name | Activity |
|---|---|---|---|
| 476 | 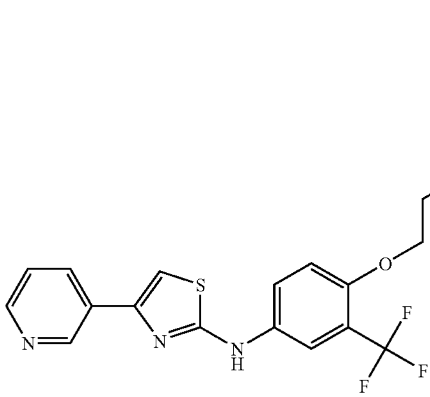 | N-(3-(trifluoromeethyl)-4-(octyloxy)phenyl)-4-(pyridin-3-yl)thiazol-2-amine | +++ |
| 477 | 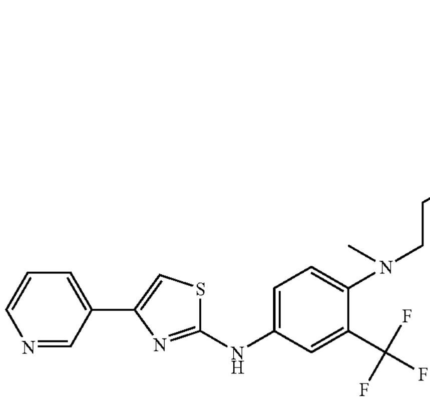 | 2-(trifluoromethyl)-N$^1$-methyl-N$^1$-octyl-N$^4$-(4-(pyridin-3-yl)thiazol-2-yl)benzene-1,4-diamine | +++ |
| 478 | 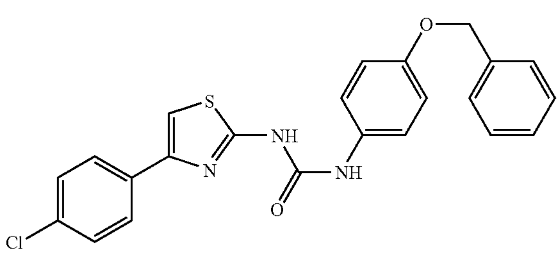 | 1-(4-(benzyloxy)phenyl)-3-(4-(4-chlorophenyl)thiazol-2-yl)urea | ++ |
| 479 | 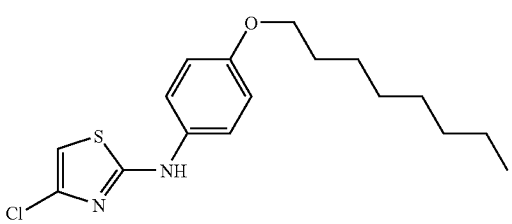 | 4-chloro-N-(4-(octyloxy)phenyl)thiazol-2-amine | +++ |

TABLE II-continued

| Cpd | Structure | Name | Activity |
|-----|-----------|------|----------|
| 480 | 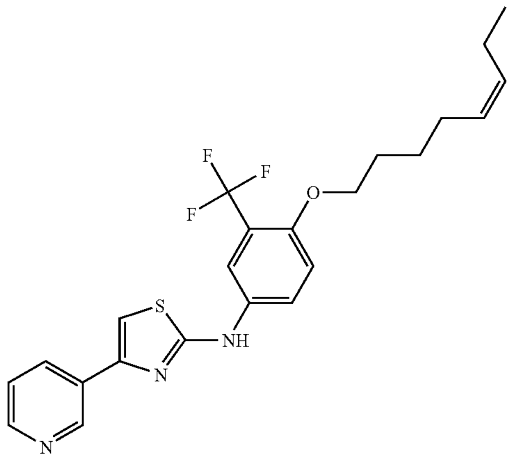 | N-(4-((Z)-oct-5-enyloxy)-3-(trifluoromethyl)phenyl)-4-(pyridin-3-yl)thiazol-2-amine | +++ |
| 481 | 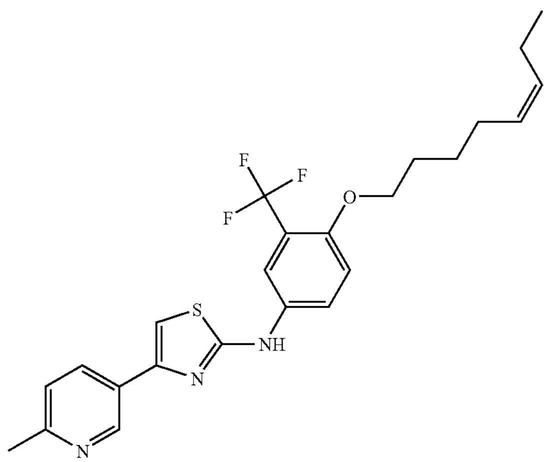 | N-(4-((Z)-oct-5-enyloxy)-3-(trifluoromethyl)phenyl)-4-(6-methylpyridin-3-yl)thiazol-2-amine | +++ |
| 482 | 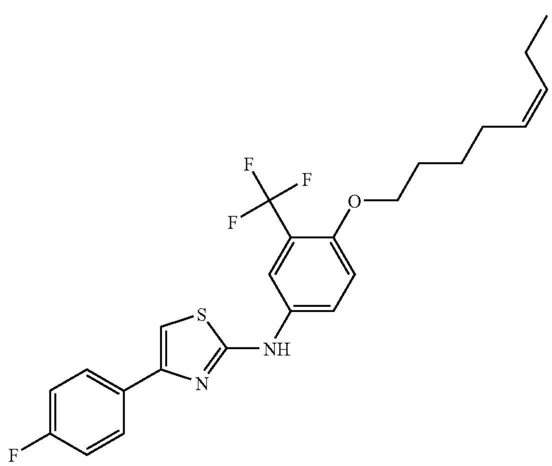 | N-(4-((Z)-oct-5-enyloxy)-3-(trifluoromethyl)phenyl)-4-(4-fluorophenyl)thiazol-2-amine | +++ |
| 483 | 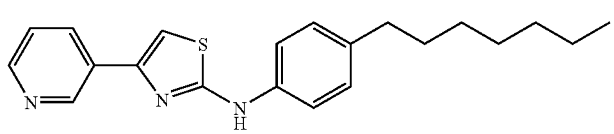 | N-(4-heptylphenyl)-4-(pyridin-3-yl)thiazol-2-amine | +++ |

TABLE II-continued

| Cpd | Structure | Name | Activity |
|---|---|---|---|
| 484 | 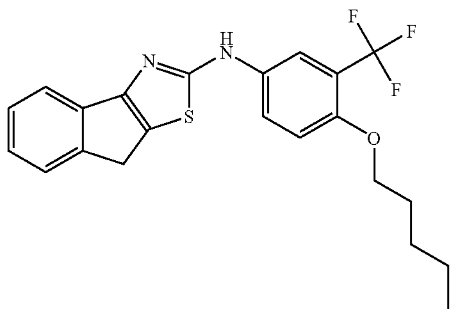 | N-(3-(trifluoromethyl)-4-(pentyloxy)phenyl)-8H-indeno[1,2-d]thiazol-2-amine | +++ |
| 485 | 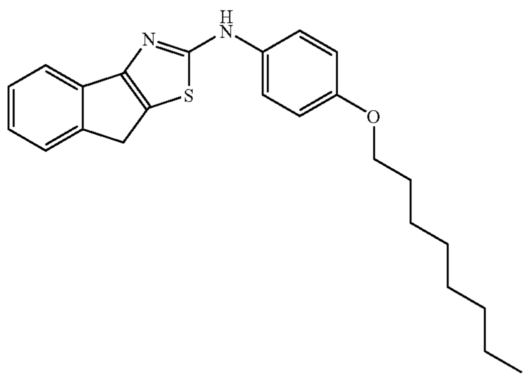 | N-(4-(octyloxy)phenyl)-8H-indeno[1,2-d]thiazol-2-amine | +++ |
| 486 | 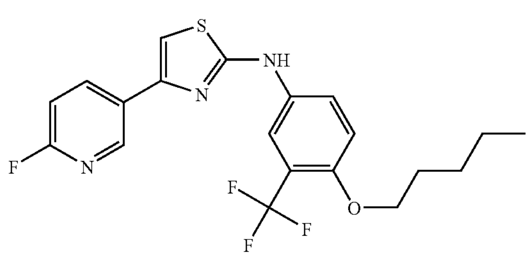 | N-(3-(trifluoromethyl)-4-(pentyloxy)phenyl)-4-(6-fluoropyridin-3-yl)thiazol-2-amine | +++ |
| 487 | 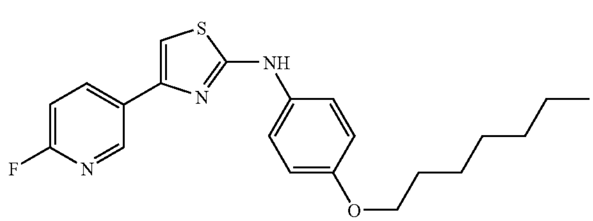 | 4-(6-fluoropyridin-3-yl)-N-(4-(heptyloxy)phenyl)thiazol-2-amine | +++ |
| 488 | 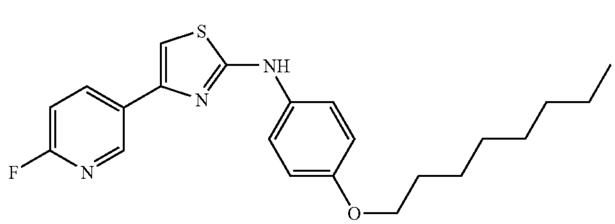 | 4-(6-fluoropyridin-3-yl)-(4-(octyloxy)phenyl)thiazol-2-amine | +++ |

TABLE II-continued

| Cpd | Structure | Name | Activity |
|---|---|---|---|
| 489 | 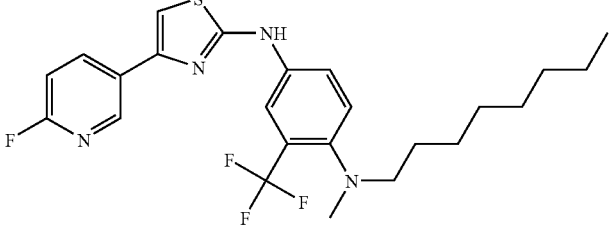 | 2-(trifluoromethyl)-$N^4$-(4-(6-fluoropyridin-3-yl)thiazol-2-yl)-$N^1$-methyl-$N^1$-octylbenzene-1,4-diamine | +++ |
| 490 | 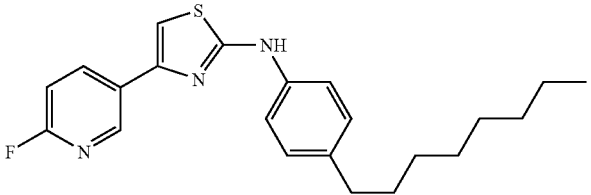 | 4-(6-fluoropyridin-3-yl)-N-(4-octylphenyl)thiazol-2-amine | +++ |
| 491 | 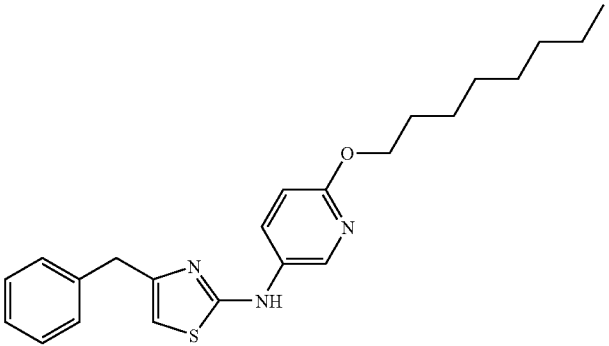 | N-(4-benzylthiazol-2-yl)-6-(octyloxy)pyridin-3-amine | ++ |
| 492 | 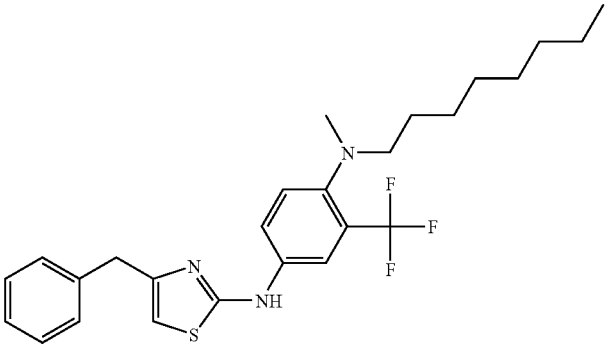 | $N^4$-(4-benzylthiazol-2-yl)-2-(trifluoromethyl)-$N^1$-methyl-$N^1$-octylbenzene-1,4-diamine | ++ |
| 493 | 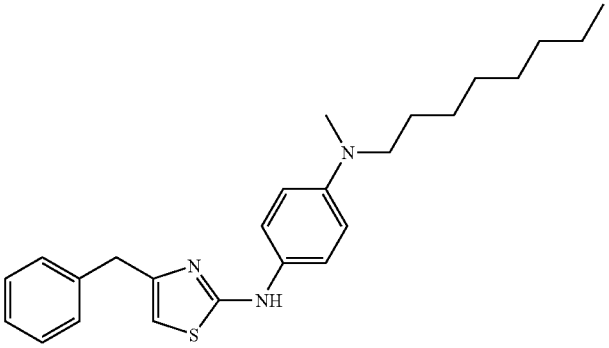 | $N^1$-(4-benzylthiazol-2-yl)-$N^4$-methyl-$N^4$-octylbenzene-1,4-diamine | ++ |

TABLE II-continued

| Cpd | Structure | Name | Activity |
|---|---|---|---|
| 494 | 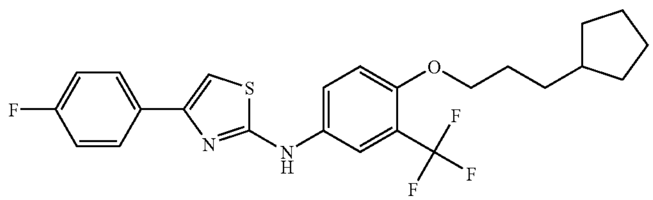 | N-(4-(3-cyclopentylpropoxy)-3-(trifluoromethyl)phenyl)-4-(4-fluorophenyl)thiazol-2-amine | +++ |
| 495 | 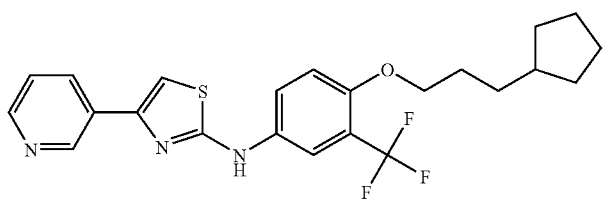 | N-(4-(3-cyclopentylpropoxy)-3-(trifluoromethyl)phenyl)-4-(pyridin-3-yl)thiazol-2-amine | +++ |
| 496 | 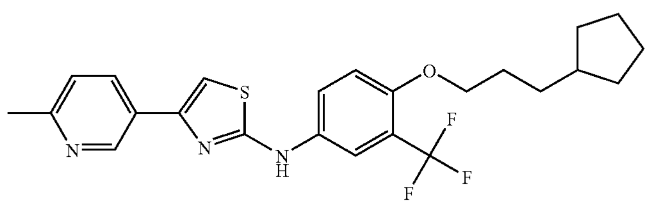 | N-(4-(3-cyclopentylpropoxy)-3-(trifluoromethyl)phenyl)-4-(6-methylpyridin-3-yl)thiazol-2-amine | +++ |
| 497 | 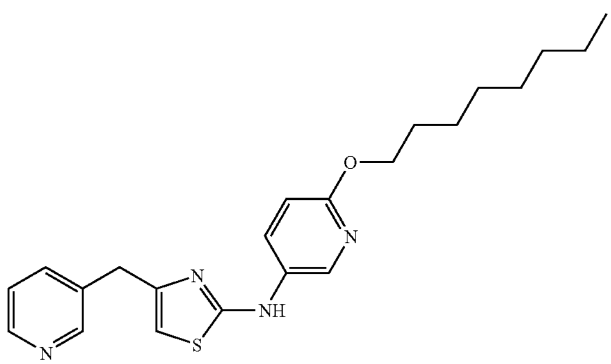 | 6-(octyloxy)-N-(4-((pyridin-3-yl)methyl)thiazol-2-yl)pyridin-3-amine | ++ |
| 498 | 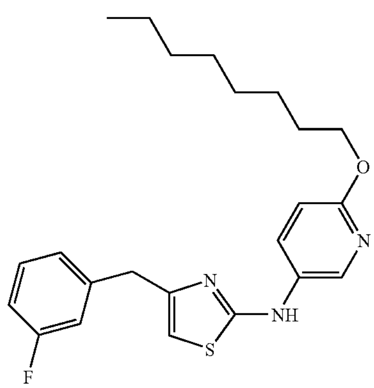 | N-(4-(3-fluorobenzyl)thiazol-2-yl)-6-(octyloxy)pyridin-3-amine | ++ |

TABLE II-continued

| Cpd | Structure | Name | Activity |
|---|---|---|---|
| 499 | 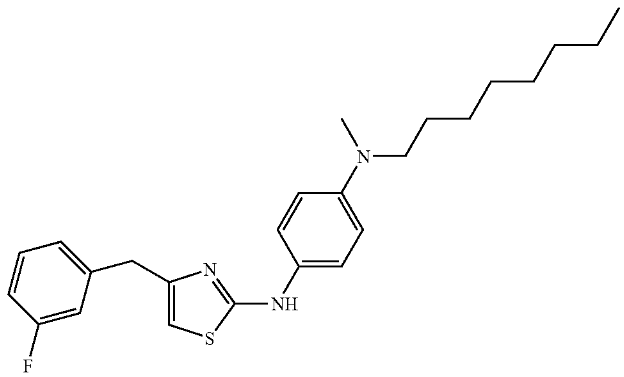 | N$^1$-(4-(3-fluorobenzyl)thiazol-2-yl)-N$^4$-methyl-N$^4$-octylbenzene-1,4-diamine | ++ |
| 500 | 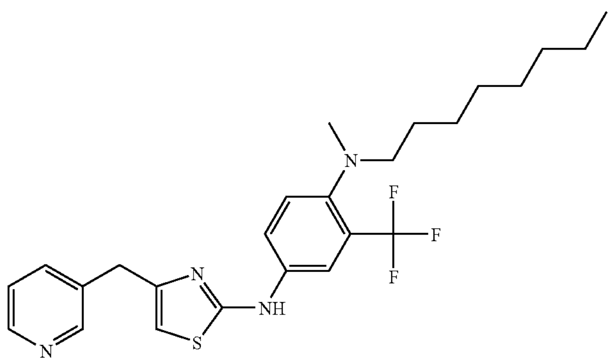 | 2-(trifluoromethyl)-N$^1$-methyl-N$^1$-octyl-N$^4$-(4-((pyridin-3-yl)methyl)thiazol-2-yl)benzene-1,4-diamine | +++ |
| 501 | 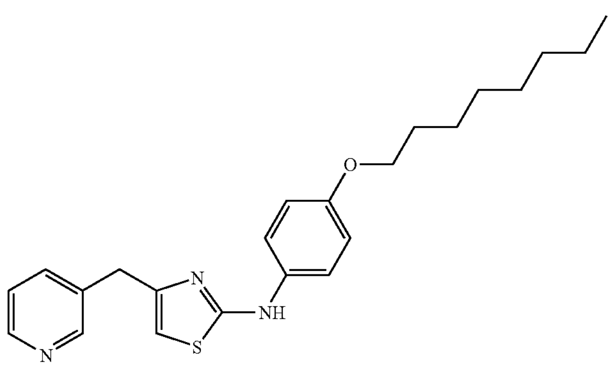 | N-(4-(octyloxy)phenyl)-4-((pyridin-3-yl)methyl)thiazol-2-amine | ++ |
| 502 | 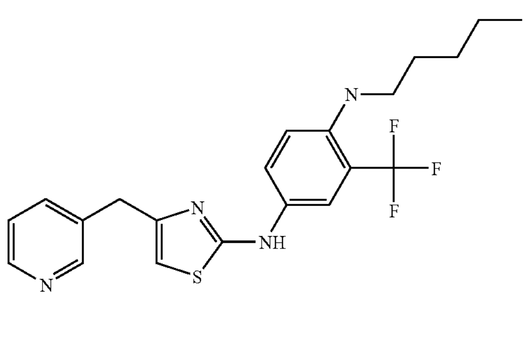 | N-(3-(trifluoromethyl)-4-(pentyloxy)phenyl)-4-((pyridin-3-yl)methyl)thiazol-2-amine | ++ |

TABLE II-continued

| Cpd | Structure | Name | Activity |
|---|---|---|---|
| 503 | 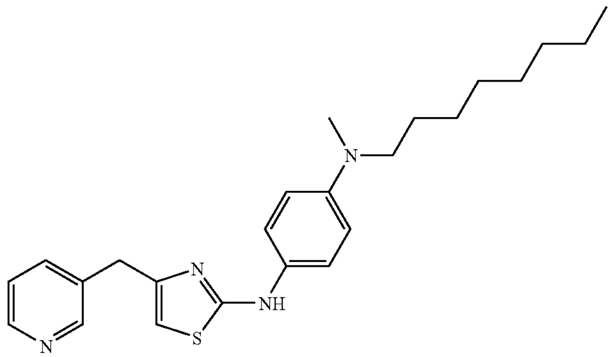 | $N^1$-methyl-$N^1$-octyl-$N^4$-(4-((pyridin-3-yl)methyl)thiazol-2-yl)benzene-1,4-diamine | + |
| 504 | 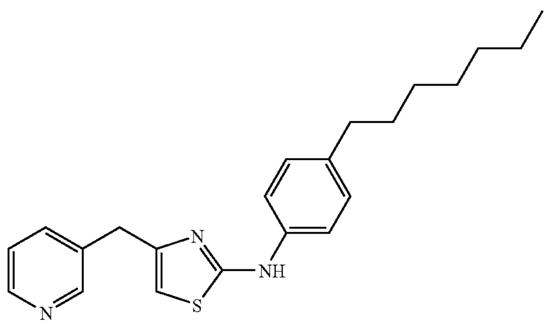 | N-(4-heptylphenyl)-4-((pyridin-3-yl)methyl)thiazol-2-amine | ++ |
| 505 | 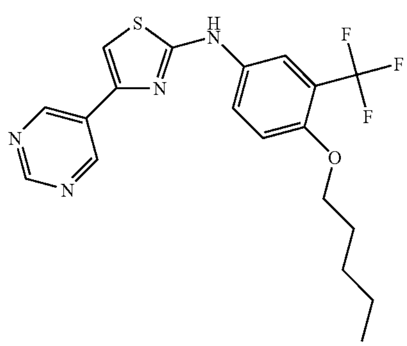 | N-(3-(trifluoromethyl)-4-(pentyloxy)phenyl)-4-(pyrimidin-5-yl)thiazol-2-amine | +++ |
| 506 | 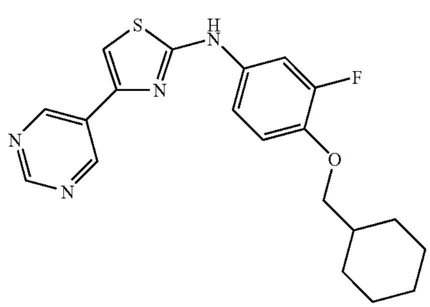 | N-(4-(cyclohexylmethoxy)-3-fluorophenyl)-4-(pyrimidin-5-yl)thiazol-2-amine | +++ |

TABLE II-continued

| Cpd | Structure | Name | Activity |
|---|---|---|---|
| 507 | 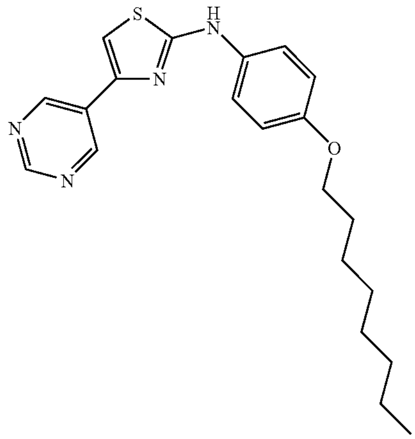 | N-(4-(octyloxy)phenyl)-4-(pyrimidin-5-yl)thiazol-2-amine | +++ |
| 508 | 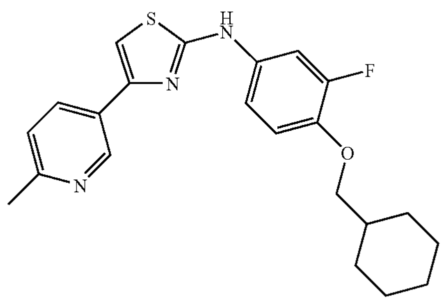 | N-(4-(cyclohexylmethoxy)-3-fluorophenyl)-4-(6-methylpyridin-3-yl)thiazol-2-amine | +++ |
| 509 | 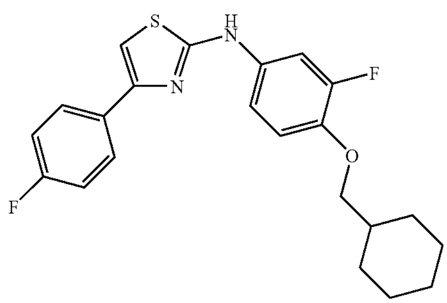 | N-(4-(cyclohexylmethoxy)-3-fluorophenyl)-4-(4-fluorophenyl)thiazol-2-amine | +++ |
| 510 | 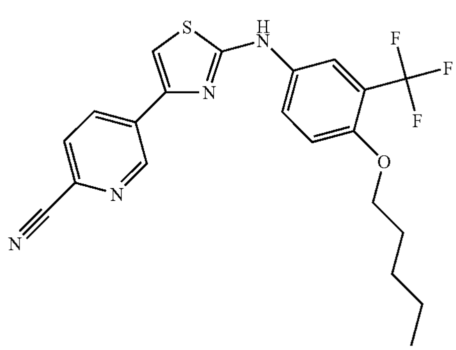 | 5-(2-(3-(trifluoromethyl)-4-(pentyloxy)phenylamino)thiazol-4-yl)pyridin-2-carbonitrile | +++ |

TABLE II-continued

| Cpd | Structure | Name | Activity |
|---|---|---|---|
| 511 | 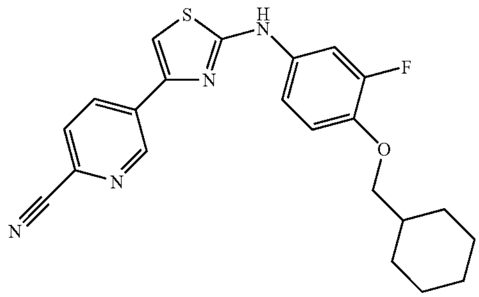 | 5-(2-(4-(cyclohexylmethoxy)-3-fluorophenylamino)thiazol-4-yl)pyridine-2-carbonitrile | + |
| 512 | 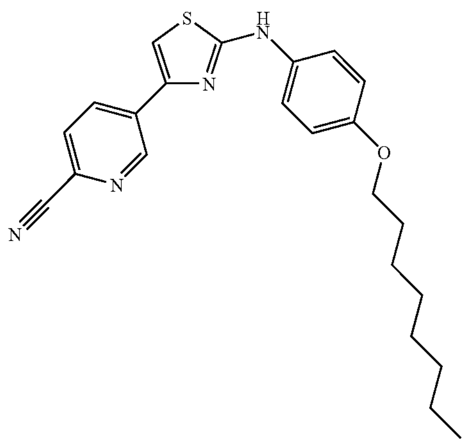 | 5-(2-(4-(octyloxy)phenylamino)thiazol-4-yl)pyridine-2-carbonitrile | +++ |
| 513 | 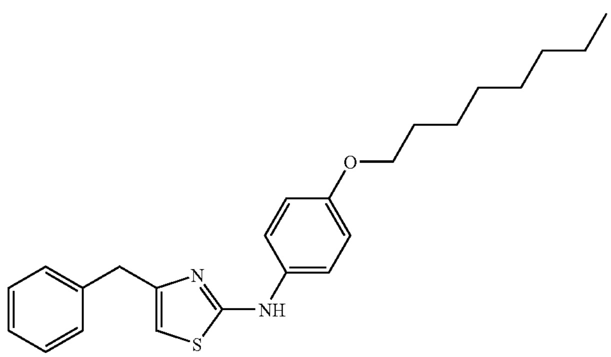 | 4-benyl-N-(4-(octyloxy)phenyl)thiazol-2-amine | + |
| 514 | 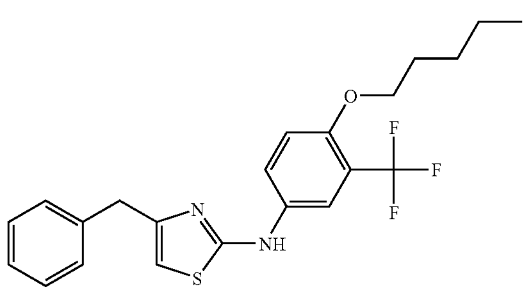 | 4-benzyl-N-(3-(trifluoromethyl)-4-(pentyloxy)phenyl)thiazol-2-amine | + |

TABLE II-continued
| Cpd | Structure | Name | Activity |
|---|---|---|---|
| 515 | 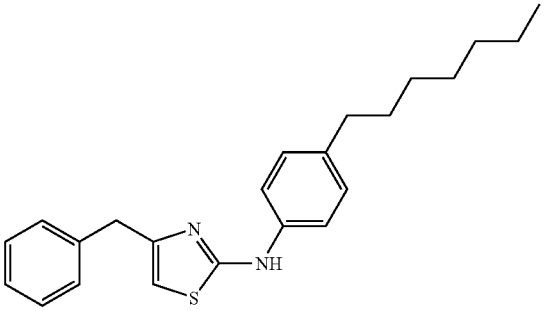 | 4-benzyl-N-(4-heptylphenyl)thiazol-2-amine | + |
| 516 | 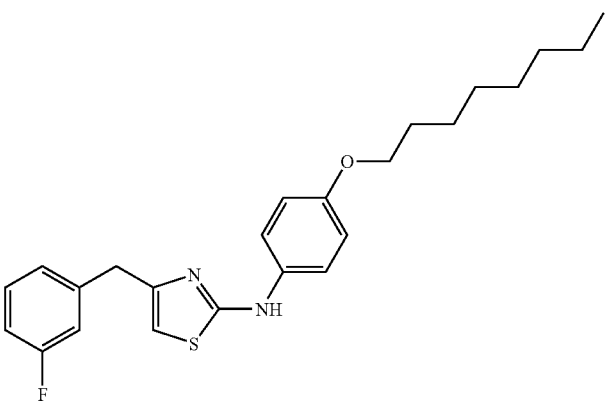 | 4-(3-fluorobenzyl)-N-(4-(octyloxy)phenyl)thiazol-2-amine | + |
| 517 | 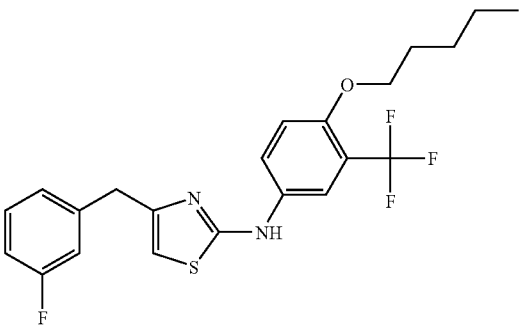 | 4-(3-fluorobenzyl)-N-(3-(trifluoromethyl)-4-(pentyloxy)phenyl)thiazol-2-amine | ++ |
| 518 | 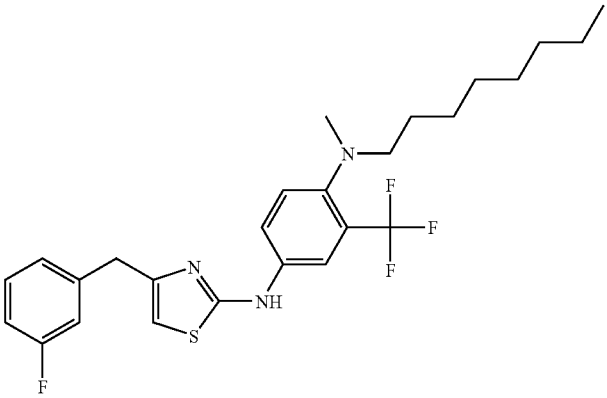 | $N^4$-(4-(3-fluorobenzyl)thiazol-2-yl)-2-(trifluoromethyl)-$N^1$-methyl-$N^1$-octylbenzene-1,4-diamine | ++ |

TABLE III
| Cpd | Structure | Name | Activity |
|---|---|---|---|
| 519 | 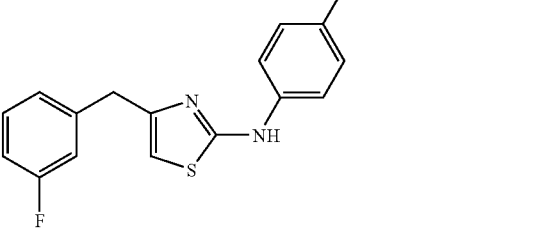 | 4-(3-fluorobenzyl)-N-(4-heptylphenyl)thiazol-2-amine | ++ |
| 520 | 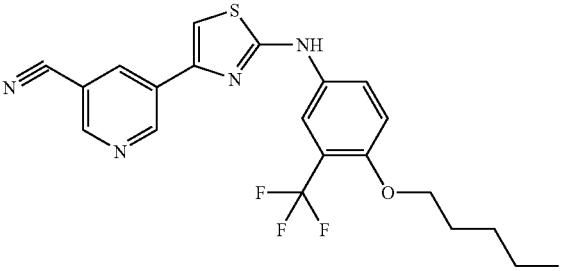 | 5-(2-(3-(trifluoromethyl)-4-(pentyloxy)phenylamino)thiazol-4-yl)pyridine-3-carbonitrile | +++ |
| 521 | 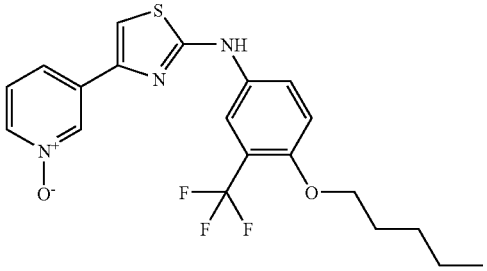 | | +++ |
| 522 | 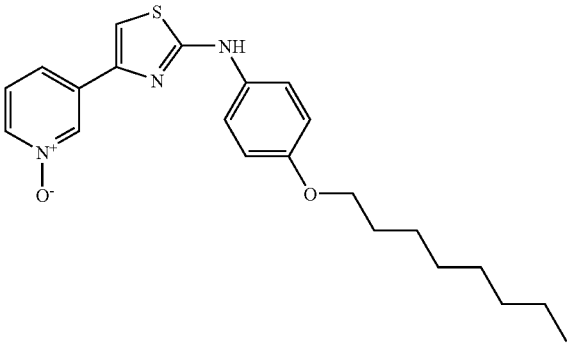 | | +++ |
| 523 | 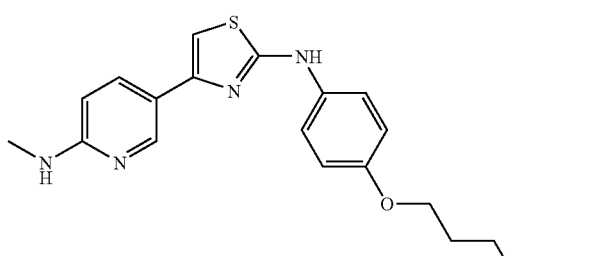 | 5-(2-(4-(heptyloxy)phenylamino)thiazol-4-yl)-N-methylpyridin-2-amine | +++ |

TABLE III-continued

| Cpd | Structure | Name | Activity |
|---|---|---|---|
| 524 | 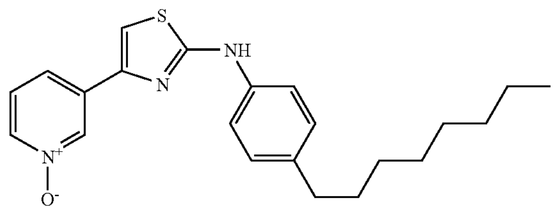 | | +++ |
| 525 | 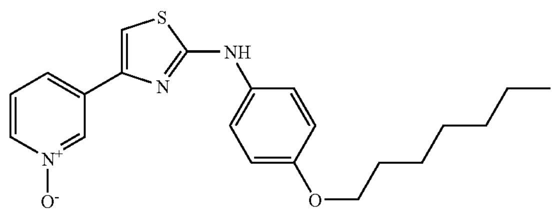 | | +++ |
| 526 | 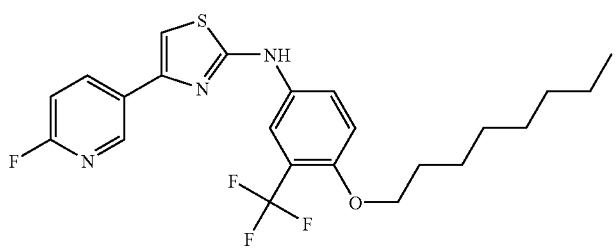 | N-(3-(trifluoromethyl)-4-(octyloxy)phenyl)-4-(6-fluoropyridin-3-yl)thiazol-2-amine | +++ |
| 527 | 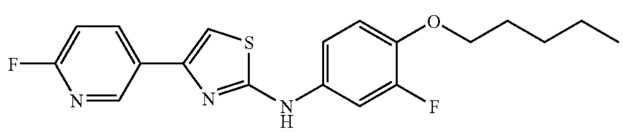 | N-(3-fluoro-4-(pentyloxy)phenyl)-4-(6-fluoropyridin-3-yl)thiazol-2-amine | +++ |
| 528 | 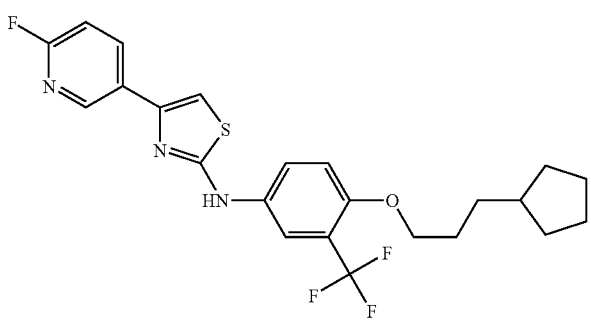 | N-(4-(3-cyclopentylpropoxy)-3-(trifluoromethyl)phenyl)-4-(6-fluoropyridin-3-yl)thiazol-2-amine | +++ |
| 529 | 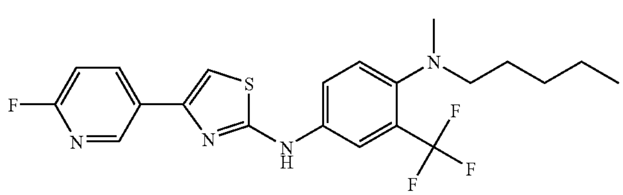 | 2-(trifluoromethyl)-N4-(4-(6-fluoropyridin-3-yl)thiazol-2-yl)-N1-methyl-N1-pentylbenzene-1,4-diamine | +++ |
| 530 | 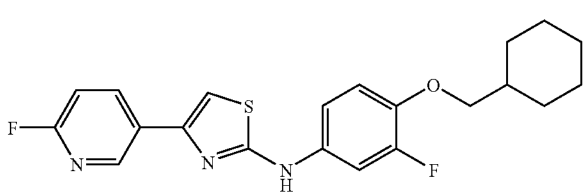 | N-(4-(cyclohexylmethoxy)-3-fluorophenyl)-4-(6-fluoropyridin-3-yl)thiazol-2-amine | +++ |

TABLE III-continued

| Cpd | Structure | Name | Activity |
|---|---|---|---|
| 531 | 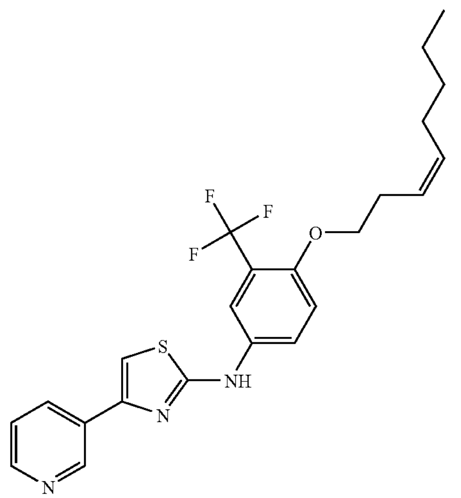 | N-(4-((Z)-oct-3-enyloxy)-3-(trifluoromethyl)phenyl)-4-(pyridin-3-yl)thiazol-2-amine | +++ |
| 532 | 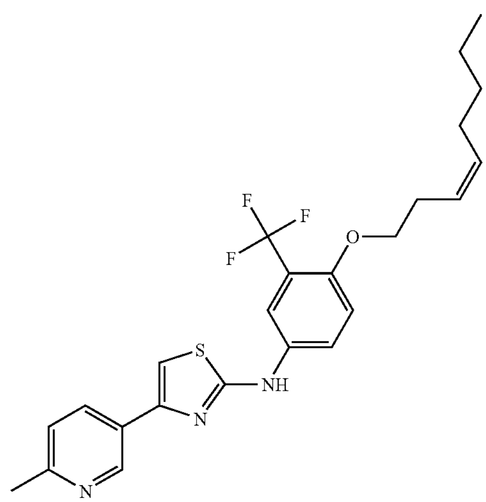 | N-(4-((Z)-oct-3-enyloxy)-3-(trifluoromethyl)phenyl)-4-(6-methylpyridin-3-yl)thiazol-2-amine | +++ |
| 533 | 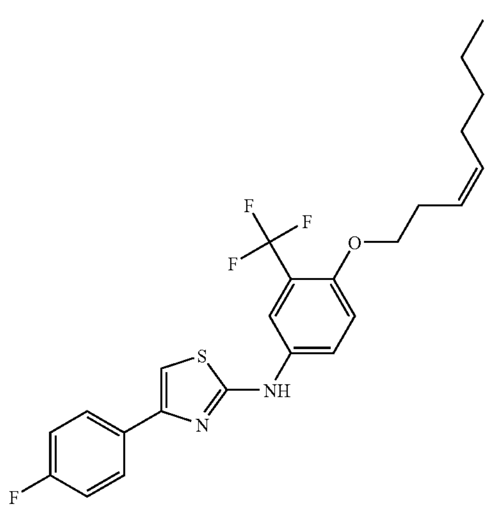 | N-(4-((Z)-oct-3-enyloxy)-3-(trifluoromethyl)phenyl)-4-(4-fluorophenyl)thiazol-2-amine | +++ |

TABLE III-continued

| Cpd | Structure | Name | Activity |
|---|---|---|---|
| 534 | 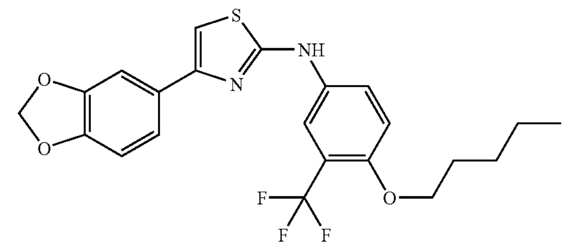 | 4-(benzo[d][1,3]dioxol-6-yl)-N-(3-(trifluoromethyl)-4-(pentyloxy)phenyl)thiazol-2-amine | +++ |
| 535 | 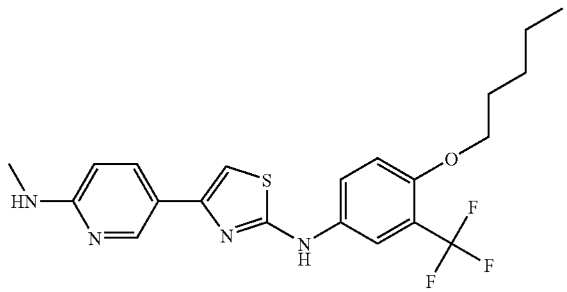 | 5-(2-(3-(trifluoromethyl)-4-(pentyloxy)phenylamino)thiazol-4-yl)-N-methylpyridin-2-amine | +++ |
| 536 | 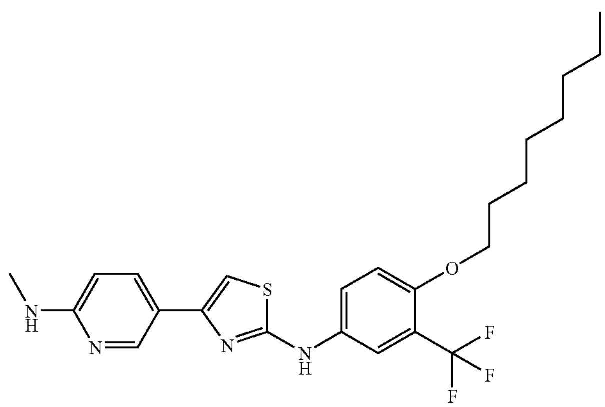 | 5-(2-(3-(trifluoromethyl)-4-(octyloxy)phenylamino)thiazol-4-yl)-N-methylpyridin-2-amine | +++ |
| 537 | 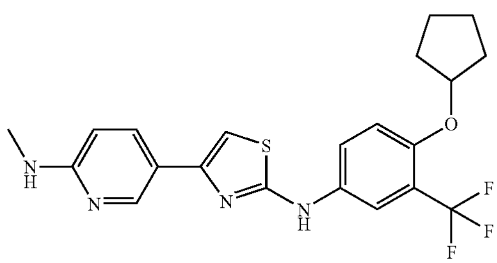 | 5-(2-(4-(cyclopentyloxy)-3-(trifluoromethyl)phenylamino)thiazol-4-yl)-N-methylpyridin-2-amine | +++ |
| 538 | 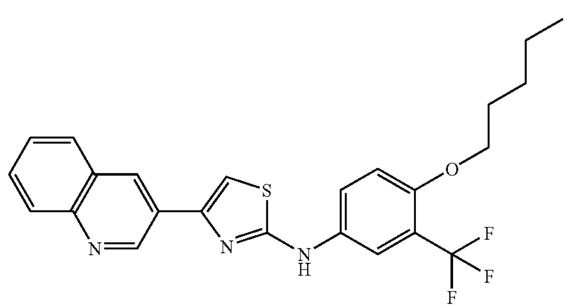 | N-(3-(trifluoromethyl)-4-(pentyloxy)phenyl)-4-(quinolin-3-yl)thiazol-2-amine | +++ |

TABLE III-continued

| Cpd | Structure | Name | Activity |
|---|---|---|---|
| 539 | 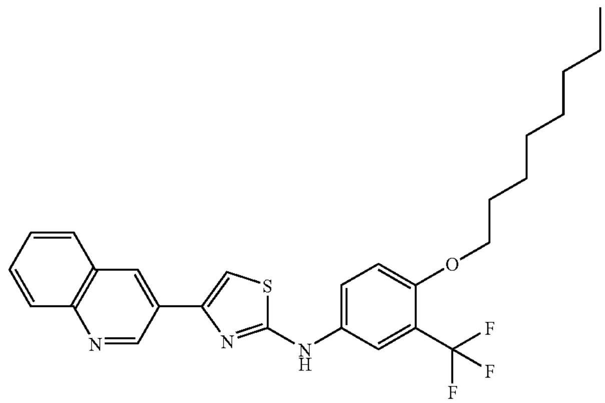 | N-(3-(trifluoromethyl)-4-(octyloxy)phenyl)-4-(quinolin-3-yl)thiazol-2-amine | +++ |
| 540 | 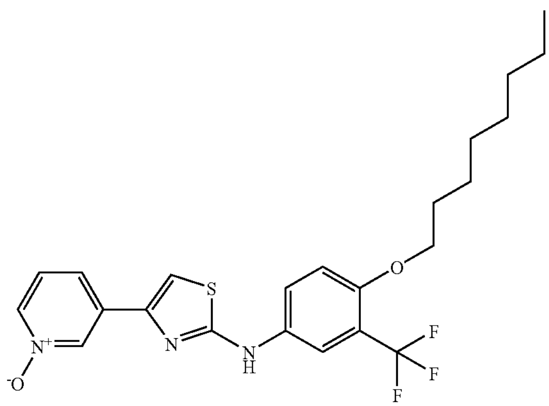 | | +++ |
| 541 | 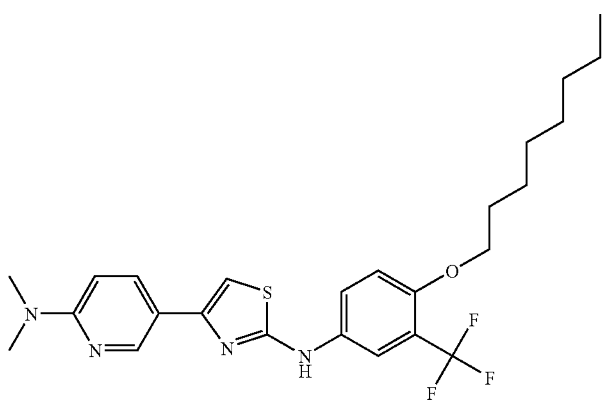 | 5-(2-(3-(trifluoromethyl)-4-(octyloxy)phenylamino)thiazol-4-yl)-N,N-dimethylpyridin-2-amine | +++ |
| 542 | 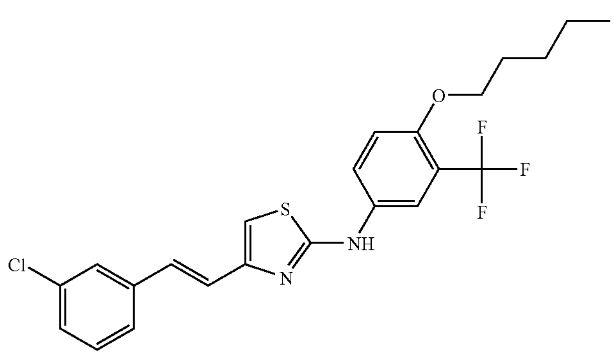 | 4-(3-chlorostyryl)-N-(3-(trifluoromethyl)-4-(pentyloxy)phenyl)thiazol-2-amine | +++ |

TABLE III-continued

| Cpd | Structure | Name | Activity |
|---|---|---|---|
| 543 | 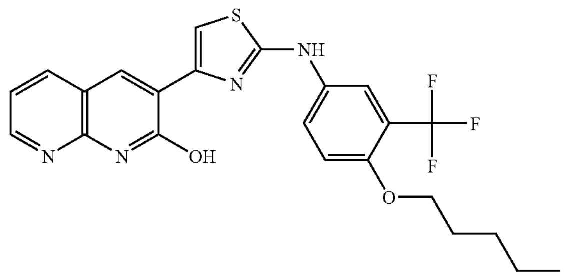 | 3-(2-(3-(trifluoromethyl)-4-(pentyloxy)phenylamino)thiazol-4-yl)-1,8-naphthyridin-2-ol | ++ |
| 544 | 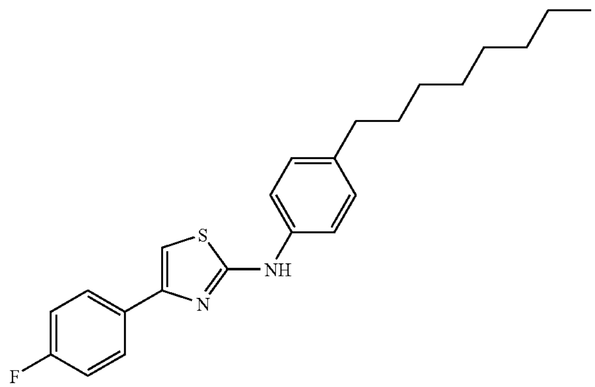 | 4-(4-fluorophenyl)-N-(4-octylphenyl)thiazol-2-amine | +++ |
| 545 | 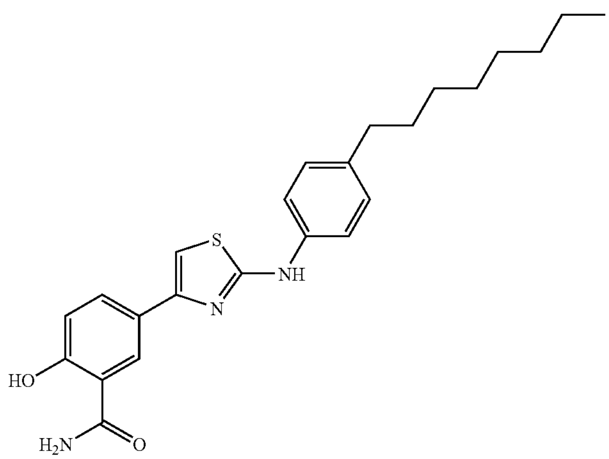 | 5-(2-(4-octylphenylamino)thiazol-4-yl)-2-hydroxybenzamide | +++ |
| 546 | 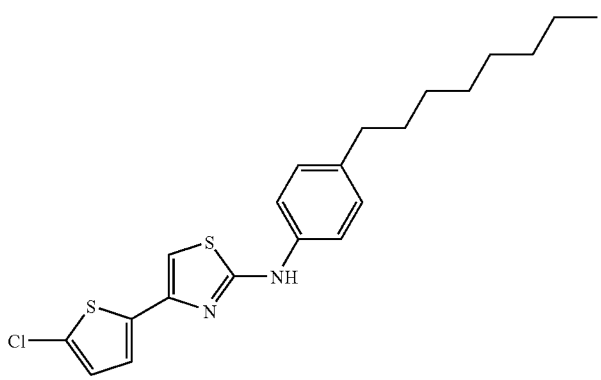 | 4-(5-chlorothiophen-2-yl)-N-(4-octylphenyl)thiazol-2-amine | +++ |

TABLE III-continued

| Cpd | Structure | Name | Activity |
|---|---|---|---|
| 547 | 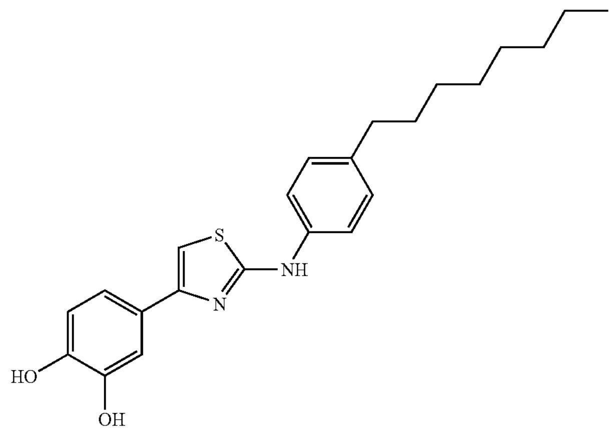 | 4-(2-(4-octylphenylamino)thiazol-4-yl)benzene-1,2-diol | +++ |
| 548 | 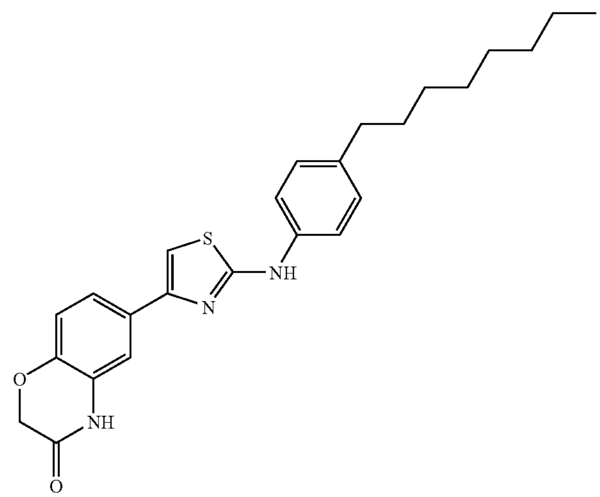 | 6-(2-(4-octylphenylamino)thiazol-4-yl)-2H-benzo[b][1,4]oxazin-3(4H)-one | +++ |
| 549 | 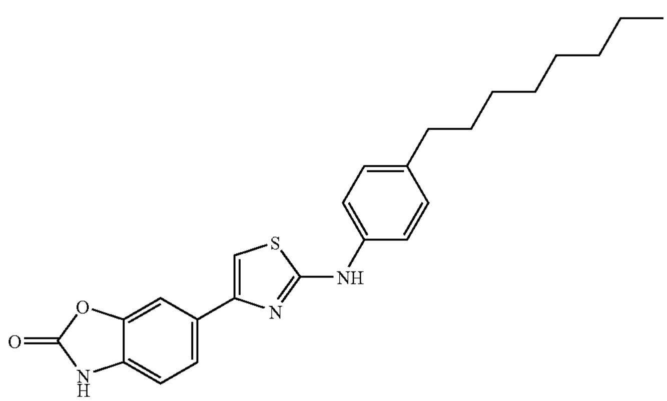 | 6-(2-(4-octylphenylamrno)thiazol-4-yl)benzo[d]oxazol-2(3H)-one | +++ |

TABLE III-continued

| Cpd | Structure | Name | Activity |
|---|---|---|---|
| 550 | 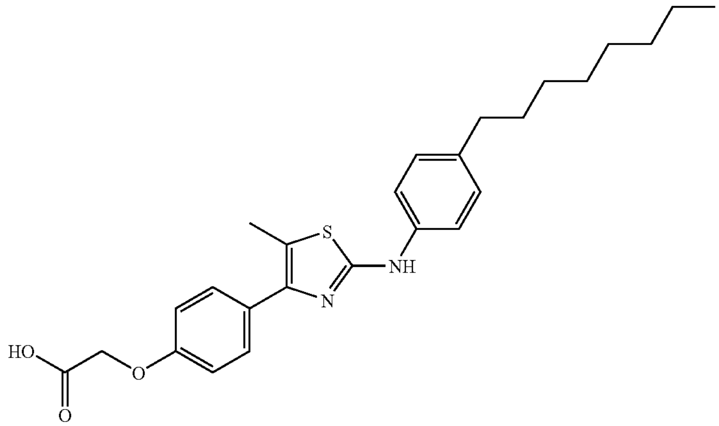 | 2-(4-(2-(4-octylphenylamino)-5-methylthiazol-4-yl)phenoxy)acetic acid | +++ |
| 551 | 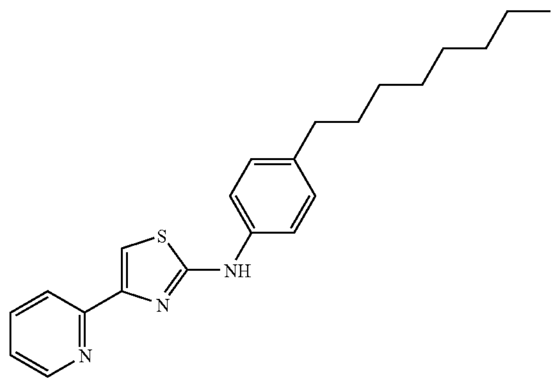 | N-(4-octylphenyl)-4-(pyridin-2-yl)thiazol-2-amine | +++ |
| 552 | 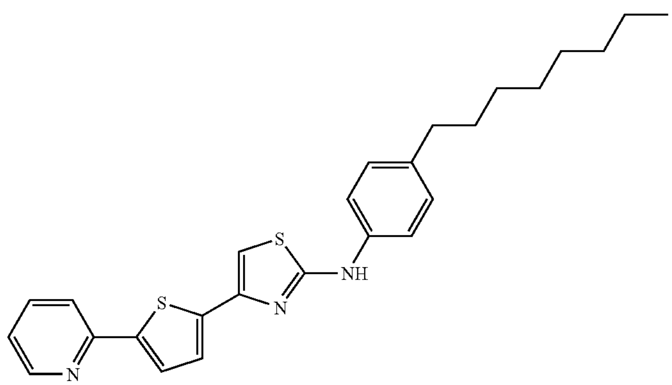 | N-(4-octylphenyl)-4-(5-(pyridin-2-yl)thiophen-2-yl)thiazol-2-amine | +++ |
| 553 | 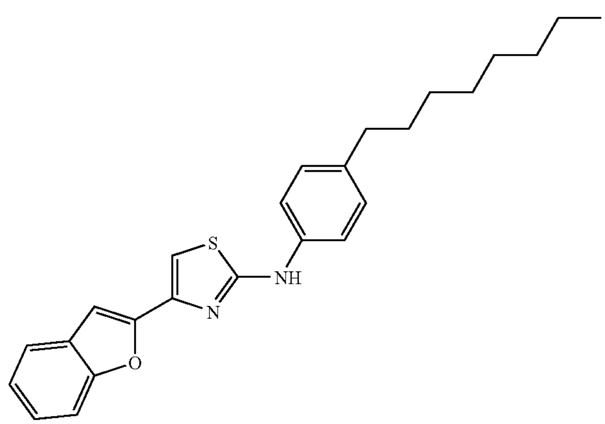 | 4-(benzofuran-2-yl)-N-(4-octylphenyl)thiazol-2-amine | ++ |

TABLE III-continued

| Cpd | Structure | Name | Activity |
|---|---|---|---|
| 554 | 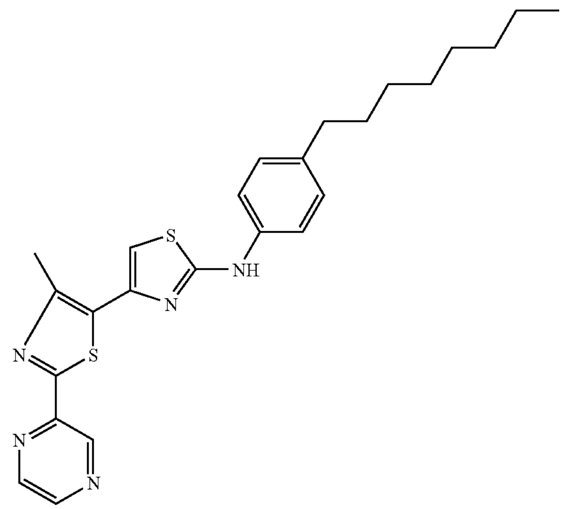 | 4-(4-methyl-2-(pyrazin-2-yl)thiazol-5-yl)-N-(4-octylphenyl)thiazol-2-amine | +++ |
| 555 | 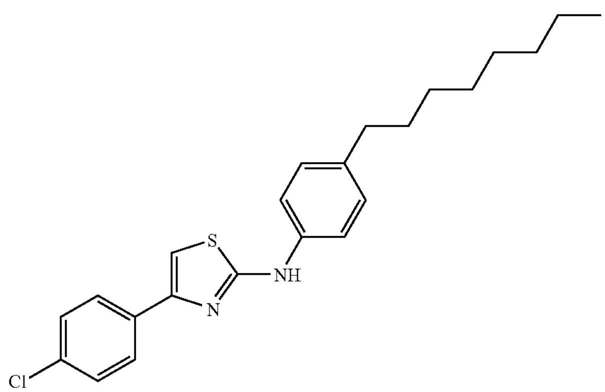 | 4-(4-chlorophenyl)-N-(4-octylphenyl)thiazol-2-amine | +++ |
| 556 | 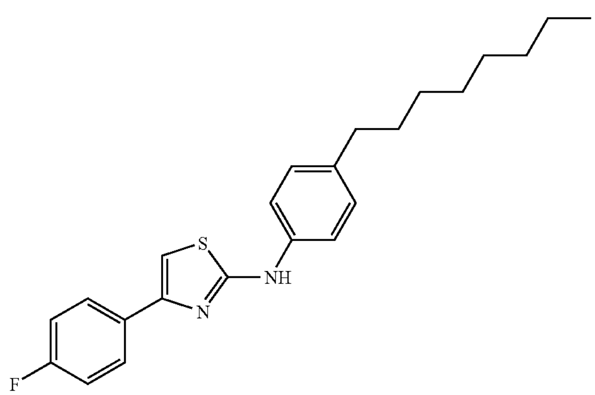 | 4-(4-fluorophenyl)-N-(4-heptylphenyl)thiazol-2-amine | +++ |

TABLE III-continued
| Cpd | Structure | Name | Activity |
|---|---|---|---|
| 557 | 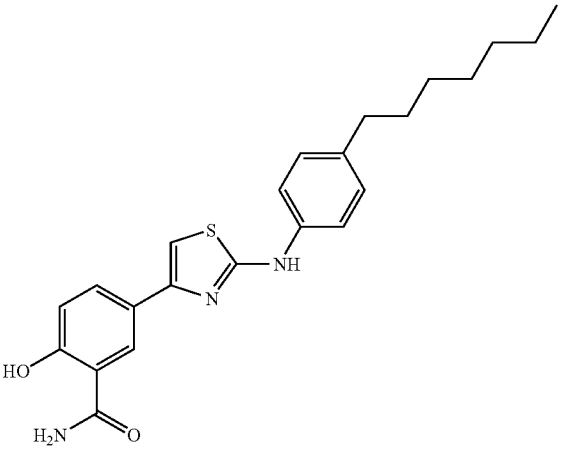 | 5-(2-(4-heptylphenylamino)thiazol-4-yl)-2-hydroxybenzamide | +++ |
| 558 | 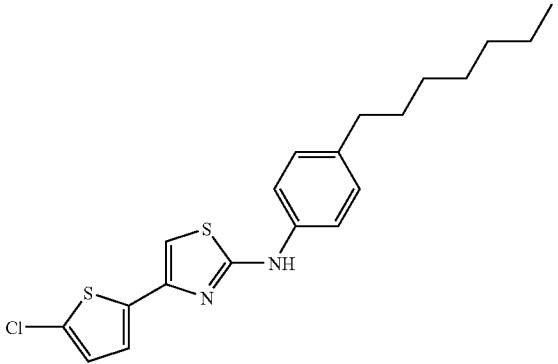 | 4-(5-chlorothiophen-2-yl)-N-(4-heptylphenyl)thiazol-2-amine | +++ |
| 559 | 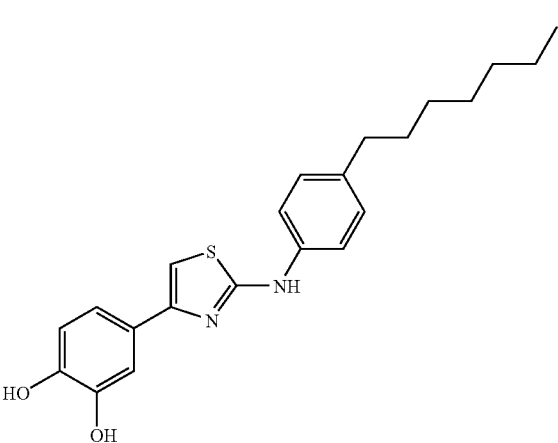 | 4-(2-(4-heptylphenylamino)thiazol-4-yl)benzene-1,2-diol | +++ |

TABLE III-continued

| Cpd | Structure | Name | Activity |
|---|---|---|---|
| 560 | 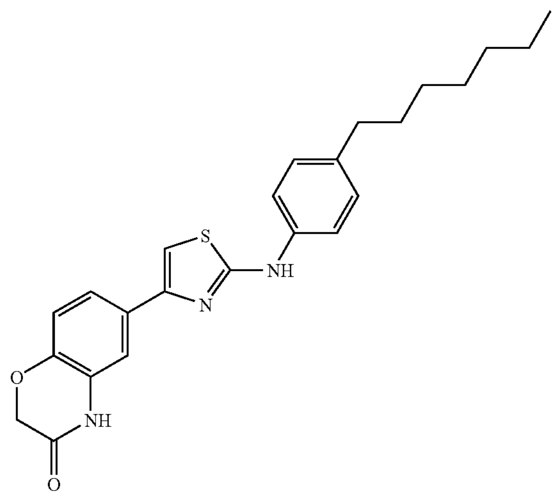 | heptylphenylamino)thiazol-4-yl)-2H-benzo[b][1,4]oxazin-3(4H)-one | +++ |
| 561 | 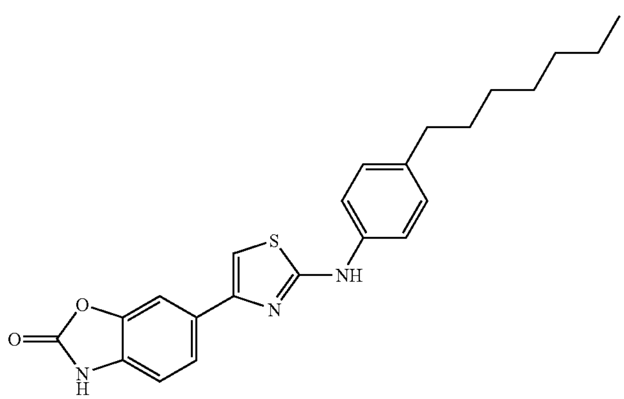 | heptylphenylamino)thiazol-4-yl)benzo[d]oxazol-2(3H)-one | +++ |
| 562 | 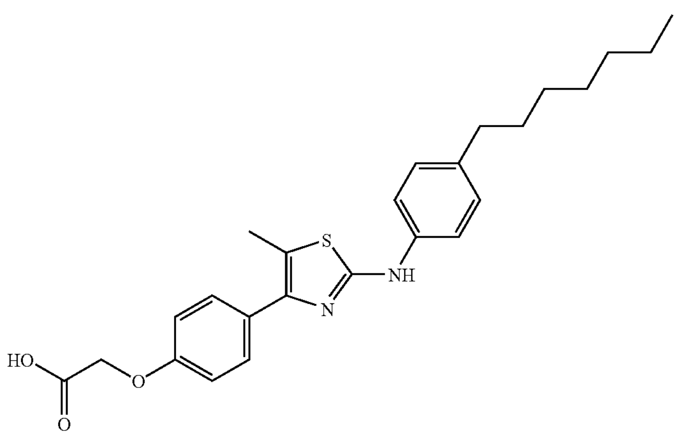 | 2-(4-(2-(4-heptylphenylamino)-5-methylthiazol-4-yl)phenoxy)acetic acid | +++ |

TABLE III-continued
| Cpd | Structure | Name | Activity |
|---|---|---|---|
| 563 | 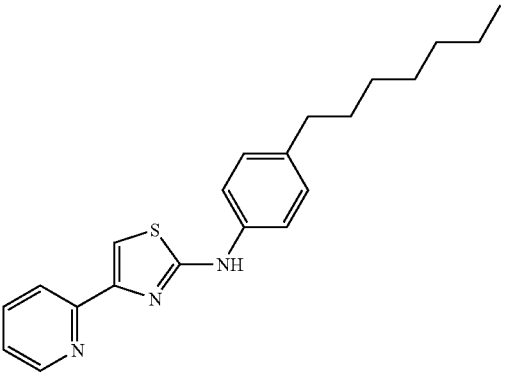 | N-(4-heptylphenyl)-4-(pyridin-2-yl)thiazol-2-amine | +++ |
| 564 | 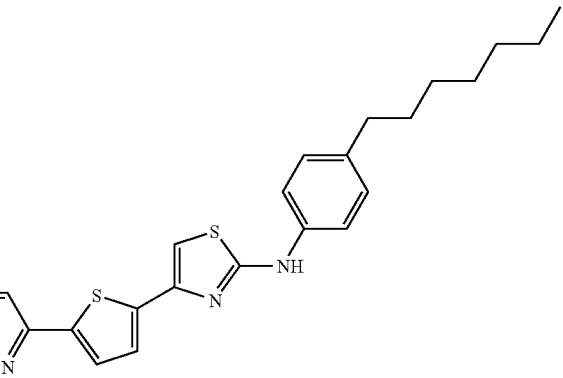 | N-(4-heptylphenyl)-4-(5-(pyridin-2-yl)thiophen-2-yl)thiazol-2-amine | +++ |
| 565 | 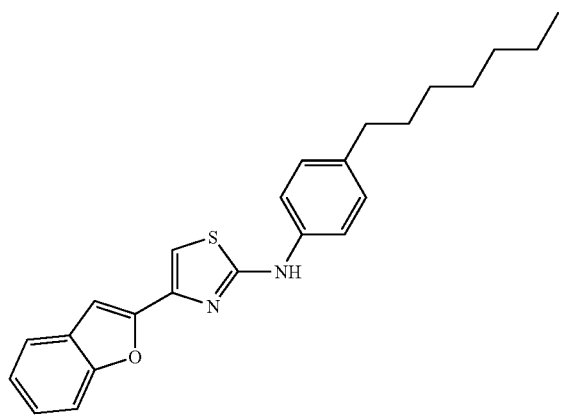 | 4-(benzofuran-2-yl)-N-(4-heptylphenyl)thiazol-2-amine | + |

TABLE III-continued
| Cpd | Structure | Name | Activity |
|---|---|---|---|
| 566 | 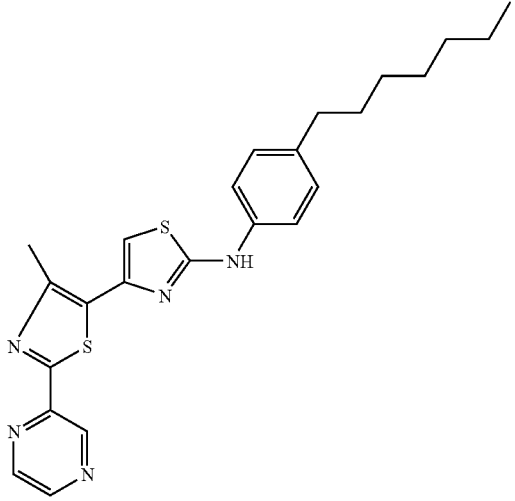 | N-(4-heptylphenyl)-4-(4-methyl-2-(pyrazin-2-yl)thiazol-5-yl)thiazol-2-amine | +++ |
| 567 | 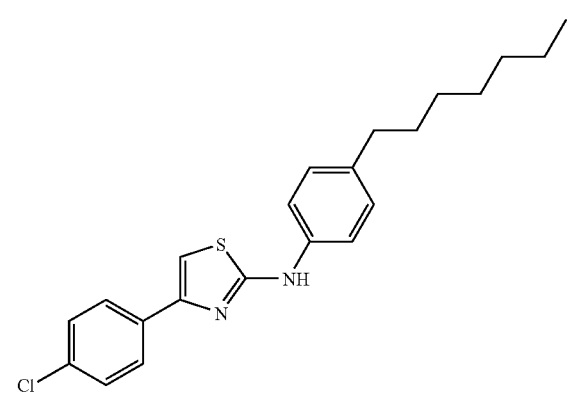 | 4-(4-chlorophenyl)-N-(4-heptylphenyl)thiazol-2-amine | +++ |
| 568 | 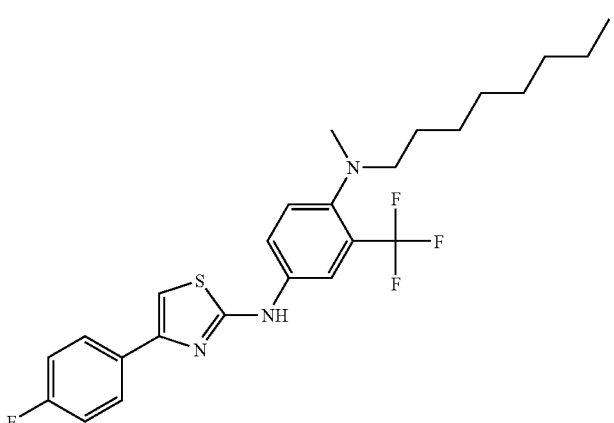 | 2-(trifluoromethyl)-$N^4$-(4-(4-fluorophenyl)thiazol-2-yl)-$N^1$-methyl-$N^1$-octylbenzene-1,4-diamine | +++ |

| Cpd | Structure | Name | Activity |
|---|---|---|---|
| 569 | 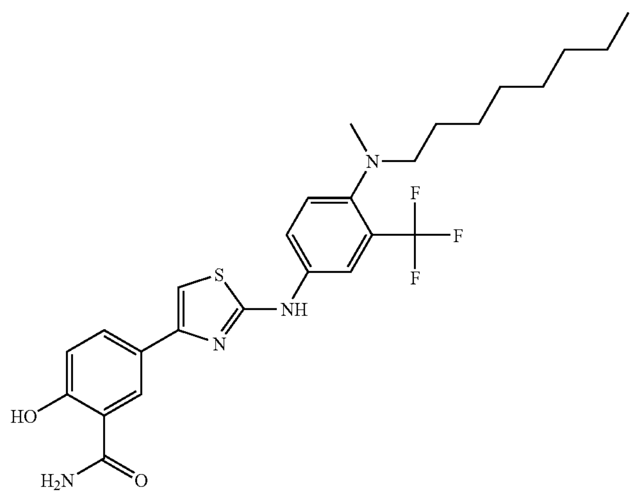 | 5-(2-(4-(N-methyl-N-octylamino)-3-(trifluoromethyl)phenylamino)thiazol-4-yl)-2-hydroxybenzamide | +++ |
| 570 | 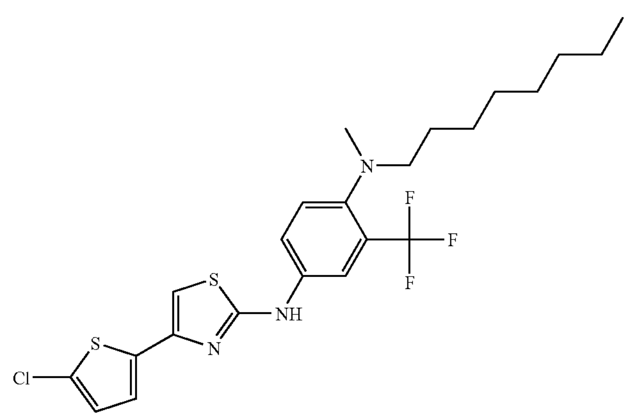 | N⁴-(4-(5-chlorothiophen-2-yl)thiazol-2-yl)-2-(trifluoromethyl)-N¹-methyl-N¹-octylbenzene-1,4-diamine | +++ |
| 571 | 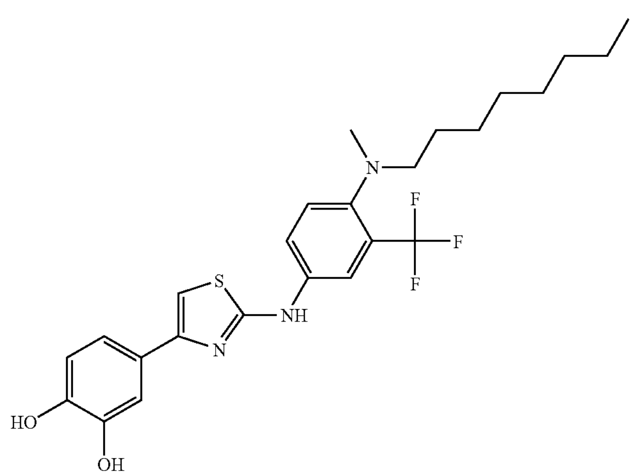 | 4-(2-(4-(N-methyl-N-octylamino)-3-(trifluoromethyl)phenylamino)thiazol-4-yl)benzene-1,2-diol | +++ |

TABLE III-continued

| Cpd | Structure | Name | Activity |
|---|---|---|---|
| 572 | 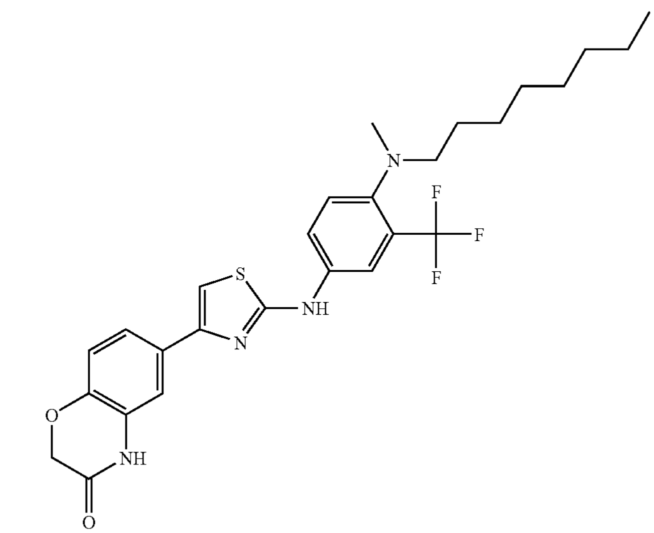 | 6-(2-(4-(N-methyl-N-octylamino)-3-(trifluoromethyl)phenylamino)thiazol-4-yl)-2H-benzo[b][1,4]oxazin-3(4H)-one | ++ |
| 573 | 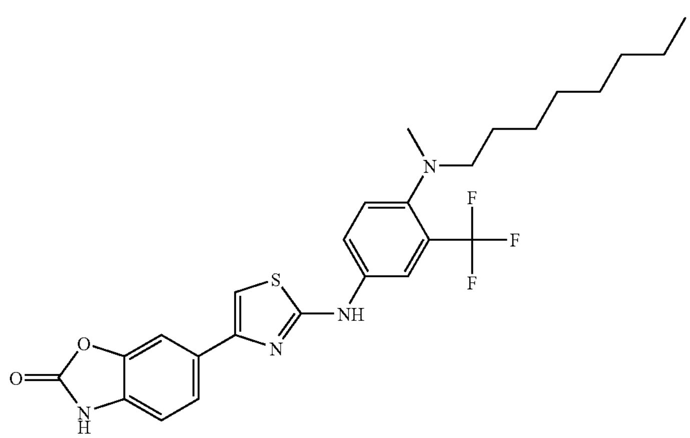 | 6-(2-(4-(N-methyl-N-octylamino)-3-(trifluoromethyl)phenylamino)azol-4-yl)benzo[d]oxazol-2(3H)-one | +++ |
| 574 | 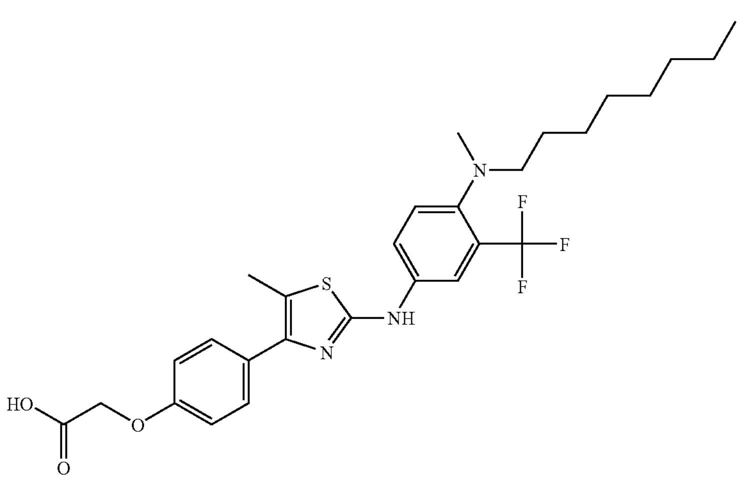 | 2-(4-(2-(4-(N-methyl-N-octylamino)-3-(trifluoromethyl)phenylamino)-5-methylthiazol-4-yl)phenoxy)acetic acid | +++ |

TABLE III-continued

| Cpd | Structure | Name | Activity |
|---|---|---|---|
| 575 | 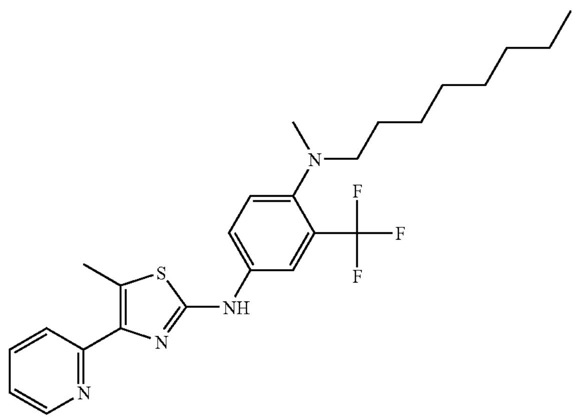 | 2-(trifluoromethyl)-$N^1$-methyl-$N^1$-octyl-$N^4$-(4-(pyridin-2-yl)thiazol-2-yl)benzene-1,4-diamine | +++ |
| 576 | 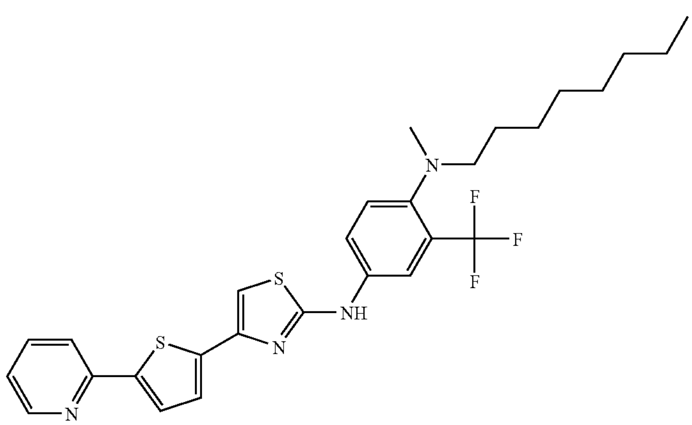 | 2-(trifluoromethyl)-$N^1$-methyl-$N^1$-octyl-$N^4$-(4-(5-(pyridin-2-yl)thiophen-2-yl)thiazol-2-yl)benzene-1,4-diamine | +++ |
| 577 | 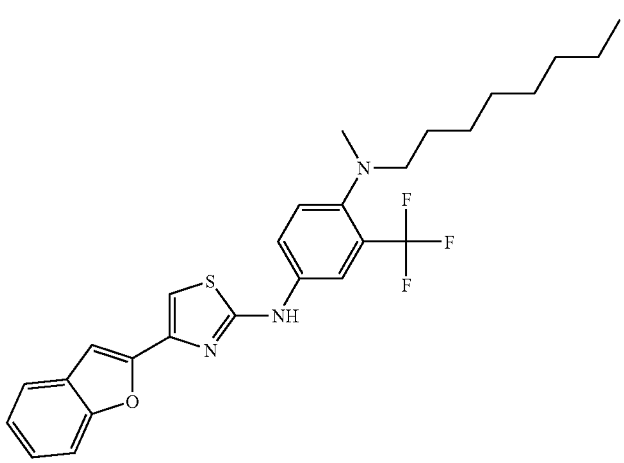 | $N^4$-(4-(benzofuran-2-yl)thiazol-2-yl)-2-(trifluoromethyl)-$N^1$-methyl-$N^1$-octylbenzene-1,4-diamine | ++ |

TABLE III-continued

| Cpd | Structure | Name | Activity |
|---|---|---|---|
| 578 | 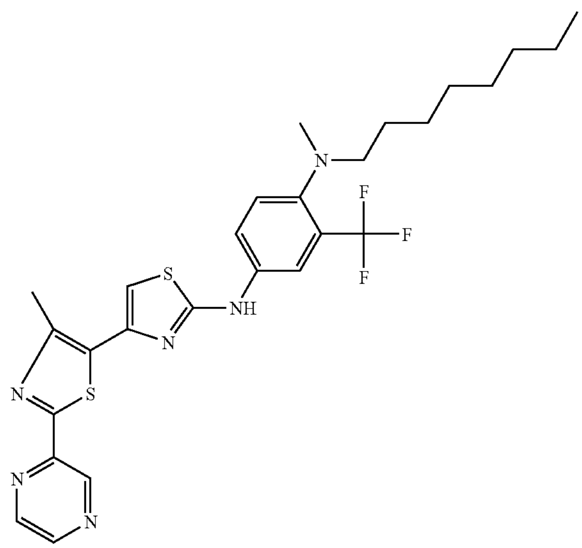 | 2-(trifluoromethyl)-N$^1$-methyl-N$^4$-(4-(4-methyl-2-(pyrazin-2-yl)thiazol-5-yl)thiazol-2-yl)-N$^1$-octylbenzene-1,4-diamine | ++ |
| 579 | 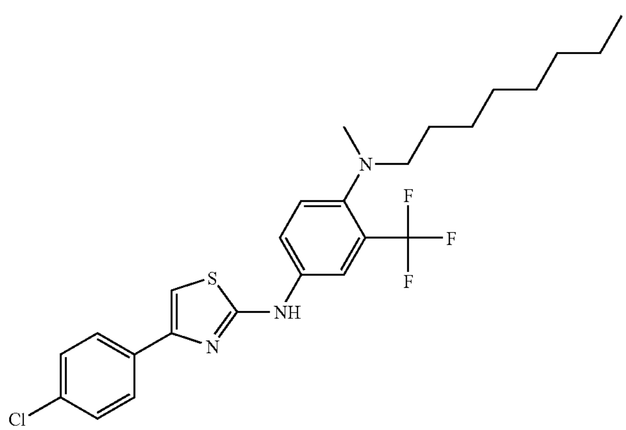 | N$^4$-(4-(4-chlorophenyl)thiazol-2-yl)-2-(trifluoromethyl)-N$^1$-methyl-N$^1$-octylbenzene-1,4-diamine | +++ |
| 580 | 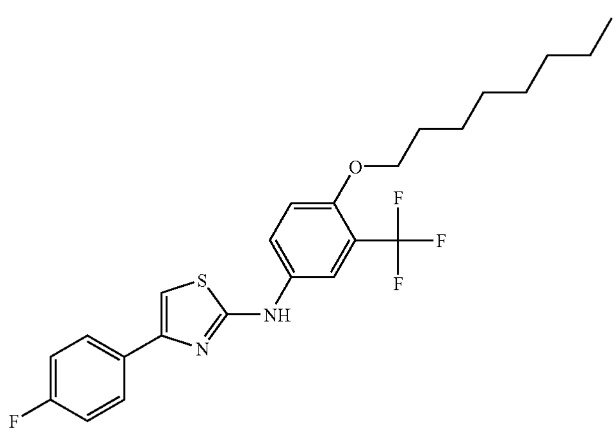 | N-(3-(trifluoromethyl)-4-(octyloxy)phenyl)-4-(4-fluorophenyl)thiazol-2-amine | +++ |

TABLE III-continued

| Cpd | Structure | Name | Activity |
|---|---|---|---|
| 581 | 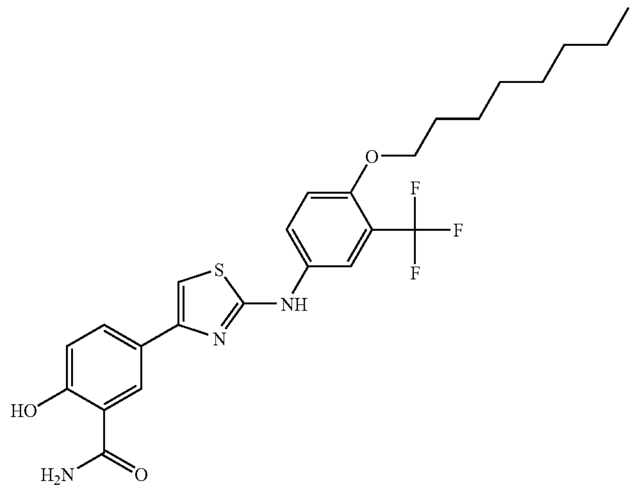 | 5-(2-(3-(trifluoromethyl)-4-(octyloxy)phenylamino)thiazol-4-yl)-2-hydroxybenzamide | +++ |
| 582 | 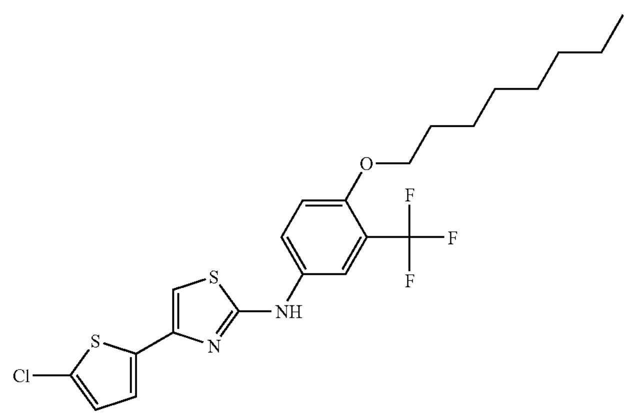 | 4-(5-chlorothiophen-2-yl)-N-(3-(trifluoromethyl)-4-(octyloxy)phenyl)thiazol-2-amine | +++ |
| 583 | 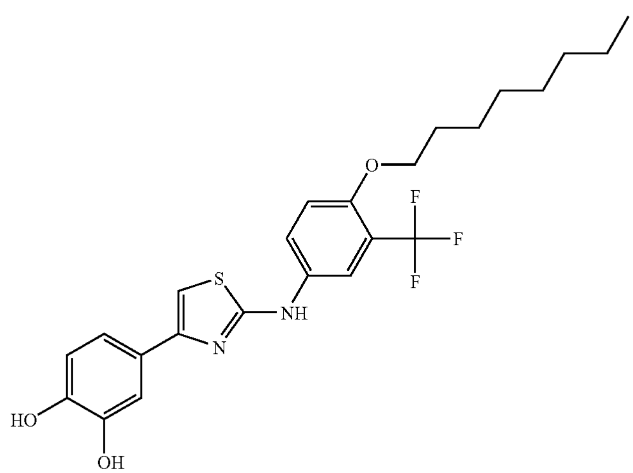 | 4-(2-(3-(trifluoromethyl)-4-(octyloxy)phenylamino)thiazol-4-yl)benzene-1,2-diol | +++ |

TABLE III-continued

| Cpd | Structure | Name | Activity |
|---|---|---|---|
| 584 | 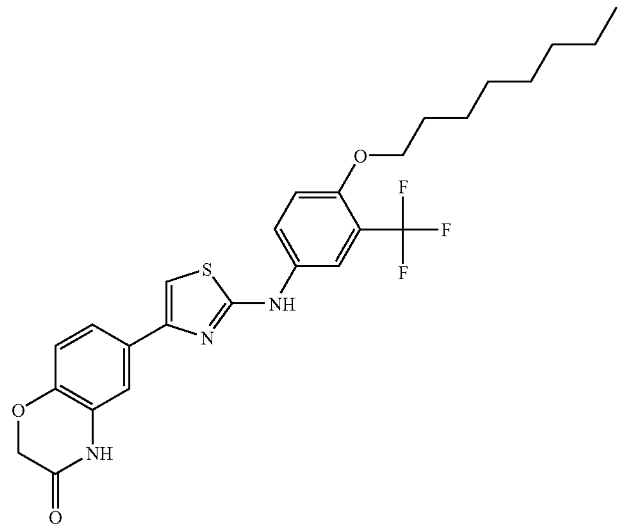 | 6-(2-(3-(trifluoromethyl)-4-(octyloxy)phenylamino)thiazol-4-yl)-2H-benzo[b][1,4]oxazin-3(4H)-one | +++ |
| 585 | 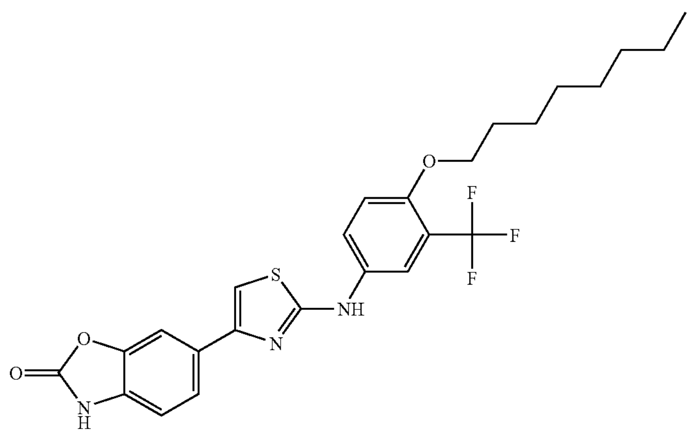 | 6-(2-(3-(trifluoromethyl)-4-(octyloxy)phenylamino)thiazol-4-yl)benzo[d]oxazol-2(3H)-one | +++ |
| 586 | 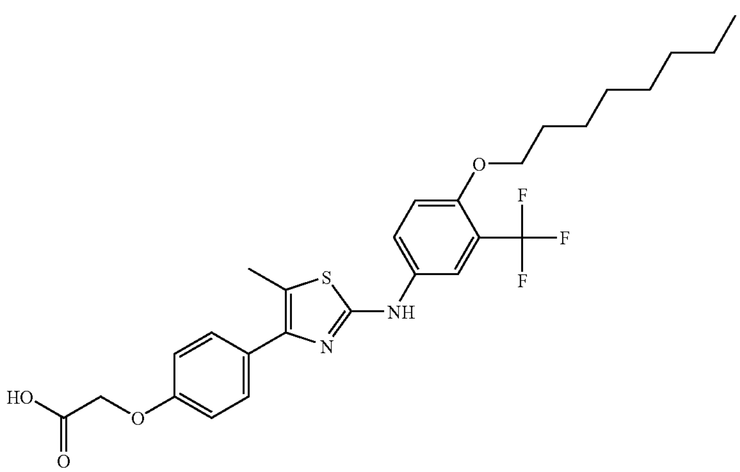 | 2-(4-(2-(3-(trifluoromethyl)-4-(octyloxy)phenylamino)-5-methylthiazol-4-yl)phenoxy)acetic acid | +++ |

TABLE III-continued
| Cpd | Structure | Name | Activity |
|---|---|---|---|
| 587 | 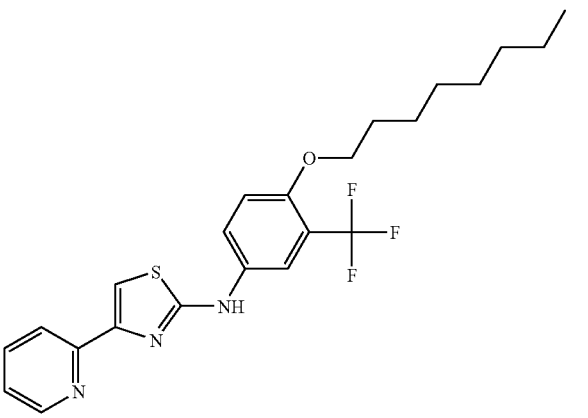 | N-(3-(trifluoromethyl)-4-(octyloxy)phenyl)-4-(pyridin-2-yl)thiazol-2-amine | +++ |
| 588 | 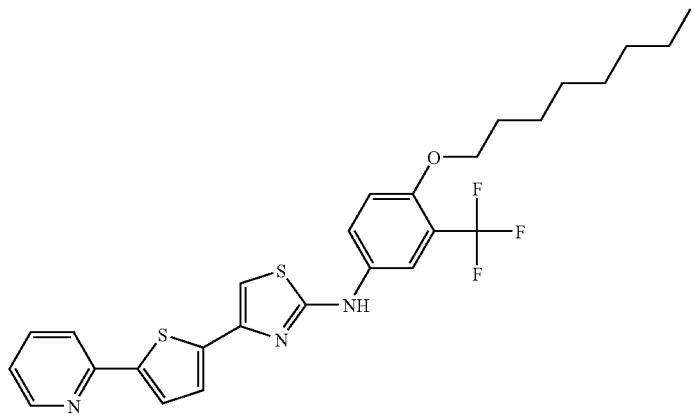 | N-(3-(trifluoromethyl)-4-(octyloxy)phenyl)-4-(5-(pyridin-2-yl)thiophen-2-yl)thiazol-2-amine | +++ |
| 589 | 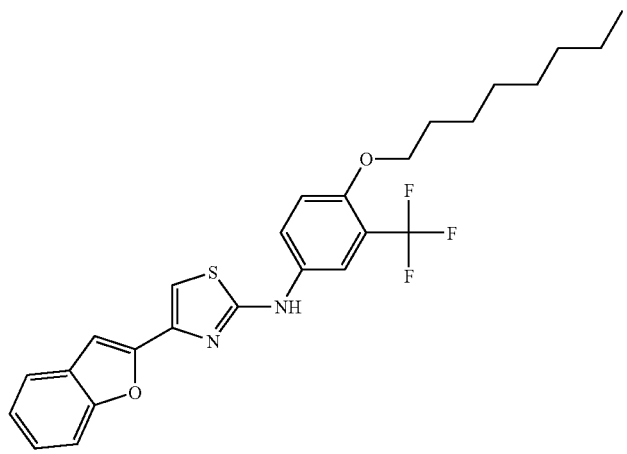 | 4-(benzofuran-2-yl)-N-(3-(trifluoromethyl)-4-(octyloxy)phenyl)thiazol-2-amine | +++ |

TABLE III-continued
| Cpd | Structure | Name | Activity |
|---|---|---|---|
| 590 | 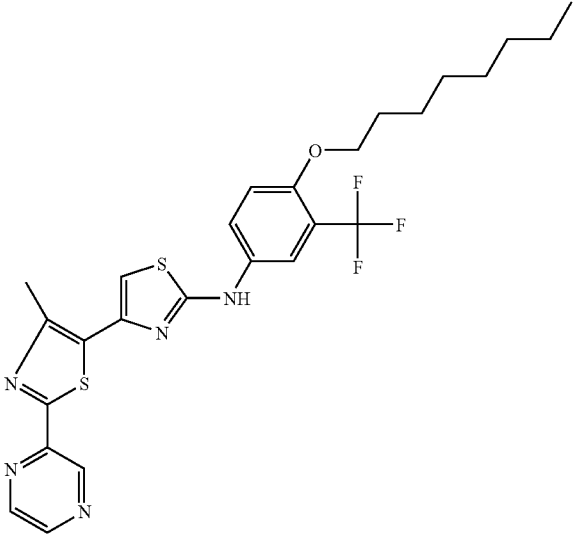 | N-(3-(trifluoromethyl)-4-(octyloxy)phenyl)-4-(4-methyl-2-(pyrazin-2-yl)thiazol-5-yl)thiazol-2-amine | +++ |
| 591 | 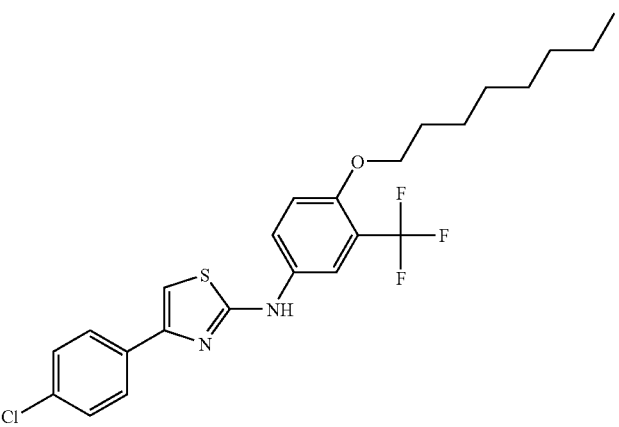 | 4-(4-chlorophenyl)-N-(3-(trifluoromethyl)-4-(octyloxy)phenyl)thiazol-2-amine | +++ |
| 592 | 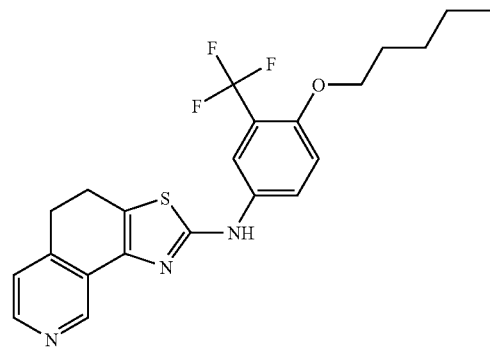 | N-(3-(trifluoromethyl)-4-(pentyloxy)phenyl)-4,5-dihydrothiazolo[5,4-h]isoquinolin-2-amine | +++ |

TABLE III-continued

| Cpd | Structure | Name | Activity |
|---|---|---|---|
| 593 | 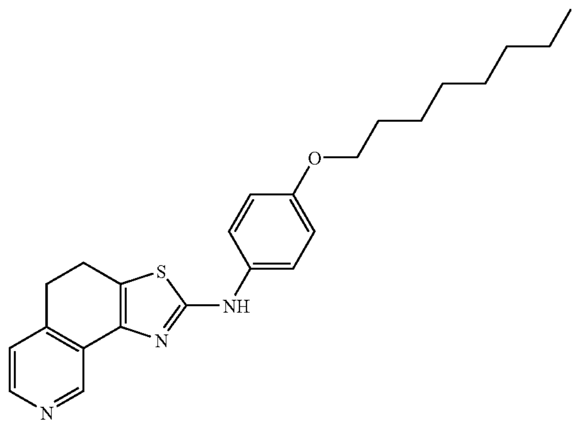 | 4,5-dihydro-N-(4-(octyloxy)phenyl)thiazolo[5,4-h]isoquinolin-2-amine | +++ |
| 594 | 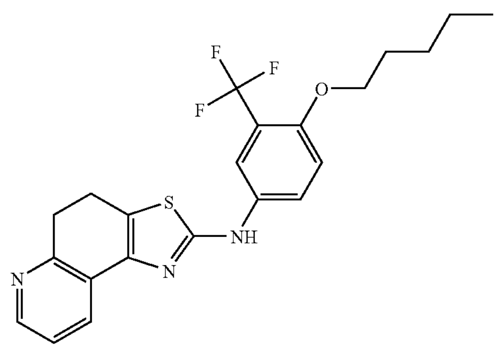 | N-(3-(trifluoromethyl)-4-(pentyloxy)phenyl)-4,5-dihydrothiazolo[4,5-f]quinolin-2-amine | +++ |
| 595 | 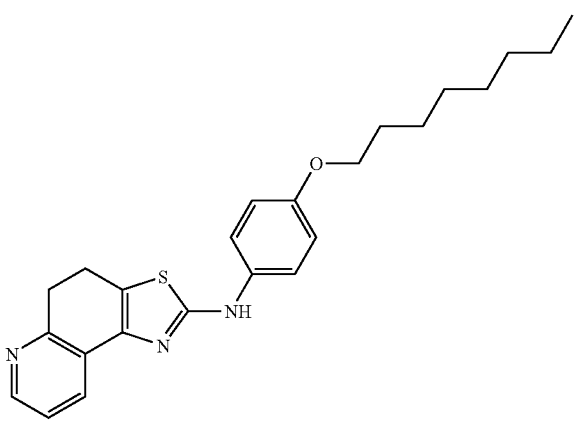 | 4,5-dihydro-N-(4-(octyloxy)phenyl)thiazolo[4,5-f]quinolin-2-amine | ++ |
| 596 | 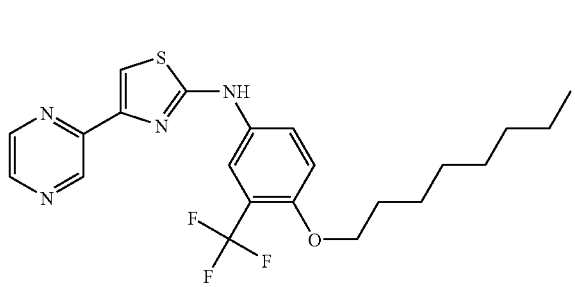 | N-(3-(trifluoromethyl)-4-(octyloxy)phenyl)-4-(pyrazin-2-yl)thiazol-2-amine | +++ |

TABLE III-continued

| Cpd | Structure | Name | Activity |
|---|---|---|---|
| 597 | 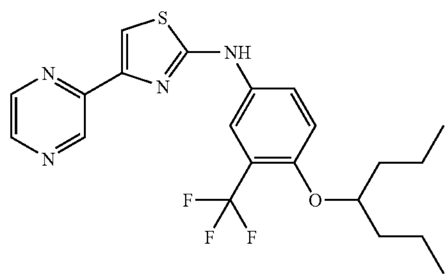 | N-(3-(trifluoromethyl)-4-(heptan-4-yloxy)phenyl)-4-(pyrazin-2-yl)thiazol-2-amine | +++ |
| 598 | 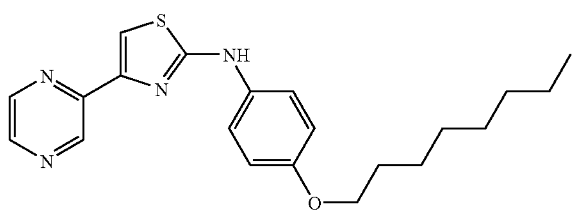 | N-(4-(octyloxy)phenyl)-4-(pyrazin-2-yl)thiazol-2-amine | +++ |
| 599 | 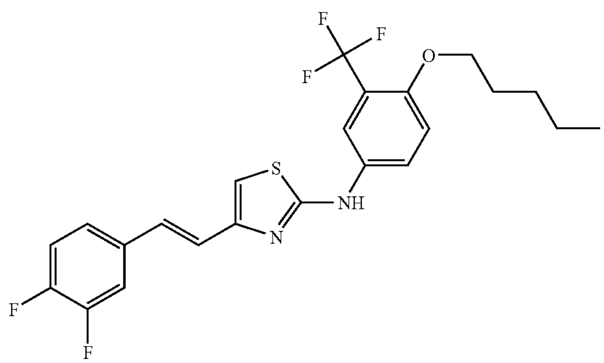 | 4-(3,4-difluorostyryl)-N-(3-(trifluoromethyl)-4-(pentyloxy)phenyl)thiazol-2-amine | +++ |
| 600 | 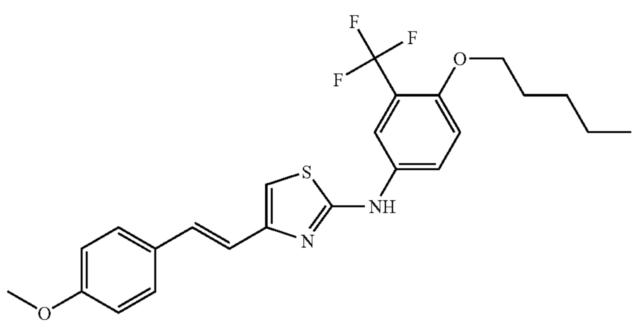 | 4-(4-methoxystyryl)-N-(3-(trifluoromethyl)-4-(pentyloxy)phenyl)thiazol-2-amine | +++ |
| 601 | 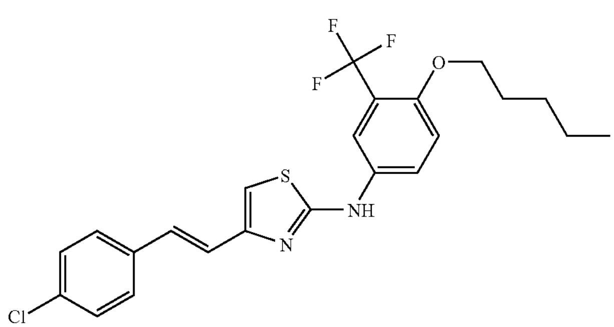 | 4-(4-chlorostyryl)-N-(3-(trifluoromethyl)-4-(pentyloxy)phenyl)thiazol-2-amine | +++ |

TABLE III-continued

| Cpd | Structure | Name | Activity |
|---|---|---|---|
| 602 | 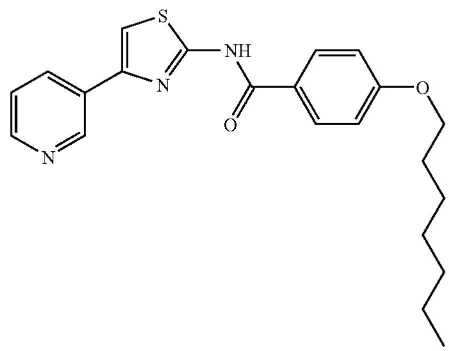 | 4-(heptyloxy)-N-(4-(pyridin-3-yl)thiazol-2-yl)benzamide | + |
| 603 | 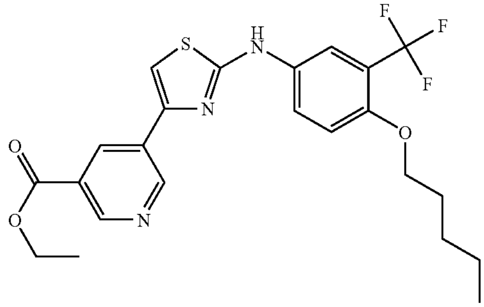 | ethyl 5-(2-(3-(trifluoromethyl)-4-(pentyloxy)phenylamino)thiazol-4-yl)pyridine-3-carboxylate | ++ |
| 604 | 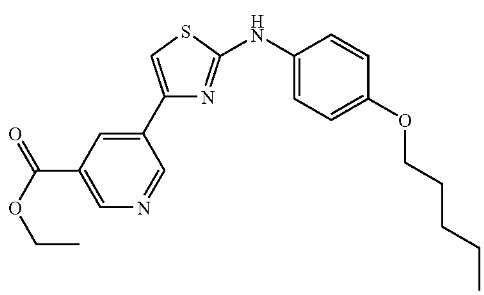 | ethyl 5-(2-(4-(octyloxy)phenylamino)thiazol-4-yl)pyridine-3-carboxylate | ++ |
| 605 | 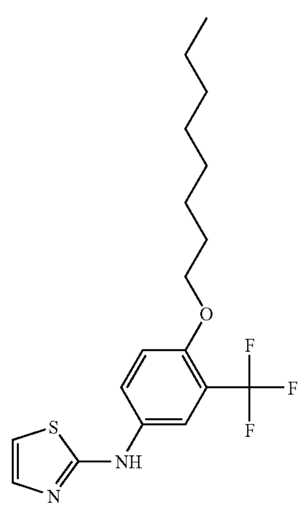 | N-(3-(trifluoromethyl)-4-(octyloxy)phenyl)thiazol-2-amine | +++ |

TABLE III-continued

| Cpd | Structure | Name | Activity |
|---|---|---|---|
| 606 | 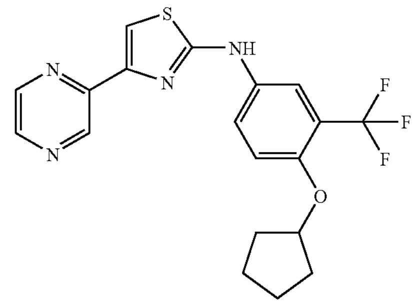 | N-(4-(cyclopentyloxy)-3-(trifluoromethyl)phenyl)-4-(pyrazin-2-yl)thiazol-2-amine | +++ |
| 607 | 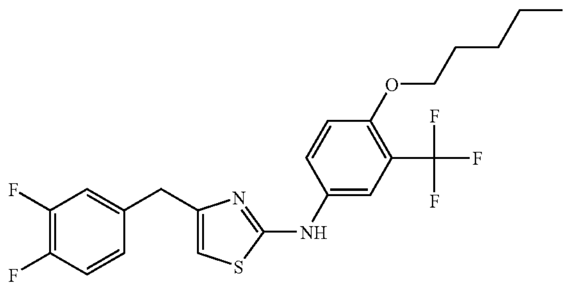 | 4-(3,4-difluorobenzyl)-N-(3-(trifluoromethyl)-4-(pentyloxy)phenyl)thiazol-2-amine | ++ |
| 608 | 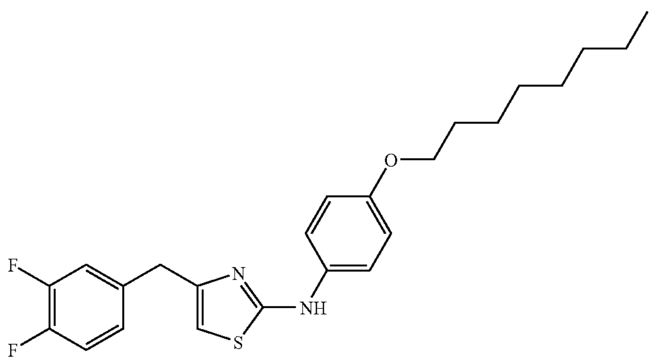 | 4-(3,4-difluorobenzyl)-N-(4-(octyloxy)phenyl)thiazol-2-amine | + |
| 609 | 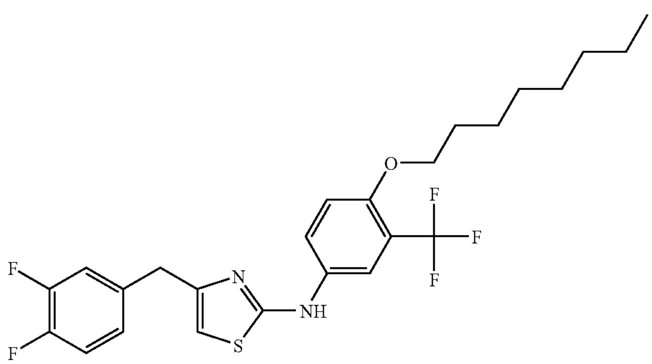 | 4-(3,4-difluorobenzyl)-N-(3-(trifluoromethyl)-4-(octyloxy)phenyl)thiazol-2-amine | ++ |
| 610 | 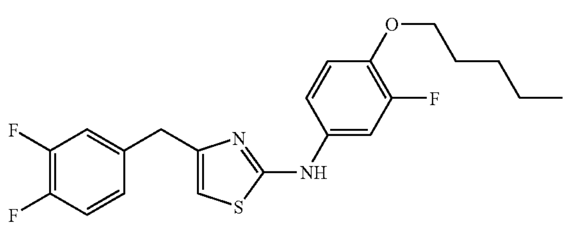 | 4-(3,4-difluorobenzyl)-N-(3-fluoro-4-(pentyloxy)phenyl)thiazol-2-amine | + |

TABLE III-continued

| Cpd | Structure | Name | Activity |
|---|---|---|---|
| 611 | 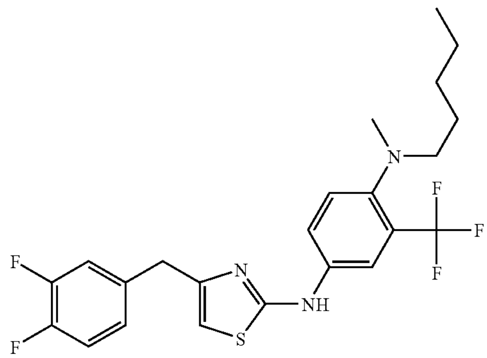 | N⁴-(4-(3,4-difluorobenzyl)thiazol-2-yl)-2-(trifluoromethyl)-N¹-methyl-N¹-pentylbenzene-1,4-diamine | + |
| 612 | 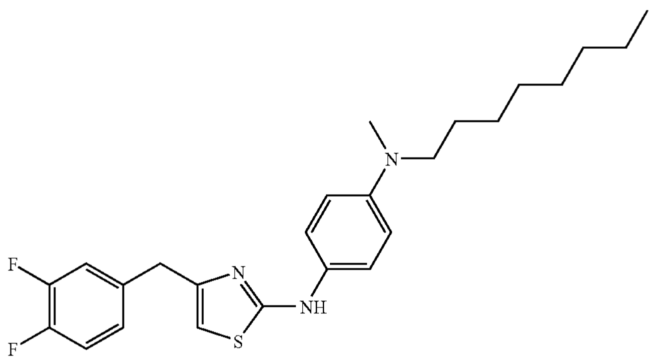 | N¹-(4-(3,4-difluorobenzyl)thiazol-2-yl)-N⁴-methyl-N⁴-octylbenzene-1,4-diamine | + |
| 613 | 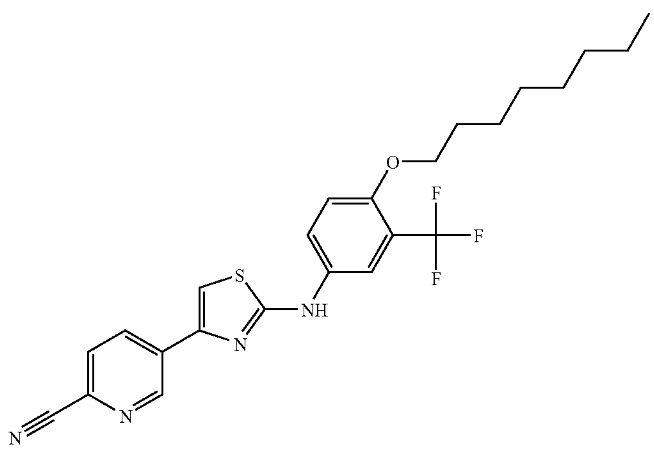 | 5-(2-(3-(trifluoromethyl)-4-(octyloxy)phenylamino)thiazol-4-yl)pyridine-2-carbonitrile | +++ |
| 614 | 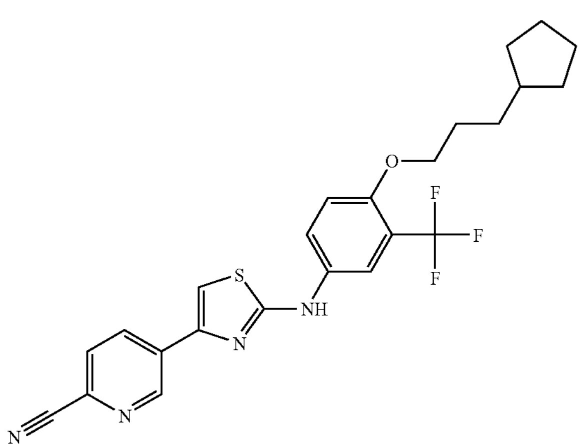 | 5-(2-(4-(3-cyclopentylpropoxy)-3-(trifluoromethyl)phenylamino)azol-4-yl)pyridine-2-carbonitrile | +++ |

TABLE III-continued

| Cpd | Structure | Name | Activity |
|---|---|---|---|
| 615 | 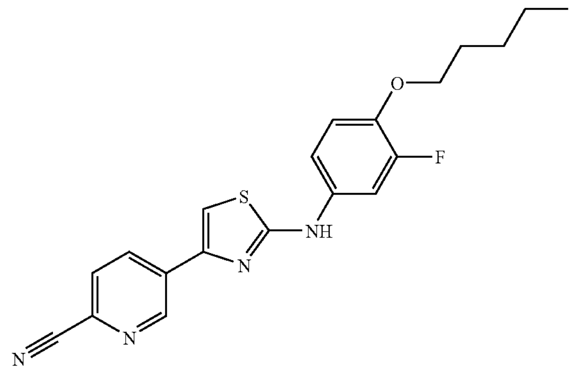 | 5-(2-(3-fluoro-4-(pentyloxy)phenylamino)thiazol-4-yl)pyridine-2-carbonitrile | +++ |
| 616 | 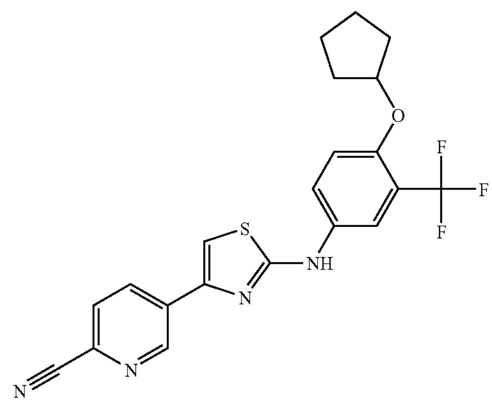 | 5-(2-(4-(cyclopentyloxy)-3-(trifluoromethyl)phenylamino)thiazol-4-yl)pyridine-2-carbonitrile | +++ |
| 617 | 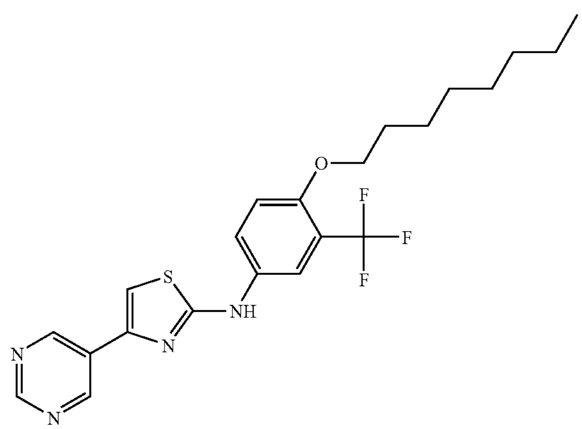 | N-(3-(trifluoromethyl)-4-(octyloxy)phenyl)-4-(pyrimidin-5-yl)thiazol-2-amine | +++ |
| 618 | 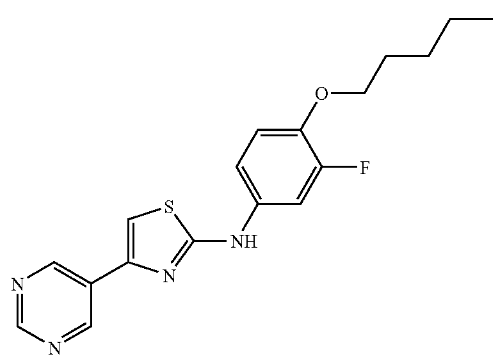 | N-(3-fluoro-4-(pentyloxy)phenyl)-4-(pyrimidin-5-yl)thiazol-2-amine | +++ |

TABLE III-continued

| Cpd | Structure | Name | Activity |
|---|---|---|---|
| 619 | 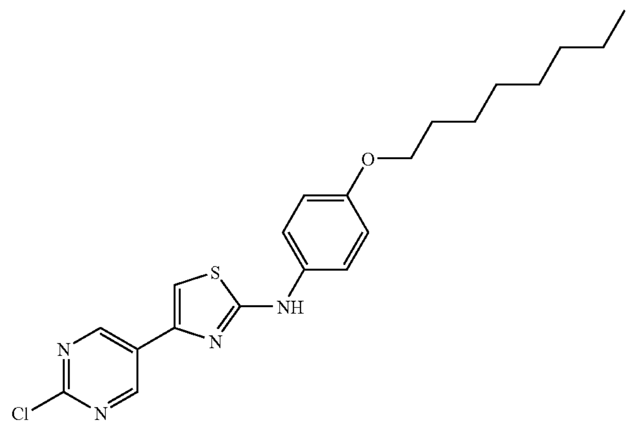 | 4-(2-chloropyrimidin-5-yl)-N-(4-(octyloxy)phenyl)thiazol-2-amine | +++ |
| 620 | 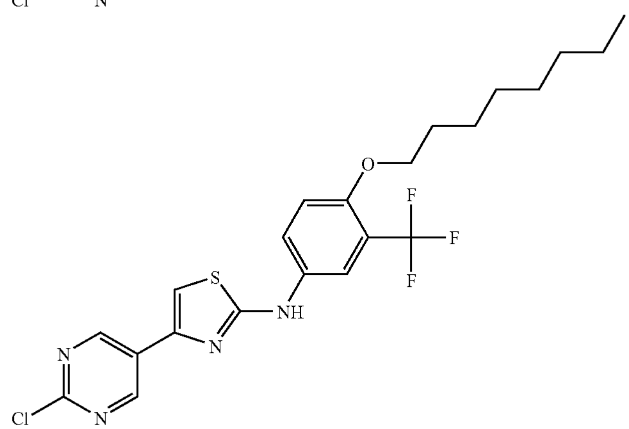 | 4-(2-chloropyrimidin-5-yl)-N-(3-(trifluoromethyl)-4-(octyloxy)phenyl)thiazol-2-amine | +++ |
| 621 | 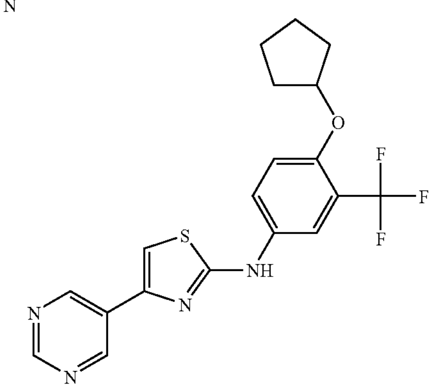 | N-(4-(cyclopentyloxy)-3-(trifluoromethyl)phenyl)-4-(pyrimidin-5-yl)thiazol-2-amine | +++ |
| 622 | 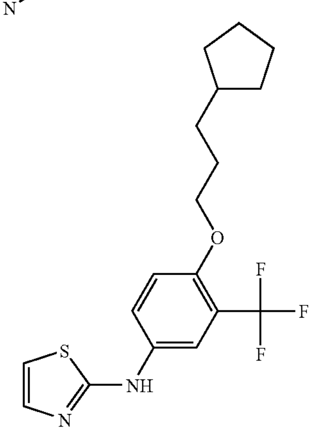 | N-(4-(3-cyclopentylpropoxy)-3-(trifluoromethyl)phenyl)thiazol-2-amine | +++ |

TABLE III-continued

| Cpd | Structure | Name | Activity |
|---|---|---|---|
| 623 | 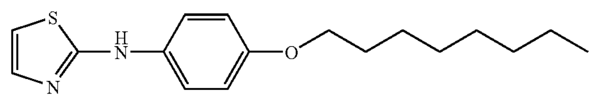 | N-(4-(octyloxy)phenyl)thiazol-2-amine | +++ |
| 624 | 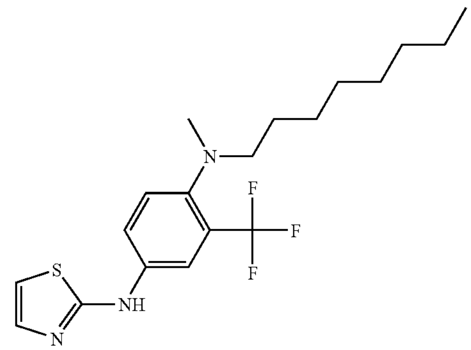 | 2-(trifluoromethyl)-N$^1$-methyl-N$^1$-octyl-N$^4$-(thiazol-2-yl)benzene-1,4-diamine | +++ |
| 625 | 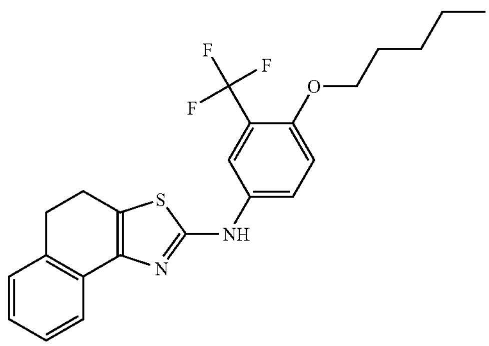 | N-(3-(trifluoromethyl)-4-(pentyloxy)phenyl)-4,5-dihydrothiazolo[4,5-f]isoquinolin-2-amine | +++ |
| 626 | 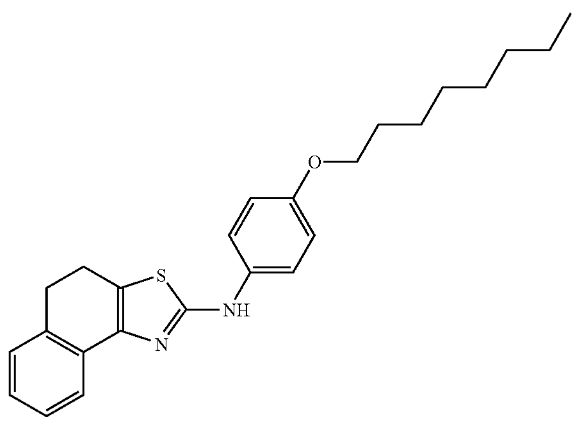 | 4,5-dihydro-N-(4-(octyloxy)phenyl)thiazolo[4,5-f]isoquinolin-2-amine | ++ |
| 627 | 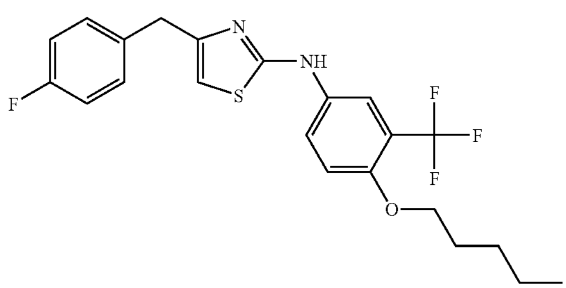 | 4-(4-fluorobenzyl)-N-(3-(trifluoromethyl)-4-(pentyloxy)phenyl)thiazol-2-amine | +++ |

TABLE III-continued

| Cpd | Structure | Name | Activity |
|---|---|---|---|
| 628 | 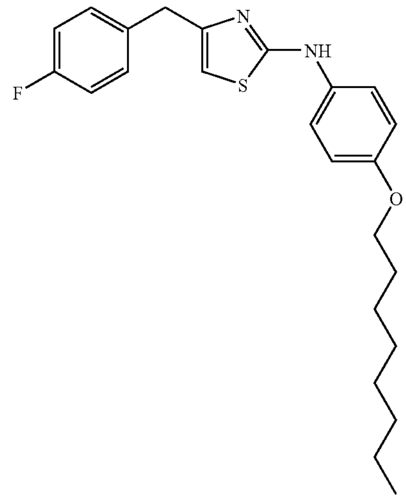 | 4-(4-fluorobenzyl)-N-(4-(octyloxy)phenyl)thiazol-2-amine | ++ |
| 629 | 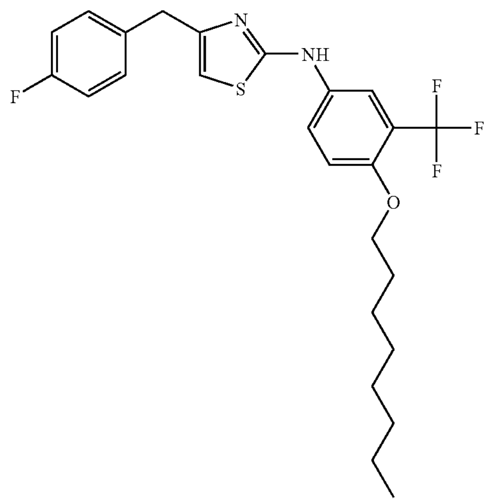 | 4-(4-fluorobenzyl)-N-(3-(trifluoromethyl)-4-(octyloxy)phenyl)thiazol-2-amine | +++ |
| 630 | 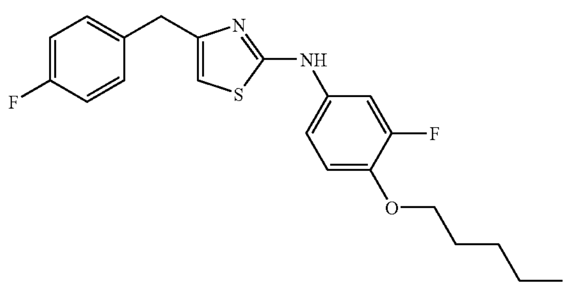 | 4-(4-fluorobenzyl)-N-(3-fluoro-4-(pentyloxy)phenyl)thiazol-2-amine | + |
| 631 | 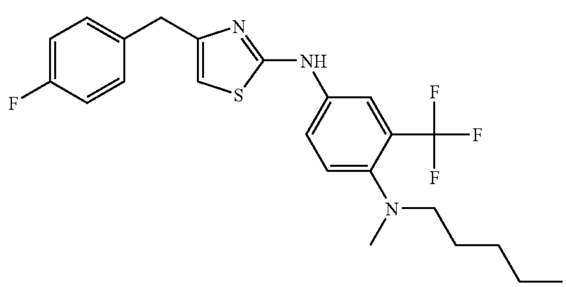 | N4-(4-(4-fluorobenzyl)thiazol-2-yl)-2-(trifluoromethyl)-N1-methyl-N1-pentylbenzene-1,4-diamine | + |

TABLE III-continued

| Cpd | Structure | Name | Activity |
|---|---|---|---|
| 632 | 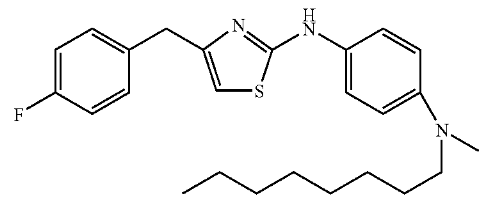 | N¹-(4-(4-fluorobenzyl)thiazol-2-yl)-N⁴-methyl-N⁴-octylbenzene-1,4-diamine | + |
| 633 | 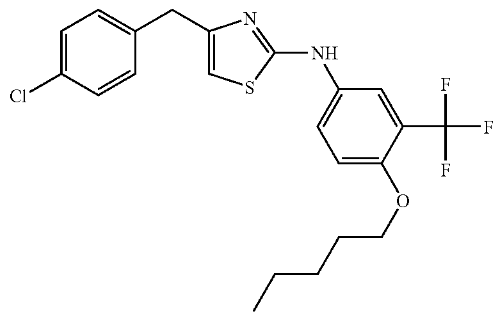 | 4-(4-chlorobenzyl)-N-(3-(trifluoromethyl)-4-(pentyloxy)phenyl)thiazol-2-amine | ++ |
| 634 | 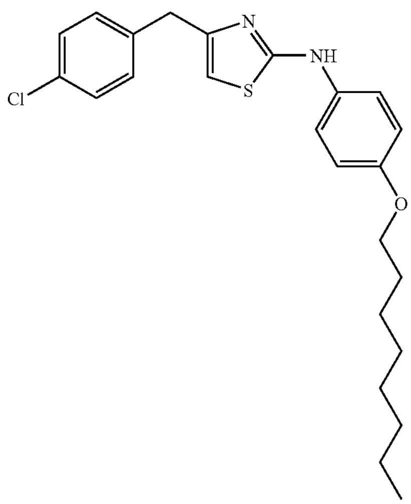 | 4-(4-chlorobenzyl)-N-(4-(octyioxy)phenyl)thiazol-2-amine | + |
| 635 | 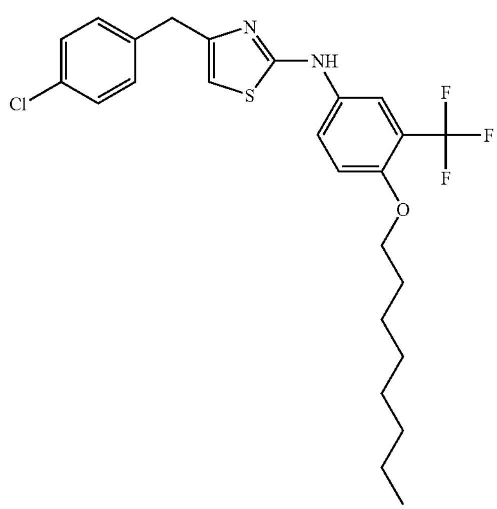 | 4-(4-chlorobenzyl)-N-(3-(trifluoromethyl)-4-(octyloxy)phenyl)thiazol-2-amine | ++ |

TABLE III-continued

| Cpd | Structure | Name | Activity |
|---|---|---|---|
| 636 | 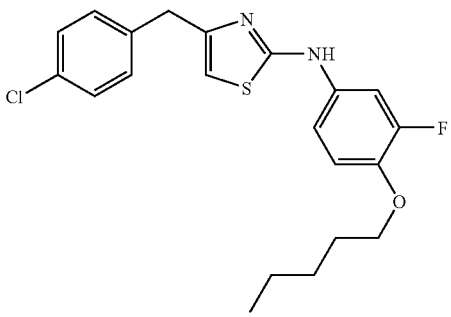 | 4-(4-chlorobenzyl)-N-(3-fluoro-4-(pentyloxy)phenyl)thiazol-2-amine | + |
| 637 | 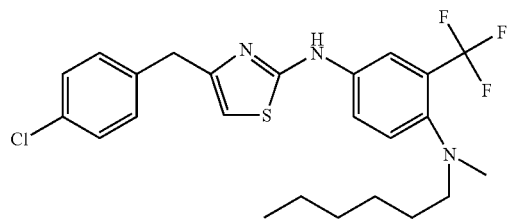 | $N^4$-(4-(4-chlorobenzyl)thiazol-2-yl)-2-(trifluoromethyl)-$N^1$-methyl-$N^1$-pentylbenzene-1,4-diamine | ++ |
| 638 | 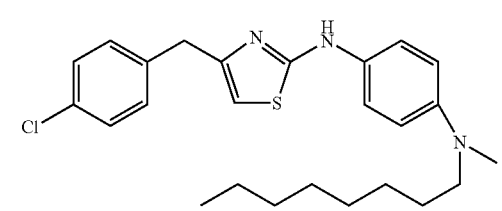 | $N^1$-(4-(4-chlorobenzyl)thiazol-2-yl)-$N^4$-methyl-$N^4$-octylbenzene-1,4-diamine | ++ |
| 639 | 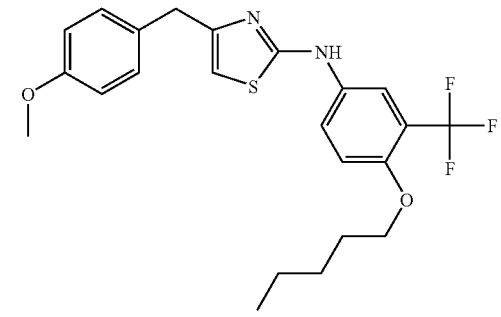 | 4-(4-methoxybenzyl)-N-(3-(trifluoromethyl)-4-(pentyloxy)phenyl)thiazol-2-amine | ++ |
| 640 | 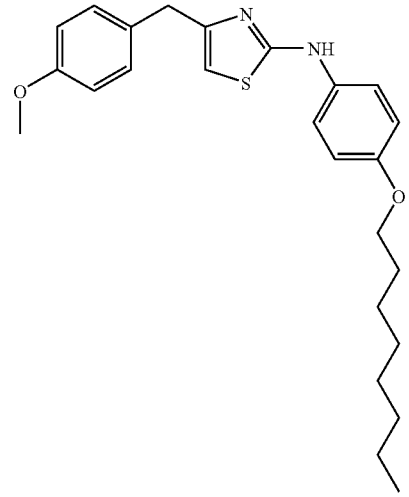 | 4-(4-methoxybenzyl)-N-(4-(octyloxy)phenyl)thiazol-2-amine | + |

TABLE III-continued

| Cpd | Structure | Name | Activity |
|---|---|---|---|
| 641 | 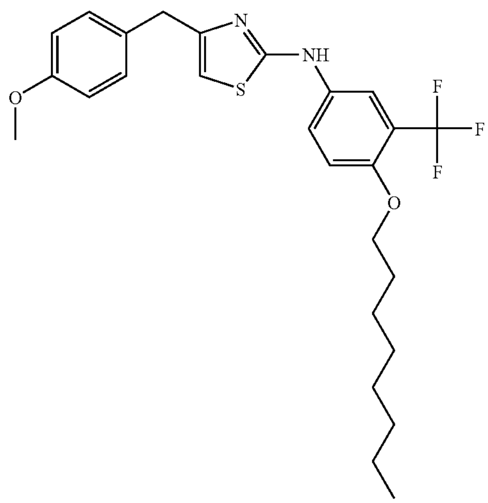 | 4-(4-methoxybenzyl)-N-(3-(trifluoromethyl)-4-(octyloxy)phenyl)thiazol-2-amine | +++ |
| 642 | 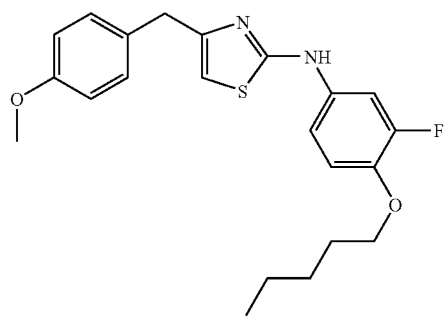 | 4-(4-methoxybenzyl)-N-(3-fluoro-4-(pentyloxy)phenyl)thiazol-2-amine | + |
| 643 | 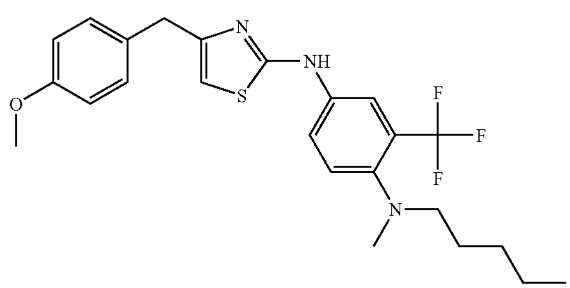 | $N^4$-(4-(4-methoxybenzyl)thiazol-2-yl)-2-(trifluoromethyl)-$N^1$-methyl-$N^1$-pentylbenzene-1,4-diamine | + |
| 644 | 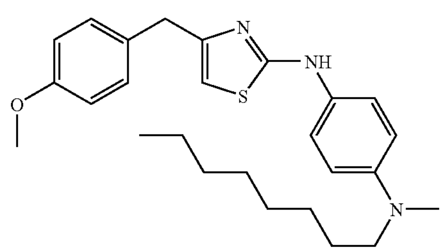 | $N^1$-(4-(4-methoxybenzyl)thiazol-2-yl)-$N^4$-methyl-$N^4$-octylbenzene-1,4-diamine | + |

TABLE III-continued

| Cpd | Structure | Name | Activity |
|---|---|---|---|
| 645 | 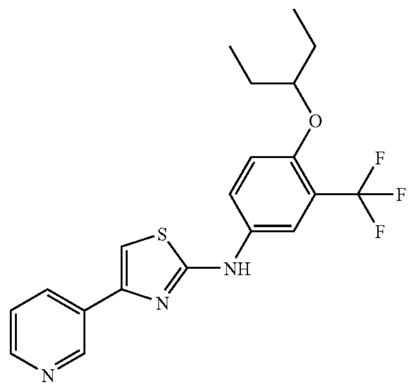 | N-(3-(trifluoromethyl)-4-(pentan-3-yloxy)phenyl)-4-(pyridin-3-yl)thiazol-2-amine | +++ |
| 646 | 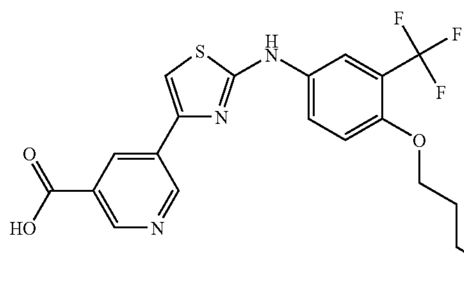 | 5-(2-(3-(trifluoromethyl)-4-(pentyloxy)phenylamino)thiazol-4-yl)pyridine-3-carboxylic acid | +++ |
| 647 | 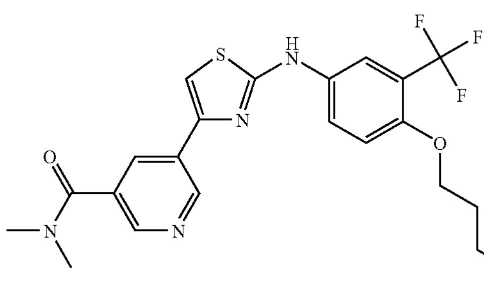 | 5-(2-(3-(trifluoromethyl)-4-(pentyloxy)phenylamino)thiazol-4-yl)-N,N-dimethylpyridine-3-carboxamide | +++ |
| 648 | 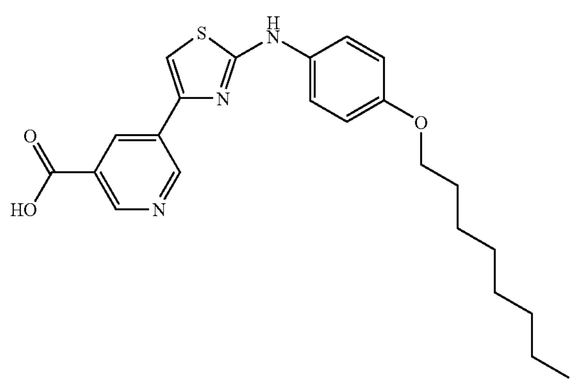 | 5-(2-(4-(octyloxy)phenylamino)thiazol-4-yl)pyridine-3-carboxylic acid | ++ |

TABLE III-continued

| Cpd | Structure | Name | Activity |
|---|---|---|---|
| 649 | 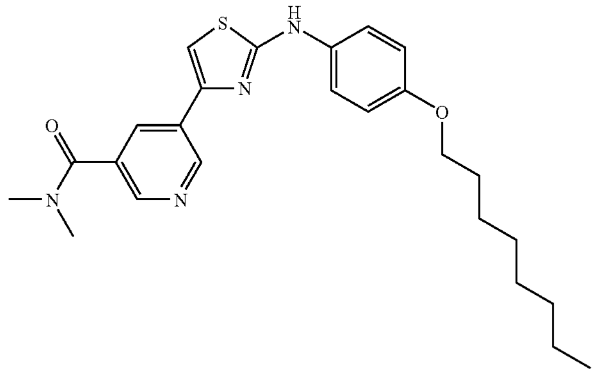 | 5-(2-(4-(octyloxy)phenylamino)thiazol-4-yl)-N,N-dimethylpyridine-3-carboxamide | ++ |
| 650 | 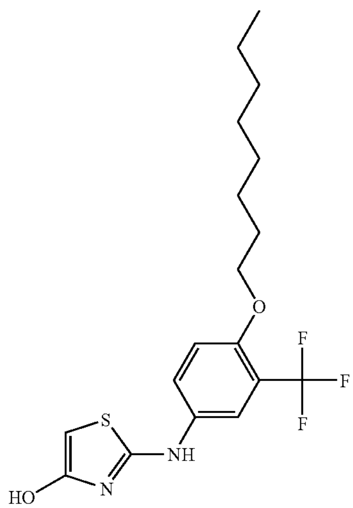 | 2-(3-(trifluoromethyl)-4-(octyloxy)phenylamino)thiazol-4-ol | ++ |
| 651 | 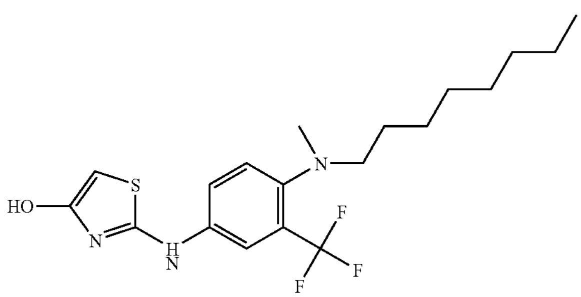 | 2-(4-(N-methyl-N-octylamino)-3-(trifluoromethyl)phenylamino)azol-4-ol | ++ |
| 652 | 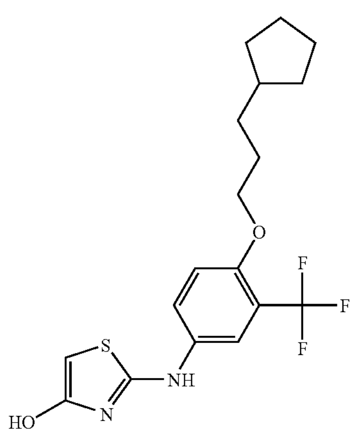 | 2-(4-(3-cyclopentylpropoxy)-3-(trifluoromethyl)phenylamino)azol-4-ol | ++ |

TABLE III-continued

| Cpd | Structure | Name | Activity |
|---|---|---|---|
| 653 | 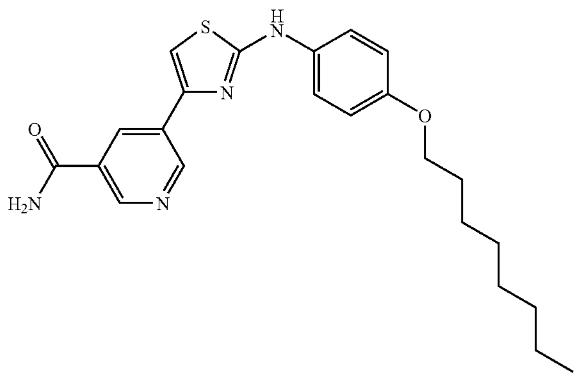 | 5-(2-(4-(octyloxy)phenylamino)thiazol-4-yl)pyridine-3-carboxamide | +++ |
| 654 | 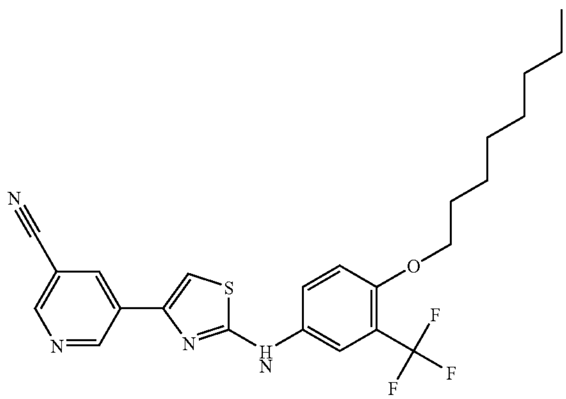 | 5-(2-(3-(trifluoromethyl)-4-(octyloxy)phenylamino)thiazol-4-yl)pyridine-3-carbonitrile | +++ |
| 655 | 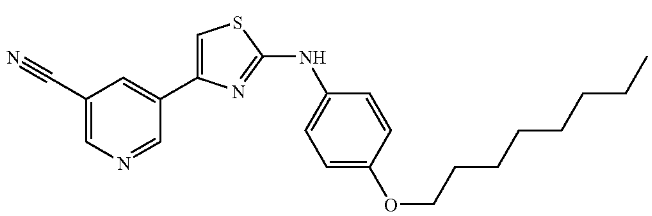 | 5-(2-(4-(octyloxy)phenylamino)thiazol-4-yl)pyridine-3-carbonitrile | +++ |
| 656 | 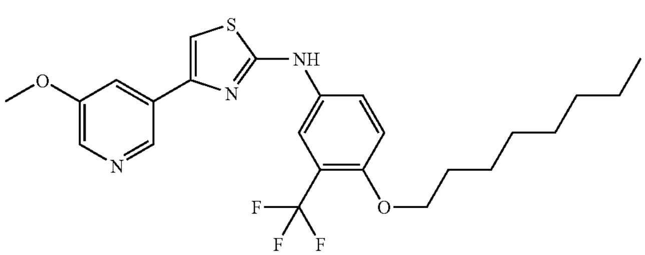 | N-(3-(trifluoromethyl)-4-(octyloxy)phenyl)-4-(5-methoxypyridin-3-yl)thiazol-2-amine | ++ |
| 657 | 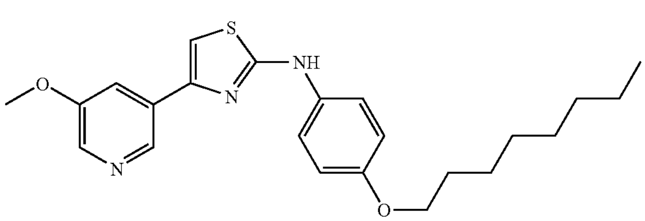 | 4-(5-methoxypyridin-3-yl)-N-(4-(octyloxy)phenyl)thiazol-2-amine | ++ |

TABLE III-continued

| Cpd | Structure | Name | Activity |
|---|---|---|---|
| 658 | 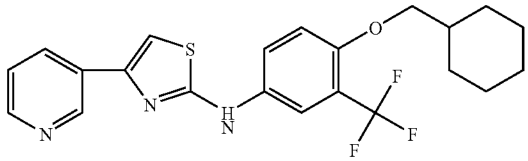 | N-(4-(cyclohexylmethoxy)-3-(trifluoromethyl)phenyl)-4-(pyridin-3-yl)thiazol-2-amine | +++ |
| 659 | 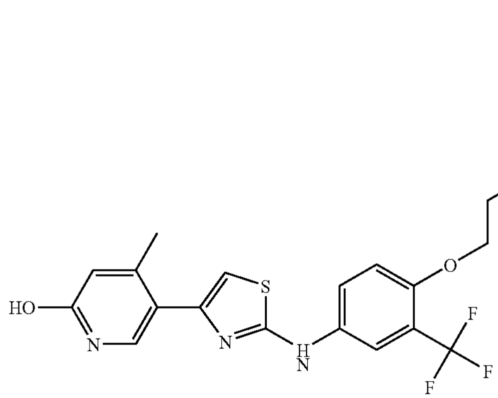 | 5-(2-(3-(trifluoromethyl)-4-(octyloxy)phenylamino)thiazol-4-yl)-4-methylpyridin-2-ol | +++ |
| 660 | 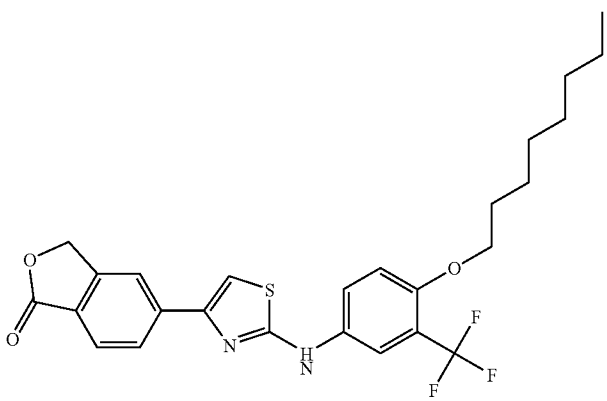 | 5-(2-(3-(trifluoromethyl)-4-(octyloxy)phenylamino)thiazol-4-yl)isobenzofuran-1(3H)-one | +++ |
| 661 | 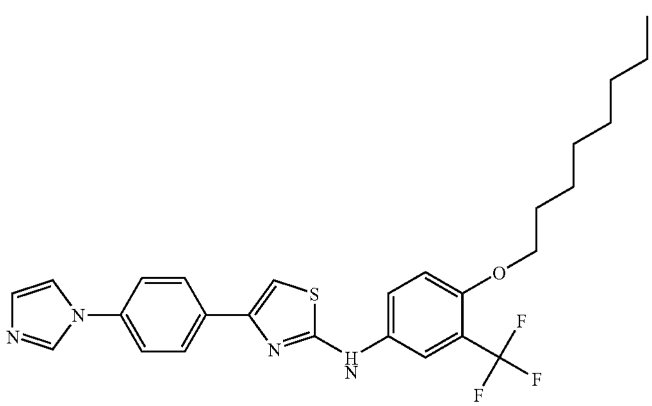 | 4-(4-(1H-imidazol-1-yl)phenyl)-N-(3-(trifluoromethyl)-4-(octyloxy)phenyl)thiazol-2-amine | +++ |

TABLE III-continued

| Cpd | Structure | Name | Activity |
|---|---|---|---|
| 662 | 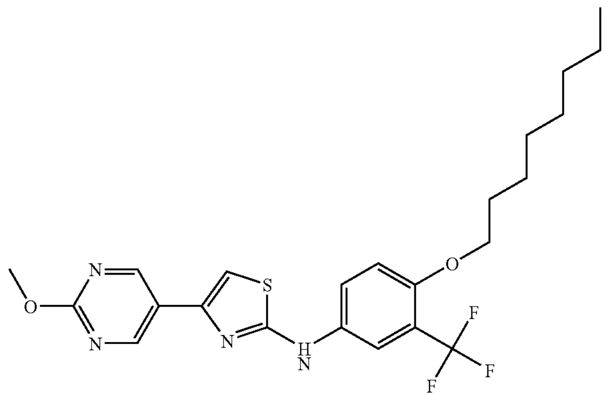 | N-(3-(trifluoromethyl)-4-(octyloxy)phenyl)-4-(2-methoxypyrimidin-5-yl)thiazol-2-amine | +++ |
| 663 | 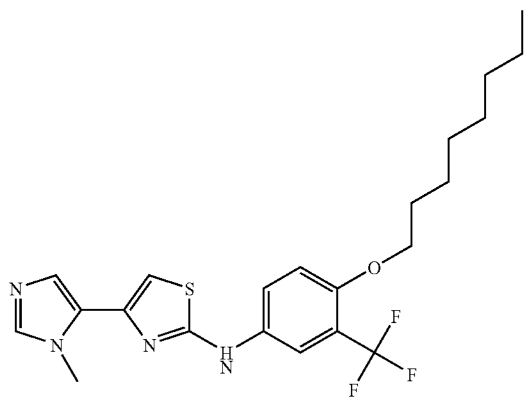 | N-(3-(trifluoromethyl)-4-(octyloxy)phenyl)-4-(1-methyl-1H-imidazol-5-yl)thiazol-2-amine | +++ |
| 664 | 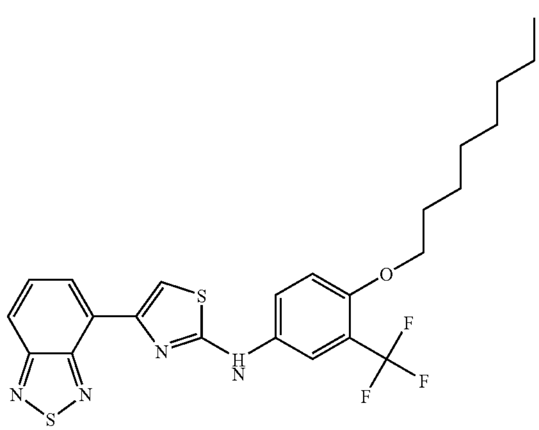 | 4-(benzo[c][1,2,5]thiadiazol-4-yl)-N-(3-(trifluoromethyl)-4-(octyloxy)phenyl)thiazol-2-amine | +++ |

TABLE III-continued

| Cpd | Structure | Name | Activity |
|---|---|---|---|
| 665 | 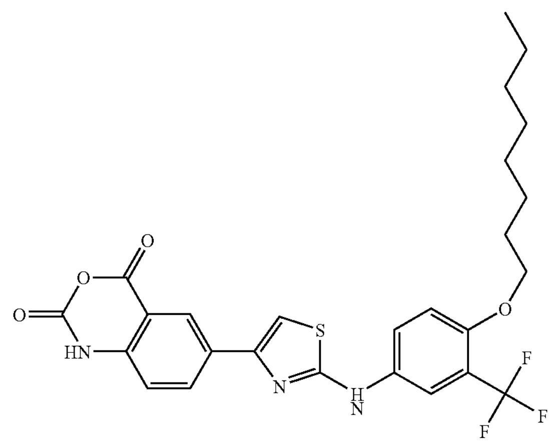 | 6-(2-(3-(trifluoromethyl)-4-(octyloxy)phenylamino)thiazol-4-yl)-1H-benzo[d][1,3]oxazine-2,4-dione | +++ |
| 666 | 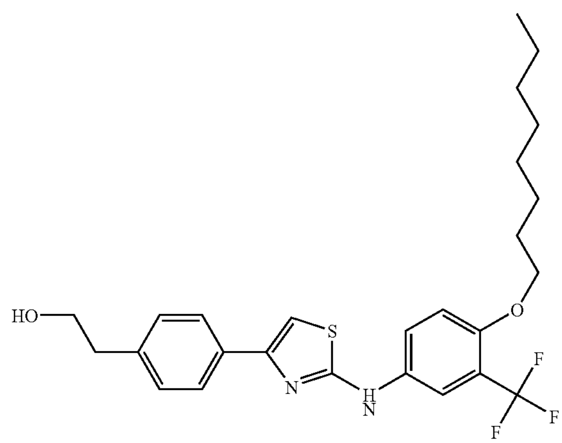 | 2-(4-(2-(3-(trifluoromethyl)-4-(octyloxy)phenylamino)thiazol-4-yl)phenyl)ethanol | +++ |
| 667 | 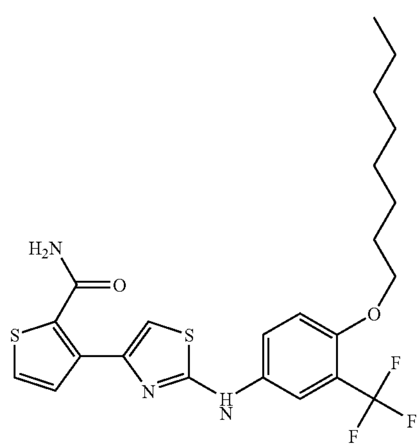 | 3-(2-(3-(trifluoromethyl)-4-(octyloxy)phenylamino)thiazol-4-yl)thiophene-2-carboxamide | +++ |

TABLE III-continued

| Cpd | Structure | Name | Activity |
|---|---|---|---|
| 668 | 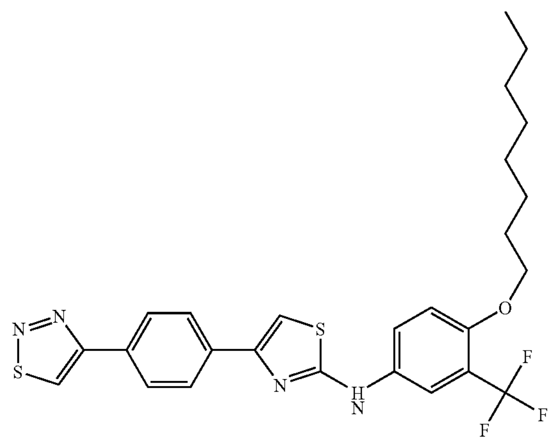 | 4-(4-(1,2,3-thiadiazol-4-yl)phenyl)-N-(3-(trifluoromethyl)-4-(octyloxy)phenyl)thiazol-2-amine | +++ |
| 669 | 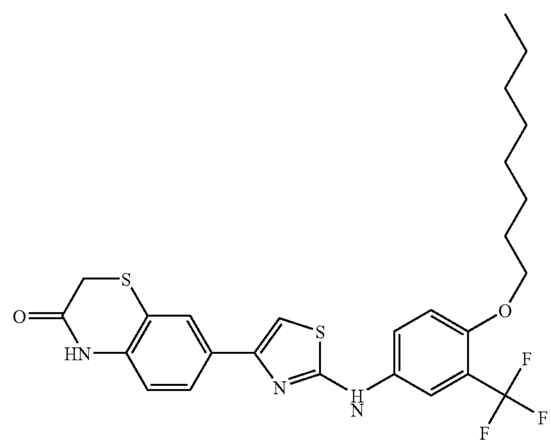 | 7-(2-(3-(trifluoromethyl)-4-(octyloxy)phenylamino)thiazol-4-yl)-2H-benzo[b][1,4]thiazin-3(4H)-one | +++ |
| 670 | 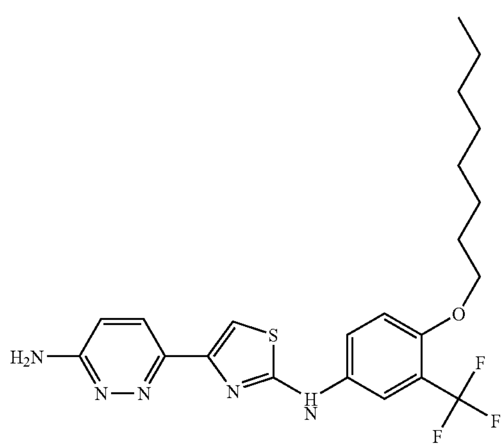 | 6-(2-(3-(trifluoromethyl)-4-(octyloxy)phenylamino)thiazol-4-yl)pyridazin-3-amine | +++ |

TABLE III-continued

| Cpd | Structure | Name | Activity |
|---|---|---|---|
| 671 | 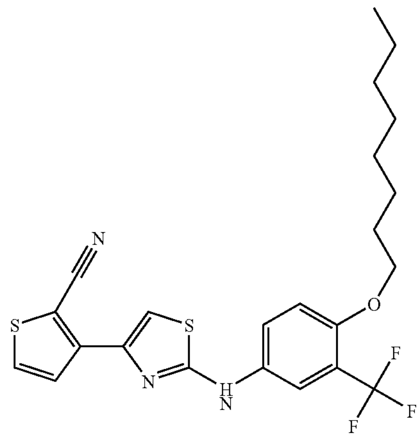 | 3-(2-(3-(trifluoromethyl)-4-(octyloxy)phenylamino)thiazol-4-yl)thiophene-2-carbonitrile | +++ |
| 672 | 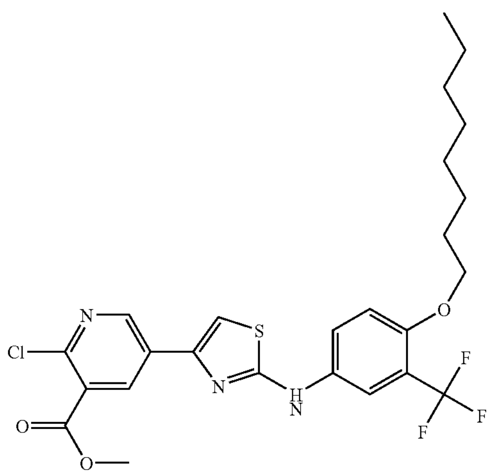 | methyl 5-(2-(3-(trifluoromethyl)-4-(octyloxy)phenylamino)thiazol-4-yl)-2-chloropyridine-3-carboxylate | +++ |
| 673 | 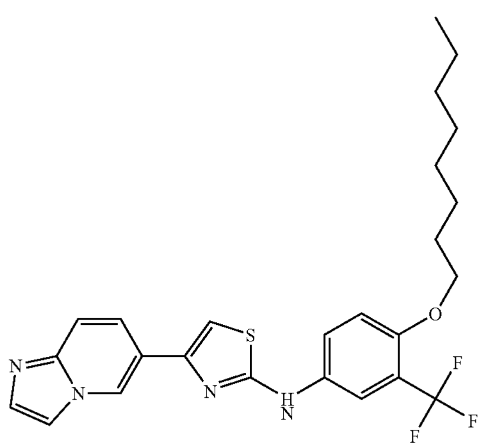 | N-(3-(trifluoromethyl)-4-(octyloxy)phenyl)-4-(H-imidazo[1,2-a]pyridin-6-yl)thiazol-2-amine | +++ |

TABLE III-continued

| Cpd | Structure | Name | Activity |
|---|---|---|---|
| 674 | 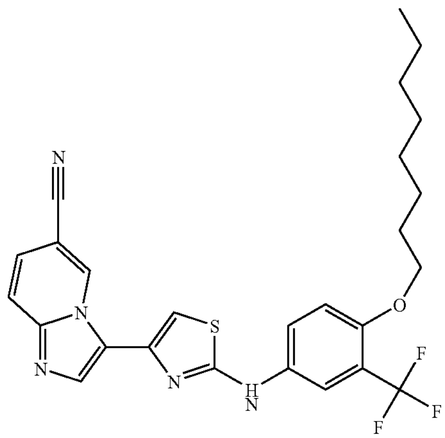 | 3-(2-(3-(trifluoromethyl)-4-(octyloxy)phenylamino)thiazol-4-yl)H-imidazo[1,2-a]pyridine-6-carbonitrile | +++ |
| 675 | 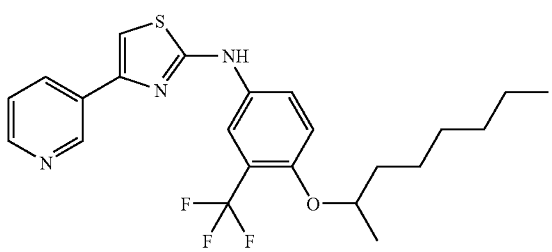 | N-(3-(trifluoromethyl)-4-(octan-2-yloxy)phenyl)-4-(pyridin-3-yl)thiazol-2-amine | +++ |
| 676 | 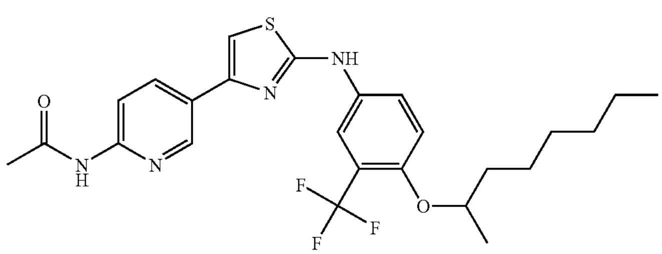 | N-(5-(2-(3-(trifluoromethyl)-4-(octan-2-yloxy)phenylamino)thiazol-4-yl)pyridin-2-yl)acetamide | +++ |
| 677 | 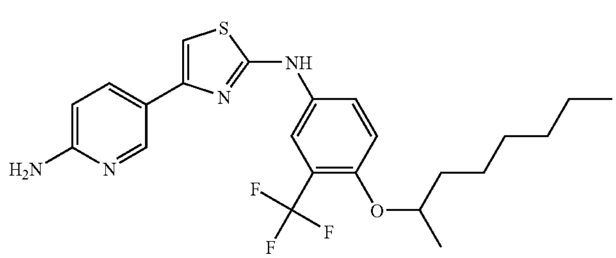 | 5-(2-(3-(trifluoromethyl)-4-(octan-2-yloxy)phenylamino)thiazol-4-yl)pyridin-2-amine | +++ |

TABLE III-continued

| Cpd | Structure | Name | Activity |
|---|---|---|---|
| 678 | 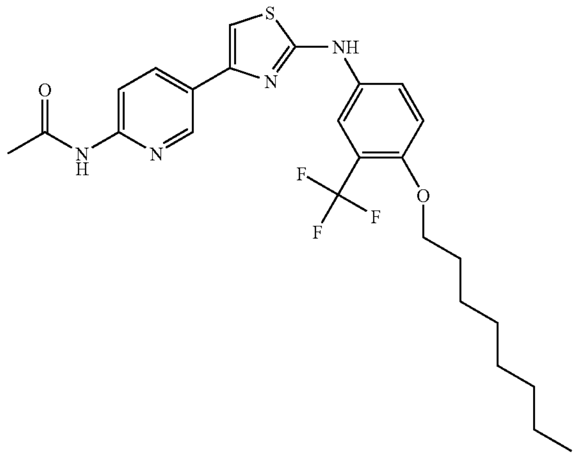 | N-(5-(2-(3-(trifluoromethyl)-4-(octyloxy)phenylamino)thiazol-4-yl)pyridin-2-yl)acetamide | +++ |
| 679 | 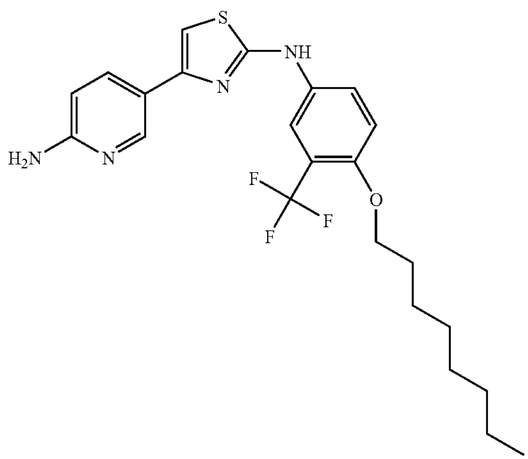 | 5-(2-(3-(trifluoromethyl)-4-(octyloxy)phenylamino)thiazol-4-yl)pyridin-2-amine | +++ |
| 680 | 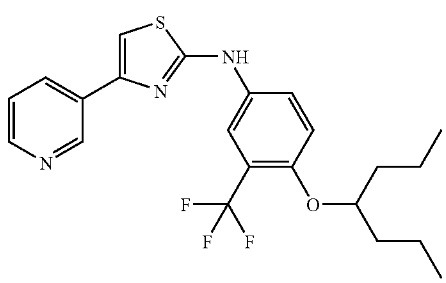 | N-(3-(trifluoromethyl)-4-(heptan-4-yloxy)phenyl)-4-(pyridin-3-yl)thiazol-2-amine | +++ |
| 681 | 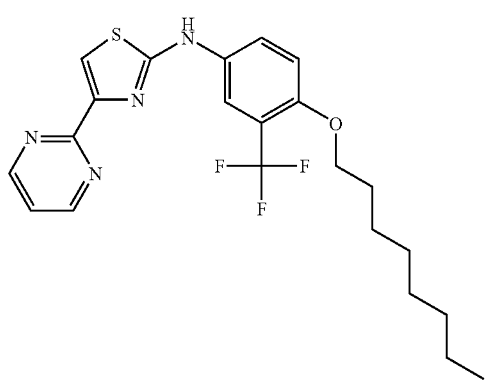 | N-(3-(trifluoromethyl)-4-(octyloxy)phenyl)-4-(pyrimidin-2-yl)thiazol-2-amine | +++ |

TABLE III-continued

| Cpd | Structure | Name | Activity |
|---|---|---|---|
| 682 | 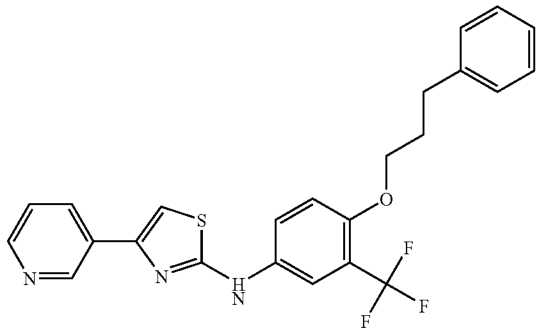 | N-(4-(3-phenylpropoxy)-3-(trifluoromethyl)phenyl)-4-(pyridin-3-yl)thiazol-2-amine | +++ |
| 683 | 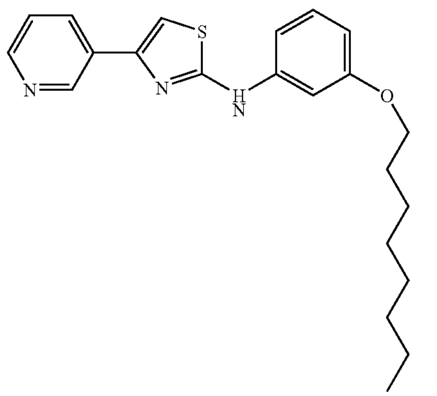 | N-(3-(octyloxy)phenyl)-4-(pyridin-3-yl)thiazol-2-amine | +++ |
| 684 | 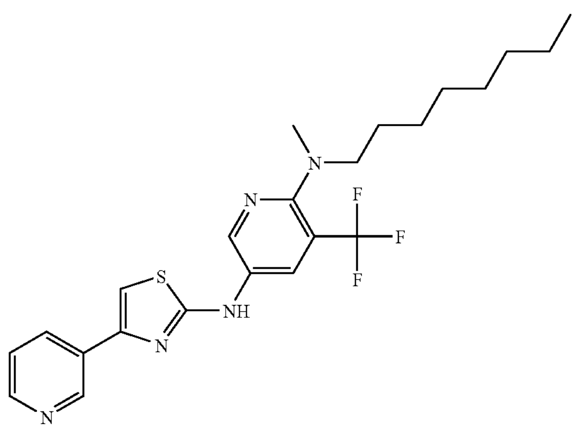 | 3-(trifluoromethyl)-$N^2$-methyl-$N^2$-octyl-$N^5$-(4-(pyridin-3-yl)thiazol-2-yl)pyridine-2,5-diamine | + |
| 685 | 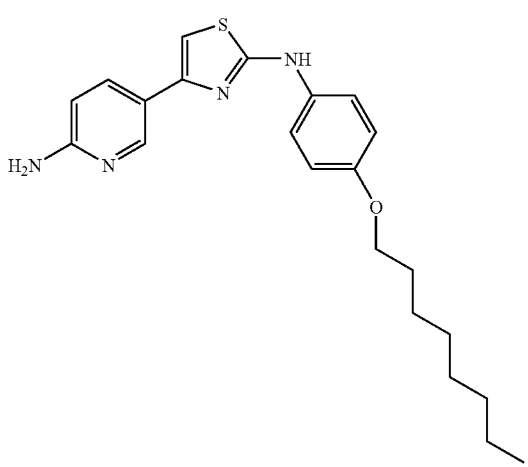 | 5-(2-(4-(octyloxy)phenylamino)thiazol-4-yl)pyridin-2-amine | +++ |

TABLE III-continued

| Cpd | Structure | Name | Activity |
|---|---|---|---|
| 686 | 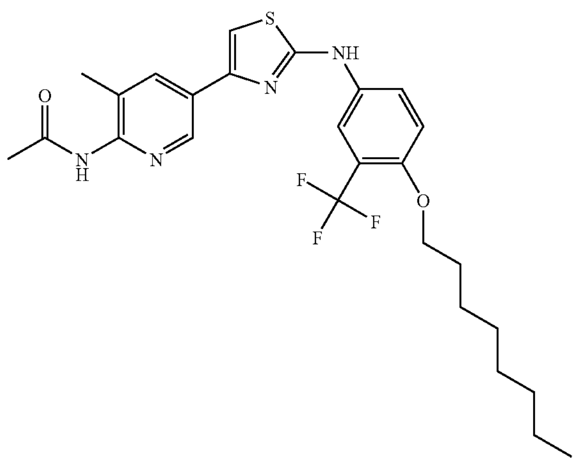 | N-(5-(2-(3-(trifluoromethyl)-4-(octyloxy)phenylamino)thiazol-4-yl)-3-methylpyridin-2-yl)acetamide | +++ |
| 687 | 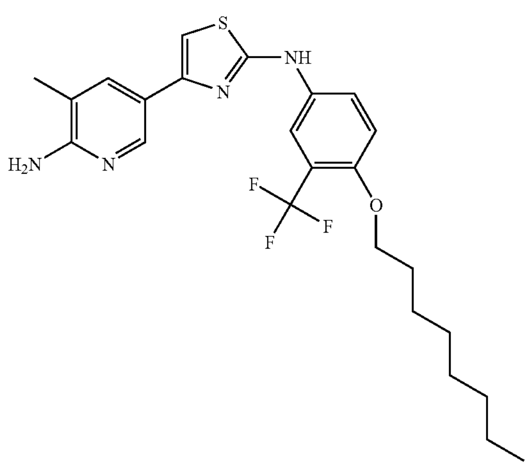 | 5-(2-(3-(trifluoromethyl)-4-(octyloxy)phenylamino)thiazol-4-yl)-3-methylpyridin-2-amine | +++ |
| 688 | 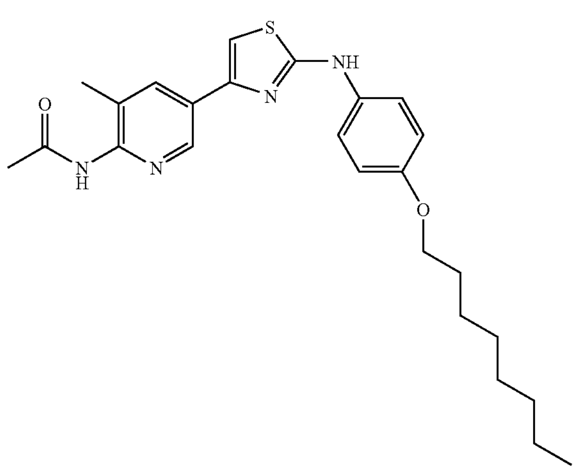 | N-(5-(2-(4-(octyloxy)phenylamino)thiazol-4-yl)-3-methylpyridin-2-yl)acetamide | ++ |

US 8,088,806 B2

TABLE III-continued

| Cpd | Structure | Name | Activity |
|---|---|---|---|
| 689 | 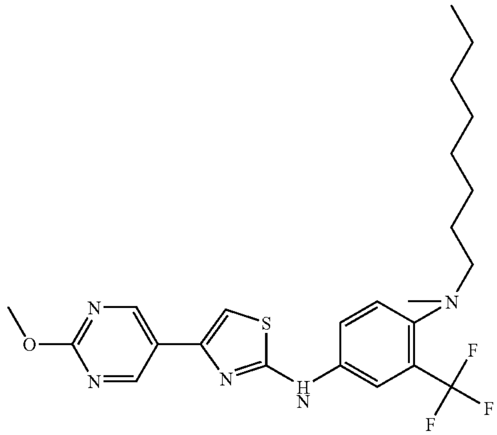 | 2-(trifluoromethyl)-N$^4$-(4-(2-methoxypyrimidin-5-yl)thiazol-2-yl)-N$^1$-methyl-N-octylbenzene-1,4-diamine | +++ |
| 690 | 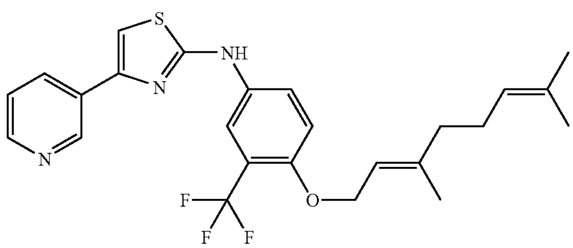 | N-(4-((E)-3,7-dimethylocta-2,6-dienyloxy)-3-(trifluoromethyl)phenyl)-4-(pyridin-3-yl)thiazol-2-amine | +++ |
| 691 | 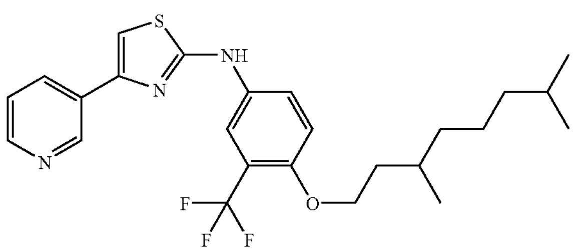 | N-(4-(3,7-dimethyloctyloxy)-3-(trifluoromethyl)phenyl)-4-(pyridin-3-yl)thiazol-2-amine | +++ |
| 692 | 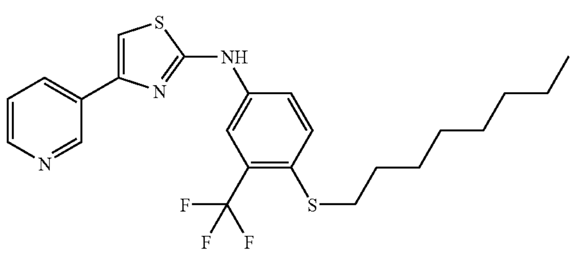 | N-(3-(trifluoromethyl)-4-(octylthio)phenyl)-4-(pyridin-3-yl)thiazol-2-amine | +++ |
| 693 | 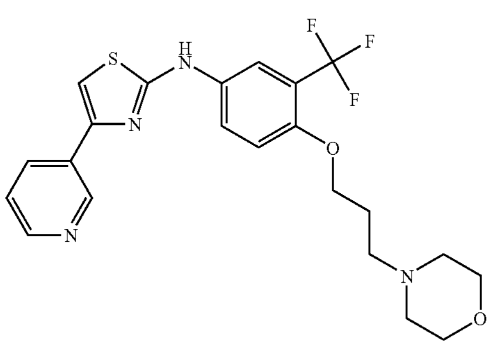 | N-(4-(3-morpholinopropoxy)-3-(trifluoromethyl)phenyl)-4-(pyridin-3-yl)thiazol-2-amine | ++ |

TABLE III-continued

| Cpd | Structure | Name | Activity |
|---|---|---|---|
| 694 | 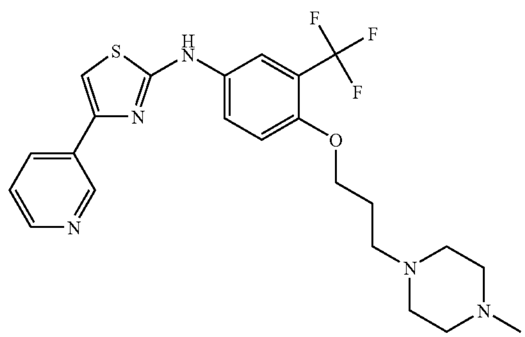 | N-(4-(3-(4-methylpiperazin-1-yl)propoxy)-3-(trifluoromethyl)phenyl)-4-(pyridin-3-yl)thiazol-2-amine | ++ |
| 695 | 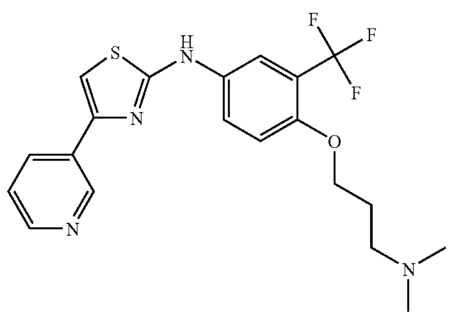 | N-(4-(3-(dimethylamino)propoxy)-3-(trifluoromethyl)phenyl)-4-(pyridin-3-yl)thiazol-2-amine | ++ |
| 696 | 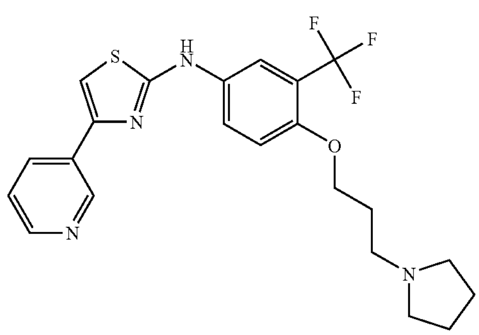 | N-(4-(3-(pyrrolidin-1-yl)propoxy)-3-(trifluoromethyl)phenyl)-4-(pyridin-3-yl)thiazol-2-amine | ++ |
| 697 | 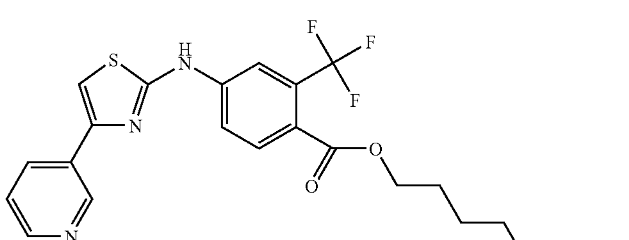 | octyl 4-(4-(pyridin-3-yl)thiazol-2-ylamino)-2-(trifluoromethyl)benzoate | +++ |
| 698 | 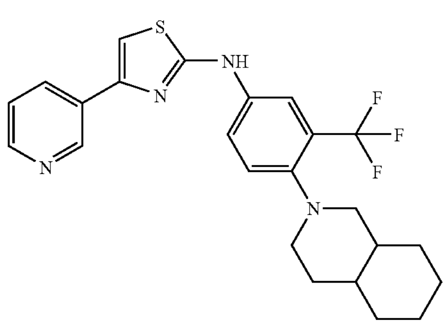 | N-(3-(trifluoromethyl)-4-(octahydroisoquinolin-2(1H)-yl)phenyl)-4-(pyridin-3-yl)thiazol-2-amine | +++ |

TABLE III-continued

| Cpd | Structure | Name | Activity |
|---|---|---|---|
| 699 | 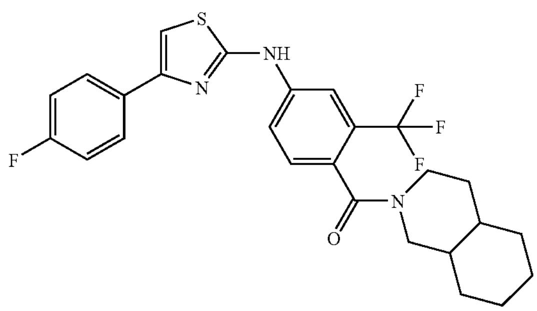 | (4-(4-(4-fluorophenyl)thiazol-2-ylamino)-2-(trifluoromethyl)phenyl)(octahydroisoquinolin-2(1H)-yl)methanone | + |
| 700 | 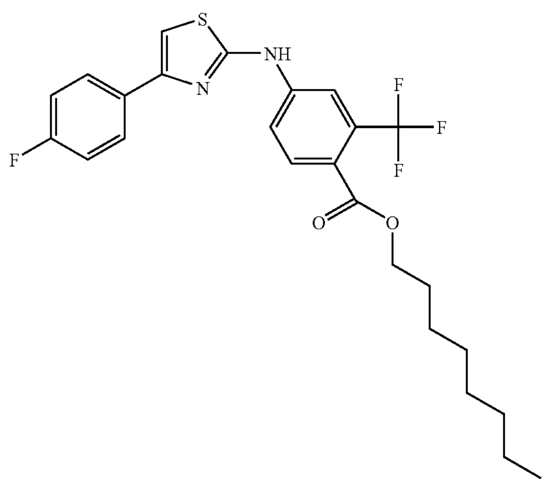 | octyl 4-(4-(4-fluorophenyl)thiazol-2-ylamino)-2-(trifluoromethyl)benzoate | +++ |
| 701 | 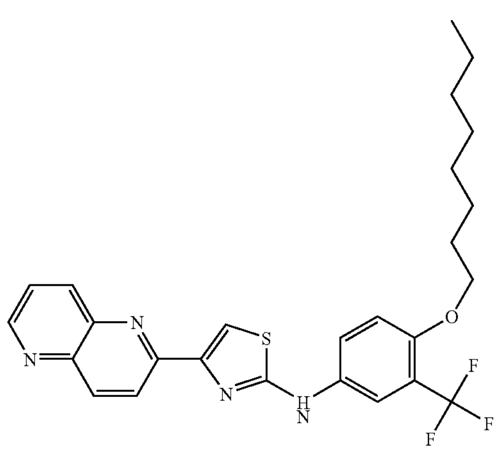 | 4-(6-deuterated-1,5-naphthyndin-2-yl)-N-(4-(octyloxy)-3-(trifluoromethyl)phenyl)thiazol-2-amine | +++ |

TABLE III-continued

| Cpd | Structure | Name | Activity |
|---|---|---|---|
| 702 | 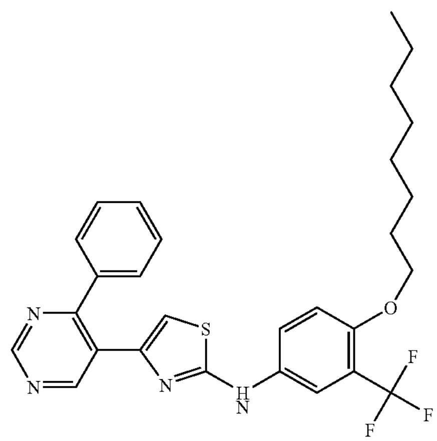 | N-(3-(trifluoromethyl)-4-(octyloxy)phenyl)-4-(4-phenylpyrimidin-5-yl)thiazol-2-amine | +++ |
| 703 | 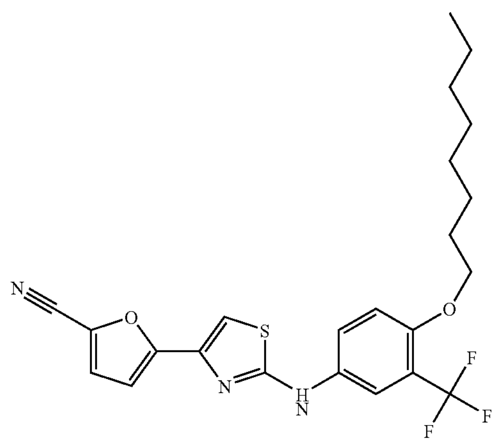 | 5-(2-(3-(trifluoromethyl)-4-(octyloxy)phenylamino)thiazol-4-yl)furan-2-carbonitrile | +++ |
| 704 | 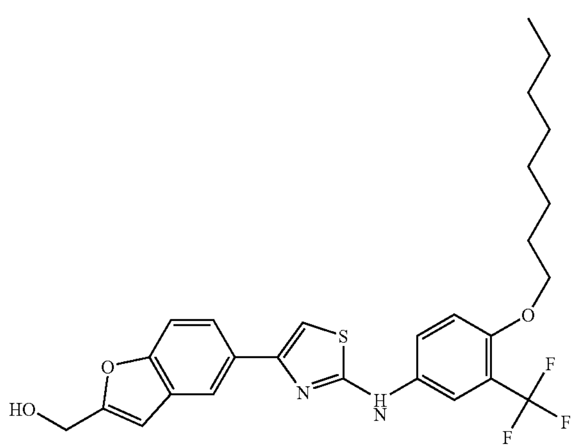 | (5-(2-(3-(trifluoromethyl)-4-(octyloxy)phenylamino)thiazol-4-yl)benzofuran-2-yl)methanol | +++ |

TABLE III-continued

| Cpd | Structure | Name | Activity |
|---|---|---|---|
| 705 | 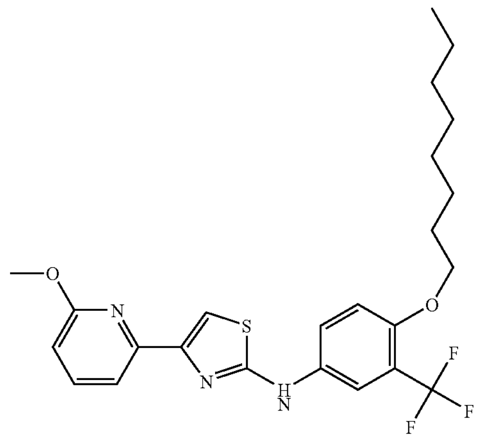 | N-(3-(trifluoromethyl)-4-(octyloxy)phenyl)-4-(6-methoxypyridin-2-yl)thiazol-2-amine | +++ |
| 706 | 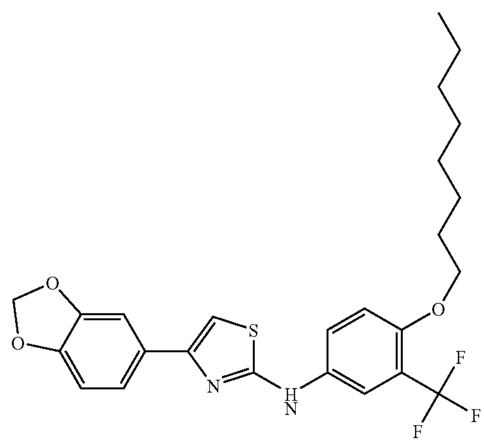 | 4-(benzo[d][1,3]dioxol-5-yl)-N-(3-(trifluoromethyl)-4-(octyloxy)phenyl)thiazol-2-amine | +++ |
| 707 | 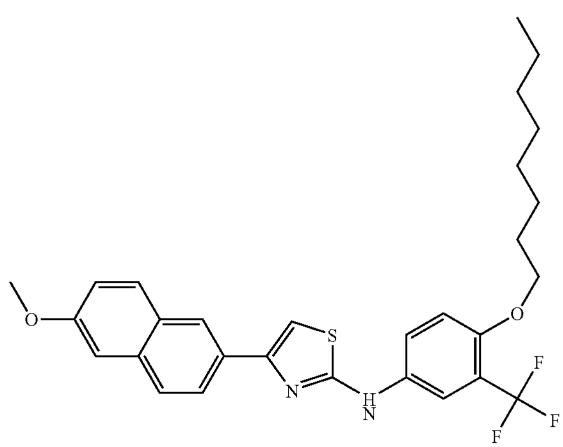 | N-(3-(trifluoromethyl)-4-(octyloxy)phenyl)-4-(2-methoxynaphthalen-6-yl)thiazol-2-amine | +++ |

TABLE III-continued

| Cpd | Structure | Name | Activity |
|---|---|---|---|
| 708 | 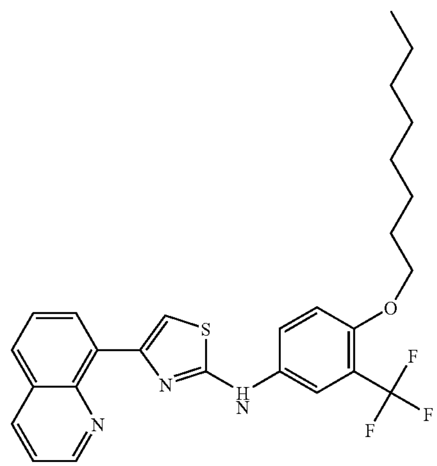 | N-(3-(trifluoromethyl)-4-(octyloxy)phenyl)-4-(quinolin-8-yl)thiazol-2-amine | +++ |
| 709 | 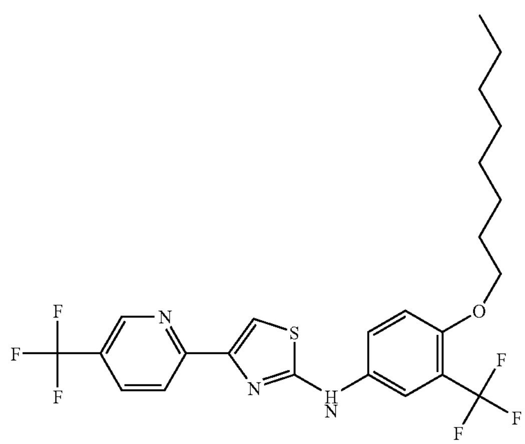 | N-(3-(trifluoromethyl)-4-(octyloxy)phenyl)-4-(5-(trifluoromethyl)pyridin-2-yl)thiazol-2-amine | +++ |
| 710 | 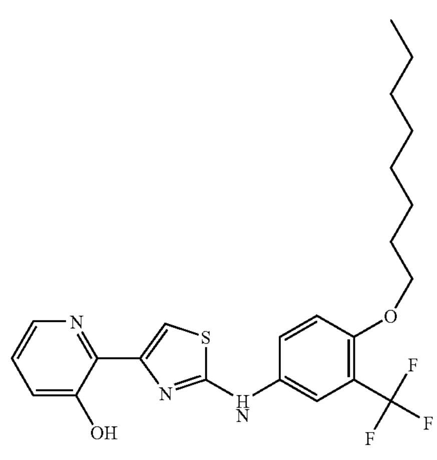 | 2-(2-(3-(trifluoromethyl)-4-(octyloxy)phenylamino)thiazol-4-yl)pyridin-3-ol | +++ |

TABLE III-continued
| Cpd | Structure | Name | Activity |
|---|---|---|---|
| 711 | 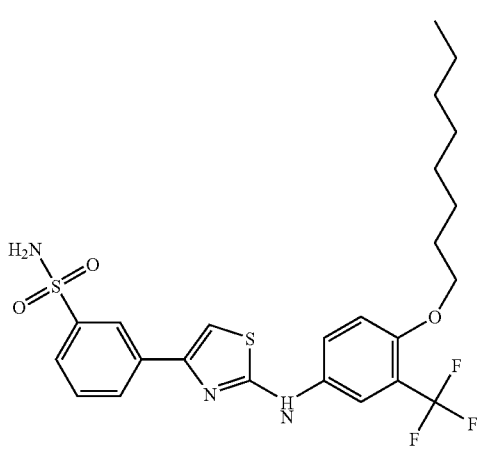 | | +++ |
| 712 | 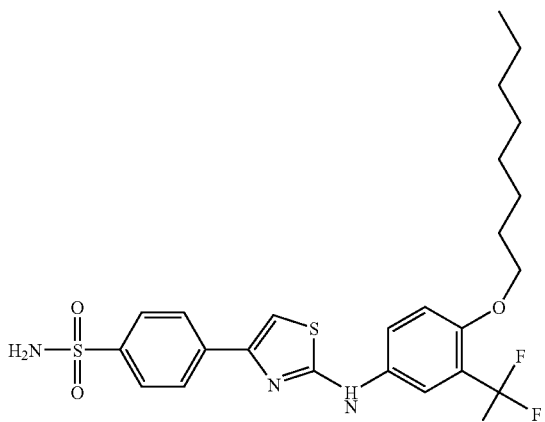 | | +++ |
| 713 | 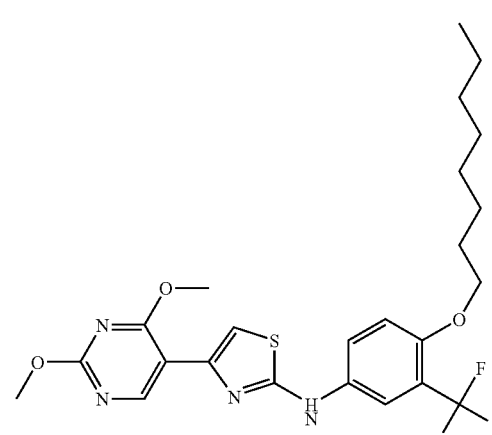 | N-(3-(trifluoromethyl)-4-(octyloxy)phenyl)-4-(2,4-dimethoxypyrimidin-5-yl)thiazol-2-amine | +++ |

TABLE III-continued
| Cpd | Structure | Name | Activity |
|---|---|---|---|
| 714 | 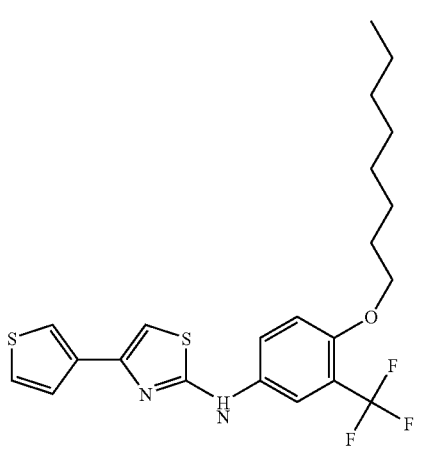 | N-(3-(trifluoromethyl)-4-(octyloxy)phenyl)-4-(thiophen-3-yl)thiazol-2-amine | +++ |
| 715 | 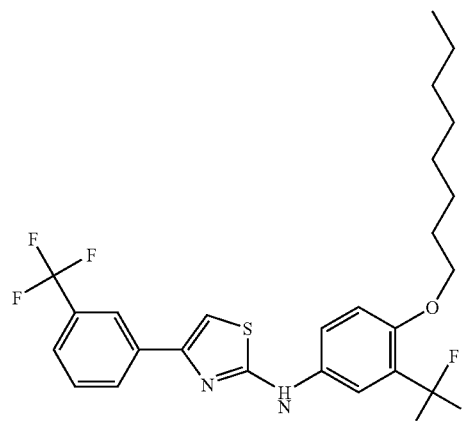 | N-(3-(trifluoromethyl)-4-(octyloxy)phenyl)-4-(3-(trifluoromethyl)phenyl)thiazol-2-amine | +++ |
| 716 | 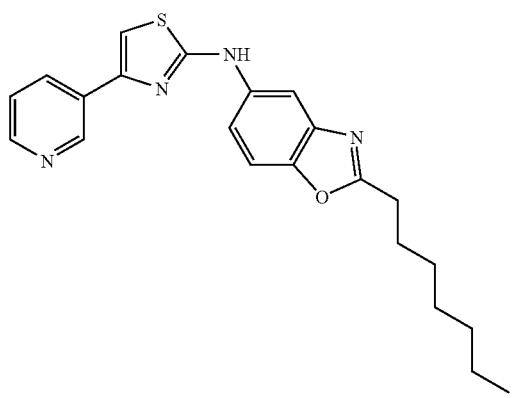 | 2-heptyl-N-(4-(pyridin-3-yl)thiazol-2-yl)benzo[d]oxazol-5-amine | +++ |

TABLE III-continued

| Cpd | Structure | Name | Activity |
|---|---|---|---|
| 717 | 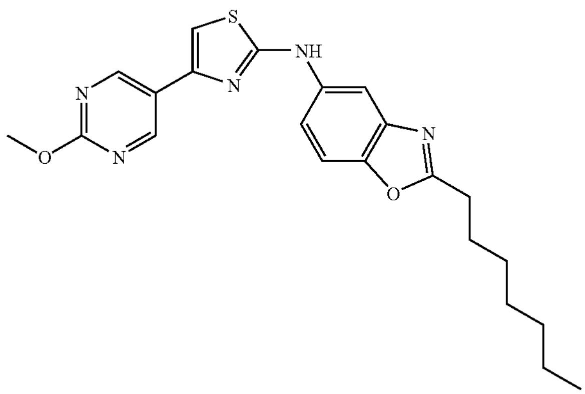 | 2-heptyl-N-(4-(2-methoxypyrimidin-5-yl)thiazol-2-yl)benzo[d]oxazol-5-amine | +++ |
| 718 | 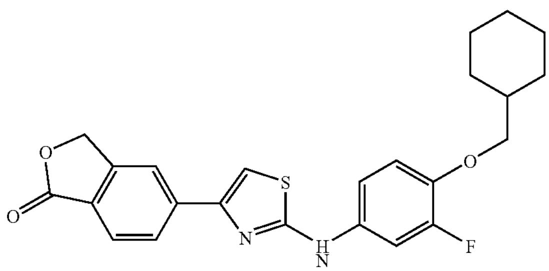 | 5-(2-(4-(cyclohexylmethoxy)-3-fluorophenylamino)thiazol-4-yl)isobenzofuran-1(3H)-one | ++ |
| 719 | 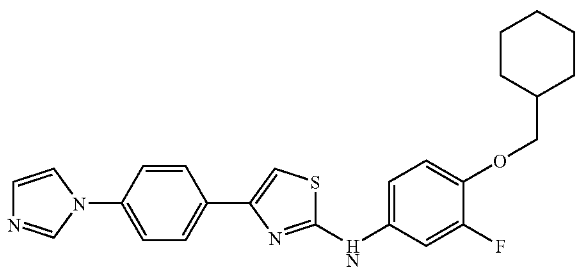 | 4-(4-(1H-imidazol-1-yl)phenyl)-N-(4-(cyclohexylmethoxy)-3-fluorophenyl)thiazol-2-amine | +++ |

TABLE IV

| Cpd | Structure | Name | Activity |
|---|---|---|---|
| 720 | 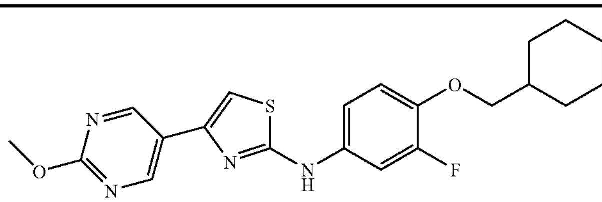 | N-(4-(cyclohexylmethoxy)-3-fluorophenyl)-4-(2-methoxypyrimidin-5-yl)thiazol-2-amine | +++ |
| 721 | 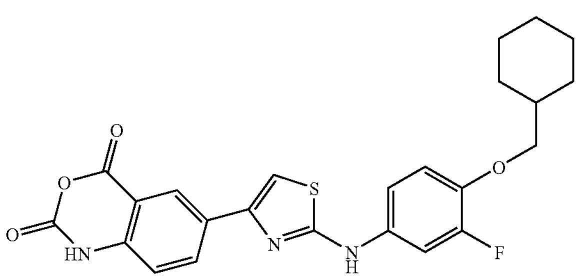 | N-(4-(cyclohexylmethoxy)-3-fluorophenyl)-4-(1-methyl-1H-imidazol-5-yl)thiazol-2-amine | +++ |

TABLE IV-continued

| Cpd | Structure | Name | Activity |
|---|---|---|---|
| 722 | 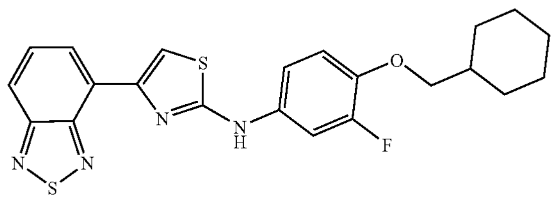 | 4-(benzo[c][1,2,5]thiadiazol-4-yl)-N-(4-(cyclohexylmethoxy)-3-fluorophenyl)thiazol-2-amine | ++ |
| 723 | 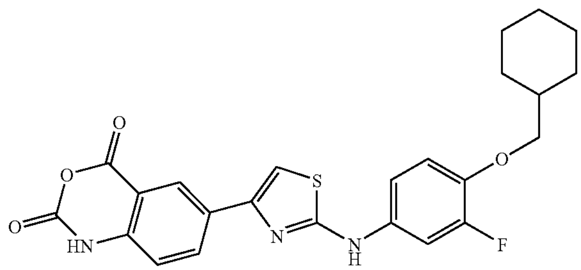 | 6-(2-(4-(cyclohexylmethoxy)-3-fluorophenylamino)thiazol-4-yl)-1H-benzo[d][1,3]oxazine-2,4-dione | ++ |
| 724 | 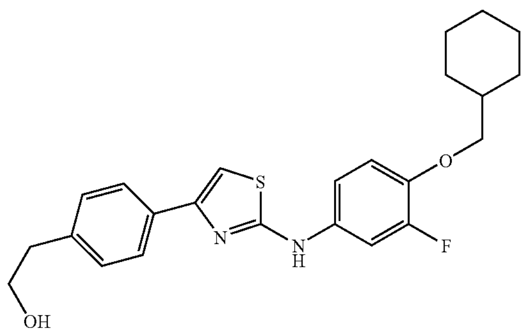 | 2-(4-(2-(4-(cyclohexylmethoxy)-3-fluorophenylamino)thiazol-4-yl)phenyl)ethanol | ++ |
| 725 | 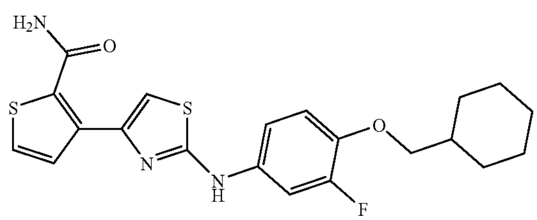 | 3-(2-(4-(cyclohexylmethoxy)-3-fluorophenylamino)thiazol-4-yl)thiophene-2-carboxamide | +++ |
| 726 | 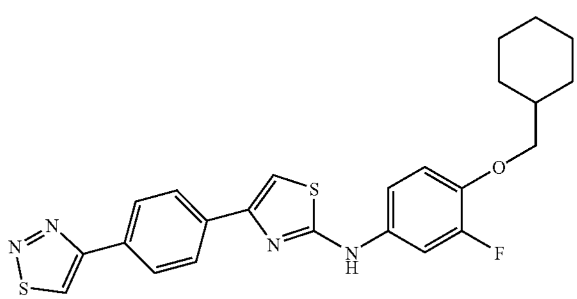 | 4-(4-(1,2,3-thiadiazol-4-yl)phenyl)-N-(4-(cyclohexylmethoxy)-3-fluorophenyl)thiazol-2-amine | ++ |
| 727 | 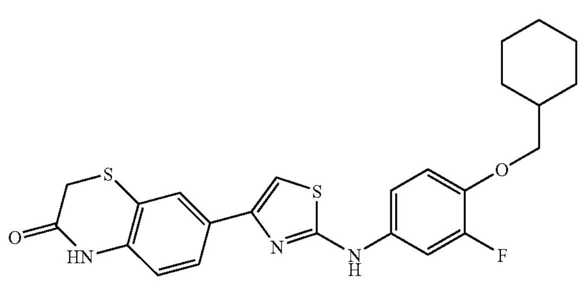 | 7-(2-(4-(cyclohexylmethoxy)-3-fluorophenylamino)thiazol-4-yl)-2H-benzo[b][1,4]thiazin-3(4H)-one | ++ |

TABLE IV-continued

| Cpd | Structure | Name | Activity |
|---|---|---|---|
| 728 | 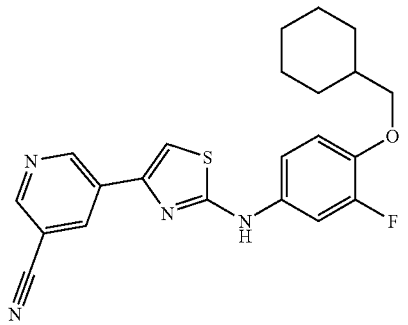 | 5-(2-(4-(cyclohexylmethoxy)-3-fluorophenylamino)thiazol-4-yl)pyridine-3-carbonitrile | +++ |
| 729 | 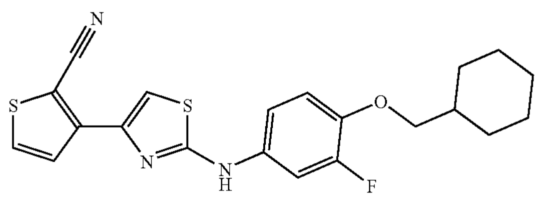 | 3-(2-(4-(cyclohexylmethoxy)-3-fluorophenylamino)thiazol-4-yl)thiophene-2-carbonitrile | +++ |
| 730 | 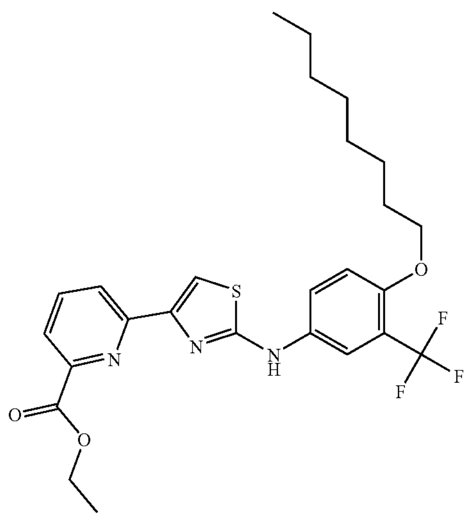 | ethyl 6-(2-(3-(trifluoromethyl)-4-(octyloxy)phenylamino)thiazol-4-yl)pyridine-2-carboxylate | +++ |
| 731 | 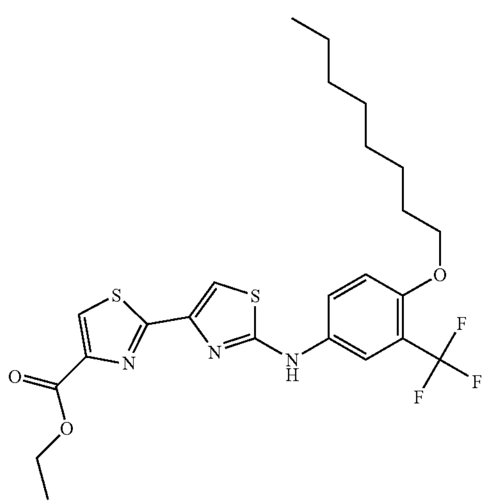 | ethyl 2-(2-(3-(trifluoromethyl)-4-(octyloxy)phenylamino)thiazol-4-yl)thiazole-4-carboxylate | +++ |

TABLE IV-continued

| Cpd | Structure | Name | Activity |
|---|---|---|---|
| 732 | 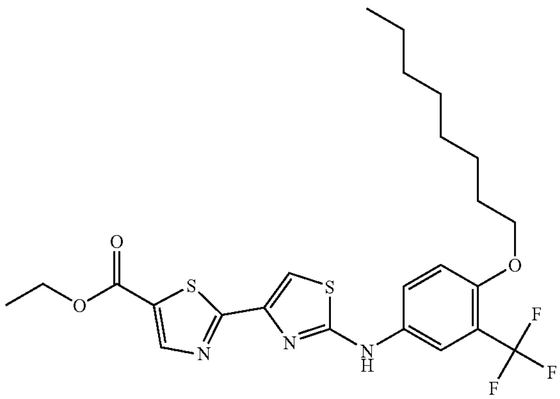 | ethyl 2-(2-(3-(trifluoromethyl)-4-(octyloxy)phenylamino)thiazol-4-yl)thiazole-5-carboxylate | +++ |
| 733 | 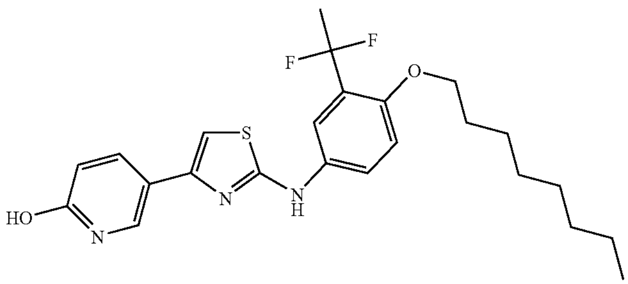 | 5-(2-(3-(trifluoromethyl)-4-(octyloxy)phenylamino)thiazol-4-yl)pyridin-2-ol | +++ |
| 734 | 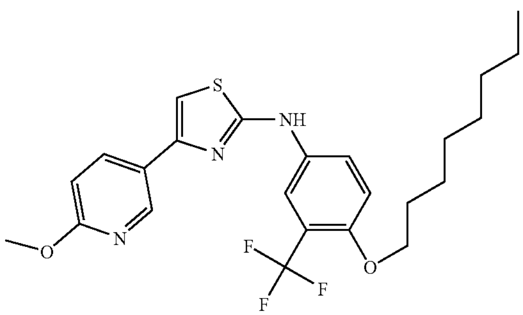 | N-(3-(trifluoromethyl)-4-(octyloxy)phenyl)-4-(6-methoxypyridin-3-yl)thiazol-2-amine | +++ |
| 735 | 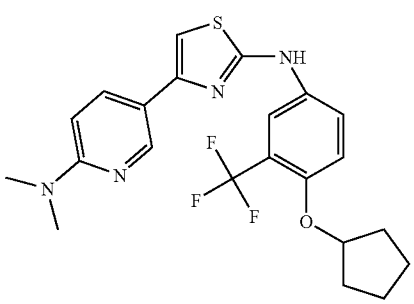 | 5-(2-(4-(cyclopentyloxy)-3-(trifluoromethyl)phenylamino)thiazol-4-yl)-N,N-dimethylpyridin-2-amine | ++ |
| 736 | 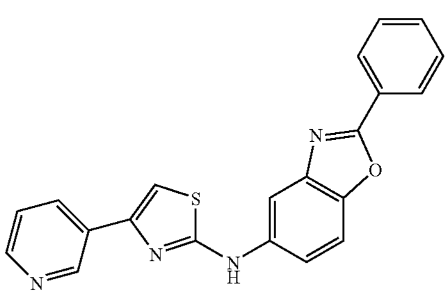 | 2-phenyl-N-(4-(pyridin-3-yl)thiazol-2-yl)benzo[d]oxazol-5-amine | +++ |

TABLE IV-continued

| Cpd | Structure | Name | Activity |
|---|---|---|---|
| 737 | 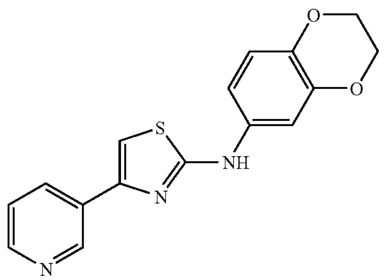 | N-(2,3-dihydrobenzo[b][1,4]dioxin-6-yl)-4-(pyridin-3-yl)thiazol-2-amine | + |
| 738 | 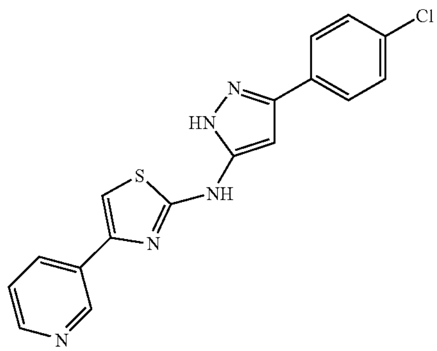 | 3-(4-chlorophenyl)-N-(4-(pyridin-3-yl)thiazol-2-yl)-1H-pyrazol-5-amine | + |
| 739 | 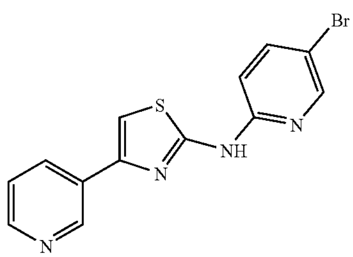 | 5-bromo-N-(4-(pyridin-3-yl)thiazol-2-yl)pyridin-2-amine | + |
| 740 | 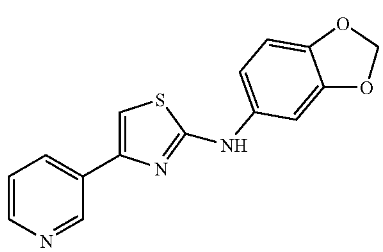 | N-(benzo[d][1,3]dioxol-6-yl)-4-(pyridin-3-yl)thiazol-2-amine | + |
| 741 | 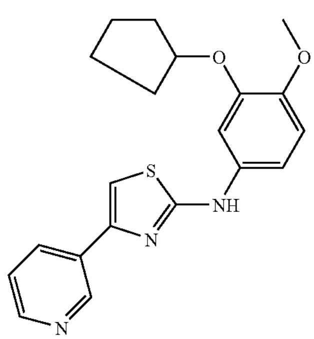 | N-(3-(cyclopentyloxy)-4-methoxyphenyl)-4-(pyridin-3-yl)thiazol-2-amine | ++ |

TABLE IV-continued

| Cpd | Structure | Name | Activity |
|---|---|---|---|
| 742 | 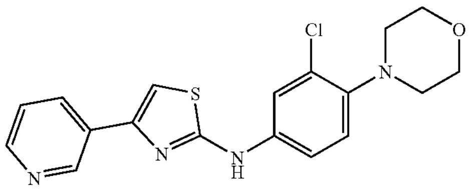 | N-(3-chloro-4-morpholinophenyl)-4-(pyridin-3-yl)thiazol-2-amine | ++ |
| 743 | 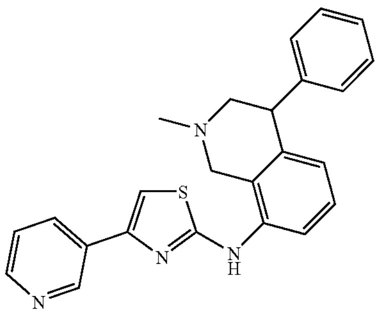 | 1,2,3,4-tetrahydro-2-methyl-4-phenyl-N-(4-(pyridin-3-yl)thiazol-2-yl)isoquinolin-8-amine | + |
| 744 | 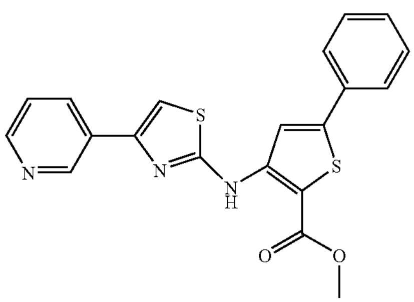 | methyl 3-(4-(pyridin-3-yl)thiazol-2-ylamino)-5-phenylthiophene-2-carboxylate | + |
| 745 | 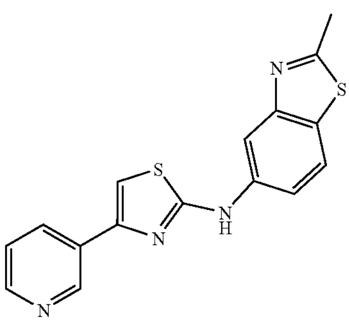 | 2-methyl-N-(4-(pyridin-3-yl)thiazol-2-yl)benzo[d]thiazol-5-amine | + |
| 746 | 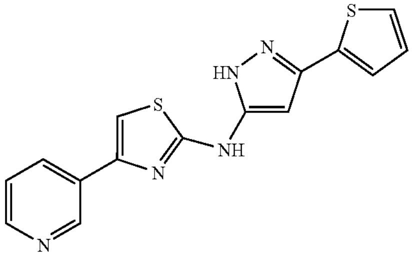 | N-(4-(pyridin-3-yl)thiazol-2-yl)-3-(thiophen-2-yl)-1H-pyrazol-5-amine | + |

TABLE IV-continued

| Cpd | Structure | Name | Activity |
|---|---|---|---|
| 747 | 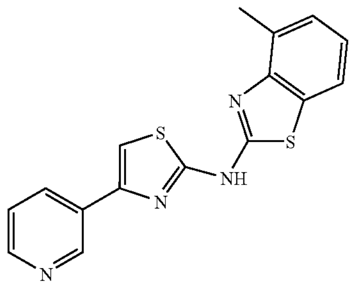 | 4-methyl-N-(4-(pyridin-3-yl)thiazol-2-yl)benzo[d]thiazol-2-amine | + |
| 748 | 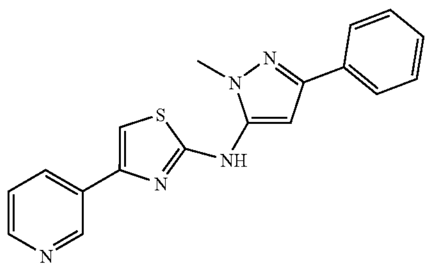 | 1-methyl-3-phenyl-N-(4-(pyridin-3-yl)thiazol-2-yl)-1H-pyrazol-5-amine | + |
| 749 | 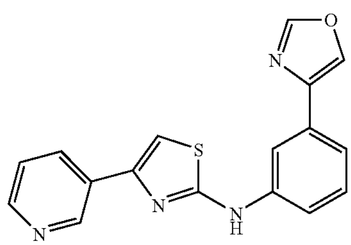 | N-(3-(oxazol-4-yl)phenyl)-4-(pyridin-3-yl)thiazol-2-amine | + |
| 750 | 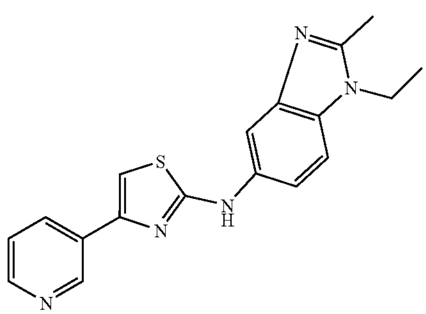 | 1-ethyl-2-methyl-N-(4-(pyridin-3-yl)thiazol-2-yl)-1H-benzo[d]imidazol-5-amine | + |
| 751 | 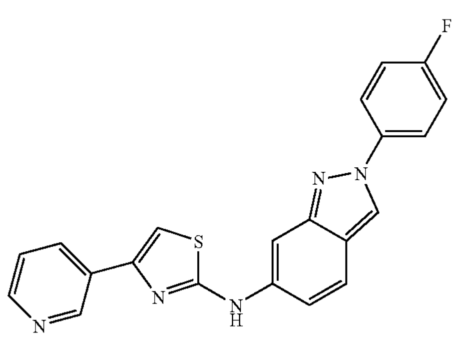 | 2-(4-fluorophenyl)-N-(4-(pyridin-3-yl)thiazol-2-yl)-2H-benzo[d][1,2,3]triazol-5-amine | +++ |

TABLE IV-continued
| Cpd | Structure | Name | Activity |
|---|---|---|---|
| 752 | 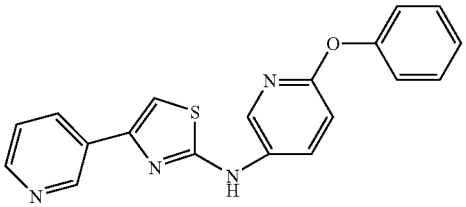 | 6-phenoxy-N-(4-(pyridin-3-yl)thiazol-2-yl)pyridin-3-amine | ++ |
| 753 | 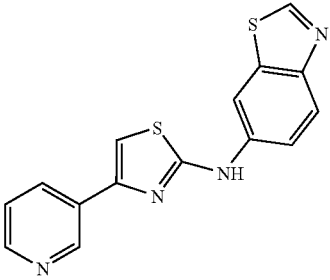 | N-(4-(pyridin-3-yl)thiazol-2-yl)benzo[d]thiazol-6-amine | + |
| 754 | 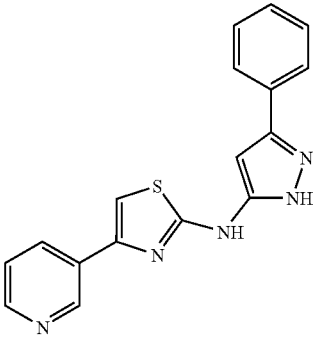 | 3-phenyl-N-(4-(pyridin-3-yl)thiazol-2-yl)-1H-pyrazol-5-amine | + |
| 755 | 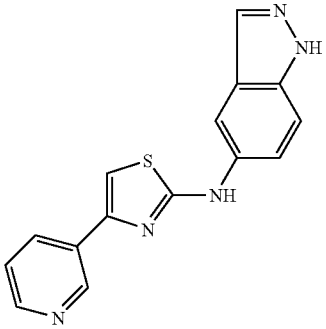 | N-(4-(pyridin-3-yl)thiazol-2-yl)-1H-indazol-5-amine | + |
| 756 | 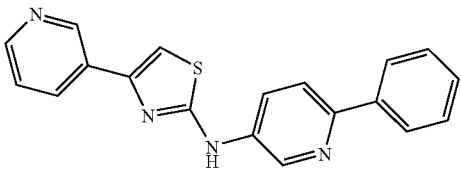 | 6-phenyl-N-(4-(pyridin-3-yl)thiazol-2-yl)pyridin-3-amine | ++ |
| 757 | 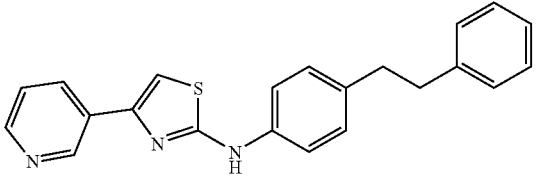 | N-(4-phenethylphenyl)-4-(pyridin-3-yl)thiazol-2-amine | +++ |

TABLE IV-continued

| Cpd | Structure | Name | Activity |
|---|---|---|---|
| 758 | 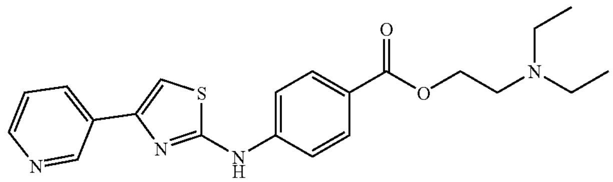 | 2-(diethylamino)ethyl 4-(4-(pyridin-3-yl)thiazol-2-ylamino)benzoate | + |
| 759 | 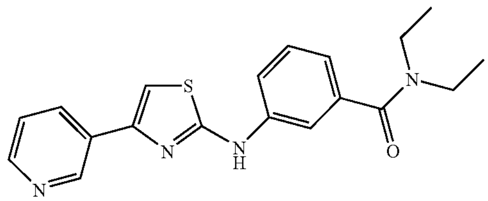 | 3-(4-(pyridin-3-yl)thiazol-2-ylamino)-N,N-diethylbenzamide | + |
| 760 | 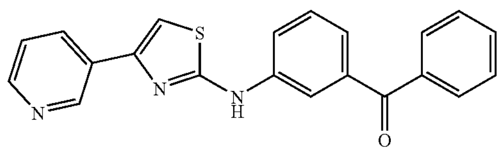 | (3-(4-(pyridin-3-yl)thiazol-2-ylamino)phenyl)(phenyl)methanone | + |
| 761 | 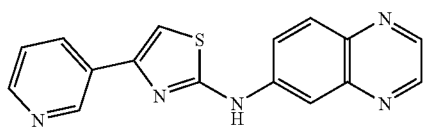 | N-(4-(pyridin-3-yl)thiazol-2-yl)quinoxalin-6-amine | + |
| 762 | 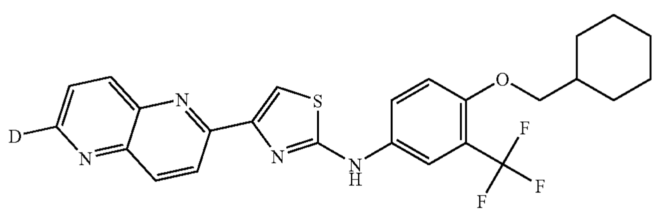 | N-(4-(cyclohexylmethoxy)-3-(trifluoromethyl)phenyl)-4-(2-deuterated-1,5-naphthyridin-6-yl)thiazol-2-amine | ++ |
| 763 | 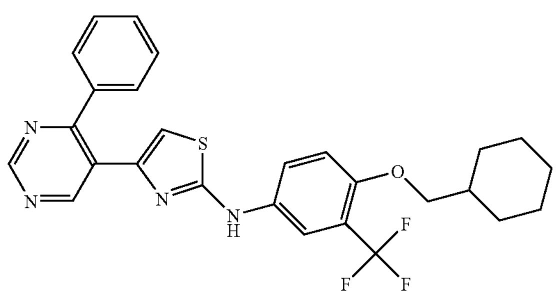 | N-(4-(cyclohexylmethoxy)-3-(trifluoromethyl)phenyl)-4-(4-phenylpyrimidin-5-yl)thiazol-2-amine | ++ |
| 764 | 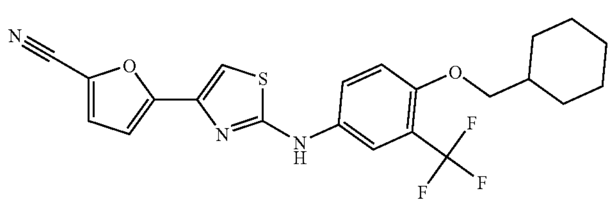 | 5-(2-(4-(cyclohexylmethoxy)-3-(trifluoromethyl)phenylamino)thiazol-4-yl)furan-2-carbonitrile | +++ |
| 765 | 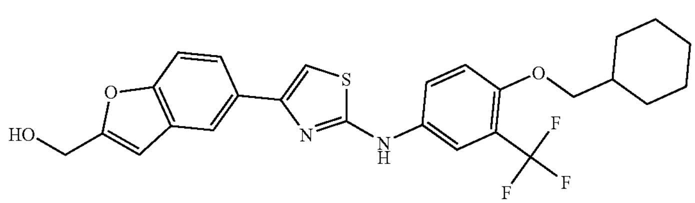 | (5-(2-(4-(cyclohexylmethoxy)-3-(trifluoromethyl)phenylamino)thiazol-4-yl)benzofuran-2-yl)methanol | +++ |

TABLE IV-continued

| Cpd | Structure | Name | Activity |
|---|---|---|---|
| 766 | 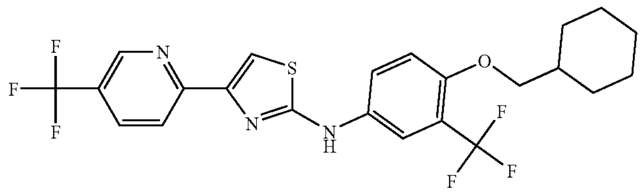 | N-(4-(cyclohexylmethoxy)-3-(trifluoromethyl)phenyl)-4-(5-(trifluoromethyl)pyridin-2-yl)thiazol-2-amine | +++ |
| 767 | 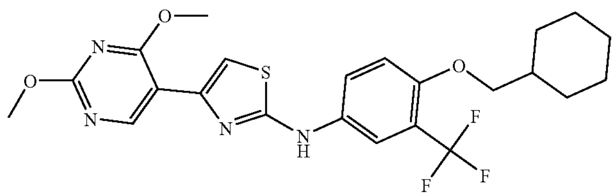 | N-(4-(cyclohexylmethoxy)-3-(trifluoromethyl)phenyl)-4-(2,4-dimethoxypyrimidin-5-yl)thiazol-2-amine | +++ |
| 768 | 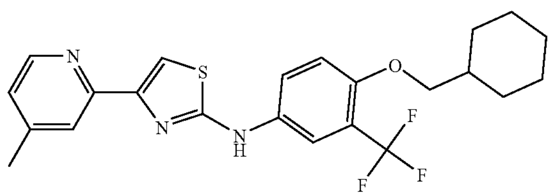 | N-(4-(cyclohexylmethoxy)-3-(trifluoromethyl)phenyl)-4-(4-methylpyridin-2-yl)thiazol-2-amine | +++ |
| 769 | 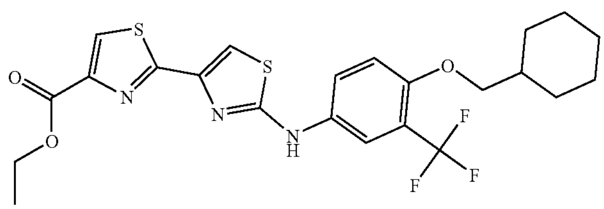 | ethyl 2-(2-(4-(cyclohexylmethoxy)-3-(trifluoromethyl)phenylamino)thiazole-4-yl)thiazole-4-carboxylate | +++ |
| 770 | 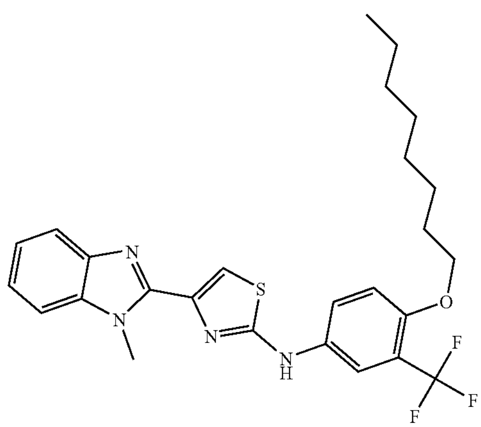 | N-(3-(trifluoromethyl)-4-(octyloxy)phenyl)-4-(1-methyl-1H-benzo[d]imidazol-2-yl)thiazol-2-amine | +++ |
| 771 | 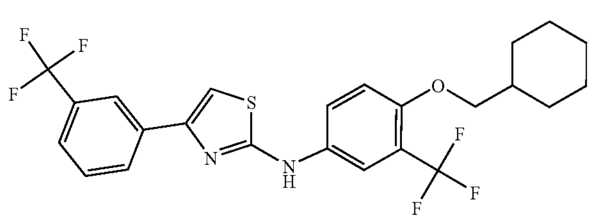 | N-(4-(cyclohexylmethoxy)-3-(trifluoromethyl)phenyl)-4-(3-(trifluoromethyl)phenyl)thiazol-2-amine | +++ |

TABLE IV-continued

| Cpd | Structure | Name | Activity |
|---|---|---|---|
| 772 | 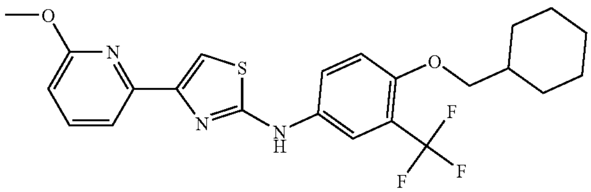 | N-(4-(cyclohexylmethoxy)-3-(trifluoromethyl)phenyl)-4-(6-methoxypyridin-2-yl)thiazol-2-amine | +++ |
| 773 | 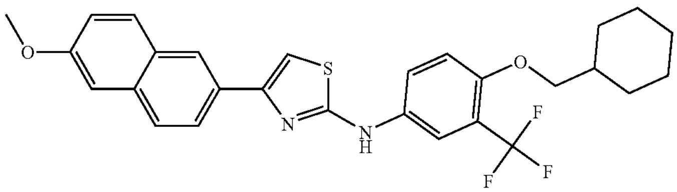 | N-(4-(cyclohexylmethoxy)-3-(trifluoromethyl)phenyl)-4-(2-methoxynaphthalen-6-yl)thiazol-2-amine | +++ |
| 774 | 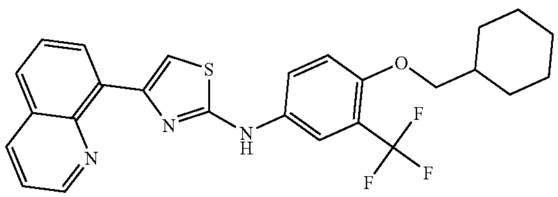 | N-(4-(cyclohexylmethoxy)-3-(trifluoromethyl)phenyl)-4-(quinolin-8-yl)thiazol-2-amine | +++ |
| 775 | 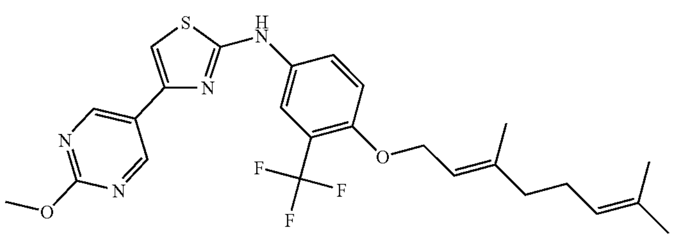 | N-(4-((E)-3,7-dimethylocta-2,6-dienyloxy)-3-(trifluoromethyl)phenyl)-4-(2-methoxypyrimidin-5-yl)thiazol-2-amine | +++ |
| 776 | 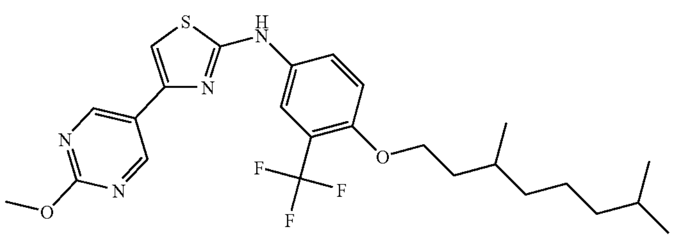 | N-(4-(3,7-dimethyloctyloxy)-3-(trifluoromethyl)phenyl)-4-(2-methoxypyrimidin-5-yl)thiazol-2-amine | +++ |
| 777 | 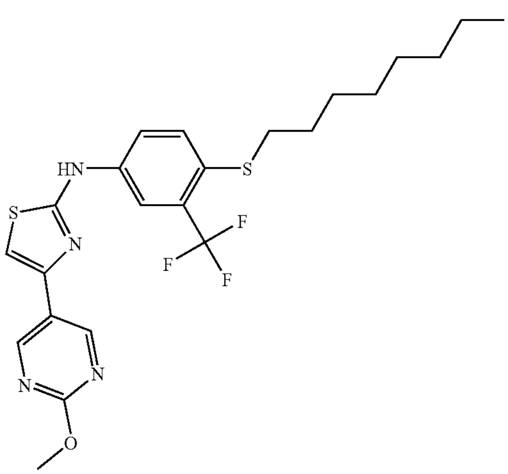 | N-(3-(trifluoromethyl)-4-(octylthio)phenyl)-4-(2-methoxypyrimidin-5-yl)thiazol-2-amine | +++ |

TABLE IV-continued

| Cpd | Structure | Name | Activity |
|---|---|---|---|
| 778 | 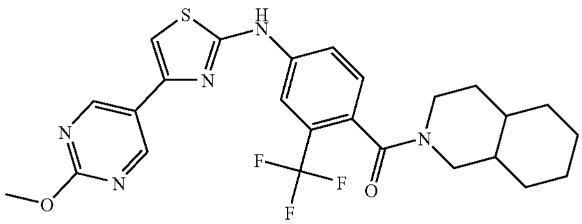 | (4-(4-(2-methoxypyrimidin-5-yl)thiazol-2-ylamino)-2-(trifluoromethyl)phenyl)(octahydroisoquinolin-2(1H)-yl)methanone | ++ |
| 779 | 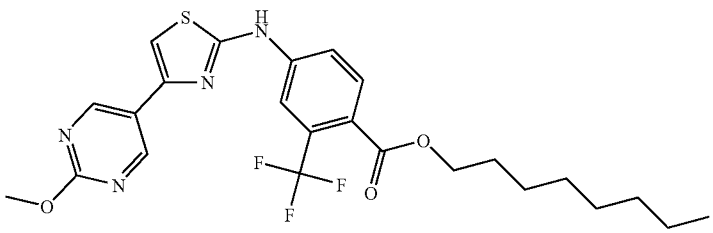 | octyl 4-(4-(2-methoxypyrimidin-5-yl)thiazol-2-ylamino)-2-(trifluoromethyl)benzoate | +++ |
| 780 | 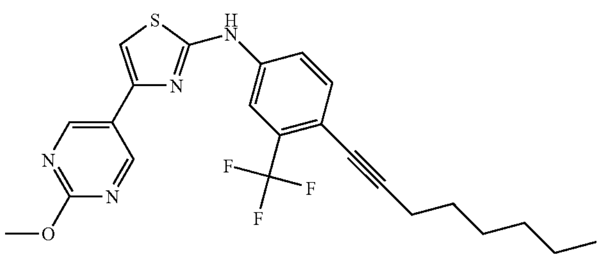 | N-(3-(trifluoromethyl)-4-(oct-1-ynyl)phenyl)-4-(2-methoxypyrimidin-5-yl)thiazol-2-amine | +++ |
| 781 | 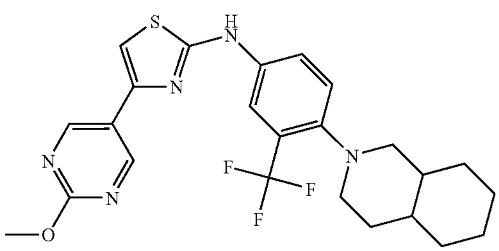 | N-(3-(trifluoromethyl)-4-(octahydroisoquinolin-2(1H)-yl)phenyl)-4-(2-methoxypyrimidin-5-yl)thiazol-2-amine | +++ |
| 782 | 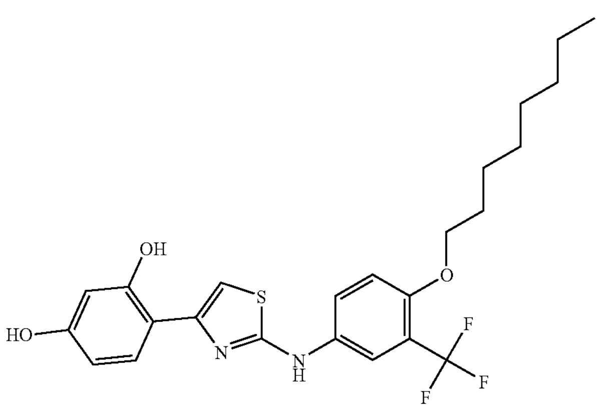 | 4-(2-(3-(trifluoromethyl)-4-(octyloxy)phenylamino)thiazol-4-yl)benzene-1,3-diol | +++ |
| 783 | 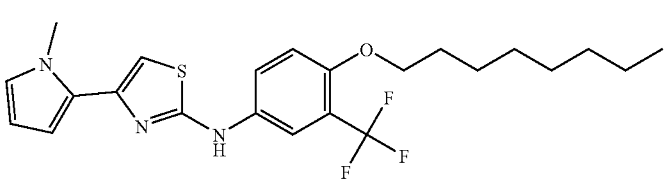 | N-(3-(trifluoromethyl)-4-(octyloxy)phenyl)-4-(1-methyl-1H-pyrrol-2-yl)thiazol-2-amine | +++ |

TABLE IV-continued

| Cpd | Structure | Name | Activity |
|---|---|---|---|
| 784 | 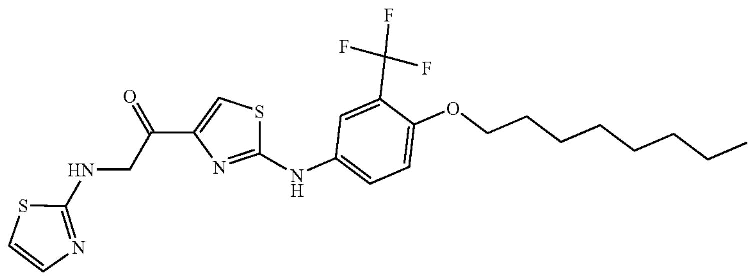 | 1-(2-(3-(trifluoromethyl)-4-(octyloxy)phenylamino)thiazol-4-yl)-2-(thiazol-2-ylamino)ethanone | +++ |
| 785 | 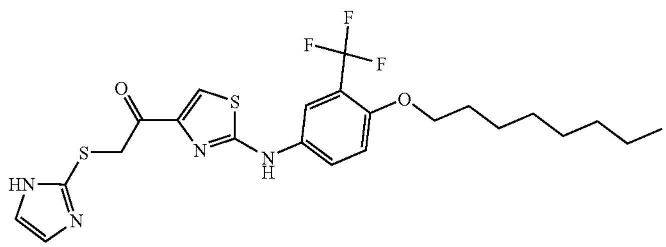 | 2-(1H-imidazol-2-ylthio)-1-(2-(3-(trifluoromethyl)-4-(octyloxy)phenylamino)thiazol-4-yl)ethanone | ++ |
| 786 | 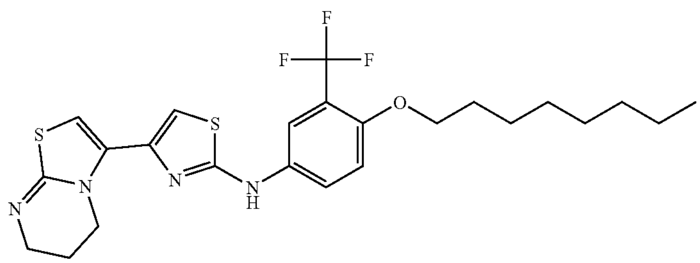 | N-(3-(trifluoromethyl)-4-(octyloxy)phenyl)-4-(6,7-dihydro-5H-thiazolo[3,2-a]pyrimidin-3-yl)thiazol-2-amine | +++ |
| 787 | 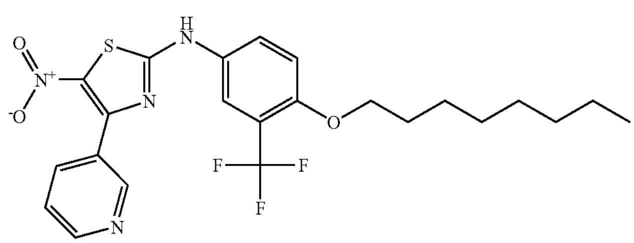 | N-(3-(trifluoromethyl)-4-(octyloxy)phenyl)-5-nitro-4-(pyridin-3-yl)thiazol-2-amine | ++ |
| 788 | 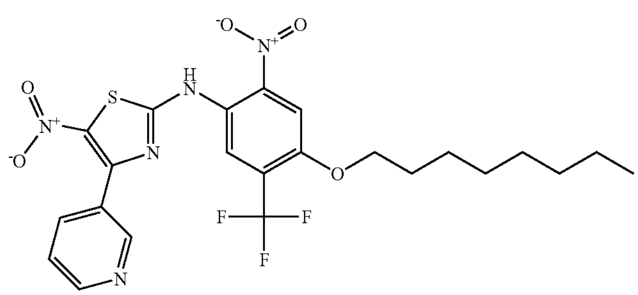 | N-(5-(trifluoromethyl)-2-nitro-4-(octyloxy)phenyl)-5-nitro-4-(pyridin-3-yl)thiazol-2-amine | ++ |

TABLE IV-continued

| Cpd | Structure | Name | Activity |
|---|---|---|---|
| 789 | 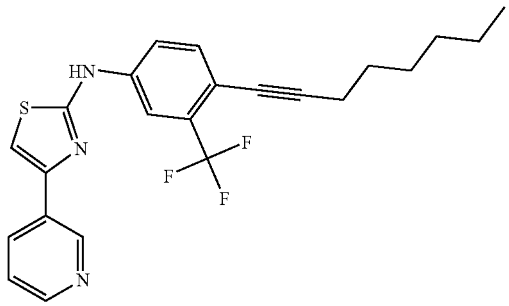 | N-(3-(trifluoromethyl)-4-(oct-1-ynyl)phenyl)-4-(pyridin-3-yl)thiazol-2-amine | +++ |
| 790 | 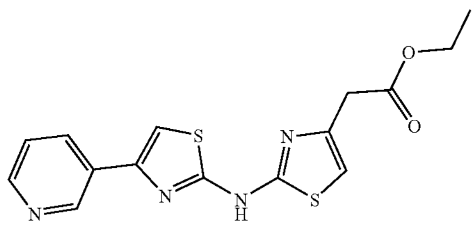 | ethyl 2-(2-(4-(pyridin-3-yl)thiazol-2-ylamino)thiazol-4-yl)acetate | + |
| 791 | 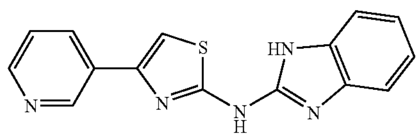 | N-(4-(pyridin-3-yl)thiazol-2-yl)-1H-benzo[d]imidazol-2-amine | + |
| 792 | 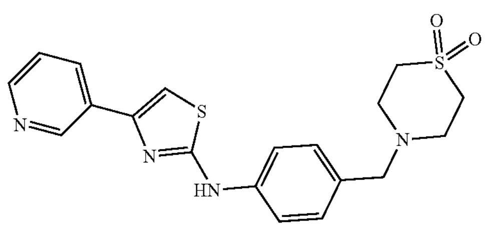 | | + |
| 793 | 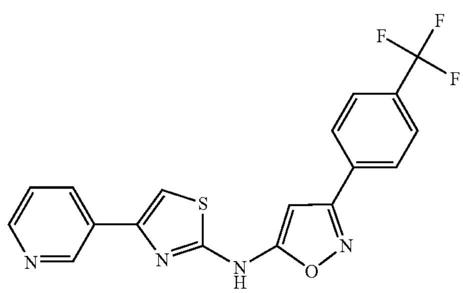 | 3-(4-(trifluoromethyl)phenyl)-N-(4-(pyridin-3-yl)thiazol-2-yl)isoxazol-5-amine | + |
| 794 | 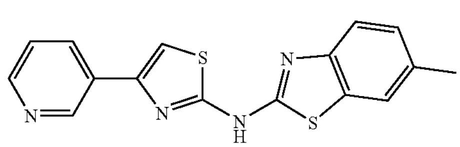 | 6-methyl-N-(4-(pyridin-3-yl)thiazol-2-yl)benzo[d]thiazol-2-amine | + |
| 795 | 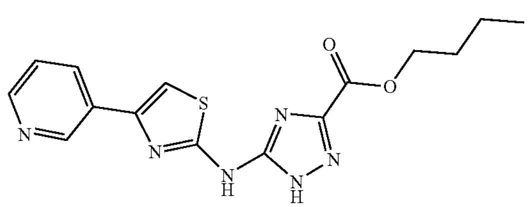 | butyl 5-(4-(pyridin-3-yl)thiazol-2-ylamino)-1H-1,2,4-triazole-3-carboxylate | + |

TABLE IV-continued

| Cpd | Structure | Name | Activity |
|---|---|---|---|
| 796 | 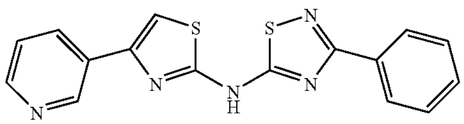 | 3-phenyl-N-(4-(pyridin-3-yl)thiazol-2-yl)-1,2,4-thiadiazol-5-amine | + |
| 797 | 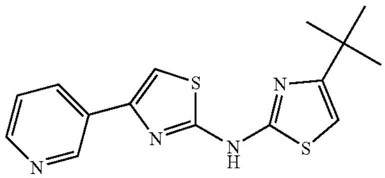 | 4-tert-butyl-N-(4-(pyridin-3-yl)thiazol-2-yl)thiazol-2-amine | + |
| 798 | 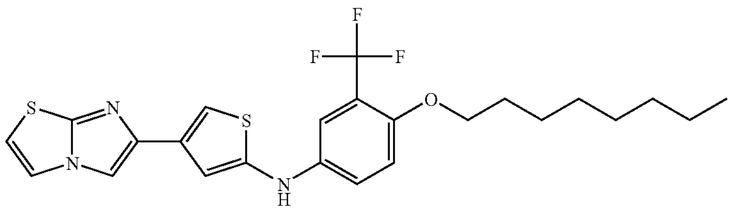 | N-(3-(trifluoromethyl)-4-(octyloxy)phenyl)-4-(imidazo[2,1-b]thiazol-6-yl)thiazol-2-amine | +++ |
| 799 | 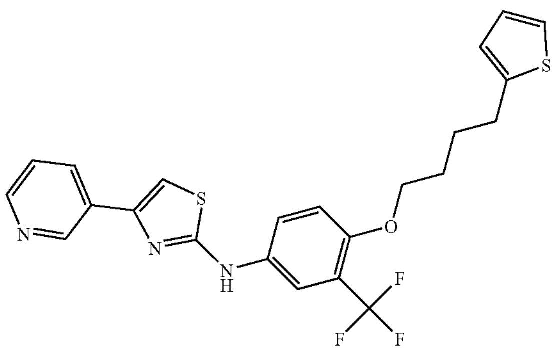 | N-(4-(4-(thiophen-2-yl)butoxy)-3-(trifluoromethyl)phenyl)-4-(pyridin-3-yl)thiazol-2-amine | +++ |
| 800 | 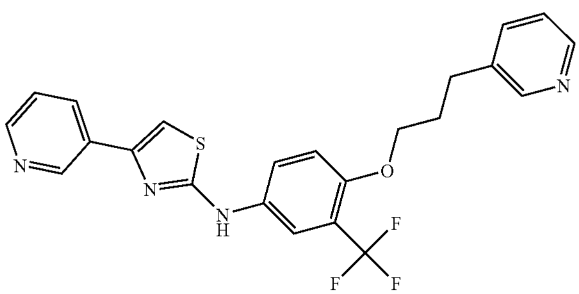 | N-(4-(3-(pyridin-3-yl)propoxy)-3-(trifluoromethyl)phenyl)-4-(pyridin-3-yl)thiazol-2-amine | +++ |
| 801 | 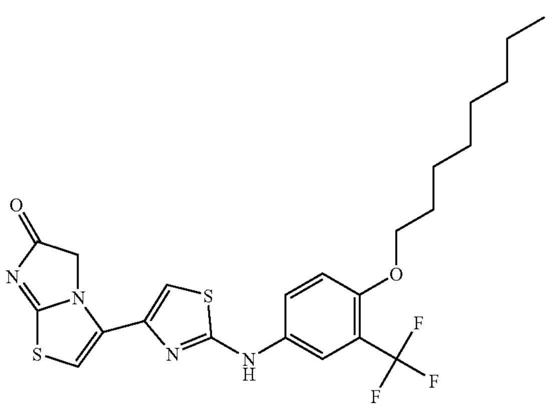 | 3-(2-(3-(trifluoromethyl)-4-(octyloxy)phenylamino)thiazol-4-yl)imidazo[2,1-b]thiazol-6(5H)-one | +++ |

TABLE IV-continued

| Cpd | Structure | Name | Activity |
|---|---|---|---|
| 802 | 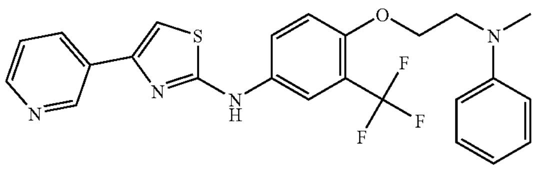 | | +++ |
| 803 | 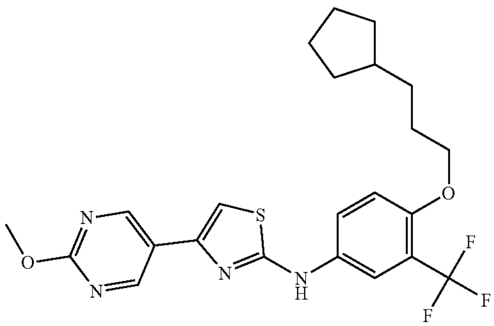 | N-(4-(3-cyclopentylpropoxy)-3-(trifluoromethyl)phenyl)-4-(2-methoxypyrimidin-5-yl)thiazol-2-amine | +++ |
| 804 | 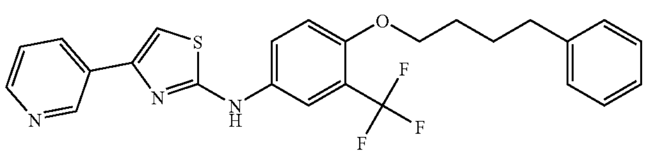 | N-(4-(4-phenylbutoxy)-3-(trifluoromethyl)phenyl)-4-(pyridin-3-yl)thiazol-2-amine | +++ |
| 805 | 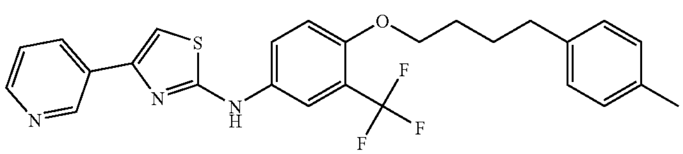 | N-(4-(4-p-tolylbutoxy)-3-(trifluoromethyl)phenyl)-4-(pyridin-3-yl)thiazol-2-amine | ++ |
| 806 | 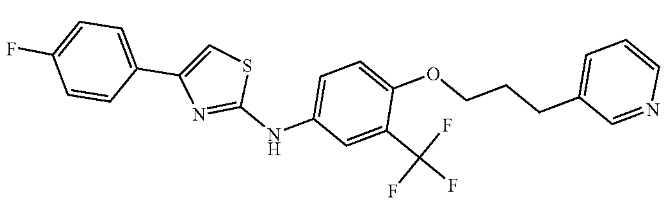 | N-(4-(3-(pyridin-3-yl)propoxy)-3-(trifluoromethyl)phenyl)-4-(4-fluorophenyl)thiazol-2-amine | ++ |
| 807 | 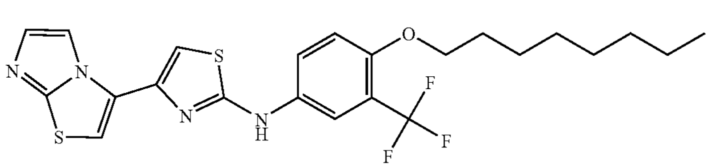 | N-(3-(trifluoromethyl)-4-(octyloxy)phenyl)-4-(imidazo[2,1-b]thiazol-3-yl)thiazol-2-amine | +++ |

TABLE IV-continued

| Cpd | Structure | Name | Activity |
|---|---|---|---|
| 808 | 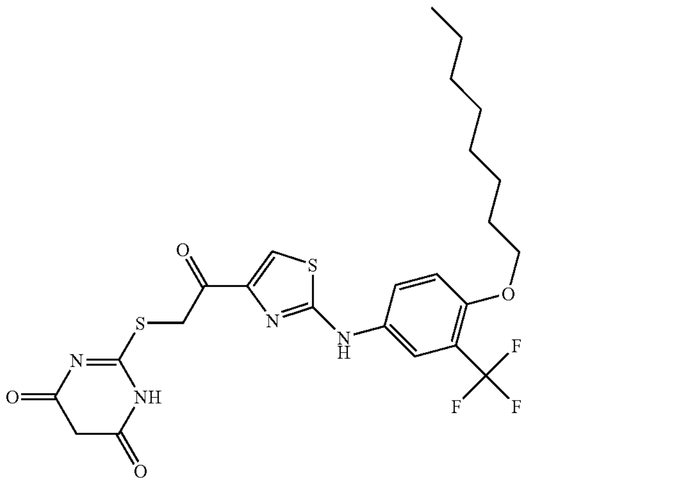 | 2-(2-(2-(3-(trifluoromethyl)-4-(octyloxy)phenylamino)thiazol-4-yl)-2-oxoethylthio)pyrimidine-4,6(1H,5H)-dione | +++ |
| 809 | 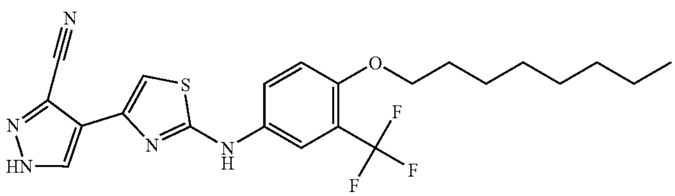 | 4-(2-(3-(trifluoromethyl)-4-(octyloxy)phenylamino)thiazol-4-yl)-1H-pyrazole-3-carbonitrile | +++ |
| 810 | 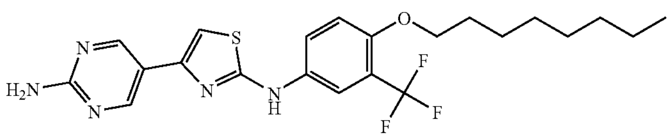 | 5-(2-(3-(trifluoromethyl)-4-(octyloxy)phenylamino)thiazol-4-yl)pyrimidin-2-amine | +++ |
| 811 | 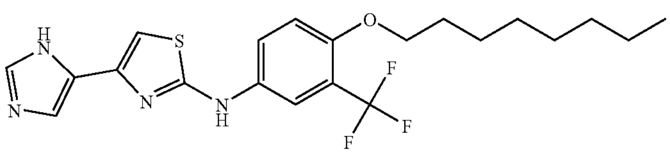 | N-(3-(trifluoromethyl)-4-(octyloxy)phenyl)-4-(1H-imidazol-5-yl)thiazol-2-amine | +++ |
| 812 | 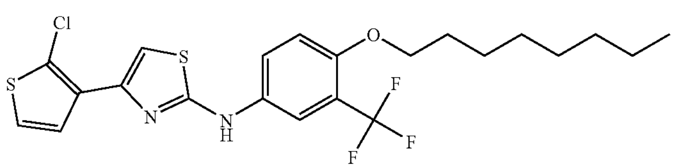 | 4-(2-chlorothiophen-3-yl)-N-(3-(trifluoromethyl)-4-(octyloxy)phenyl)thiazol-2-amine | +++ |
| 813 | 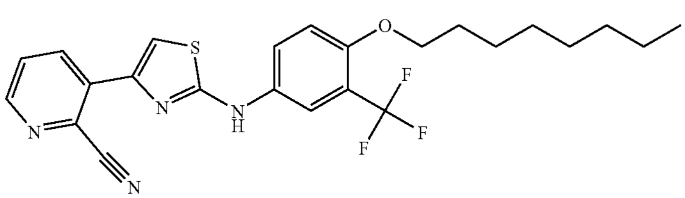 | 3-(2-(3-(trifluoromethyl)-4-(octyloxy)phenylamino)thiazol-4-yl)pyridine-2-carbonitrile | +++ |
| 814 | 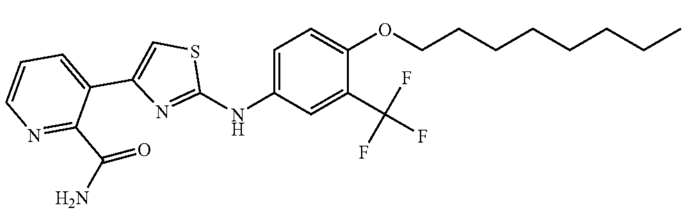 | 3-(2-(3-(trifluoromethyl)-4-(octyloxy)phenylamino)thiazol-4-yl)pyridine-2-carboxamide | ++ |

TABLE IV-continued

| Cpd | Structure | Name | Activity |
|---|---|---|---|
| 815 | 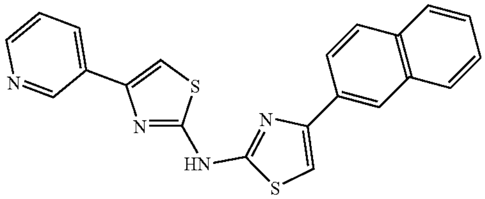 | 4-(naphthalen-2-yl)-N-(4-(pyridin-3-yl)thiazol-2-yl)thiazol-2-amine | ++ |
| 816 | 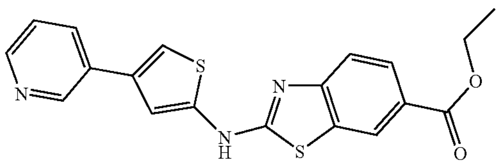 | ethyl 2-(4-(pyridin-3-yl)thiazol-2-ylamino)benzo[d]thiazole-6-carboxylate | + |
| 817 | 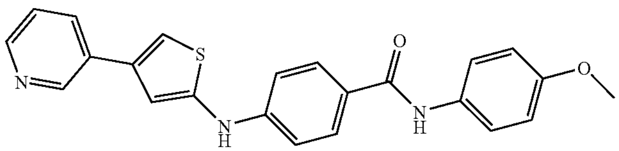 | 4-(4-(pyridin-3-yl)thiazol-2-ylamino)-N-(4-methoxyphenyl)benzamide | + |
| 818 | 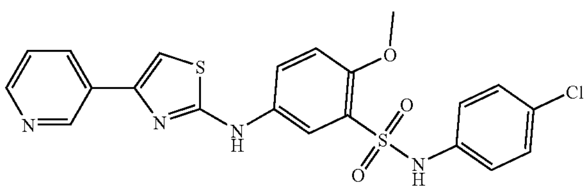 | | + |
| 819 | 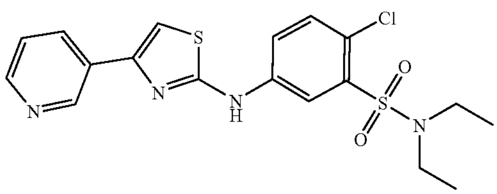 | | + |
| 820 | 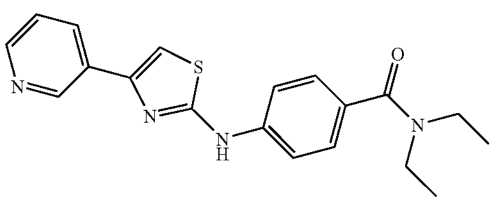 | 4-(4-(pyridin-3-yl)thiazol-2-ylamino)-N,N-diethylbenzamide | + |
| 821 | 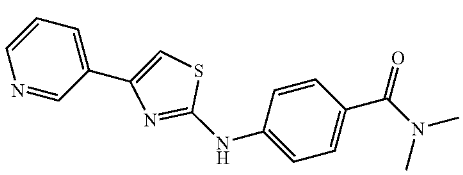 | 4-(4-(pyridin-3-yl)thiazol-2-ylamino)-N,N-dimethylbenzamide | + |
| 822 | 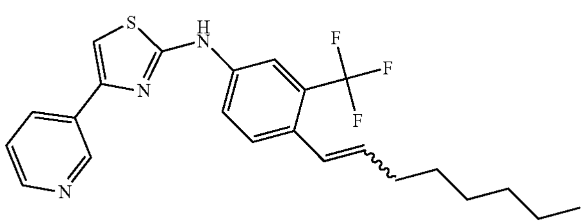 | N-(3-(trifluoromethyl)-4-(oct-1-enyl)phenyl)-4-(pyridin-3-yl)thiazol-2-amine | +++ |

TABLE IV-continued

| Cpd | Structure | Name | Activity |
|---|---|---|---|
| 823 | 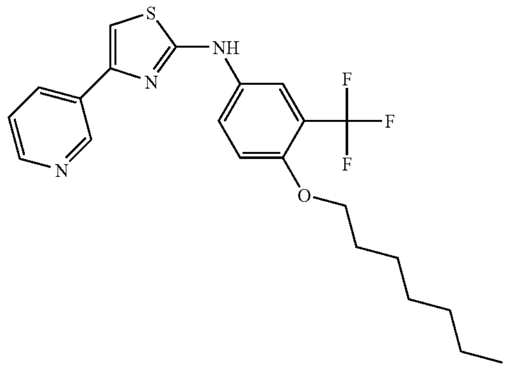 | N-(3-(trifluoromethyl)-4-(heptyloxy)phenyl)-4-(pyridin-3-yl)thiazol-2-amine | +++ |
| 824 | 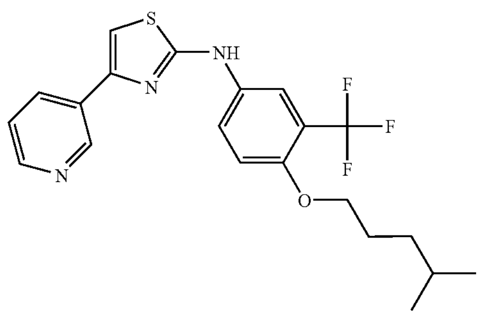 | N-(4-(4-methylpentyloxy)-3-(trifluoromethyl)phenyl)-4-(pyridin-3-yl)thiazol-2-amine | +++ |
| 825 | 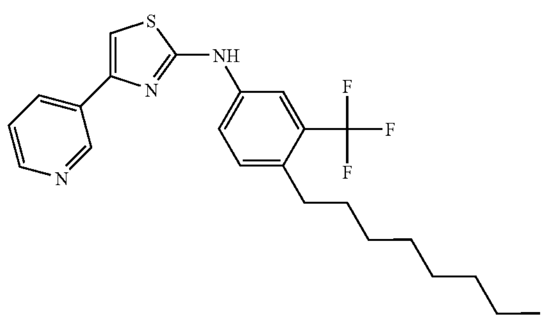 | N-(3-(trifluoromethyl)-4-octylphenyl)-4-(pyridin-3-yl)thiazol-2-amine | +++ |
| 826 | 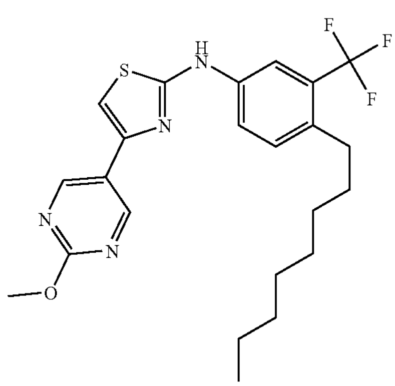 | N-(3-(trifluoromethyl)-4-octylphenyl)-4-(2-methoxypyrimidin-5-yl)thiazol-2-amine | +++ |

TABLE IV-continued

| Cpd | Structure | Name | Activity |
|---|---|---|---|
| 827 | 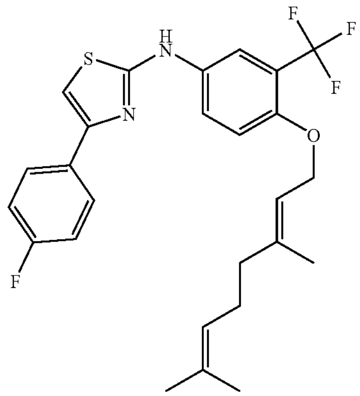 | N-(4-((E)-3,7-dimethylocta-2,6-dienyloxy)-3-(trifluoromethyl)phenyl)-4-(4-fluorophenyl)thiazol-2-amine | + |
| 828 | 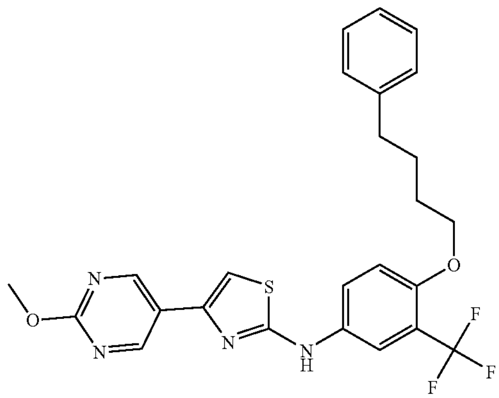 | N-(4-(4-phenylbutoxy)-3-(trifluoromethyl)phenyl)-4-(2-methoxypyrimidin-5-yl)thiazol-2-amine | +++ |
| 829 | 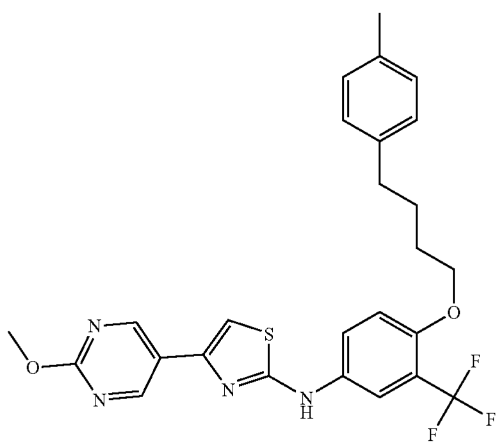 | N-(4-(4-p-tolylbutoxy)-3-(trifluoromethyl)phenyl)-4-(2-methoxypyrimidin-5-yl)thiazol-2-amine | +++ |
| 830 | 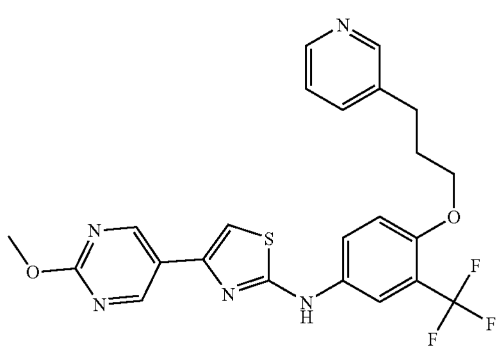 | N-(4-(3-(pyridin-3-yl)propoxy)-3-(trifluoromethyl)phenyl)-4-(2-methoxypyrimidin-5-yl)thiazol-2-amine | ++ |

TABLE IV-continued

| Cpd | Structure | Name | Activity |
|---|---|---|---|
| 831 | 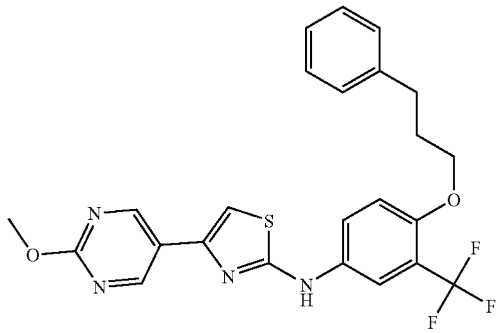 | N-(4-(3-phenylpropoxy)-3-(trifluoromethyl)phenyl)-4-(2-methoxypyrimidin-5-yl)thiazol-2-amine | +++ |
| 832 | 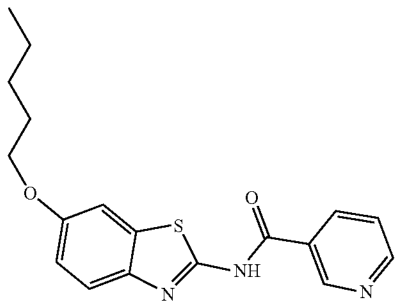 | N-(6-(pentyloxy)benzo[d]thiazol-2-yl)nicotinamide | + |
| 833 | 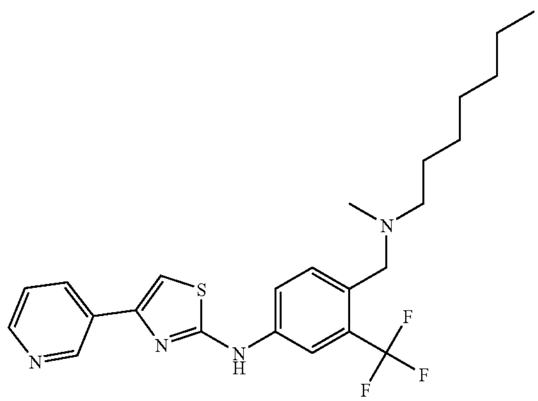 | N-(4-((heptyl(methyl)amino)methyl)-3-(trifluoromethyl)phenyl)-4-(pyridin-3-yl)thiazol-2-amine | +++ |
| 834 | 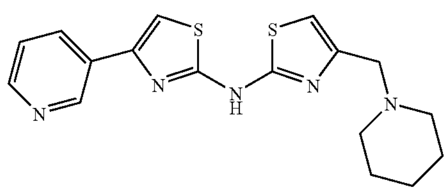 | 4-((piperidin-1-yl)methyl)-N-(4-(pyridin-3-yl)thiazol-2-yl)thiazol-2-amine | + |
| 835 | 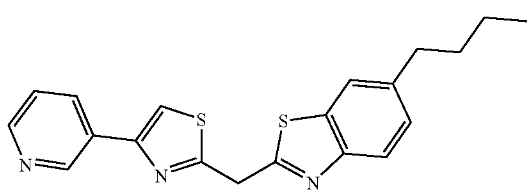 | 6-butyl-N-(4-(pyridin-3-yl)thiazol-2-yl)benzo[d]thiazol-2-amine | + |
| 836 | 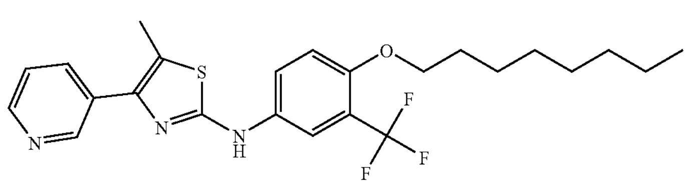 | N-(3-(trifluoromethyl)-4-(octyloxy)phenyl)-5-methyl-4-(pyridin-3-yl)thiazol-2-amine | +++ |

TABLE IV-continued

| Cpd | Structure | Name | Activity |
|---|---|---|---|
| 837 | 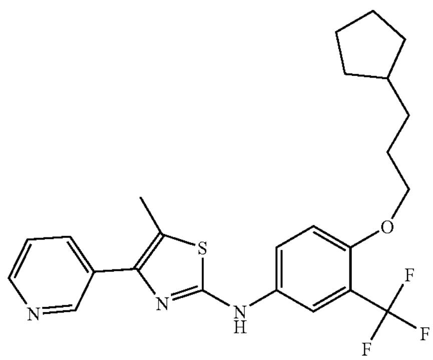 | N-(4-(3-cyclopentylpropoxy)-3-(trifluoromethyl)phenyl)-5-methyl-4-(pyridin-3-yl)thiazol-2-amine | +++ |
| 838 | 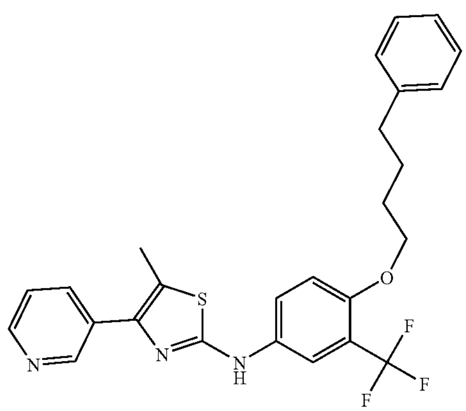 | N-(4-(4-phenylbutoxy)-3-(trifluoromethyl)phenyl)-5-methyl-4-(pyridin-3-yl)thiazol-2-amine | +++ |
| 839 | 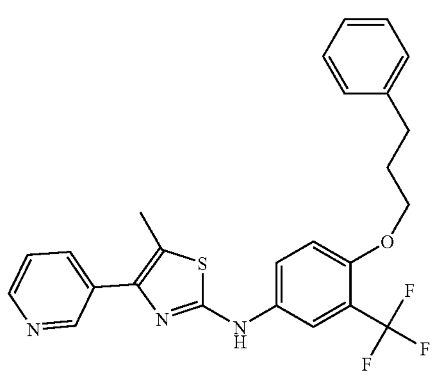 | N-(4-(3-phenylpropoxy)-3-(trifluoromethyl)phenyl)-5-methyl-4-(pyridin-3-yl)thiazol-2-amine | +++ |

TABLE IV-continued

| Cpd | Structure | Name | Activity |
|---|---|---|---|
| 840 | 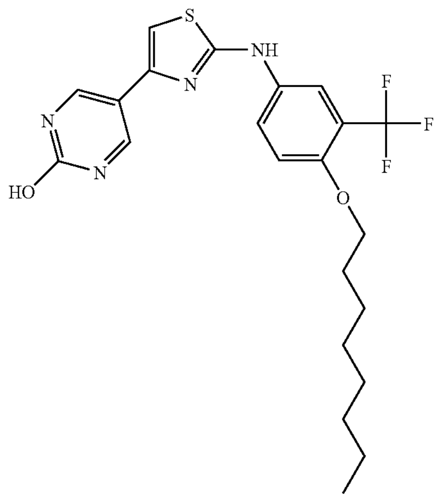 | 5-(2-(3-(trifluoromethyl)-4-(octyloxy)phenylamino)thiazol-4-yl)pyrimidin-2-ol | +++ |
| 841 | 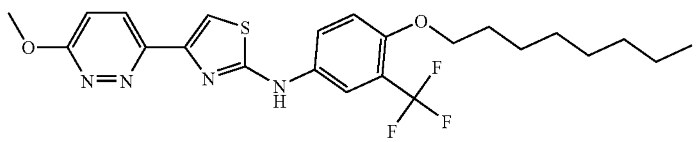 | N-(3-(trifluoromethyl)-4-(octyloxy)phenyl)-4-(6-methoxypyridazin-3-yl)thiazol-2-amine | +++ |
| 842 | 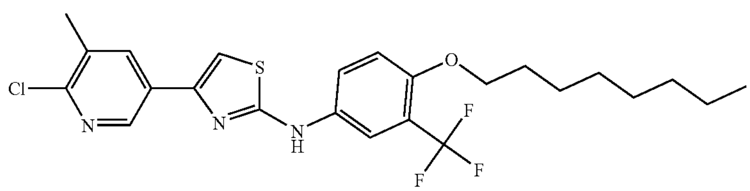 | 4-(6-chloro-5-methylpyridin-3-yl)-N-(3-(trifluoromethyl)-4-(octyloxy)phenyl)thiazol-2-amine | +++ |
| 843 | 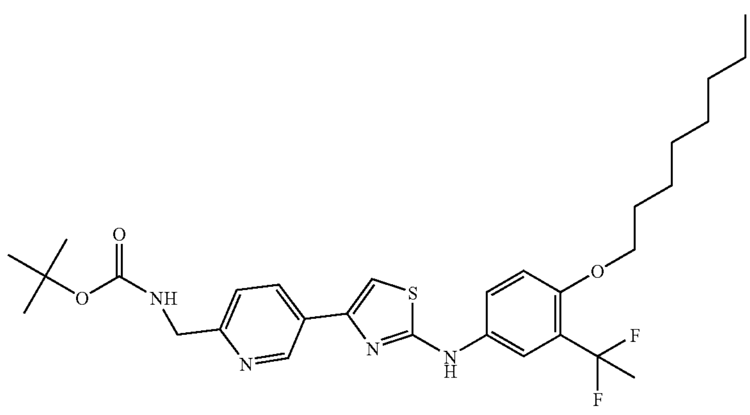 | tert-butyl (5-(2-(3-(trifluoromethyl)-4-(octyloxy)phenylamino)thiazol-4-yl)pyridin-2-yl)methylcarbamate | +++ |
| 844 | 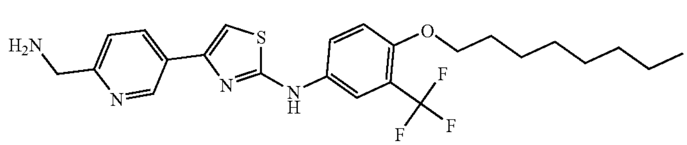 | 4-(6-(aminomethyl)pyridin-3-yl)-N-(3-(trifluoromethyl)-4-(octyloxy)phenyl)thiazol-2-amine | +++ |

TABLE IV-continued

| Cpd | Structure | Name | Activity |
|---|---|---|---|
| 845 | 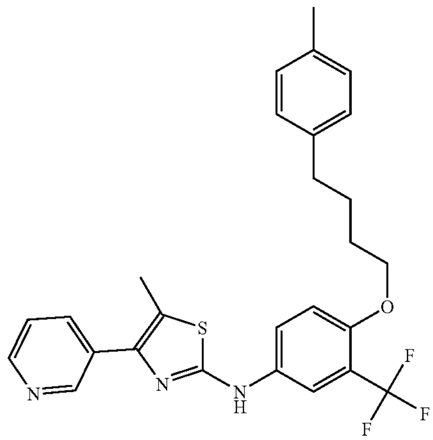 | N-(4-(4-p-tolylbutoxy)-3-(trifluoromethyl)phenyl)-5-methyl-4-(pyridin-3-yl)thiazol-2-amine | +++ |
| 846 | 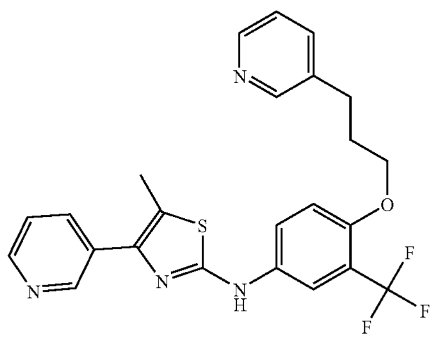 | N-(4-(3-(pyridin-3-yl)propoxy)-3-(trifluoromethyl)phenyl)-5-methyl-4-(pyridin-3-yl)thiazol-2-amine | + |
| 847 | 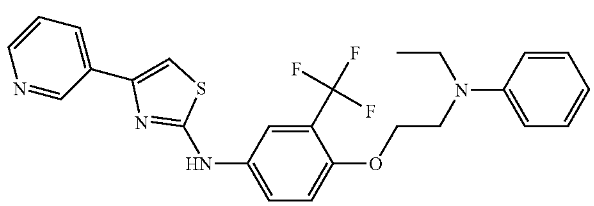 | CHEMDRAW COULD NOT NAME STRUCTURE | +++ |
| 848 | 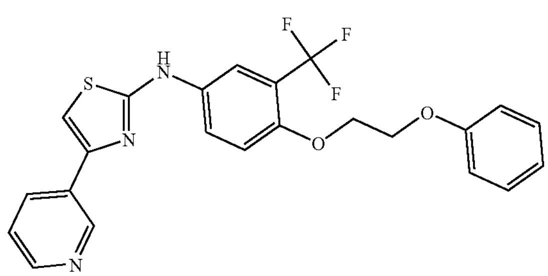 | N-(4-(2-phenoxyethoxy)-3-(trifluoromethyl)phenyl)-4-(pyridin-3-yl)thiazol-2-amine | +++ |

TABLE IV-continued

| Cpd | Structure | Name | Activity |
|---|---|---|---|
| 849 | 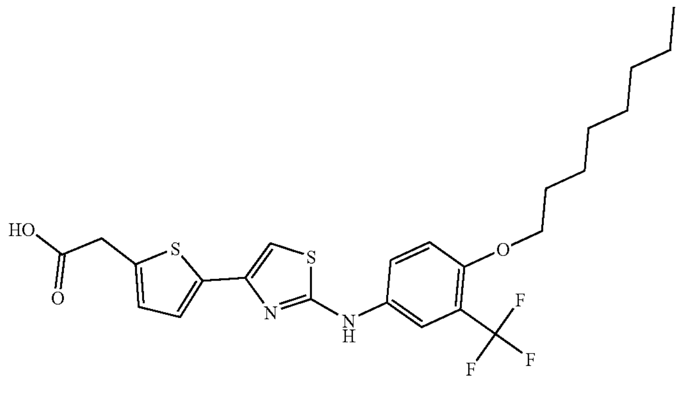 | 2-(5-(2-(3-(trifluoromethyl)-4-(octyloxy)phenylamino)thiazol-4-yl)thiophen-2-yl)acetic acid | +++ |
| 850 | 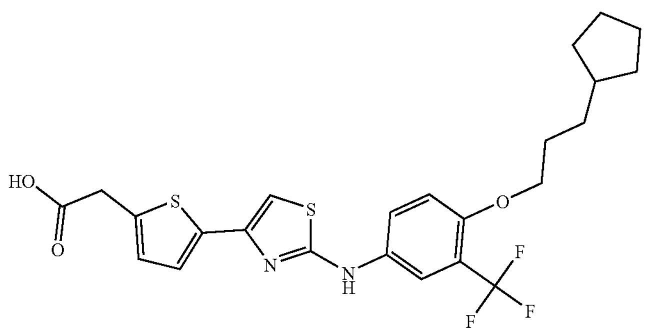 | 2-(5-(2-(4-(3-cyclopentylpropoxy)-3-(trifluoromethyl)phenylamino)thiazol-4-yl)thiophen-2-yl)acetic acid | +++ |
| 851 | 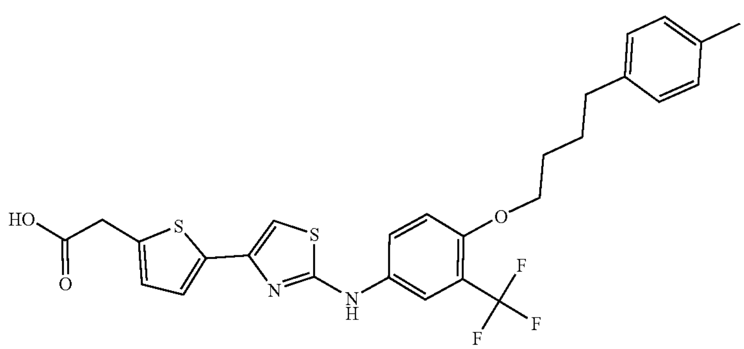 | 2-(5-(2-(4-(4-p-tolylbutoxy)-3-(trifluoromethyl)phenylamino)thiazol-4-yl)thiophen-2-yl)acetic acid | +++ |
| 852 | 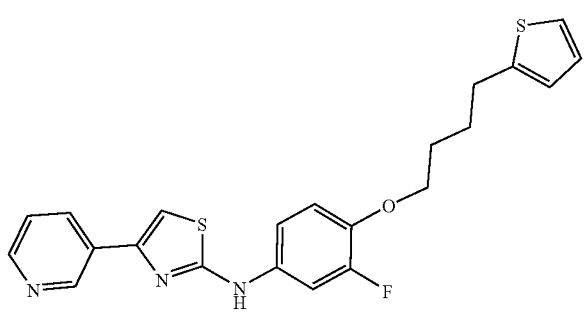 | N-(4-(4-(thiophen-2-yl)butoxy)-3-fluorophenyl)-4-(pyridin-3-yl)thiazol-2-amine | +++ |

TABLE IV-continued

| Cpd | Structure | Name | Activity |
|---|---|---|---|
| 853 | 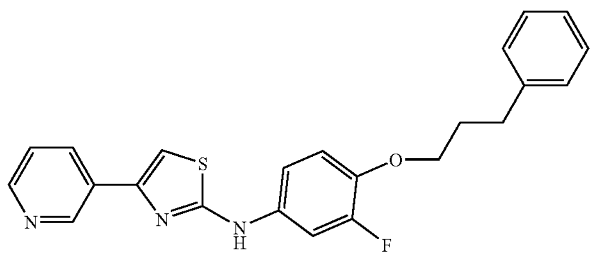 | N-(4-(3-phenylpropoxy)-3-fluorophenyl)-4-(pyridin-3-yl)thiazol-2-amine | +++ |
| 854 | 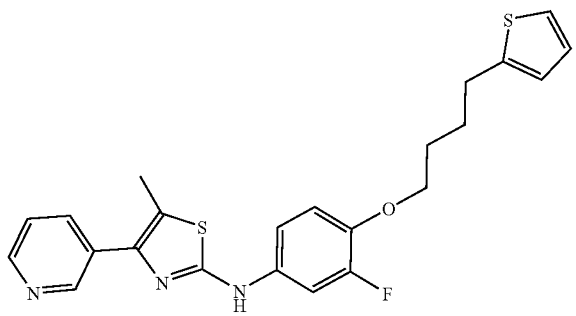 | N-(4-(4-(thiophen-2-yl)butoxy)-3-fluorophenyl)-5-methyl-4-(pyridin-3-yl)thiazol-2-amine | ++ |
| 855 | 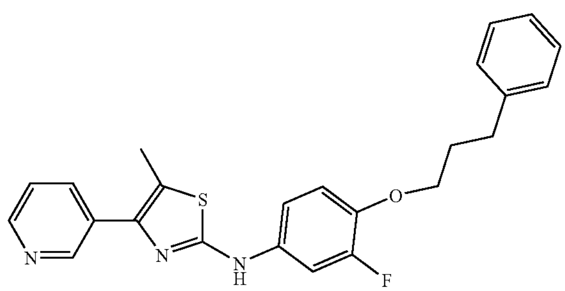 | N-(4-(3-phenylpropoxy)-3-fluorophenyl)-5-methyl-4-(pyridin-3-yl)thiazol-2-amine | + |
| 856 | 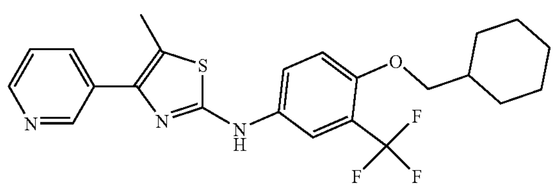 | N-(4-(cyclohexylmethoxy)-3-(trifluoromethyl)phenyl)-5-methyl-4-(pyridin-3-yl)thiazol-2-amine | +++ |
| 857 | 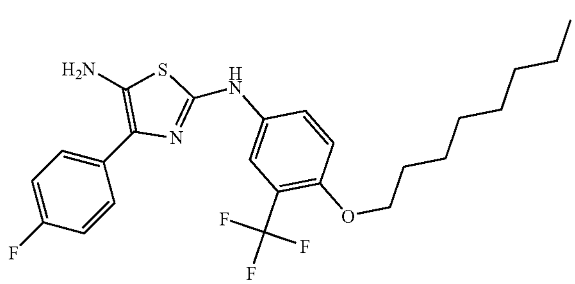 | $N^2$-(3-(trifluoromethyl)-4-(octyloxy)phenyl)-4-(4-fluorophenyl)thiazole-2,5-diamine | +++ |

TABLE IV-continued

| Cpd | Structure | Name | Activity |
|---|---|---|---|
| 858 | 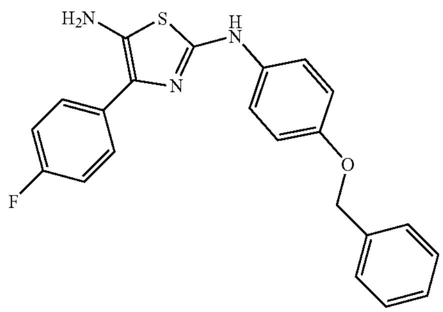 | $N^2$-(4-(benzyloxy)phenyl)-4-(4-fluorophenyl)thiazole-2,5-diamine | ++ |
| 859 | 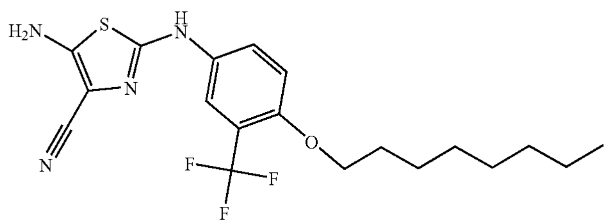 | 2-(3-(trifluoromethyl)-4-(octyloxy)phenylamino)-5-aminothiazole-4-carbonitrile | +++ |
| 860 | 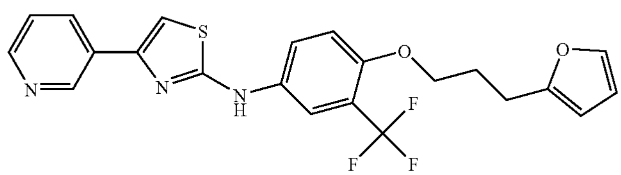 | N-(4-(3-(furan-2-yl)propoxy)-3-(trifluoromethyl)phenyl)-4-(pyridin-3-yl)thiazol-2-amine | +++ |
| 861 | 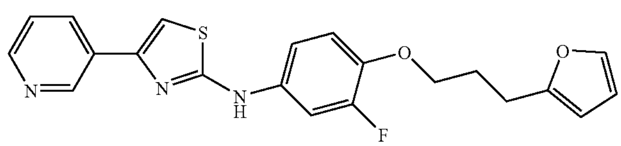 | N-(4-(3-(furan-2-yl)propoxy)-3-fluorophenyl)-4-(pyridin-3-yl)thiazol-2-amine | +++ |
| 862 | 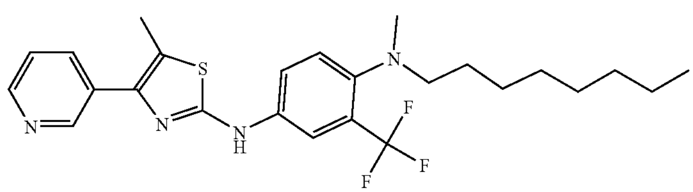 | 2-(trifluoromethyl)-$N^1$-methyl-$N^4$-(5-methyl-4-(pyridin-3-yl)thiazol-2-yl)-$N^1$-octylbenzene-1,4-diamine | +++ |
| 863 | 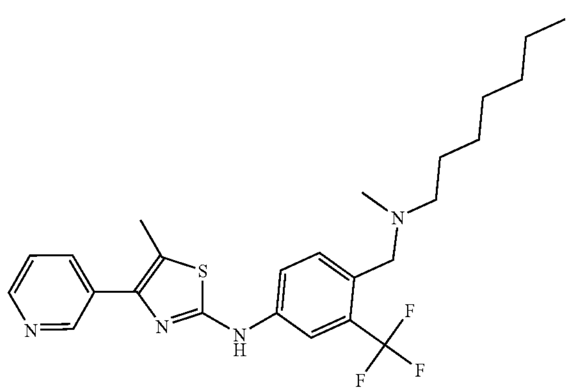 | CHEMDRAW COULD NOT NAME STRUCTURE | ++ |

TABLE IV-continued

| Cpd | Structure | Name | Activity |
|---|---|---|---|
| 864 | 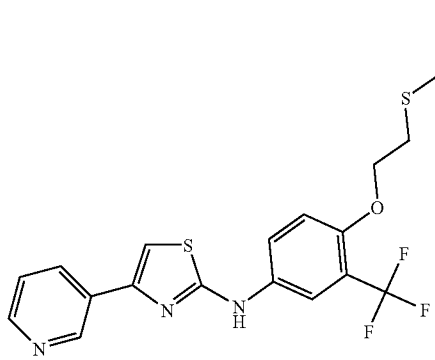 | N-(4-(2-(phenylthio)ethoxy)-3-(trifluoromethyl)phenyl)-4-(pyridin-3-yl)thiazol-2-amine | +++ |
| 865 | 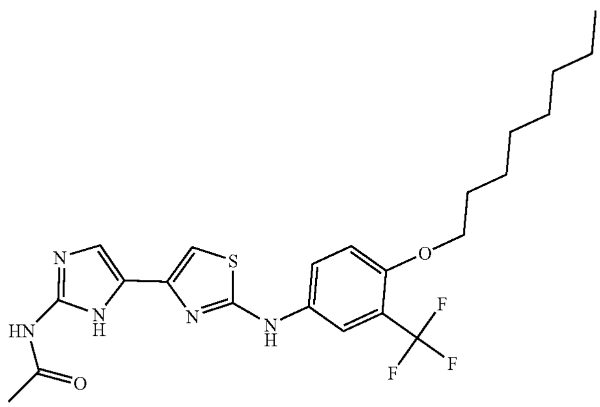 | N-(5-(2-(3-(trifluoromethyl)-4-(octyloxy)phenylamino)thiazol-4-yl)-1H-imidazol-2-yl)acetamide | +++ |
| 866 | 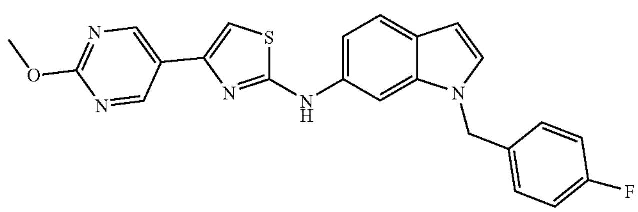 | 1-(4-fluorobenzyl)-N-(4-(2-methoxypyrimidin-5-yl)thiazol-2-yl)-1H-indol-6-amine | +++ |
| 867 | 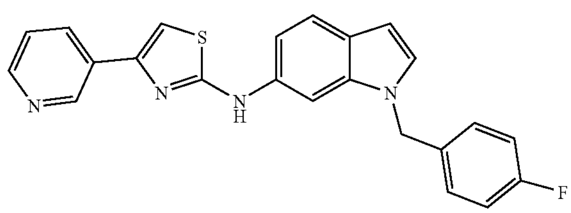 | 1-(4-fluorobenzyl)-N-(4-(pyridin-3-yl)thiazol-2-yl)-1H-indol-6-amine | +++ |
| 868 | 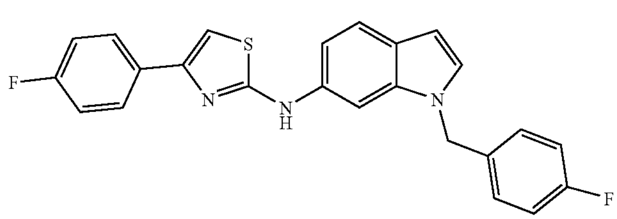 | 1-(4-fluorobenzyl)-N-(4-(4-fluorophenyl)thiazol-2-yl)-1H-indol-6-amine | +++ |

TABLE IV-continued

| Cpd | Structure | Name | Activity |
|---|---|---|---|
| 869 | 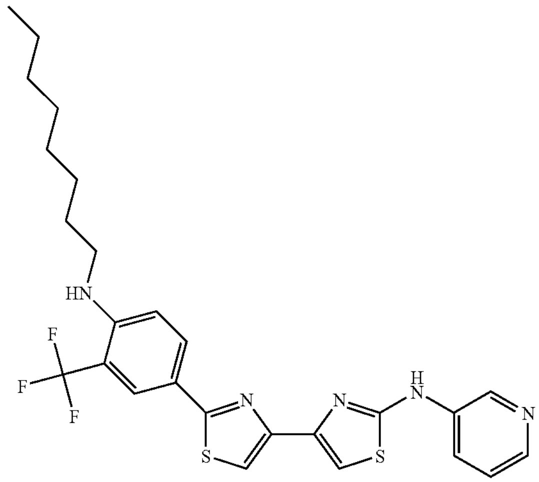 | N-(4-(2-(3-(trifluoromethyl)-4-(octylamino)phenyl)thiazol-4-yl)thiazol-2-yl)pyridin-3-amine | +++ |
| 870 | 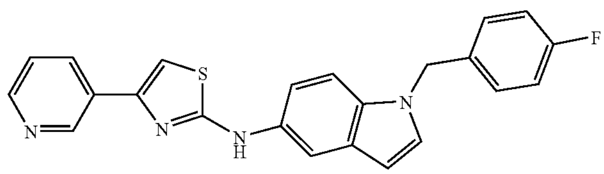 | 1-(4-(fluorobenzyl)-N-(4-(pyridin-3-yl)thiazol-2-yl)-1H-indol-5-amine | +++ |
| 871 | 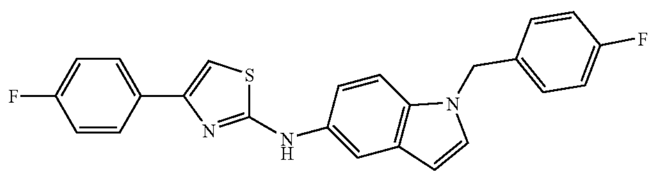 | 1-(4-fluorobenzyl)-N-(4-(4-fluorophenyl)thiazol-2-yl)-1H-indol-5-amine | + |
| 872 | 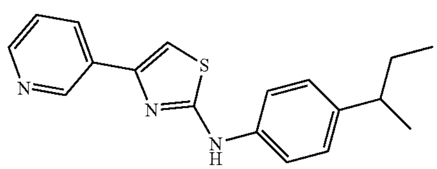 | N-(4-sec-butylphenyl)-4-(pyridin-3-yl)thiazol-2-amine | ++ |
| 873 | 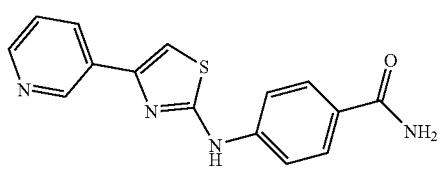 | 4-(4-(pyridin-3-yl)thiazol-2-ylamino)benzamide | + |
| 874 | 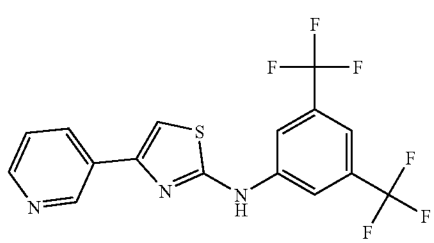 | N-(3,5-bis(trifluoromethyl)phenyl)-4-(pyridin-3-yl)thiazol-2-amine | ++ |
| 875 | 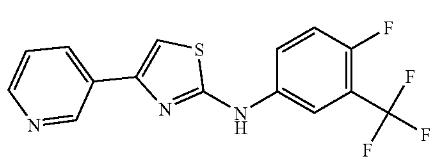 | N-(4-fluoro-3-(trifluoromethyl)phenyl)-4-(pyridin-3-yl)thiazol-2-amine | ++ |

TABLE IV-continued

| Cpd | Structure | Name | Activity |
|---|---|---|---|
| 876 | 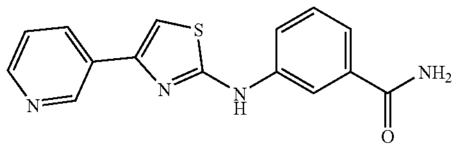 | 3-(4-(pyridin-3-yl)thiazol-2-ylamino)benzamide | + |
| 877 | 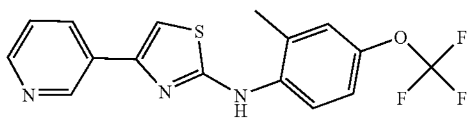 | N-(2-methyl-4-(trifluoromethoxy)phenyl)-4-(pyridin-3-yl)thiazol-2-amine | + |
| 878 | 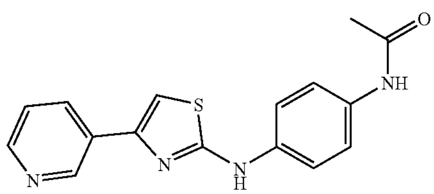 | N-(4-(4-(pyridin-3-yl)thiazol-2-ylamino)phenyl)acetamide | + |
| 879 | 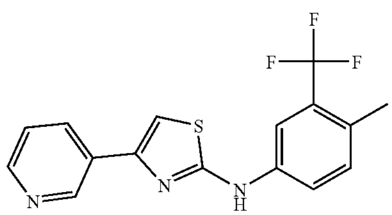 | N-(3-(trifluoromethyl)-4-methylphenyl)-4-(pyridin-3-yl)thiazol-2-amine | +++ |
| 880 | 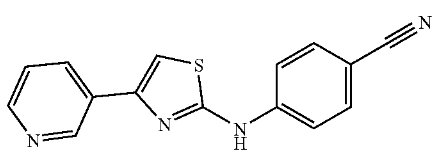 | 4-(4-(pyridin-3-yl)thiazol-2-ylamino)benzonitrile | ++ |
| 881 | 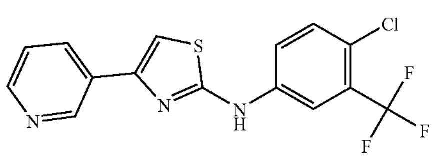 | N-(4-chloro-3-(trifluoromethyl)phenyl)-4-(pyridin-3-yl)thiazol-2-amine | +++ |
| 882 | 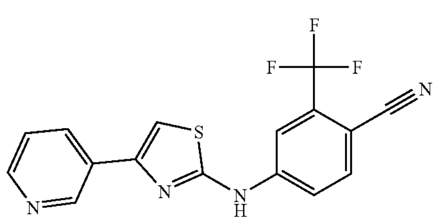 | 4-(4-(pyridin-3-yl)thiazol-2-ylamino)-2-(trifluoromethyl)benzonitrile | + |
| 883 | 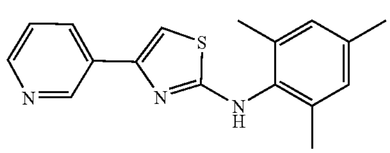 | N-mesityl-4-(pyridin-3-yl)thiazol-2-amine | + |
| 884 | 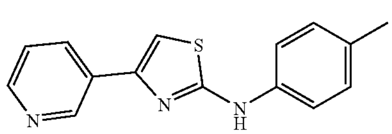 | 4-(pyridin-3-yl)-N-p-tolylthiazol-2-amine | + |

TABLE IV-continued

| Cpd | Structure | Name | Activity |
|---|---|---|---|
| 885 | 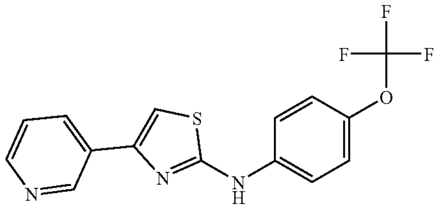 | 4-(pyridin-3-yl)-N-(4-(trifluoromethoxy)phenyl)thiazol-2-amine | ++ |
| 886 | 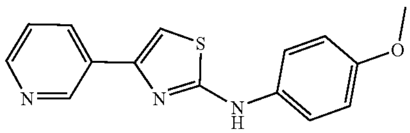 | N-(4-methoxyphenyl)-4-(pyridin-3-yl)thiazol-2-amine | + |
| 887 | 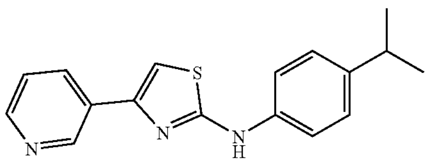 | N-(4-isopropylphenyl)-4-(pyridin-3-yl)thiazol-2-amine | ++ |
| 888 | 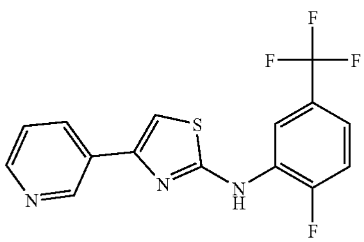 | N-(2-fluoro-5-(trifluoromethyl)phenyl)-4-(pyridin-3-yl)thiazol-2-amine | ++ |
| 889 | 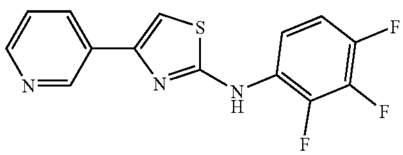 | N-(2,3,4-trifluorophenyl)-4-(pyridin-3-yl)thiazol-2-amine | + |
| 890 | 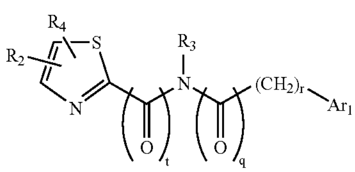 | N-(2-fluoro-3-(trifluoromethyl)phenyl)-4-(pyridin-3-yl)thiazol-2-amine | ++ |
| 891 | 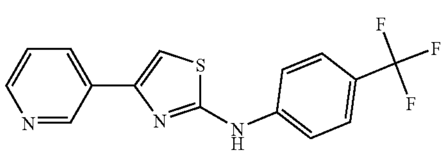 | N-(4-(trifluoromethyl)phenyl)-4-(pyridin-3-yl)thiazol-2-amine | ++ |
| 892 | 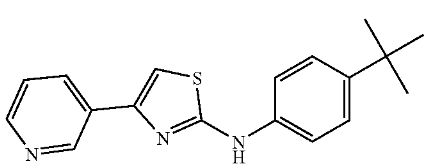 | N-(4-tert-butylphenyl)-4-(pyridin-3-yl)thiazol-2-amine | ++ |

TABLE IV-continued

| Cpd | Structure | Name | Activity |
|---|---|---|---|
| 893 | 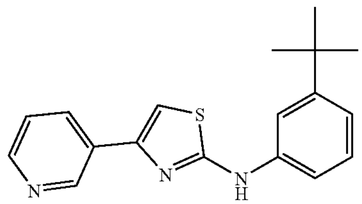 | N-(3-tert-butylphenyl)-4-(pyridin-3-yl)thiazol-2-amine | + |
| 894 | 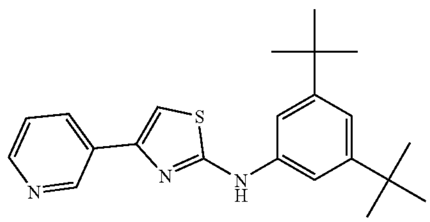 | N-(3,5-di-tert-butylphenyl)-4-(pyridin-3-yl)thiazol-2-amine | +++ |
| 895 | 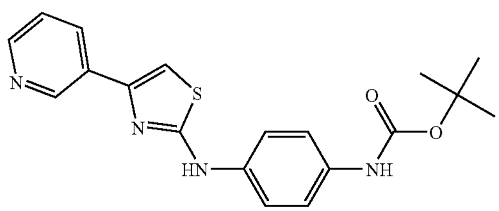 | tert-butyl 4-(4-(pyridin-3-yl)thiazol-2-ylamino)phenylcarbamate | + |
| 896 | 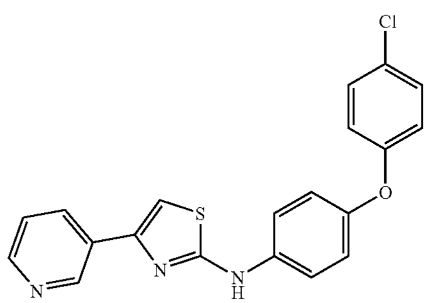 | N-(4-(4-chlorophenoxy)phenyl)-4-(pyridin-3-yl)thiazol-2-amine | +++ |
| 897 | 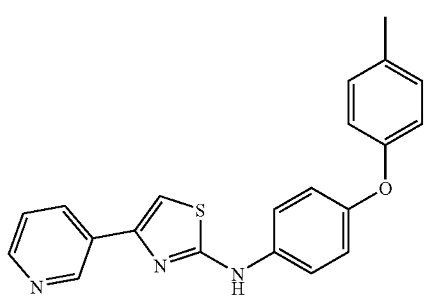 | N-(4-(p-tolyloxy)phenyl)-4-(pyridin-3-yl)thiazol-2-amine | +++ |
| 898 | 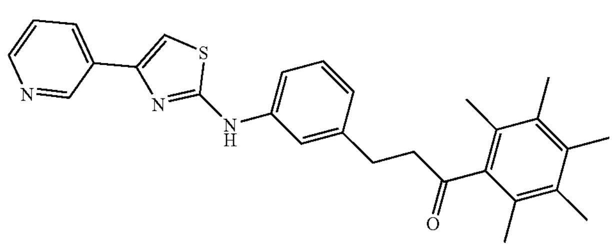 | 3-(3-(4-(pyridin-3-yl)thiazol-2-ylamino)phenyl)-1-(2,3,4,5,6-pentamethylphenyl)propan-1-one | +++ |

TABLE IV-continued

| Cpd | Structure | Name | Activity |
|---|---|---|---|
| 899 | 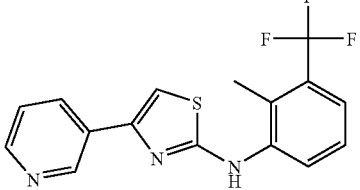 | N-(3-(trifluoromethyl)-2-methylphenyl)-4-(pyridin-3-yl)thiazol-2-amine | ++ |
| 900 | 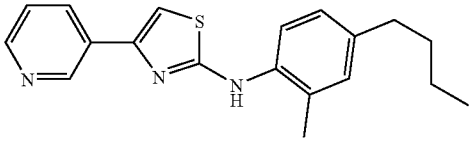 | N-(4-butyl-2-methylphenyl)-4-(pyridin-3-yl)thiazol-2-amine | +++ |
| 901 | 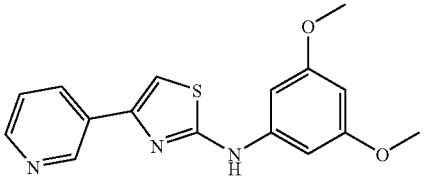 | N-(3,5-dimethoxyphenyl)-4-(pyridin-3-yl)thiazol-2-amine | ++ |
| 902 | 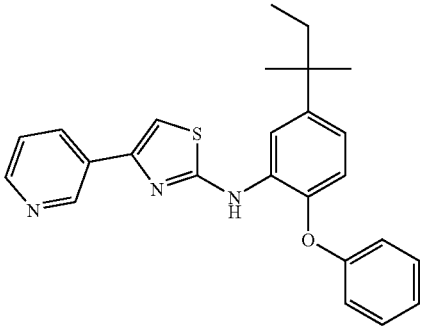 | N-(5-tert-pentyl-2-phenoxyphenyl)-4-(pyridin-3-yl)thiazol-2-amine | +++ |
| 903 | 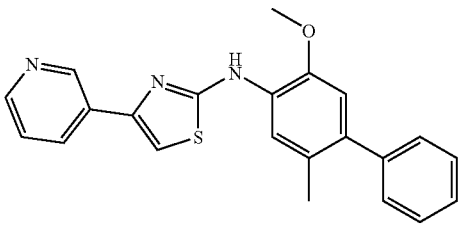 | CHEMDRAW COULD NOT NAME STRUCTURE | +++ |
| 904 | 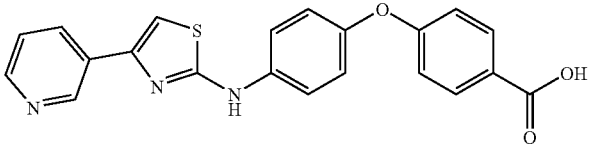 | 4-(4-(4-(pyridin-3-yl)thiazol-2-ylamino)phenoxy)benzoic acid | +++ |
| 905 | 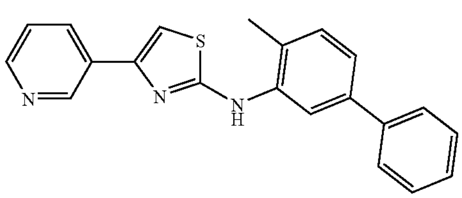 | CHEMDRAW COULD NOT NAME STRUCTURE | + |

TABLE IV-continued

| Cpd | Structure | Name | Activity |
|---|---|---|---|
| 906 | 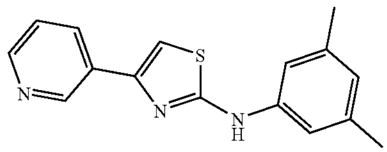 | N-(3,5-dimethylphenyl)-4-(pyridin-3-yl)thiazol-2-amine | ++ |
| 907 | 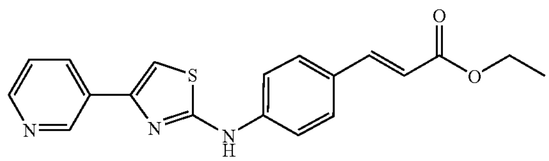 | (E)-ethyl 3-(4-(4-(pyridin-3-yl)thiazol-2-ylamino)phenyl)acrylate | + |
| 908 | 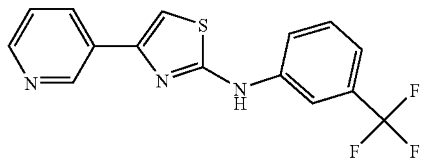 | N-(3-(trifluoromethyl)phenyl)-4-(pyridin-3-yl)thiazol-2-amine | +++ |
| 909 | 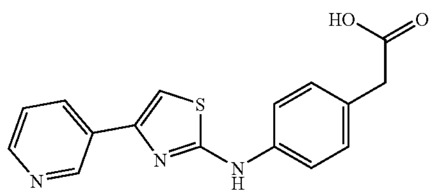 | 2-(4-(4-(pyridin-3-yl)thiazol-2-ylamino)phenyl)acetic acid | + |
| 910 | 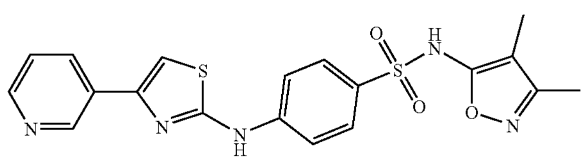 | CHEMDRAW COULD NOT NAME STRUCTURE | + |
| 911 | 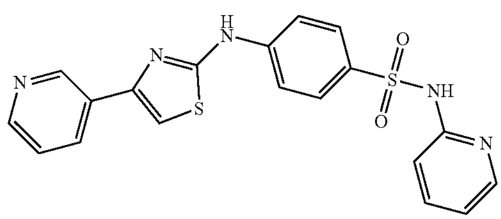 | CHEMDRAW COULD NOT NAME STRUCTURE | + |
| 912 | 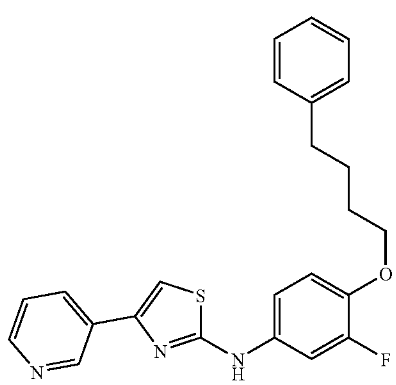 | N-(4-(4-phenylbutoxy)-3-fluorophenyl)-4-(pyridin-3-yl)thiazol-2-amine | +++ |

| Cpd | Structure | Name | Activity |
|---|---|---|---|
| 913 | 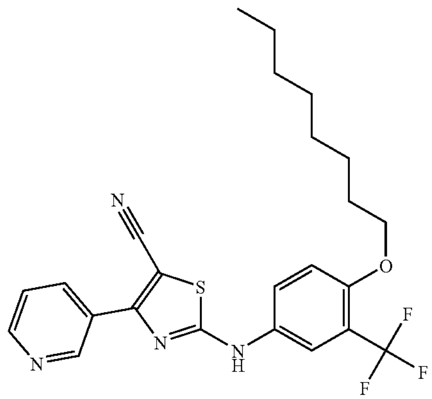 | 2-(3-(trifluoromethyl)-4-(octyloxy)phenylamino)-4-(pyridin-3-yl)thiazole-5-carbonitrile | ++ |
| 914 | 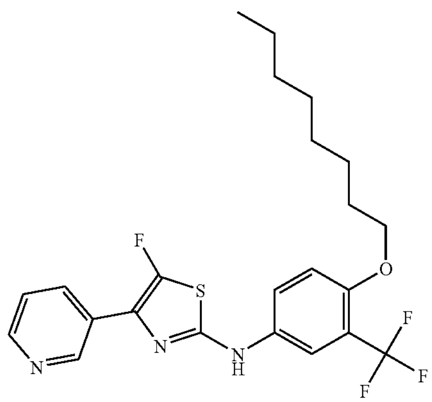 | 5-fluoro-N-(3-(trifluoromethyl)-4-(octyloxy)phenyl)-4-(pyridin-3-yl)thiazol-2-amine | +++ |
| 915 | 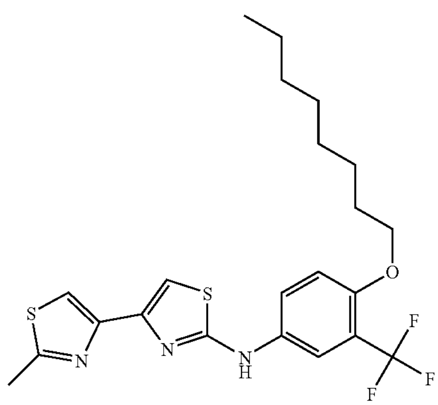 | N-(3-(trifluoromethyl)-4-(octyloxy)phenyl)-4-(2-methylthiazol-4-yl)thiazol-2-amine | +++ |
| 916 | 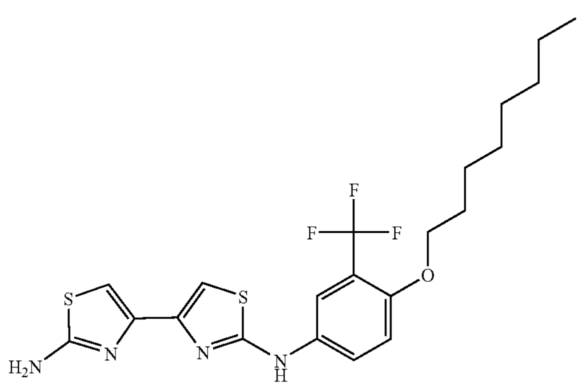 | 4-(2-(3-(trifluoromethyl)-4-(octyloxy)phenylamino)thiazol-4-yl)thiazol-2-amine | +++ |

TABLE IV-continued

| Cpd | Structure | Name | Activity |
|---|---|---|---|
| 917 | 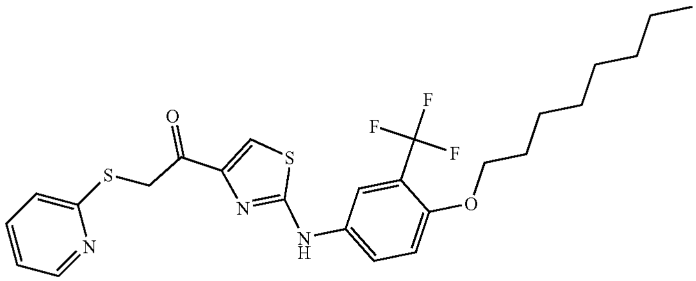 | 1-(2-(3-(trifluoromethyl)-4-(octyloxy)phenylamino)thiazol-4-yl)-2-(pyridin-2-ylthio)ethanone | ++ |
| 918 | 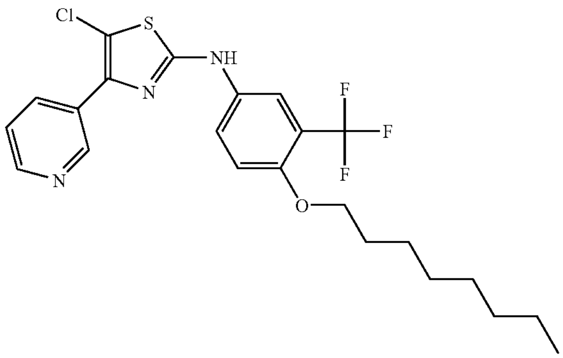 | 5-chloro-N-(3-(trifluoromethyl)-4-(octyloxy)phenyl)-4-(pyridin-3-yl)thiazol-2-amine | +++ |
| 919 | 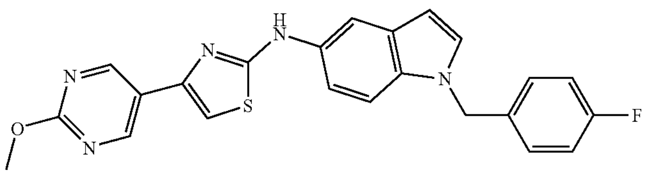 | 1-(4-fluorobenzyl)-N-(4-(2-methoxypyrimidin-5-yl)thiazol-2-yl)-1H-indol-5-amine | ++ |
| 920 | 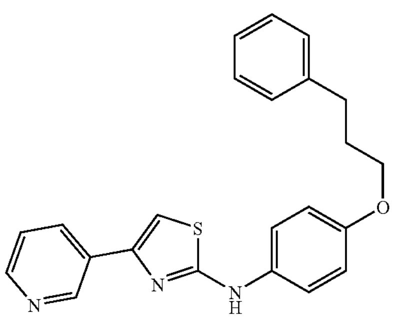 | N-(4-(3-phenylpropoxy)phenyl)-4-(pyridin-3-yl)thiazol-2-amine | +++ |
| 921 | 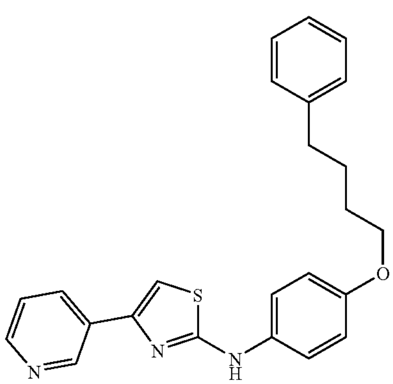 | N-(4-(4-phenylbutoxy)phenyl)-4-(pyridin-3-yl)thiazol-2-amine | +++ |

TABLE IV-continued

| Cpd | Structure | Name | Activity |
|---|---|---|---|
| 922 | 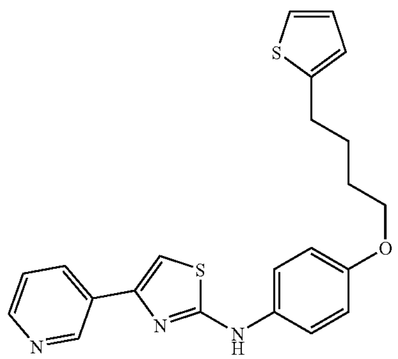 | N-(4-(4-(thiophen-2-yl)butoxy)phenyl)-4-(pyridin-3-yl)thiazol-2-amine | +++ |
| 923 | 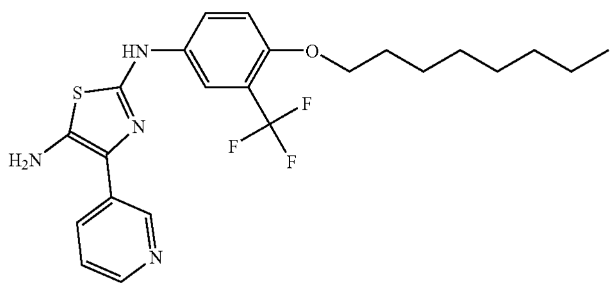 | $N^2$-(3-(trifluoromethyl)-4-(octyloxy)phenyl)-4-(pyridin-3-yl)thiazole-2,5-diamine | +++ |
| 924 | 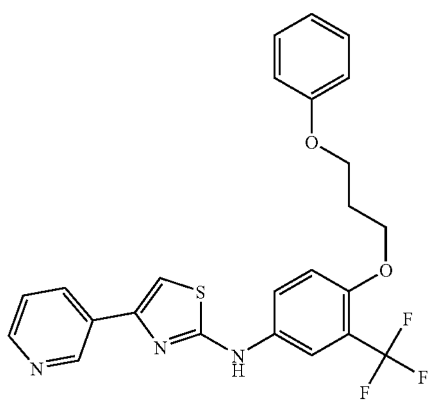 | N-(4-(3-phenoxypropoxy)-3-(trifluoromethyl)phenyl)-4-(pyridin-3-yl)thiazol-2-amine | +++ |
| 925 | 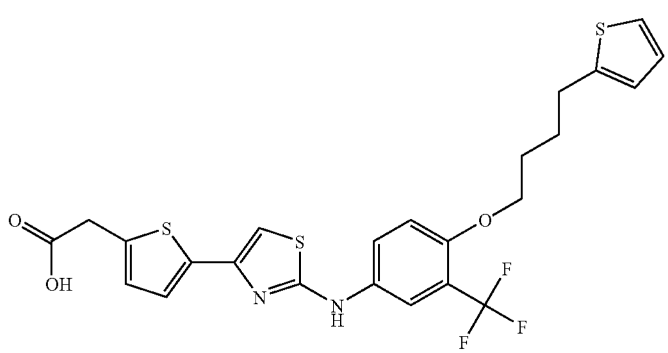 | 2-(5-(2-(4-(4-(thiophen-2-yl)butoxy)-3-(trifluoromethyl)phenylamino)thiazol-4-yl)thiophen-2-yl)acetic acid | +++ |

TABLE IV-continued

| Cpd | Structure | Name | Activity |
|---|---|---|---|
| 926 | 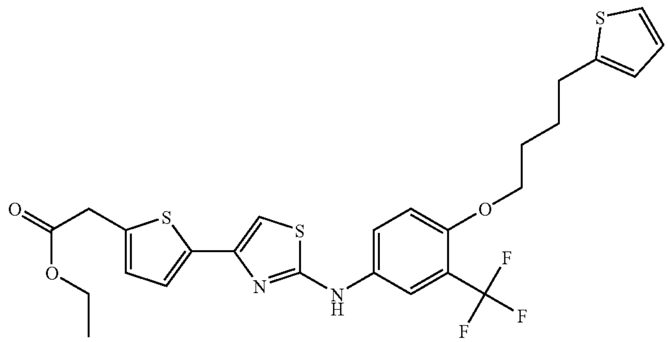 | ethyl 2-(5-(2-(4-(4-(thiophen-2-yl)butoxy)-3-(trifluoromethyl)phenylamino)thiazol-4-yl)thiophen-2-yl)acetate | ++ |
| 927 | 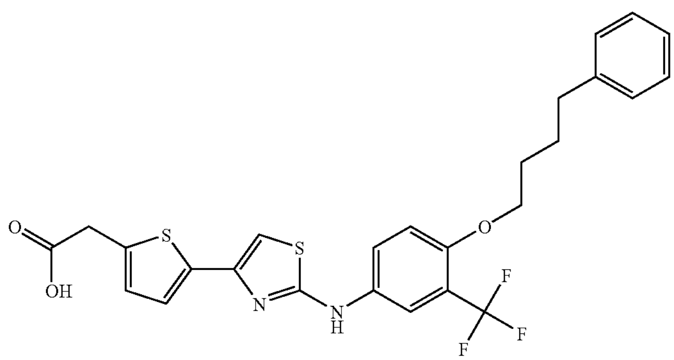 | 2-(5-(2-(4-(4-phenylbutoxy)-3-(trifluoromethyl)phenylamino)thiazol-4-yl)thiophen-2-yl)acetic acid | +++ |
| 928 | 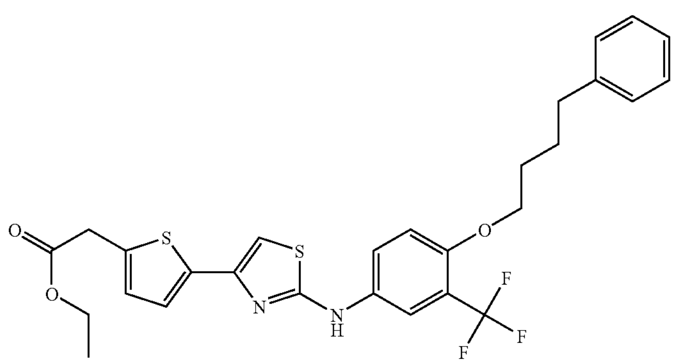 | ethyl 2-(5-(2-(4-(4-phenylbutoxy)-3-(trifluoromethyl)phenylamino)thiazol-4-yl)thiophen-2-yl)acetate | ++ |
| 929 | 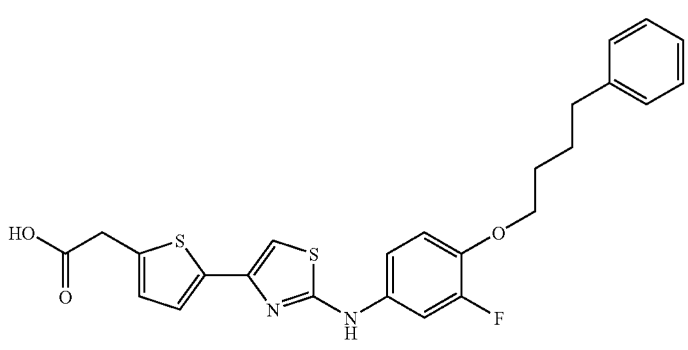 | 2-(5-(2-(4-(4-phenylbutoxy)-3-fluorophenylamino)thiazol-4-yl)thiophen-2-yl)acetic acid | +++ |

TABLE IV-continued
| Cpd | Structure | Name | Activity |
|---|---|---|---|
| 930 | 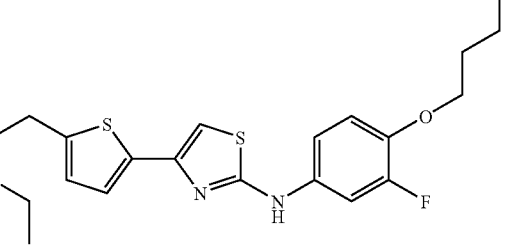 | ethyl 2-(5-(2-(4-(4-phenylbutoxy)-3-fluorophenylamino)thiazol-4-yl)thiophen-2-yl)acetate | ++ |
| 931 | 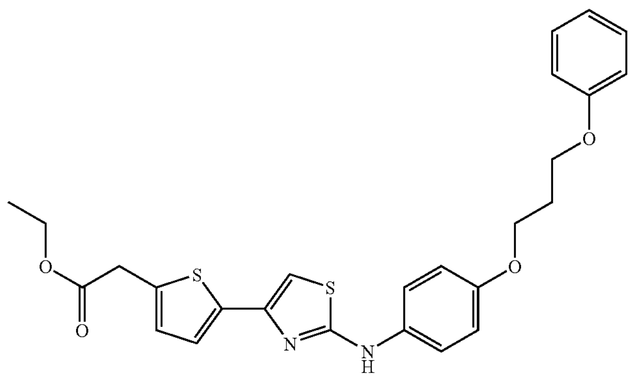 | ethyl 2-(5-(2-(4-(3-phenoxypropoxy)phenylamino)thiazol-4-yl)thiophen-2-yl)acetate | ++ |
| 932 | 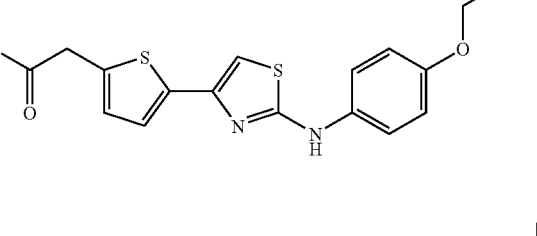 | CHEMDRAW COULD NOT NAME STRUCTURE | ++ |
| 933 | 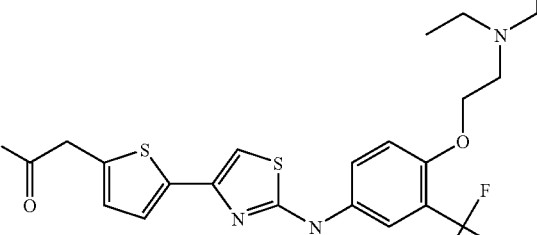 | ethyl 2-(5-(2-(4-(2-phenoxyethoxy)-3-(trifluoromethyl)phenylamino)thiazol-4-yl)thiophen-2-yl)acetate | ++ |

TABLE IV-continued

| Cpd | Structure | Name | Activity |
|---|---|---|---|
| 934 | 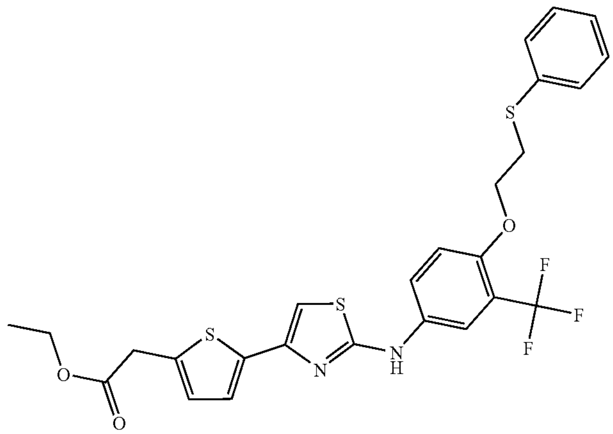 | ethyl 2-(5-(2-(4-(2-(phenylthio)ethoxy)-3-(trifluoromethyl)phenylamino)thiazol-4-yl)thiophen-2-yl)acetate | ++ |
| 935 | 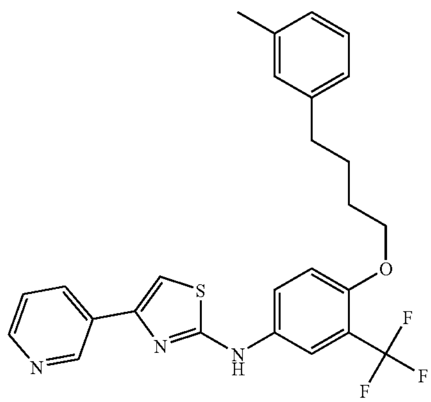 | N-(4-(4-m-tolylbutoxy)-3-(trifluoromethyl)phenyl)-4-(pyridin-3-yl)thiazol-2-amine | +++ |
| 936 | 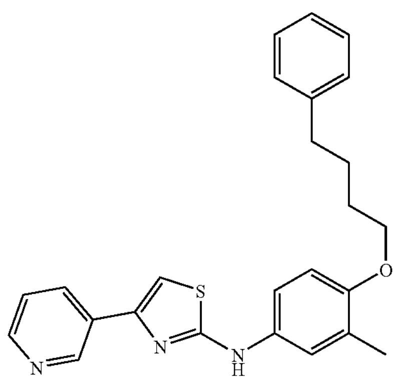 | N-(4-(4-phenylbutoxy)-3-methylphenyl)-4-(pyridin-3-yl)thiazol-2-amine | +++ |
| 937 | 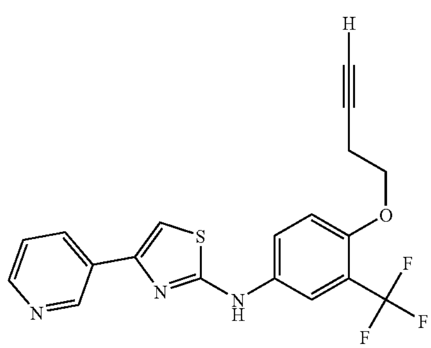 | N-(4-(but-3-ynyloxy)-3-(trifluoromethyl)phenyl)-4-(pyridin-3-yl)thiazol-2-amine | +++ |

TABLE IV-continued

| Cpd | Structure | Name | Activity |
|---|---|---|---|
| 938 | 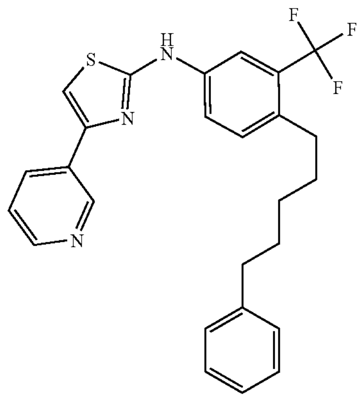 | N-(3-(trifluoromethyl)-4-(5-phenylpentyl)phenyl)-4-(pyridin-3-yl)thiazol-2-amine | +++ |
| 939 | 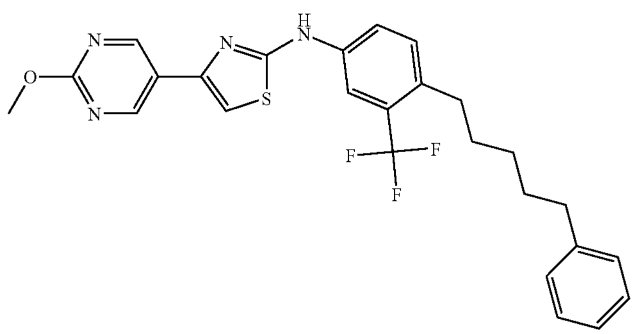 | N-(3-(trifluoromethyl)-4-(5-phenylpentyl)phenyl)-4-(2-methoxypyrimidin-5-yl)thiazol-2-amine | +++ |
| 940 | 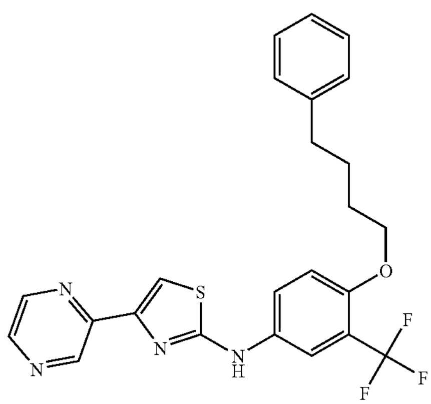 | N-(4-(4-phenylbutoxy)-3-(trifluoromethyl)phenyl)-4-(pyrazin-2-yl)thiazol-2-amine | +++ |
| 941 | 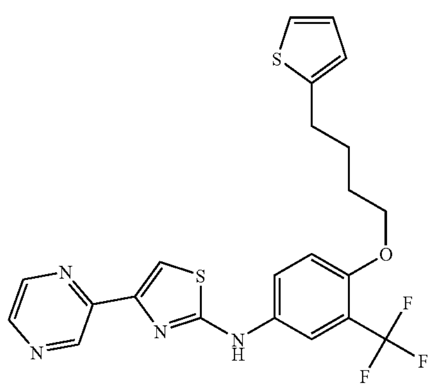 | N-(4-(4-(thiophen-2-yl)butoxy)-3-(trifluoromethyl)phenyl)-4-(pyrazin-2-yl)thiazol-2-amine | +++ |

TABLE IV-continued

| Cpd | Structure | Name | Activity |
|---|---|---|---|
| 942 | 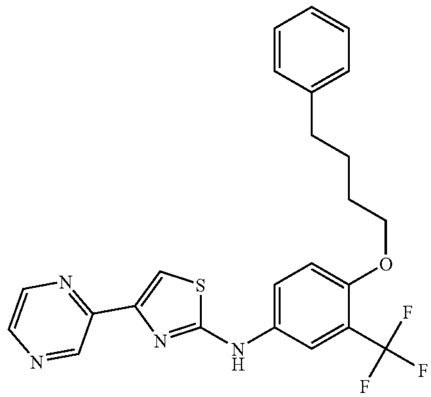 | N-(4-(4-phenylbutoxy)-3-fluorophenyl)-4-(pyrazin-2-yl)thiazol-2-amine | +++ |
| 943 | 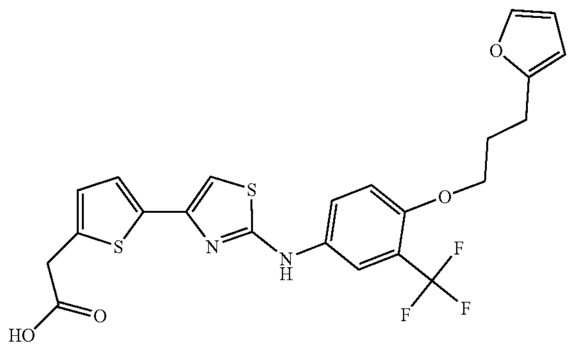 | 2-(5-(2-(4-(3-(furan-2-yl)propoxy)-3-(trifluoromethyl)phenylamino)thiazol-4-yl)thiophen-2-yl)acetic acid | +++ |
| 944 | 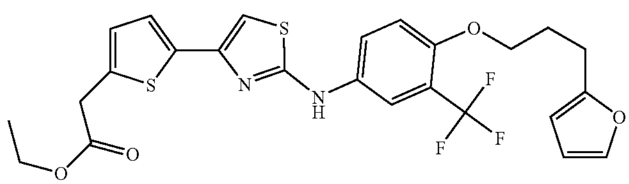 | ethyl 2-(5-(2-(4-(3-(furan-2-yl)propoxy)-3-(trifluoromethyl)phenylamino)thiazol-4-yl)thiophen-2-yl)acetate | +++ |
| 945 | 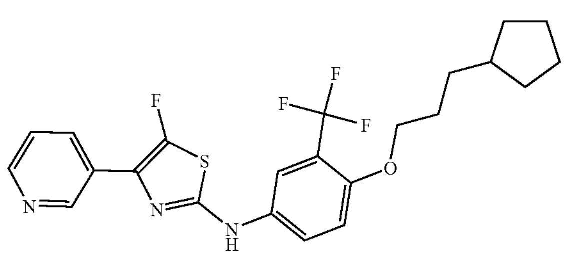 | N-(4-(3-cyclopentylpropoxy)-3-(trifluoromethyl)phenyl)-5-fluoro-4-(pyridin-3-yl)thiazol-2-amine | +++ |
| 946 | 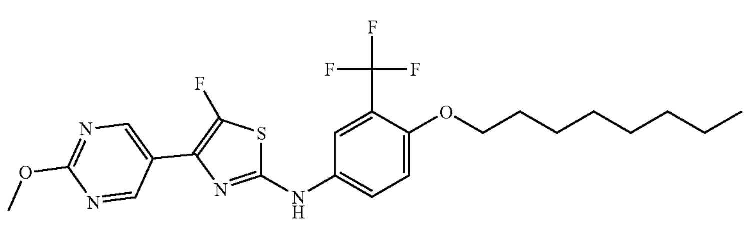 | 5-fluoro-N-(3-(trifluoromethyl)-4-(octyloxy)phenyl)-4-(2-methoxypyrimidin-5-yl)thiazol-2-amine | +++ |

TABLE IV-continued

| Cpd | Structure | Name | Activity |
|---|---|---|---|
| 947 | 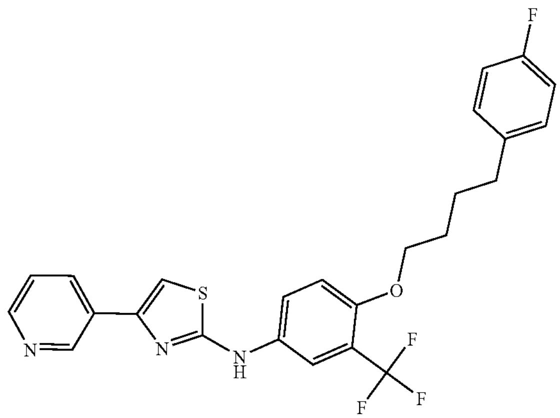 | N-(4-(4-(4-fluorophenyl)butoxy)-3-(trifluoromethyl)phenyl)-4-(pyridin-3-yl)thiazol-2-amine | +++ |
| 948 | 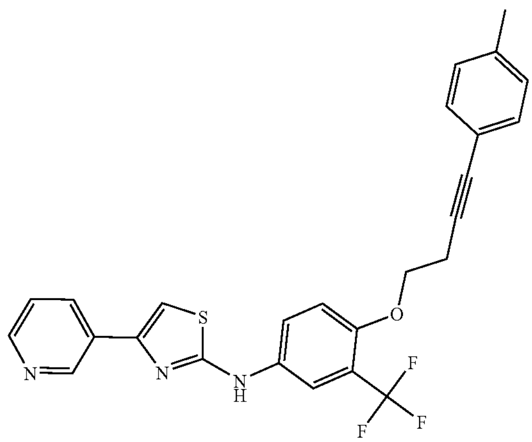 | N-(4-(4-p-tolylbut-3-ynyloxy)-3-(trifluoromethyl)phenyl)-4-(pyridin-3-yl)thiazol-2-amine | +++ |
| 949 | 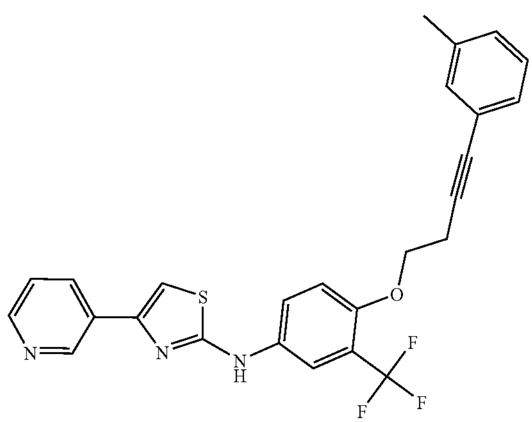 | N-(4-(4-m-tolylbut-3-ynyloxy)-3-(trifluoromethyl)phenyl)-4-(pyridin-3-yl)thiazol-2-amine | +++ |
| 950 | 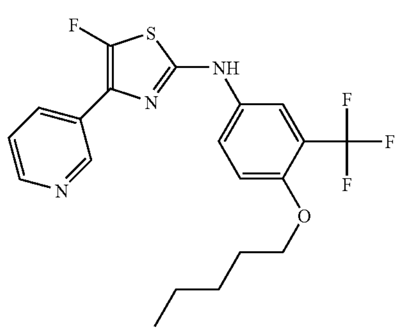 | 5-fluoro-N-(3-(trifluoromethyl)-4-(pentyloxy)phenyl)-4-(pyridin-3-yl)thiazol-2-amine | +++ |

TABLE IV-continued

| Cpd | Structure | Name | Activity |
|---|---|---|---|
| 951 | 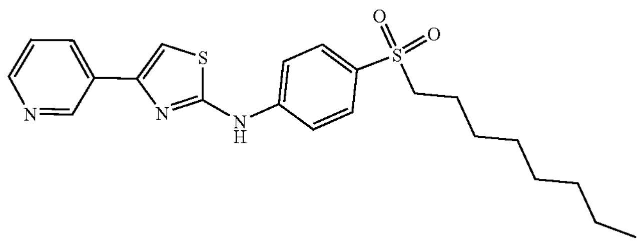 | N-(4-(octylsulfonyl)phenyl)-4-(pyridin-3-yl)thiazol-2-amine | +++ |
| 952 | 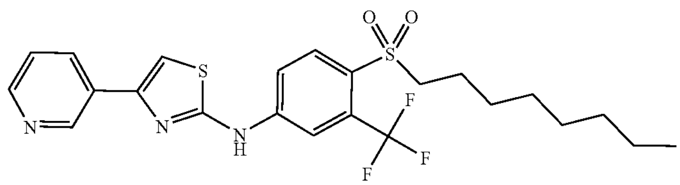 | N-(3-(trifluoromethyl)-4-(octylsulfonyl)phenyl)-4-(pyridin-3-yl)thiazol-2-amine | +++ |
| 953 | 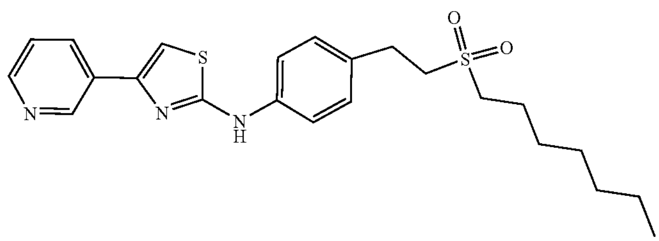 | N-(4-(2-(heptylsulfonyl)ethyl)phenyl)-4-(pyridin-3-yl)thiazol-2-amine | ++ |

Example 4

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

4A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

4B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N11, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×10$^5$ cells/10 ml/plate). The plates are then incubated at 37° C. in a 5% CO2 incubator.

Cells are examined under a microscope approximated 24 hours after seeding and prior to adding drugs. If counting and dilution were performed correctly, cells are 60-70% confluent and nearly all cells should attach and spread evenly in the well.

4C. Treatment of HCV-replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml penstrep (BRL # 15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 cells/100 μl/well of 96 well plate (6-7.5×105 cells/10 ml/plate). Plates are placed into 37° C. 5% $CO_2$ incubator overnight.

4D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 μl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 μl of PBS. The PBS is then decanted and the plates tapped in a paper towel to remove any remaining PBS. Cells are fixed in situ with 100 μl/well of pre-cooled (−20° C.) methanol: acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

Test Results:

Compounds described in the "TABLE OF COMPOUNDS" is Example 3 have been tested in an HCV replication assay, essentially as described in this example, and found to inhibit replication of the HCV replicon with an $EC_{50}$ value of less than 10 micromolar.

Example 5

Cytotoxicity Assays

To insure that the decrease in replicon replication is due to compound activity against the HCV replicon rather than non-specific toxicity assays are used to quantitate compound cytotoxicity.

Example 5A

Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

Example 5B

MTS Assay for Cytotoxicity

Cell viability may also be determined by CELLTITER 96 AQUEOUS ONE Solution Cell Proliferation Assay (Promega, Madison Wis.), a calorimetric assay for determining the number of viable cells. In this method, before fixing the cells, 10-20 μl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Album and MTS methods for determining cytotoxicity may be obtained as follows: Cells are treated with different concentrations of test compound or Helioxanthin for a three day-period. Prior to lysis for detection album as described above, the MTS reagent is added according to manufacturer's instruction to each well and incubate at 37° C. and read at OD 490 nm. The cellular album quantitation is then performed as described above.

What is claimed is:

1. A method of relieving one or more symptoms of Hepatitis C Infection in a patient, comprising administering to a patient in need thereof, a therapeutically effective amount of a compound of the formula

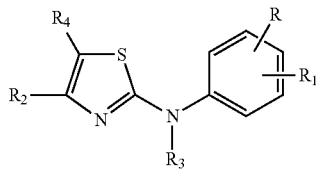

or pharmaceutically acceptable salt or hydrate thereof; wherein:

R is 0 or one or more substituents independently chosen from halogen, hydroxyl, amino, cyano, nitro, $C_1$-$C_2$alkyl, $C_1$-$C_2$alkoxy, $C_1$-$C_2$haloalkyl, and $C_1$-$C_2$haloalkoxy;

$R_1$ is one substituent independently chosen from $C_4$-$C_{10}$ alkyl, $C_2$-$C_{io}$ alkenyl, $C_2$-$C_{io}$ alkynyl, $C_4$-$C_{io}$ alkoxy, and a group-YZ, where Y is a bond, or Y is $C_1$-$C_{10}$alkyl optionally having 1 or 2 oxygen or nitrogen atoms within the alkyl chain; and Z is $C_3$-$C_7$cycloalkyl, phenyl, or ($C_3$-$C_7$cycloalkyl)$C_0$-$C_{10}$alkoxy, wherein each group listed in the definition of $R_1$ is substituted with 0 or one or more substituents independently chosen from:

halogen, hydroxyl, amino, cyano, nitro, oxo, $C_1$-$C_4$alkyl, $C_1$-$C_4$alkoxy, $C_1$-$C_2$haloalkyl, and $C_1$-$C_2$haloalkoxy;

wherein there is an $R_1$ substituent in either the meta or para positions of the phenyl it substitutes;

$R_2$ is pyridyl, which is substituted with 0 or one or more substituents independently chosen from halogen, hydroxyl, cyano, —C(O)NH$_2$, $C_1$-$C_2$haloalkyl, $C_1$-$C_2$haloalkoxy, mono- and di-$C_1$-$C_6$alkylamino, mono- and di-($C_1$-$C_4$alkyl)carboxamide, and mono- and di($C_1$-$C_4$alkyl)sulfonamide, $R_3$ is hydrogen; and $R_4$ is hydrogen, halogen, cyano, trifluoromethyl or $C_1$-$C_2$alkyl.

2. The method of claim 1, wherein R is 0 substituents.

3. The method of claim 2, wherein $R_1$ is $C_4$-$C_{10}$ alkyl or $C_4$-$C_{10}$ alkoxy.

4. The method of claim 2, wherein $R_1$ is a group-YZ.

5. The method of claim 1, wherein $R_4$ is hydrogen; and $R_2$ is 3-pyridyl.

6. The method of claim 1, wherein the patient has antibodies to hepatitis C virus.

7. The method of claim 6, additionally comprising administering to the patient an amount of at least one anti-HCV agent that is not a compound or salt of the formula

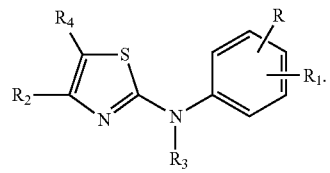

8. The method of claim 7, further comprising administering to the patient an amount of one or more of pegylated alpha interferon, un-pegylated alpha interferon, ribavirin, protease inhibitor, polymerase inhibitor, p7 inhibitor, entry inhibitor, fusion inhibitor, anti-fibrotic, drug which targets inosine monophosphate dehydrogenase inhibitors (IMPDH), synthetic thymosin alpha 1, therapeutic vaccine, immunomodulator, and helicase inhibitor.

9. The method of claim 1, wherein the compound is combined with at least one pharmaceutically acceptable excipient and administered as a pharmaceutical composition.

10. The method of claim 9 wherein the pharmaceutical composition is formulated for oral administration.

11. A method of relieving one or more symptoms of a Hepatitis C Infection in a patient, comprising administering to a patient in need thereof, a therapeutically effective amount of a compound, wherein the compound is N-(3-(trifluoromethyl)-4-(pentyloxy)phenyl)-4-(pyridin-3-yl)thiazol-2-amine;
N-(3-fluoro-4-(pentyloxy)phenyl)-4-(pyridin-3-yl)thiazol-2-amine;
N-(4-(cyclohexylmethoxy)-3-fluorophenyl)-4-(pyridin-3-yl)thiazol-2-amine;
N-(3-methyl-4-(pentyloxy)phenyl)-4-(pyridin-3-yl)thiazol-2-amine;
N-(4-butoxy-3-(trifluoromethyl)phenyl)-4-(pyridin-3-yl)thiazol-2-amine;
N-(4-(pentyloxy)phenyl)-4-(pyridin-3-yl)thiazol-2-amine;
N-(4-pentylphenyl)-4-(pyridin-3-yl)thiazol-2-amine;
N-(3-(benzyloxy)phenyl)-4-(pyridin-3-yl)thiazol-2-amine;
N-(3-phenoxyphenyl)-4-(pyridin-3-yl)thiazol-2-amine;
N-(3-(phenethyloxy)phenyl)-4-(pyridin-3-yl)thiazol-2-amine;
N-(4-(hexyloxy)phenyl)-4-(pyridin-3-yl)thiazol-2-amine;
N-(4-butoxyphenyl)-4-(pyridin-3-yl)thiazol-2-amine;
N-(4-(heptyloxy)phenyl)-4-(pyridin-3-yl)thiazol-2-amine;
N-(4-(octyloxy)phenyl)-4-(pyridin-3-yl)thiazol-2-amine;
N-(4-hexylphenyl)-4-(pyridin-3-yl)thiazol-2-amine;
N-(4-octylphenyl)-4-(pyridin-3-yl)thiazol-2-amine;
N-(4-butylphenyl)-4-(pyridin-3-yl)thiazol-2-amine;
N-(3-benzylphenyl)-4-(pyridin-3-yl)thiazol-2-amine;
N-(4-cyclohexylphenyl)-4-(pyridin-3-yl)thiazol-2-amine;
N-(4-phenoxyphenyl)-4-(pyridin-3-yl)thiazol-2-amine;
N-(4-(cyclopentyloxy)-3-(trifluoromethyl)phenyl)-4-(pyridin-3-yl)thiazol-2-amine;
N-(4-isobutoxy-3-(trifluoromethyl)phenyl)-4-(pyridin-3-yl)thiazol-2-amine;
N-(4-(cyclopropylmethoxy)-3-(trifluoromethyl)phenyl)-4-(pyridin-3-yl)thiazol-2-amine;
N-methyl-5-(2-(4-(pentyloxy)-3-(trifluoromethyl)phenylamino)thiazol-4-yl)picolinamide;
N-(5-cyclohexyl-2-methoxyphenyl)-4-(pyridin-3-yl)thiazol-2-amine;
N-(2-methoxy-5-phenoxyphenyl)-4-(pyridin-3-yl)thiazol-2-amine;

N-cyclopropyl-5-(2-(4-(pentyloxy)-3-(trifluoromethyl) phenylamino)thiazol-4-yl)picolinamide;
N-(4-(pentyloxy)-3-(trifluoromethyl)phenyl)-4-(pyridin-4-yl)thiazol-2-amine;
N-(4-(heptyloxy)phenyl)-4-(pyridin-4-yl)thiazol-2-amine;
N-(3-phenoxyphenyl)-4-(pyridin-4-yl)thiazol-2-amine;
N-(4-(heptyloxy)phenyl)-4-(6-methylpyridin-3-yl)thiazol-2-amine;
4-(6-methylpyridin-3-yl)-N-(4-(octyloxy)phenyl)thiazol-2-amine;
5-(2-(4-(pentyloxy)-3-(trifluoromethyl)phenylamino) thiazol-4-yl)pyridin-2-ol;
4-(6-methoxypyridin-3-yl)-N-(4-(pentyloxy)-3-(trifluoromethyl)phenyl)thiazol-2-amine;
N-(4-(octyloxy)phenyl)-4-(pyridin-2-yl)thiazol-2-amine;
N-(4-(octyloxy)phenyl)-4-(5-(pyridin-2-yl)thiophen-2-yl)thiazol-2-amine;
N-(4-(heptyloxy)phenyl)-4-(pyridin-2-yl)thiazol-2-amine;
N-(3-(trifluoromethyl)-4-(pentyloxy)phenyl)-4-(pyridin-2-yl)thiazol-2-amine;
N-(4-(octyloxy)phenyl)-4-(pyridin-4-yl)thiazol-2-amine;
N-(3-fluoro-4-(pentyloxy)phenyl)-4-(pyridin-4-yl)thiazol-2-amine;
N-(3-fluoro-4-(pentyloxy)phenyl)-4-(pyridin-2-yl)thiazol-2-amine;
N-(3,5-difluoro-4-(pentyloxy)phenyl)-4-(pyridin-3-yl)thiazol-2-amine;
4-(6-bromopyridin-3-yl)-N-(3-(trifluoromethyl)-4-(pentyloxy)phenyl)thiazol-2-amine;
4-(6-chloropyridin-3-yl)-N-(3-(trifluoromethyl)-4-(pentyloxy)phenyl)thiazol-2-amine;
N-(3-(trifluoromethyl)-4-(octyloxy)phenyl)-4-(pyridin-3-yl)thiazol-2-amine;
N-(4-heptylphenyl)-4-(pyridin-3-yl)thiazol-2-amine;
N-(3-(trifluoromethyl)-4-(pentyloxy)phenyl)-4-(6-fluoropyridin-3-yl)thiazol-2-amine;
4-(6-fluoropyridin-3-yl)-N-(4-(heptyloxy)phenyl)thiazol-2-amine;
4-(6-fluoropyridin-3-yl)-N-(4-(octyloxy)phenyl)thiazol-2-amine;
4-(6-fluoropyridin-3-yl)-N-(4-octylphenyl)thiazol-2-amine;
N-(4-(3-cyclopentylpropoxy)-3-(trifluoromethyl)phenyl)-4-(pyridin-3-yl)thiazol-2-amine;
N-(4-(3-cyclopentylpropoxy)-3-(trifluoromethyl)phenyl)-4-(6-methylpyridin-3-yl)thiazol-2-amine;
6-(octyloxy)-N-(4-((pyridin-3-yl)methyl)thiazol-2-yl)pyridin-3-amine;
N-(4-(octyloxy)phenyl)-4-((pyridin-3-yl)methyl)thiazol-2-amine;
N-(3-(trifluoromethyl)-4-(pentyloxy)phenyl)-4-((pyridin-3-yl)methyl)thiazol-2-amine;
5-(2-(3-(trifluoromethyl)-4-(pentyloxy)phenylamino) thiazol-4-yl)pyridine-2-carbonitrile;
5-(2-(4-(cyclohexylmethoxy)-3-fluorophenylamino)thiazol-4-yl)pyridine-2-carbonitrile;
5-(2-(4-(octyloxy)phenylamino)thiazol-4-yl)pyridine-2-carbonitrile;
5-(2-(3-(trifluoromethyl)-4-(pentyloxy)phenylamino) thiazol-4-yl)pyridine-3-carbonitrile;
5-(2-(4-(heptyloxy)phenylamino)thiazol-4-yl)-N-methylpyridin-2-amine;
N-(3-(trifluoromethyl)-4-(octyloxy)phenyl)-4-(6-fluoropyridin-3-yl)thiazol-2-amine;
N-(3-fluoro-4-(pentyloxy)phenyl)-4-(6-fluoropyridin-3-yl)thiazol-2-amine;
N-(4-(3-cyclopentylpropoxy)-3-(trifluoromethyl)phenyl)-4-(6-fluoropyridin-3-yl)thiazol-2-amine;
2-(trifluoromethyl)-N4-(4-(6-fluoropyridin-3-yl)thiazol-2-yl)-N$^1$-methyl-N$^1$-pentylbenzene-1,4-diamine;
N-(4-(cyclohexylmethoxy)-3-fluorophenyl)-4-(6-fluoropyridin-3-yl)thiazol-2-amine;
N-(4((Z)-oct-3-enyloxy)-3-(trifluoromethyl)phenyl)-4-(pyridin-3-yl)thiazol-2-amine;
N-(4((Z)-oct-3-enyloxy)-3-(trifluoromethyl)phenyl)-4-(6-methylpyridin-3-yl)thiazol-2-amine;
5-(2-(3-(trifluoromethyl)-4-(pentyloxy)phenylamino) thiazol-4-yl)-N-methylpyridin-2-amine;
5-(2-(3-(trifluoromethyl)-4-(octyloxy)phenylamino)thiazol-4-yl)-N-methylpyridin-2-amine;
5-(2-(4-(cyclopentyloxy)-3-(trifluoromethyl)phenylamino)thiazol-4-yl)-N-methylpyridin-2-amine;
5-(2-(3-(trifluoromethyl)-4-(octyloxy)phenylamino)thiazol-4-yl)-N,N-dimethylpyridin-2-amine;
N-(4-octylphenyl)-4-(pyridin-2-yl)thiazol-2-amine;
N-(4-octylphenyl)-4-(5-(pyridin-2-yl)thiophen-2-yl)thiazol-2-amine;
N-(4-heptylphenyl)-4-(pyridin-2-yl)thiazol-2-amine;
2-(trifluoromethyl)-N$^1$-methyl-N$^1$-octyl-N$^4$-(4-(pyridin-2-yl)thiazol-2-yl)benzene-1,4-diamine;
N-(3-(trifluoromethyl)-4-(octyloxy)phenyl)-4-(pyridin-2-yl)thiazol-2-amine;
4-(heptyloxy)-N-(4-(pyridin-3-yl)thiazol-2-yl)benzamide;
ethyl 5-(2-(3-(trifluoromethyl)-4-(pentyloxy)phenylamino)thiazol-4-yl)pyridine-3-carboxylate;
ethyl 5-(2-(4-(octyloxy)phenylamino)thiazol-4-yl)pyridine-3-carboxylate;
5-(2-(3-(trifluoromethyl)-4-(octyloxy)phenylamino)thiazol-4-yl)pyridine-2-carbonitrile;
5-(2-(4-(3-cyclopentylpropoxy)-3-(trifluoromethyl)phenylamino)thiazol-4-yl)pyridine-2-carbonitrile;
5-(2-(3-fluoro-4-(pentyloxy)phenylamino)thiazol-4-yl) pyridine-2-carbonitrile;
5-(2-(4-(cyclopentyloxy)-3-(trifluoromethyl)phenylamino)thiazol-4-yl)pyridine-2-carbonitrile;
N-(3-(trifluoromethyl)-4-(pentan-3-yloxy)phenyl)-4-(pyridin-3-yl)thiazol-2-amine;
5-(2-(3-(trifluoromethyl)-4-(pentyloxy)phenylamino) thiazol-4-yl)pyridine-3-carboxylic acid;
5-(2-(4-(octyloxy)phenylamino)thiazol-4-yl)-N,N-dimethylpyridine-3-carboxamide;
5-(2-(4-(octyloxy)phenylamino)thiazol-4-yl)pyridine-3-carboxamide;
5-(2-(3-(trifluoromethyl)-4-(octyloxy)phenylamino)thiazol-4-yl)pyridine-3-carbonitrile;
5-(2-(4-(octyloxy)phenylamino)thiazol-4-yl)pyridine-3-carbonitrile;
N-(3-(trifluoromethyl)-4-(octyloxy)phenyl)-4-(5-methoxypyridin-3-yl)thiazol-2-amine;
N-(4-(cyclohexylmethoxy)-3-(trifluoromethyl)phenyl)-4-(pyridin-3-yl)thiazol-2-amine;
5-(2-(3-(trifluoromethyl)-4-(octyloxy)phenylamino)thiazol-4-yl)-4-methylpyridin-2-ol;
N-(3-(trifluoromethyl)-4-(octan-2-yloxy)phenyl)-4-(pyridin-3-yl)thiazol-2-amine;
N-(5-(2-(3-(trifluoromethyl)-4-(octan-2-yloxy)phenylamino)thiazol-4-yl)pyridin-2-yl)acetamide;
5-(2-(3-(trifluoromethyl)-4-(octan-2-yloxy)phenylamino) thiazol-4-yl)pyridin-2-amine;

N-(5-(2-(3-(trifluoromethyl)-4-(octyloxy)phenylamino)thiazol-4-yl)pyridin-2-yl)acetamide;
5-(2-(3-(trifluoromethyl)-4-(octyloxy)phenylamino)thiazol-4-yl)pyridin-2-amine;
N-(3-(trifluoromethyl)-4-(heptan-4-yloxy)phenyl)-4-(pyridin-3-yl)thiazol-2-amine;
N-(4-(3-phenylpropoxy)-3-(trifluoromethyl)phenyl)-4-(pyridin-3-yl)thiazol-2-amine;
N-(3-(octyloxy)phenyl)-4-(pyridin-3-yl)thiazol-2-amine;
5-(2-(4-(octyloxy)phenylamino)thiazol-4-yl)pyridin-2-amine;
N-(5-(2-(3-(trifluoromethyl)-4-(octyloxy)phenylamino)thiazol-4-yl)-3-methylpyridin-2-yl)acetamide;
N-(5-(2-(4-(octyloxy)phenylamino)thiazol-4-yl)-3-methylpyridin-2-yl)acetamide;
N-(4-(3,7-dimethyloctyloxy)-3-(trifluoromethyl)phenyl)-4-(pyridin-3-yl)thiazol-2-amine;
N-(3-(trifluoromethyl)-4-(octylthio)phenyl)-4-(pyridin-3-yl)thiazol-2-amine;
N-(3-(trifluoromethyl)-4-(octyloxy)phenyl)-4-(5-(trifluoromethyl)pyridin-2-yl)thiazol-2-amine;
2-(2-(3-(trifluoromethyl)-4-(octyloxy)phenylamino)thiazol-4-yl)pyridin-3-ol;
5-(2-(4-(cyclohexylmethoxy)-3-fluorophenylamino)thiazol-4-yl)pyridine-3-carbonitrile;
Ethyl 6-(2-(3-(trifluoromethyl)-4-(octyloxy)phenylamino)thiazol-4-yl)pyridine-2-carboxylate;
5-(2-(3-(trifluoromethyl)-4-(octyloxy)phenylamino)thiazol-4-yl)pyridin-2-ol;
N-(3-(cyclopentyloxy)-4-methoxyphenyl)-4-(pyridin-3-yl)thiazol-2-amine;
6-Phenoxy-N-(4-(pyridin-3-yl)thiazol-2-yl)pyridin-3-amine;
N-(4-phenethylphenyl)-4-(pyridin-3-yl)thiazol-2-amine;
N-(4-(cyclohexylmethoxy)-3-(trifluoromethyl)phenyl)-4-(5-(trifluoromethyl)pyridin-2-yl)thiazol-2-amine;
N-(3-(trifluoromethyl)-4-(oct-1-ynyl)phenyl)-4-(pyridin-3-yl)thiazol-2-amine;
N-(4-(4-phenylbutoxy)-3-(trifluoromethyl)phenyl)-4-(pyridin-3-yl)thiazol-2-amine;
N-(4-(4-p-tolylbutoxy)-3-(trifluoromethyl)phenyl)-4-(pyridin-3-yl)thiazol-2-amine;
3-(2-(3-(trifluoromethyl)-4-(octyloxy)phenylamino)thiazol-4-yl)pyridine-2-carbonitrile   3-(2-(3-(trifluoromethyl)-4-(octyloxy)phenylamino)thiazol-4-yl)pyridine-2-carboxamide   4-(4-(pyridin-3-yl)thiazol-2-ylamino)-N-(4-methoxyphenyl)benzamide;
N-(3-(trifluoromethyl)-4-(oct-1-enyl)phenyl)-4-(pyridin-3-yl)thiazol-2-amine;
N-(3-(trifluoromethyl)-4-(heptyloxy)phenyl)-4-(pyridin-3-yl)thiazol-2-amine;
N-(4-(4-methylpentyloxy)-3-(trifluoromethyl)phenyl)-4-(pyridin-3-yl)thiazol-2-amine;
N-(3-(trifluoromethyl)-4-octylphenyl)-4-(pyridin-3-yl)thiazol-2-amine;
N-(3-(trifluoromethyl)-4-(octyloxy)phenyl)-5-methyl-4-(pyridin-3-yl)thiazol-2-amine;
N-(4-(3-cyclopentylpropoxy)-3-(trifluoromethyl)phenyl)-5-methyl-4-(pyridin-3-yl)thiazol-2-amine;
N-(4-(4-phenylbutoxy)-3-(trifluoromethyl)phenyl)-5-methyl-4-(pyridin-3-yl)thiazol-2-amine;
N-(4-(3-phenylpropoxy)-3-(trifluoromethyl)phenyl)-5-methyl-4-(pyridin-3-yl)thiazol-2-amine;
N-(4-(4-p-tolylbutoxy)-3-(trifluoromethyl)phenyl)-5-methyl-4-(pyridin-3-yl)thiazol-2-amine;
N-(4-(3-phenylpropoxy)-3-fluorophenyl)-4-(pyridin-3-yl)thiazol-2-amine;
N-(4-(3-phenylpropoxy)-3-fluorophenyl)-5-methyl-4-(pyridin-3-yl)thiazol-2-amine;
N-(4-(cyclohexylmethoxy)-3-(trifluoromethyl)phenyl)-5-methyl-4-(pyridin-3-yl)thiazol-2-amine;
N-(4-sec-butylphenyl)-4-(pyridin-3-yl)thiazol-2-amine;
4-(4-(pyridin-3-yl)thiazol-2-ylamino)benzamide;
N-(4-fluoro-3-(trifluoromethyl)phenyl)-4-(pyridin-3-yl)thiazol-2-amine;
3-(4-(pyridin-3-yl)thiazol-2-ylamino)benzamide;
N-(2-methyl-4-(trifluoromethoxy)phenyl)-4-(pyridin-3-yl)thiazol-2-amine;
N-(4-(4-(pyridin-3-yl)thiazol-2-ylamino)phenyl)acetamide;
4-(4-(pyridin-3-yl)thiazol-2-ylamino)benzonitrile;
N-(4-chloro-3-(trifluoromethyl)phenyl)-4-(pyridin-3-yl)thiazol-2-amine;
4-(4-(pyridin-3-yl)thiazol-2-ylamino)-2-(trifluoromethyl)benzonitrile;
N-(4-tert-butylphenyl)-4-(pyridin-3-yl)thiazol-2-amine;
N-(3-tert-butylphenyl)-4-(pyridin-3-yl)thiazol-2-amine;
N-(3,5-di-tert-butylphenyl)-4-(pyridin-3-yl)thiazol-2-amine;
tert-butyl  4-(4-(pyridin-3-yl)thiazol-2-ylamino)phenylcarbamate;
N-(4-(4-chlorophenoxy)phenyl)-4-(pyridin-3-yl)thiazol-2-amine;
N-(4-(p-tolyloxy)phenyl)-4-(pyridin-3-yl)thiazol-2-amine;
N-(4-butyl-2-methylphenyl)-4-(pyridin-3-yl)thiazol-2-amine;
N-(5-tert-pentyl-2-phenoxyphenyl)-4-(pyridin-3-yl)thiazol-2-amine;

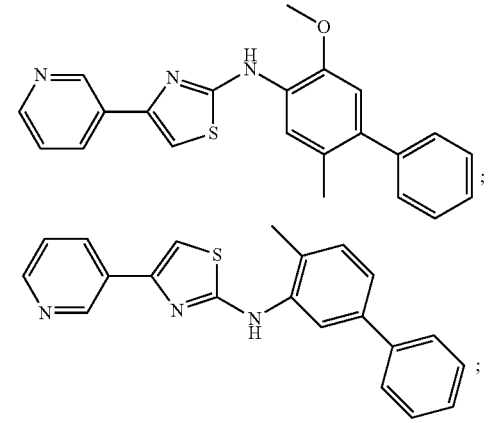

N-(4-(4-phenylbutoxy)-3-fluorophenyl)-4-(pyridin-3-yl)thiazol-2-amine;
2-(3-(trifluoromethyl)-4-(octyloxy)phenylamino)-4-(pyridin-3-yl)thiazole-5-carbonitrile;
5-Fluoro-N-(3-(trifluoromethyl)-4-(octyloxy)phenyl)-4-(pyridin-3-yl)thiazol-2-amine;
5-Chloro-N-(3-(trifluoromethyl)-4-(octyloxy)phenyl)-4-(pyridin-3-yl)thiazol-2-amine;
N-(4-(3-phenylpropoxy)phenyl)-4-(pyridin-3-yl)thiazol-2-amine;
N-(4-(4-phenylbutoxy)phenyl)-4-(pyridin-3-yl)thiazol-2-amine;
N-(4-(4-(thiophen-2-yl)butoxy)phenyl)-4-(pyridin-3-yl)thiazol-2-amine;

N-(4-(3-phenoxypropoxy)-3-(trifluoromethyl)phenyl)-4-(pyridin-3-yl)thiazol-2-amine;

N-(4-(4-m-tolylbutoxy)-3-(trifluoromethyl)phenyl)-4-(pyridin-3-yl)thiazol-2-amine;

N-(4-(4-phenylbutoxy)-3-methylphenyl)-4-(pyridin-3-yl)thiazol-2-amine;

N-(4-(but-3-ynyloxy)-3-(trifluoromethyl)phenyl)-4-(pyridin-3-yl)thiazol-2-amine;

N-(3-(trifluoromethyl)-4-(5-phenylpentyl)phenyl)-4-(pyridin-3-yl)thiazol-2-amine;

N-(4-(3-cyclopentylpropoxy)-3-(trifluoromethyl)phenyl)-5-fluoro-4-(pyridin-3-yl)thiazol-2-amine;

N-(4-(4-(4-fluorophenyl)butoxy)-3-(trifluoromethyl)phenyl)-4-(pyridin-3-yl)thiazol-2-amine;

N-(4-(4-p-tolylbut-3-ynyloxy)-3-(trifluoromethyl)phenyl)-4-(pyridin-3-yl)thiazol-2-amine;

N-(4-(4-m-tolylbut-3-ynyloxy)-3-(trifluoromethyl)phenyl)-4-(pyridin-3-yl)thiazol-2-amine; or 5-fluoro-N-(3-(trifluoromethyl)-4-(pentyloxy)phenyl)-4-(pyridin-3-yl)thiazol-2-amine;

or a pharmaceutically acceptable salt or hydrate of any of the foregoing.

12. The method of claim 1, wherein $R_4$ is halogen.

13. The method of claim 11, wherein the compound is N-(3-(trifluoromethyl)-4-(octyloxy)phenyl)-4-(pyridin-3-yl)thiazol-2-amine;

N-(3-(trifluoromethyl)-4-octylphenyl)-4-(pyridin-3-yl)thiazol-2-amine;

N-(3-(trifluoromethyl)-4-(octyloxy)phenyl)-5-methyl-4-(pyridin-3-yl)thiazol-2-amine;

5-Fluoro-N-(3-(trifluoromethyl)-4-(octyloxy)phenyl)-4-(pyridin-3-yl)thiazol-2-amine; or 5-Chloro-N-(3-(trifluoromethyl)-4-(octyloxy)phenyl)-4-(pyridin-3-yl)thiazol-2-amine.

\* \* \* \* \*